(12) United States Patent
Wu et al.

(10) Patent No.: US 6,831,080 B2
(45) Date of Patent: Dec. 14, 2004

(54) CINNAMIDE DERIVATIVES AS KCNQ POTASSIUM CHANNEL MODULATORS

(75) Inventors: Yong-Jin Wu, Madison, CT (US); Li-Quang Sun, Glastonbury, CT (US); Jie Chen, Madison, CT (US); Huan He, Wallingford, CT (US); Alexandre L'Heureux, Longueuil (CA); Pierre Dextraze, Laprairie (CA); Jean-Paul Daris, St. Hubert (CA); Gene G. Kinney, Collegeville, PA (US); Steven I. Dworetzky, Middlefield, CT (US); Piyasena Hewawasam, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 3 days.

(21) Appl. No.: 10/160,582

(22) Filed: May 31, 2002

(65) Prior Publication Data

US 2003/0166650 A1 Sep. 4, 2003

Related U.S. Application Data

(60) Provisional application No. 60/294,815, filed on May 31, 2001.

(51) Int. Cl.[7] .................. C07C 237/20; C07D 311/74; C07D 333/74; A61K 31/33; A61K 31/165
(52) U.S. Cl. .................. 514/230.5; 544/168; 544/146; 544/105; 544/335; 544/336; 544/393; 546/337; 546/175; 546/265; 514/237.8; 514/231.5; 514/357; 514/311; 514/256; 514/332; 514/252.1; 514/255.03
(58) Field of Search ........................ 544/168, 146, 544/105, 335, 336, 393; 514/237.8, 231.5, 230.5, 357, 311, 256, 332, 252.1, 255.03; 546/337, 175, 265

(56) References Cited

U.S. PATENT DOCUMENTS

| | | | |
|---|---|---|---|
| 4,927,838 A | 5/1990 | Guthrie et al. | 514/337 |
| 6,046,239 A | 4/2000 | Lennox et al. | 514/563 |

FOREIGN PATENT DOCUMENTS

| | | |
|---|---|---|
| EP | 810220 A1 | 12/1997 |
| EP | 1-142-875 A1 | 12/2001 |
| JP | 45-14291 | 5/1970 |
| JP | 2-138159 | 5/1990 |
| WO | WO 00/07993 | 2/2000 |
| WO | WO 01/10380 | 2/2001 |
| WO | WO 01/10381 | 2/2001 |

OTHER PUBLICATIONS

Jensen, BNS–204352: A potassium channel opener developed for the treatment of stroke, CNS Drug Rev. 8: 353–360, 2002.*

Bell et al. Generation and Cycloadditions of 2–(N–Acylamino)–1–Thia–1,3–Dienes Part III, Control of Diasteroselectivity Using Homochiral Auxiliaries. Tetrahedron 54:3219–3234, 1998.*

H.–S. Wang, et al., "KCNQ2 and KCNQ3 Potassium Channel Subunits: Modular Correlates of the M–Channel", *Science*, 282, pp. 1890–1893 (1998).

* cited by examiner

*Primary Examiner*—Richard L. Raymon
*Assistant Examiner*—Hong Liu
(74) *Attorney, Agent, or Firm*—Aldo A. Algieri

(57) ABSTRACT

There is provided novel cinnamide derivatives of Formula I:

wherein R is $C_{1-4}$ alkyl or trifluoromethyl; $R^1$ is selected from the group consisting of pyridinyl, quinolinyl, thienyl, furanyl, 1,4-benzodioxanyl, 1,3-benzodioxolyl, chromanyl, indanyl, biphenylyl, phenyl and substituted phenyl in which said substituted phenyl is substituted with one or two substituents each independently selected-from the group consisting of halogen, $C_{1-4}$ alkyl, $C_{1-4}$ alkoxy, trifluoromethyl, trifluoromethoxy and nitro; $R^2$ and $R^3$ are each independently selected from the group consisting of hydrogen, $C_{1-4}$ alkyl, and halogen; $R^4$ is selected from the group consisting of di($C_{1-4}$ alkyl)amino, trifluoromethoxy and optionally substituted morpholin-4-yl, pyridinyl, pyrimidinyl, piperazinyl, and pyrazinyl with one or two substituents in which said substituent is independently selected from the group consisting of $C_{1-4}$ alkyl, aminomethyl, hydroxymethyl, chloro or fluoro; $R^5$ is hydrogen, chloro or fluoro; or $R^4$ and $R^5$ taken together are —CH=CH—CH=CH— or —X($CH_2$)$_m$Y— in which X and Y are each independently selected from the group consisting of $CH_2$, ($CH_2$)$_n$N($R^9$)— and O, wherein m is 1 or 2; n is 0 or 1; and $R^6$, $R^7$, and $R^8$ are each independently selected from hydrogen, chloro and fluoro; and $R^9$ is selected from the group consisting of hydrogen, $C_{1-4}$ alkyl, hydroxyethyl, $C_{1-4}$ alkoxyethyl, cyclopropylmethyl, —$CO_2$($C_{1-4}$alkyl), and —$CH_2CH_2NR^{10}R^{11}$ in which $R^{10}$ and $R^{11}$ are each independently hydrogen or $C_{1-4}$ alkyl, which are openers of the KCNQ potassium channels and are useful in the treatment of disorders which are responsive to the opening of the KCNQ potassium channels.

27 Claims, No Drawings

CINNAMIDE DERIVATIVES AS KCNQ POTASSIUM CHANNEL MODULATORS

CROSS-REFERENCE TO RELATED APPLICATIONS

This is a non-provisional application which claims the benefit of U.S. Provisional Application No. 60/294,815 filed May 31, 2001.

FIELD OF THE INVENTION

The present invention is directed to novel cinnamide derivatives which are modulators of KCNQ potassium channels and are therefore useful in treating disorders responsive to the modulation of the potassium channels. The present invention also provides a method of treatment with the novel cinnamide derivatives and to pharmaceutical compositions thereof.

BACKGROUND OF THE INVENTION

Potassium ($K^+$) channels are considered to be the most diverse class of ion channels and have several critical roles in cell function. This has been demonstrated in neurons where $K^+$ channels are responsible, in part, for determining cell excitability by contributing to membrane repolarization following depolarization, resting membrane potential, and regulation of neurotransmitter release. The M-current has long been described, by electrophysiology recording methods and by pharmacology, as a dominant conductance in controlling neuronal excitability. Pharmacological activation or suppression of M-currents by small molecules could have profound effects in controlling neuronal excitability. Recently, Wang et al., Science, 282:1890–1893, (1998) reported that co-assembly of the KCNQ2 and KCNQ3 potassium channels underlies the native M-current in neurons.

Activation or opening of the KCNQ channel(s), particularly the KCNQ2 or KCNQ2/3 channel(s), mutated or wild type, may prove to be beneficial in increasing hyperpolarization of neurons, thereby resulting in protection from abnormal synchronous firing during a migraine attack. The present invention provides a solution to the problem of abnormal synchronous firing of neurons related to migraine headache by demonstrating that modulators, preferably openers, of KCNQ potassium channels increases hyperpolarization of neurons which protects against abnormal synchronous neuron firing involved in migraine attacks.

Although the symptom pattern varies among migraine sufferers, the severity of migraine pain justifies a need for vigorous, yet safe and effective, treatments and therapies for the great majority of cases. Needed in the art are agents that can be used to combat and relieve migraine (and diseases similar to and mechanistically related to migraine), and even prevent the recurrence of migraine. Also needed are anti-migraine agents which are effective in the treatment of acute migraine, as well as in the prodrome phase of a migraine attack. Thus, a clear goal in the art is to discover new, safe, nontoxic and effective anti-migraine compounds for use as drugs, and in anti-migraine compositions and treatments.

Because migraine afflicts a large percentage of the population, there is a need to discover compounds and agents that are useful in therapeutics and treatments, and as components of pharmaceutical compositions, for reducing, ameliorating, or alleviating the pain and discomfort of migraine headache and other symptoms of migraine. The present invention satisfies such a need by providing compounds that function as openers of the KCNQ family of potassium channel proteins to serve as anti-migraine agents or drugs and to comprise compositions to treat migraine, as described herein.

A broad range of cinnamide compounds are known and new compounds continue to be reported with a broad range of utility. Some of these compounds can be found in the disclosures of WO 00/07993 published Feb. 17, 2000, EP 810220A1, published Dec. 3, 1997, U.S. Pat. No. 4,927,838 issued May 22, 1990 to Guthrie, et al., U.S. Pat. No. 6,046,239 issued Apr. 4, 2000 to Lennox, et al., WO 00.42013, published Jul. 20, 2000, WO 01/10381 published Feb. 15, 2001, WO 01/10380 published Feb. 15, 2001, JP45-14291 published May 21, 1970, and JP2-138159 published May 28, 1990. The compounds described in these patents are distinct from those of the present invention.

SUMMARY OF THE INVENTION

The present invention provides novel cinnamides and related derivatives having the general Formula I:

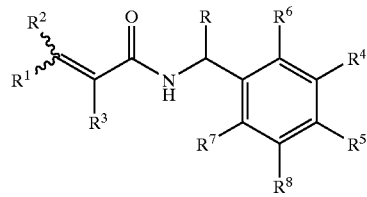

I wherein R, $R^1$, $R^2$, $R^3$, $R^4$, $R^5$, $R^6$, $R^7$, $R^8$ and $R^9$ are as defined below, or a nontoxic pharmaceutically acceptable salt, solvate or hydrate thereof which are openers or activators of KCNQ potassium channels. The present invention also provides pharmaceutical compositions comprising said cinnamides and to the method of treatment of disorders sensitive to KCNQ potassium channel opening activity such as migraine or a migraine attack, bipolar disorders, epilepsy, acute and chronic pain and anxiety.

DETAILED DESCRIPTION OF THE INVENTION

The present invention provides novel cinnamide and related derivatives which are modulators of the KCNQ potassium channels and which have the general Formula I or a pharmaceutically acceptable salt thereof:

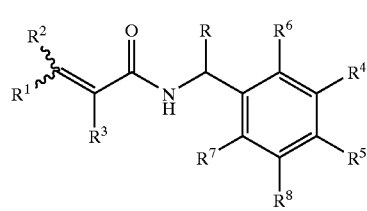

I wherein R is $C_{1-4}$ alkyl or trifluoromethyl; $R^1$ is selected from the group consisting of pyridinyl, quinolinyl, thienyl, furanyl, 1,4-benzodioxanyl, 1,3-benzodioxolyl, chromanyl, indanyl, biphenylyl, phenyl and substituted phenyl, in which said substituted phenyl is substituted with substituent independently selected from the group consisting of halogen, $C_{1-4}$ alkyl, $C_{1-4}$ alkoxy, trifluoromethyl, trifluoromethoxy and nitro; $R^2$ and $R^3$ are each independently selected from the group consisting of hydrogen, $C_{1-4}$ alkyl and halogen; $R^4$ is selected from the group consisting of di($C_4$ alkyl)amino, trifluoromethoxy and optionally substituted morpholin-4-yl, pyridinyl, pyrimidinyl, piperazinyl, and pyrazinyl with one or two substituents in which said substituent is independently selected from the group consisting of $C_{1-4}$alkyl, aminomethyl, hydroxymethyl, chloro or fluoro; $R^5$ is hydrogen, chloro or fluoro; or $R^4$ and $R^5$ taken together are —CH=CH—CH=CH— or —X$(CH_2)_m$Y— in which X and Y are each independently selected from the group consisting of $CH_2$, $(CH_2)_n$N($R^9$)— and O, wherein m is 1 or 2; n is 0 or 1; $R^6$, $R^7$, and $R^8$ are each independently selected from hydrogen, chloro and fluoro; and $R^9$ is selected from the group consisting of hydrogen, $C_{1-4}$alkyl, hydroxyethyl, $C_{1-4}$ alkoxyethyl, cyclopropylmethyl, —$CO_2$($C_{1-4}$alkyl), and —$CH_2CH_2NR^{10}R^{11}$ in which $R^{10}$ and $R^{11}$ are each independently hydrogen or $C_{1-4}$alkyl.

The present invention also provides a method for the treatment or alleviation of disorders associated with KCNQ potassium channel polypeptides and, in particular, human KCNQ potassium channel polypeptides in a mammal in need thereof which comprises administering together with a conventional adjuvant, carrier or diluent a therapeutically effective amount of a compound of Formula I or a pharmaceutically acceptable salt thereof. Preferably, the compounds of Formula I are useful in the treatment of migraine or a migraine attack, cluster headaches, bipolar disorder, convulsions, mania, acute mania, epilepsy, anxiety, depression, schizophrenia, functional bowel disorders, stroke, traumatic brain injury, multiple sclerosis, neurodegenerative disorders or alleviating pain such as musculoskeletal pain, post operative pain, surgical pain, inflammatory pain, neuropathic pain such as diabetic neuropathy and pain associated with cancer and fibromyalgia.

The term "pain" as used herein and in the claims means all types of acute and chronic pain, such as neuropathic pain, post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis and the term also is intended to include nociceptive pain or nociception.

The term "$C_{1-4}$ alkyl" as used herein and in the claims means straight or branched chain alkyl groups such as methyl, ethyl, propyl, isopropyl, butyl, isobutyl, and tert-butyl. The term "$C_{1-4}$ alkoxy" as used herein and in the claims means an oxygen substituted with straight or branched chain alkyl groups and includes groups such as methoxy, ethoxy, propoxy, isopropoxy, butoxy, isobutoxy, and tert-butoxy. The term "halogen" as used herein and in the claims is intended to include bromine, chlorine, iodine and fluorine.

As the compounds of the present invention contain a substituted carbon-carbon double bond as part of the structure, the compounds of the invention exist in either of two geometric isomeric forms, namely as cis or trans isomers. Preferred are the trans isomers in which the group $R^1$ and the amide group, C(O)NH, are trans to each other. As the compounds of the present invention possess an asymmetric carbon atom, such as the carbon adjacent to the amide nitrogen and to which the phenyl is attached, the present invention includes the racemate as well as the individual enantiomeric forms of the compounds of Formula I as described herein and in the claims. Preferred embodiments of compounds of Formula I include the racemate, a single enantiomer, and in certain instances a single enantiomer wherein the carbon adjacent to the amide nitrogen and to which the phenyl is attached has the (S) stereochemistry. Mixtures of isomers of the compounds of Formula I or chiral precursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns, according to procedures described herein.

Certain of the compounds of the present invention can exist in unsolvated forms as well as solvated forms including hydrated forms such as monohydrate, dihydrate, trihydrate, hemihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

In the method of the present invention, the term "therapeutically effective amount" means the total amount of each active component of the method that is sufficient to show a meaningful patient benefit, i.e., amelioration or healing of conditions which respond to modulation of the KCNQ potassium channels. When applied to an individual active ingredient, administered alone, the term refers to that ingredient alone. When applied to a combination, the term refers to combined amounts of the active ingredients that result in the therapeutic effect, whether administered in combination, serially or simultaneously. The term "KCNQ" as used herein and in the claims means the family of KCNQ2, KCNQ3, KCNQ4, and KCNQ5 potassium channel polypeptides as well as heteromultimers of different individual family members which include but are not limited to KCNQ2/3, KCNQ2/5 and KCNQ3/5. The terms "treat, treating, treatment" as used herein and in the claims means preventing, alleviating or ameliorating diseases and/or symptoms associated with dysfunction of cellular membrane polarization and conductance of human KCNQ2, KCNQ3, KCNQ4, and KCNQ5 potassium channel polypeptides and, in particular, migraine and/or symptoms that precede a full-blown migraine attack, neuropathic pain, mania and anxiety.

The general procedures used to synthesize intermediates and the compounds of Formula I are described in Reaction Schemes 1–4 and are illustrated in the preparations and examples. Reasonable variations of the described procedures, which would be evident to one skilled in the art, are intended to be within the scope of the present invention.

Reaction Scheme 1

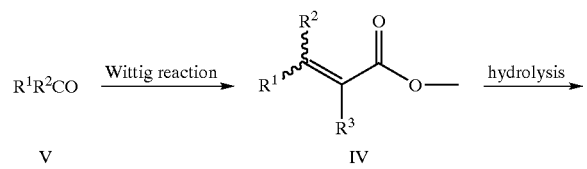

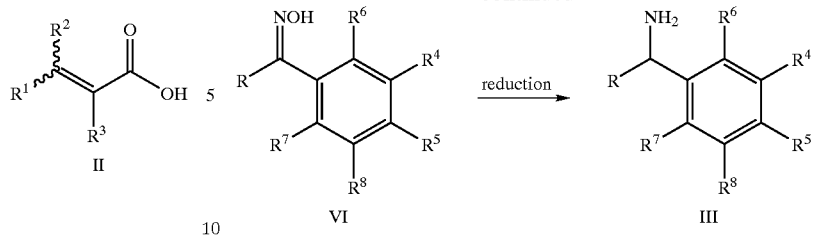

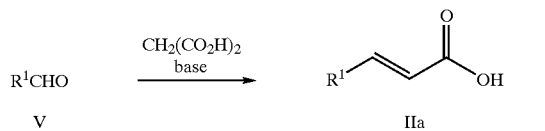

Reaction Scheme 1 depicts the preparation of cinnamic acid derivatives useful as intermediates in the synthesis of compounds of Formula I. Step 1 of Scheme 1 depicts the Wittig reaction of an appropriate aldehyde or ketone of Formula V with an appropriate Wittig reagent to provide the methyl ester of Formula IV. Hydrolysis of the methyl ester of Formula IV can be accomplished using an appropriate base such as sodium hydroxide or lithium hydroxide in an appropriate solvent followed by acidification with an appropriate acid such as 1N hydrochloric acid to provide the cinnamic acid of Formula II.

Scheme 2 depicts an alternative preparation of a cinnamic acid derivative of Formula IIa which can be then used to prepare compounds within general Formula I.

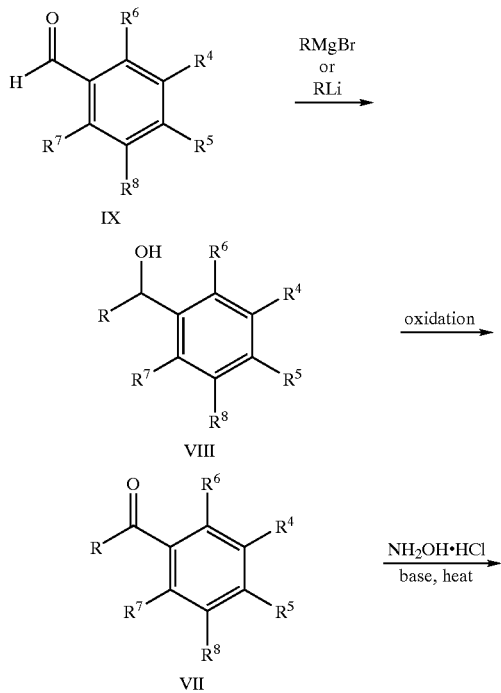

Reaction Scheme 3 depicts a general method useful for the preparation of amines of Formula III which are useful intermediates for the preparation of compounds of Formula I. The benzaldehyde derivative of general Formula IX may be reacted with RMgBr or RLi to provide the alcohol of Formula VIII, which can then be oxidized using Swern oxidation, Dess-Martin periodinane or pyridinium chloro chromate (PCC) to provide the acetophenone derivative of general Formula VII. The compound of Formula VII may then be reacted with hydroxylamine, in the presence of base and with heating to provide the oxime of general Formula VI. The oxime may then be reduced using Raney nickel or palladium on carbon under hydrogenation to provide the amine of general Formula III.

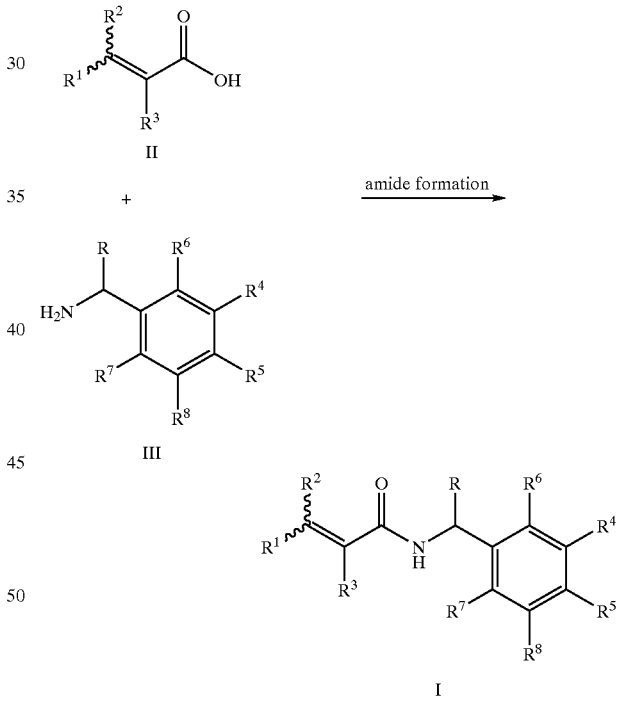

Reaction Scheme 4 depicts the preparation of compounds of general Formula I from the acid of general Formula II and amine of general Formula III. The coupling of the acid, II, and amine, III is carried out by methodology well known in the art for the conversion of an acid and an amine to form an amide. Useful reactive derivatives of the acid of Formula II include, but are not limited to, activated esters, reactive mixed anhydrides, and acid halides (such as the acid chloride, prepared e.g. with thionyl chloride or oxalyl chloride). A preferred method is to condense the acid of Formula II with the amine of Formula III in the presence of an appropriate condensing agent, for example, 1-(3- dimethylaminopropyl)-3-ethylcarbodiimide (EDC) or dicyclohexylcarbodiimide (DCC), and a basic tertiary amine, such as 4-dimethylaminopyridine (DMAP), in an inert solvent such as dichloromethane. The more preferred method is to couple the acid of Formula II with the amine of Formula III in the presence of 1-(3-dimethylaminopropyl)-3-ethylcarbodiimide, hydrochloride (EDC) in the presence of 4-dimethylaminopyridine (DMAP), triethylamine (Et₃N), in dichloromethane.

In a preferred embodiment, the present invention includes compounds of Formula Ia or a pharmaceutically acceptable salt thereof:

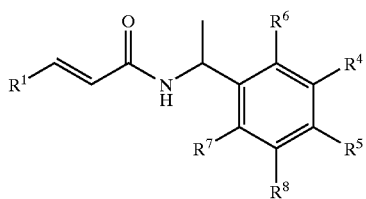

Ia wherein $R^1$ is selected from the group consisting of pyridinyl, 3-quinolinyl, 2-thienyl, benzodioxanyl, 1,3-benzodioxol-5-yl, chroman-5-yl, indan-5-yl, 4-biphenylyl, phenyl and substituted phenyl, in which said substituted phenyl is substituted with substituent independently selected from the group consisting of halogen, $C_{1-4}$ alkyl, $C_{1-4}$ alkoxy, trifluoromethyl, trifluoromethoxy and nitro; $R^4$ is selected from the group consisting of optionally substituted di($C_{1-4}$ alkyl)amino, trifluoromethoxy and optionally substituted morpholin-4-yl, pyridinyl, pyrimidinyl, piperazinyl, and pyrazinyl with one or two substituents in which said substituent is independently selected from the group consisting of $C_{1-4}$ alkyl, aminomethyl, hydroxymethyl, chloro or fluoro; $R^5$ is hydrogen or fluoro; or $R^4$ and $R^5$ taken together are —CH=CH—CH=CH— or —X(CH₂)$_m$Y—, in which X and Y are each independently selected from the group consisting of CH₂, (CH₂)$_n$N(R⁹)— and O, wherein m is 1 or 2; n is 0 or 1; $R^6$, $R^7$, and $R^8$ are each independently selected from hydrogen, chloro and fluoro; and $R^9$ is selected from the group consisting of hydrogen, $C_{1-4}$ alkyl, hydroxyethyl, $C_{1-4}$ alkoxyethyl, cyclopropylmethyl, —CO₂($C_{1-4}$alkyl), and —CH₂CH₂NR¹⁰R¹¹ in which $R^{10}$ and $R^{11}$ are each independently hydrogen or $C_{1-4}$ alkyl.

In another preferred embodiment, the invention includes compounds of Formula Ib or a pharmaceutically acceptable salt thereof

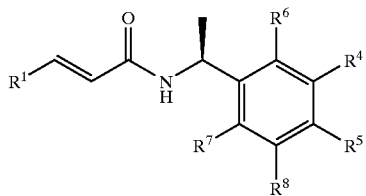

Ib wherein $R^1$ is selected from the group consisting of pyridinyl, 3-quinolinyl, 2-thienyl, benzodioxanyl, 1,3-benzodioxol-5-yl, chroman-5-yl, indan-5-yl, 4-biphenylyl, phenyl and substituted phenyl, in which said substituted phenyl is substituted with substituent independently selected from the group consisting of halogen, $C_{1-4}$ alkyl, $C_{1-4}$ alkoxy, trifluoromethyl, trifluoromethoxy and nitro; $R^4$ is selected from the group consisting of optionally substituted di($C_{1-4}$alkyl)amino, trifluoromethoxy and optionally substituted morpholin-4-yl, pyridinyl, pyrimidinyl, piperazinyl, and pyrazinyl with one or two substituents in which said substituent is independently selected from the group consisting of $C_{1-4}$ alkyl, aminomethyl, hydroxymethyl, chloro or fluoro; $R^5$ is hydrogen or fluoro; or $R^4$ and $R^5$ taken together are —CH=CH—CH=CH— or —X(CH₂)$_m$Y—, in which X and Y are each independently selected from the group consisting of CH₂, (CH₂)$_n$N(R⁹)— and O, wherein m is 1 or 2; n is 0 or 1; $R^6$, $R^7$, and $R^8$ are each independently selected from hydrogen, chloro and fluoro; and $R^9$ is selected from the group consisting of hydrogen, $C_{1-4}$ alkyl, hydroxyethyl, $C_{1-4}$ alkoxyethyl, cyclopropylmethyl, —CO₂($C_{1-4}$alkyl), and —CH₂CH₂NR¹⁰R¹¹ in which $R^{10}$ and $R^{11}$ are each independently hydrogen or $C_{1-4}$ alkyl.

Preferred compounds for use in the method of the present invention include the compounds of Formula I listed below:

2-Methyl-3-phenyl-but-2-enoic acid (1-naphthalen-2-ylethyl)-amide;

N-(1-Benzo[1,3]dioxol-5-yl-ethyl)-3-(3-methoxyphenyl)-acrylamide;

N-[1-(2,3-Dihydrobenzofuran-5-yl)ethyl]-3-(3-methoxyphenyl)-acrylamide;

(S)-3-Phenyl-N-[1-(3-morpholin-4-yl-phenyl)ethyl]acrylamide;

3-(3-Fluorophenyl)-N-[1-(2,3-dihydrobenzo[1,4]dioxin-6-yl)-ethyl]acrylamide;

(±)-7-{1-[3-(4-Fluorophenyl)acryloylamino]ethyl}-3,4-dihydro-1H-isoquinoline-2-carboxylic acid methyl ester;

3-(2-Fluorophenyl)-N-[1-(4-methyl-3,4-dihydro-2H-benzo[1,4]oxazin-6-yl)ethyl]-acrylamide;

(S)-N-(1-Naphthalen-2-yl-ethyl)-3-phenyl-acrylamide;

(S)-3-(4-Fluoro-phenyl)-N-(1-naphthalen-2-yl-ethyl)-acrylamide;

(±)-N-(1-Benzo[1,3]dioxol-5-yl-ethyl)-3-(2,4-difluoro-phenyl)-acrylamide;

(±)-N-[1-(2,3-Dihydro-benzofuran-5-yl)-ethyl]-3-(2-fluoro-phenyl)-acrylamide;

(±)-3-(2,4-Difluoro-phenyl)-N-[1-(2,3-dihydro-benzofuran-5-yl)-ethyl]-acrylamide;

(S)-3-(2,4-Difluoro-phenyl)-N-[1-(3-morpholin-4-yl-phenyl)-ethyl]-acrylamide;

(S)-N-[1-(3-(2,6-Dimethyl-morpholin)-4-yl-phenyl)-ethyl]-3-phenyl-acrylamide;

[(S)-3-(2-Fluoro-phenyl)-N-[1-(3-morpholin-4-yl-phenyl)-ethyl]-acrylamide;

(S)-N-[1-(3-Morpholin-4-yl-phenyl)-ethyl]-3-thiophen-3-yl-acrylamide;

(S)-3-(4-Fluoro-phenyl)-N-[1-(3-morpholin-4-yl-phenyl)-ethyl]-acrylamide;

(S)-N-{1-[3-(cis-2,6-Dimethyl-morpholin-4-yl)-phenyl]-ethyl}-3-(4-fluoro-phenyl)-acrylamide;

(S)-3-(2,4-Difluoro-phenyl)-N-{1-[3-(cis-2,6-dimethyl-morpholin-4-yl)-phenyl]-ethyl}-acrylamide;

(S)-3-(3,4-Difluoro-phenyl)-N-{1-[3-(cis-2,6-dimethyl-morpholin-4-yl)-phenyl]-ethyl}-acrylamide;

(S)-3-(2,5-Difluoro-phenyl)-N-{1-[3-(cis-2,6-dimethyl-morpholin-4-yl)-phenyl]-ethyl}-acrylamide;

(S)-3-(2-Fluoro-phenyl)-N-{1-[3-(2-methyl-morpholin-4-yl)-phenyl]-ethyl}-acrylamide;

(S)-3-(3-Fluoro-phenyl)-N-{1-[3-(2-methyl-morpholin-4-yl)-phenyl]-ethyl}-acrylamide;

(S)-3-(4-Fluoro-phenyl)-N-{1-[3-(2-methyl-morpholin-4-yl)-phenyl]-ethyl}-acrylamide;
(S)-3-(2,4-Difluoro-phenyl)-N-{1-[3-(2-methyl-morpholin-4-yl)-phenyl]-ethyl}-acrylamide;
(S)-N-{1-[3-(2-Oxa-5-aza-bicyclo[2.2.1]hept-5-yl) phenyl]ethyl}-3-phenyl-acrylamide;
(S)-N-{1-[3-(2-Hydroxymethyl-morpholin-4-yl)-phenyl]-ethyl}-3-phenyl-acrylamide;
(±)-N-[1-(3-Morpholin-4-yl-phenyl)-propyl]-3-phenyl-acrylamide;
(±)-3-(2,4-Difluoro-phenyl)-N-[1-(3-morpholin-4-yl-phenyl)-propyl]-acrylamide;
(±)-3-(2-Fluoro-phenyl)-N-[1-(3-morpholin-4-yl-phenyl)-propyl]-acrylamide;
(±)-3-(3-Fluoro-phenyl)-N-[1-(3-morpholin-4-yl-phenyl)-propyl]-acrylamide;
(±)-N-[1-(4-Fluoro-3-morpholin-4-yl-phenyl)-ethyl]-3-(2-fluoro-phenyl)-acrylamide;
(±)-N-[1-(4-Fluoro-3-morpholin-4-yl-phenyl)-ethyl]-3-(4-fluoro-phenyl)-acrylamide;
(±)-3-(2,4-Difluoro-phenyl)-N-[1-(4-fluoro-3-morpholin-4-yl-phenyl)-ethyl]-acrylamide;
(S)-N-[1-(4-Fluoro-3-morpholin-4-yl-phenyl)-ethyl]-3-(4-fluoro-phenyl)-acrylamide;
(±)-3-(3,4-Difluoro-phenyl)-N-[1-(4-fluoro-3-morpholin-4-yl-phenyl)-ethyl]-acrylamide;
(±)-3-(2,5-Difluoro-phenyl)-N-[1-(4-fluoro-3-morpholin-4-yl-phenyl)-ethyl]-acrylamide;
(±)-N-[1-(4-Fluoro-3-morpholin-4-yl-phenyl)-ethyl]-3-(3-fluoro-phenyl)-acrylamide;
(±)-N-[1-(4-Fluoro-3-morpholin-4-yl-phenyl)-ethyl]-3-(2-fluoro-phenyl)-acrylamide;
(±)-3-(3-Fluoro-phenyl)-N-[1-(1,2,3,4-tetrahydro-quinolin-7-yl)-ethyl]-acrylamide;
(±)-3-(4-Fluoro-phenyl)-N-[1-(1,2,3,4-tetrahydro-quinolin-7-yl)ethyl]-acrylamide;
(±)-3-(2-Fluoro-phenyl)-N-[1-(1-methyl-1,2,3,4-tetrahydro-quinolin-7-yl)ethyl]acrylamide;
(±)-N-{1-[1-(2-Hydroxy-ethyl)-1,2,3,4-tetrahydro-quinolin-7-yl]-ethyl}-3-phenyl-acrylamide;
(±)-3-(2,5-Difluoro-phenyl)-N-{1-[1-(2-hydroxy-ethyl)-1,2,3,4-tetrahydro-quinolin-7-yl]-ethyl}-acrylamide;
(±)-3-(3,5-Difluoro-phenyl)-N-{1-[1-(2-hydroxy-ethyl)-1,2,3,4-tetrahydro-quinolin-6-yl]-ethyl}-acrylamide;
(S)-3-Phenyl-N-[1-(3-pyridyl-phenyl)-ethyl]acrylamide;
(S)-(2,4-Difluoro-phenyl)-N-[1-(3-pyridin-3-yl-phenyl)-ethyl]-acrylamide;
(S)-3-Phenyl-N-[1-(3-pyridin-4-yl-phenyl)-ethyl]-acrylamide;
(S)-N-{1-[3-(6-Chloro-pyridin-3-yl)-phenyl]-ethyl}-3-(2-fluoro-phenyl)-acrylamide;
(S)-3-Phenyl-N-[1-(3-pyrimidin-5-yl-phenyl)-ethyl]-acrylamide;
(S)-3-Phenyl-N-[1-(3-pyridin-2-yl-phenyl)-ethyl]-acrylamide;
(S)-3-(2-Fluoro-phenyl)-N-[1-(3-pyridin-2-yl-phenyl)-ethyl]-acrylamide;
(S)-3-(2-Fluoro-phenyl)-N-{1-[3-(6-fluoro-pyridin-3-yl)-phenyl]ethyl}-acrylamide;
(S)-3-(4-Fluoro-phenyl)-N-{1-[3-(6-fluoro-pyridin-3-yl)-phenyl]-ethyl}-acrylamide;
(S)-N-{1-[3-(6-Fluoro-pyridin-3-yl)-phenyl]-ethyl}-3-pyridin-3-yl-acrylamide;
(S)-N-{1-[3-(6-Fluoro-pyridin-3-yl)-phenyl]-ethyl}-3-pyridin-4-yl-acrylamide;
(S)-N-{1-[3-(6-Chloro-pyridin-3-yl)-phenyl]-ethyl}-3-(3-fluoro-phenyl)-acrylamide;
(S)-N-{1-[3-(6-Chloro-pyridin-3-yl)-phenyl]-ethyl}-3-pyridin-3-yl-acrylamide;
(S)-N-{1-[3-(6-Chloro-pyridin-3-yl)-phenyl]-ethyl}-3-pyridin-2-yl-acrylamide;
(S)-N-{1-[3-(6-Chloro-pyridin-3-yl)-phenyl]-ethyl}-3-pyridin-4-yl-acrylamide;
(S)-N-{1-[3-(6-Chloro-pyridin-3-yl)-phenyl]-ethyl}-3-(2-fluoro-phenyl)-acrylamide;
(S)-N-{1-[3-(6-Chloro-pyridin-3-yl)-phenyl]-ethyl}-3-(2,4-difluoro-phenyl)-acrylamide;
(S)-N-{1-[3-(6-Chloro-pyridin-3-yl)-phenyl]-ethyl}-3-(4-fluoro-phenyl)-acrylamide;
(S)-3-(2-Fluoro-phenyl)-N-[1-(3-pyridin-3-yl-phenyl) ethyl]acrylamide;
(S)-N-{1-[3-(6-Fluoro-pyridin-3-yl)-phenyl]-ethyl}-3-phenyl-acrylamide;
(S)-N-{1-[3-(6-Chloro-pyridin-3-yl)-phenyl]-ethyl}-3-phenyl-acrylamide;
(S)-3-(2-Fluoro-phenyl)-N-[1-(3-pyridin-4-yl-phenyl) ethyl]acrylamide;
(S)-3-(2-Fluoro-phenyl)-N-[1-(3-pyrazin-2-yl-phenyl) ethyl]acrylamide;
(S)-3-(2-Fluoro-phenyl)-N-[1-(3-pyrimidin-5-yl-phenyl) ethyl]acrylamide;
(S)-3-(2-Fluoro-phenyl)-N-{1-[3-(4-methyl-pyridin-3-yl) phenyl]ethyl}acrylamide;
(S)-3-(4-Fluorophenyl)-N-{1-[3-(4-methylpiperazin-1-yl)phenyl]ethyl}acrylamide; and
(S)-3-(2,3-Difluoro-phenyl)-N-{1-[3-(4-methyl-piperazin-1-yl)-phenyl]-ethyl}-acrylamide;
or a pharmaceutically acceptable salt thereof.

BIOLOGICAL ACTIVITY

KCNQ Oocyte Methods and Results

Potassium ($K^+$) channels are structurally and functionally diverse families of $K^+$-selective channel proteins which are ubiquitous in cells, indicating their central importance in regulating a number of key cell functions [Rudy, B., Neuroscience, 25: 729–749 (1988)]. While widely distributed as a class, $K^+$ channels are differentially distributed as individual members of this class or as families. [Gehlert, D. R., et al., Neuroscience, 52: 191–205 (1993)]. In general, activation of $K^+$ channels in cells, and particularly in excitable cells such as neurons and muscle cells, leads to hyperpolarization of the cell membrane, or in the case of depolarized cells, to repolarization. In addition to acting as an endogenous membrane voltage clamp, $K^+$ channels can respond to important cellular events such as changes in the intracellular concentration of ATP or the intracellular concentration of calcium ($Ca^{2+}$). The central role of $K^+$ channels, in regulating numerous cell functions makes them particularly important targets for therapeutic development. [Cook, N. S., Potassium channels: Structure, classification, function and therapeutic potential. Ellis Horwood, Chinchester (1990)]. One class of $K^+$ channels, the KCNQ family exemplified by KCNQ2, KCNQ2/3 heteromultimers, and KCNQ5, is regulated by transmembrane voltage and plays a potentially important role in the regulation of neuronal excitability [Biervert, C., et al., Science, 279: 403–406 (1998); Lerche, C. et al., J. Biol. Chem. 275:22395–22400 (2000); Wang, H. et al., Science, 282:1890–1893 (1998)].

An opener of KCNQ channels, such as the KCNQ2 and KCNQ2/3 channel opener retigabine, exerts its cellular effects by increasing the open probability of these channels [Main J., Mol Pharmacol 58(2):253–62 (2000); Wickenden, A. et al., Mol. Pharm. 58:591–600 (2000)]. This increase in the opening of individual KCNQ channels collectively results in the hyperpolarization of cell membranes, particularly in depolarized cells, produced by significant increases in whole-cell KCNQ-mediated conductance.

The ability of compounds described in the present invention to open KCNQ channels and increase whole-cell outward ($K^+$) KCNQ-mediated currents was assessed under voltage-clamp conditions by determining their ability to increase cloned mouse KCNQ2 (mKCNQ2)-mediated, heteromultimeric KCNQ2/3 (mKCNQ2/hKCNQ3)-mediated, and human KCNQ5 (hKCNQ5)-mediated outward currents heterologously expressed in Xenopus oocytes. Oocytes were prepared and injected using standard techniques; each oocyte was injected with approximately 50 nl of mKCNQ2, or hKCNQ5 cRNA. In the case of mKCNQ2/h3 heteromultimeric channel expression, equal amounts (25–50 nL) of each cRNA were co-injected. Injection of equivalent amounts of water (50 nl) did not result in expression of outward currents at the voltage steps used to detect KCNQ expression. Following injection, oocytes were maintained at 17° in ND96 medium consisting of (in mM): NaCl, 90; KCl, 1.0; $CaCl_2$, 1.0; $MgCl_2$, 1.0; HEPES, 5.0; pH 7.5. Horse serum (5%) and penicillin/streptomycin (5%) were added to the incubation medium. Recording commenced 2–6 days following mRNA injection. Prior to the start of an experiment oocytes were placed in a recording chamber and incubated in Modified Barth's Solution (MBS) consisting of (in mM): NaCl, 88; $NaHCO_3$, 2.4; KCl, 1.0; HEPES, 10; $MgSO_4$, 0.82; $Ca(NO_3)_2$, 0.33; $CaCl_2$, 0.41; pH 7.5.

Oocytes were impaled with electrodes (1–2 MΩ) and standard 2-electrode voltage clamp techniques were employed to record whole-cell membrane currents. Recordings were accomplished using standard two-electrode voltage clamp techniques [Stuhmer, W., et al., Methods in Enzymology, Vol. 207: 319–339 (1992)]. Voltage-clamp protocols typically consisted of a series of voltage steps 1–5 sec duration, in +10 mV steps from a holding potential of −90 mV to a maximal potential of +40 mV; records were digitized at 5 kHz and stored on a computer using pClamp data acquisition and analysis software (Axon Instruments). Compounds were evaluated at a single concentration and at a single holding potential (−40 μM); the effect of the selected compounds of Formula I on KCNQ2 current was expressed as the percent of control current and is listed in Table I.

TABLE 1

| Example No. | Concentration | KCNQ2 Current |
|---|---|---|
| 2 | 5 μM | 160 |
| 6 | 1 μM | 110 |
| 19 | 1 μM | 123 |
| 79 | 1 μM | 123 |
| 82 | 10 μM | 197 |
| 183 | 10 μM | 135 |
| 197 | 10 μM | 187 |
| 199 | 5 μM | 138 |
| 200 | 10 μM | 126 |
| 201 | 5 μM | 157 |

KCNQ Patch-Clamp Methods and Results

Whole-cell patch-clamp recordings were made from an HEK 293 stable cell line expressing mKCNQ2 channels, maintained in culture for 1–2 days. Patch pipettes had initial resistances of 2.5–4 MΩ. Currents were recorded with an EPC-9 amplifier (HEKA, Lambrecht, Germany) controlled with software (Pulse, HEKA) run on a standard lab PC. Series resistance compensation was used during current recording, and set at 80%. The series resistance (R) and cell capacitance (C) were determined electronically by subtracting the capacitive currents at the onset and offset of a 5 mV voltage step. The cancellation of whole-cell capacitance transients was virtually complete in all cells. Analog current signals were low-pass filtered at 2.9 kHz using a four-pole Bessel filter −3 dB) and stored on a local network server computer at a sampling rate of 1.5 kHz. All recordings were performed at room temperature (20–22° C.). The pipette solution contained (mM): KCl, 150; $CaCl_2$, 2.5; EGTA, 5; $MgCl_2$, 1; HEPES, 10; pH to 7.3 with KOH, and Osmolality of 290–300 mOsm. The extracellular solution contained (mM): NaCl, 140; KCl, 2.5; $CaCl_2$, 2.5; $MgCl_2$, 1; glucose, 10; HEPES, 10; pH to 7.3 with NaOH, and Osmolality of 305–310 mOsm For analysis of agents effects on mKCNQ2 currents, the raw current records were displayed on the digital oscilloscope of the Pulse software application. Concentration response data were generated by measuring the difference in the steady-state amplitude of current in the presence of compound at the end of a 600 ms voltage-clamp step from a holding potential of −80 mV. The concentration-response data were fitted with Hill-type equations:

$$I=I_{max}/(I+EC_{50}/[A]^{nH}),$$

where I is the steady-state current at a given concentration of agonist [A]; and $I_{max}$, $EC_{50}$ and nH are parameters estimated from the curve fit. In some cases the concentration-response data were fitted with equations consisting of the sum of two Hill-type components. Current-voltage (I/V) relationships for agonist-evoked currents were obtained by performing 600 ms voltage steps (−110 mV to +40 mV) in the absence and presence of agonist. The effect of the representative compounds of Formula I on KCNQ currents is listed in Table 2.

TABLE 2

| Example No. | $EC_{50}$ (μM) @ −40 mv) | $I_{max}$ (%) |
|---|---|---|
| 1 | 9.2 | 237 |
| 38 | 4.2 | 550 |
| 46 | 0.0006 | 260 |
| 90 | 1.2 | 523 |
| 97 | 2.9 | 1500 |
| 169 | 1 | 1750 |
| 214 | 0.0009 | 260 |
| 215 | 5.4 | 2030 |
| 242 | 1.4 | 1740 |
| 248 | 5 | 290 |

In vivo Electrophysiology

Cortical spreading depression (CSD) is defined as a wave of neuronal excitation, followed by long-lasting inhibition, that spreads from a focal point at a rate of 2–3 mm/min (Lashley, K. S. (1941) *Arch. Neurol. Phsychiatry*, 46: 331–339). It has been suggested that spreading depression may underlie some of the prodromal events that precede migraine, particularly visual aura (Lauritzen, M. (1994) *Brain*, 117: 199–210). Clinical neurological prodromal migraine symptoms proceed in a temporal fashion that is correlated with the expected rate of spreading depression (Lauritzen, M., Olesen, J. (1984) *Brian* 107: 447–461). These neurological symptoms are correlated with associated changes in blood flow that correlate well with the spreading depression phenomena (Lauritzen, M., et al., (1983) *Ann. Neurol.*, 13: 633–641). Finally, spreading depression has been visualized during migraine in humans using functional magnetic resonance imaging based on blood oxygenation level dependent imaging (Cao, Y., et al., (1999) *Arch. Neurol.*, 56: 548–554). This evidence lends support to the hypothesis that CSD may underlie both the visual aura, and possibly other prodomal symptoms, that precede migraine as well as the ensuing migraine attack and accompanying pain (Hardebo, J. E. (1991) *Headache*, 3: 213–21; Hardebo, J. E. (1992) *Cephalalgia*, 12: 75–80.). It follows that compounds that interrupt cortical spreading depression may be useful for the treatment of migraine headache (Obrenovitch, T. P., Zilkha, E. (1996) *Br. J. Pharmacol.*, 117: 931–937; Chan, W. N., et al., A. A. (1999) *Bioorg. & Med. Chem. Lett.*, 9: 285–290; Read, S. J., et al., *Cephalalgia*, 20: 92–99).

Male Long-Evans rats (300–450 g) were used in the present studies (Harlan). Rats were anesthetized with urethane anesthesia (1.2 g/kg i.p.) and placed in a stereotaxic frame. Under anesthesia a Silastic catheter was placed in the jugular vein of the rats. The skull was exposed using a scalpel. A small hole (approximately 2 mm by 3 mm) was drilled in to the skull rostral to the lambdoid suture using a microdrill and steel burr. The dura was disrupted and a drop of mineral oil was placed in this hole to prevent dehydration of the underlying cortex. Ultimately this hole was used for the application of crystalline KCl (described below).

Two additional holes were place in the skull unilaterally at 4 and 8 mm rostral to the application hole. Silver wire electrodes were placed in these latter holes and secured to the skull using acrylic cement. A similar silver wire electrode was sutured to the nuchal muscle to serve as a reference electrode. Electrical DC recordings were obtained using a standard differential amplifier (Warner, DP-304) and commercially available data acquisition equipment (Cambridge Electronic Design, 1401 A-D converter and Spike2 software).

Treatment and Analysis Procedure

All experimental procedures were conducted while the rats were maintained under anesthesia. Rats were injected with test compound, valproic acid or vehicle (100% PEG-400) 15 min prior to the application of crystalline KCl to the application site described above. All injections were given via the jugular vein at a volume of $\leq 0.5$ ml/kg. Only one treatment was tested per animal. The effect of valproic acid was also determined in this study due to the fact that Depakote™ (divalproex sodium) is one of only three drugs currently indicated for the prophylatic treatment of migraine headache. Valproic acid (30–200 mg/kg i.v.) was obtained from Sigma Chemical Company and was dissolved in a vehicle of isotonic saline.

KCl was applied to the application site for 10 min and was then removed using a saline soaked cotton swab. Mineral oil was subsequently reapplied to the application site. Typically, this application produced a long-lasting series of spreading depressions. The number of spreading depressions produced by this KCl application was the primary measure used to access the effectiveness of compounds in this assay.

Data were analyzed using analyses of variance followed by the Dunnett post-hoc test for pairwise comparisons, when appropriate. A difference was considered significant when $p \leq 0.05$.

The effect of representative compounds of Formula I on spreading depression is expressed as the percent reduction from vehicle control and is listed in Table 3.

TABLE 3

| Example Number | % Reduction |
|---|---|
| Valproic acid | 31 (100 mg/kg, i.v.) |
| 1 | 25 (1 mg/kg, i.v.) |
| 82 | 27 (1 mg/kg, i.v.) |
| 84 | 37 (1 mg/kg, i.v.) |
| 90 | 37 (1 mg/kg, i.v.) |
| 169 | 25 (1 mg/kg, i.v.) |

The results in Table 3 suggest that compounds that open KCNQ channels, in general, are efficacious in reducing the number of spreading depressions produced by cortical KCl applications, and therefore compounds of Formula I may be useful in the treatment of migraine headache.

Mania and Bipolar Methods and Results

In animals, combination treatment with amphetamine and chlordiazepoxide increases spontaneous activity in novel environments relative to the effect of vehicle or amphetamine alone (Rushton R., et al., (1963) *Br. J. Pharmacol.* 20: 99–105; Rushton R., Steinberg H. (1966) *Nature* 211:1312–1313). The behavior produced by this combination treatment has been described as "compulsive" or "manic" in a manner consistent with the hyperactivity seen clinically during mania (Cox C., et al., (1971) *Nature* 232: 336–338; Aylmer C G G, et al., (1987) *Psychopharmacology* 91: 198–206). Acute pretreatment with lithium or valproate selectively attenuates this combination-induced hyperactivity (Cox C., et al. (1971) *Nature* 232: 336–338; Vale A. L., Ratcliffe F, (1987) *Psychopharmacology* 91: 325–355; Aylmer C G G, et al., (1987) *Psychopharmacology* 91: 198–206; Cao B. J., Peng N. A. (1993) *Eur. J. Pharmacol.* 237: 177–181; Serpa K. A., Meltzer L. T. (1999) *Soc. Neurosci. Abst.* 25:1321). Since both lithium and valproate are well accepted as efficacious for the treatment of acute mania and the prophylaxis of bipolar disorder (Goldberg, (2000) *J. Clin. Psychiatry* 61 (Supl. 13): 12–18) this model is utilized as an animal surrogate model for mania and bipolar disorder.

Subjects: Female Sprague Dawley rats (Hilltop Lab Animals, Scottdale, Pa.), weighing 150–200 g at the beginning of the experiment, were used in the experiment described in this example. Animals were individually housed in standard shoebox cages and maintained on a 12:12 h light-dark cycle (lights on at 0600). All animals were allowed food and water ad libitum throughout the experimental procedure. Prior to arrival to the testing facility, the rats were anesthetized with vaporized Isoflurane and catheters were surgically implanted into the jugular vein. The catheters were made of silastic medical grade tubing (15 cm long, 0.02" internal diameter, 0.037" external diameter), fastened with sutures to muscle near the jugular vein and at the nape of the neck, then sealed with smooth pieces of monofilament that were secured at the nape of the neck.

Procedure: Approximately 10 days after surgery, rats were randomly divided into 5 groups according to the following table:

Injection Time Pre-test

| Group | 28 hours | 4 hours | 45 minutes | 30 minutes |
|---|---|---|---|---|
| LiCl | LiCl | LiCl | Vehicle | C + A |
| Test Compound | Vehicle | Vehicle | Compound of Example 1 | C + A |

-continued

| Group | 28 hours | 4 hours | 45 minutes | 30 minutes |
|---|---|---|---|---|
| C + A | Vehicle | Vehicle | Vehicle | C + A |
| Amph | Vehicle | Vehicle | Vehicle | A |
| Veh | Vehicle | Vehicle | Vehicle | Vehicle |

Abbreviations: LiCl, lithium chloride; C, chlordiazepoxide hydrochloride; A, d-amphetamine sulfate Lithium chloride (LiCl), chlordiazepoxide hydrochloride (CDP) and d-amphetamine sulfate (Amph) were obtained from Sigma Chemical Company (St. Louis, Mo.). LiCl was dissolved in a vehicle of isotonic saline and injected intraperitoneally (i.p.) at a dose of 2 mEq/kg. CDP and Amph were dissolved in a vehicle of sterile water (Phoenix Scientific, Inc., St. Joseph, Mo.) and injected subcutaneously (s.c.) at a dose of 12.5 mg/kg and 1.18 mg/kg, respectively. Combination treatment of CDP and Amph represented the s.c. injection of a 1:1 mixture of both compounds at the above referenced doses. Compound of Example 1 was dissolved in dimethylsulfoxide (DMSO) and brought to volume with propylene glycol (PG) such that the final vehicle represented a 4% DMSO/96% PG solution. Compound of Example 1 or vehicle solution was administered intravenously (i.v.) at a dose of 5 mg/kg through a 23 gauge needle that was connected to polyethylene tubing (PE-50) and a 3 ml syringe on a programmable Harvard infusion pump. Compound of Example 1 or vehicle solution was administered at a rate of 0.1 ml/minutes, the injectors were left in place for 30 seconds, then 0.2 ml of 250 units/ml heparinized saline was injected into the catheter. The catheter was fitted into the monofilament seal before returning the animal to its home cage. All drugs were delivered at a volume of 1 ml/kg. All doses, where appropriate, represent the dose of the base.

Thirty minutes after final s.c. dosing with either CDP+Amph, Amph alone or vehicle, rats were placed in locomotor activity testing apparatus. Locomotion testing was performed in clear, rectangular Plexiglas boxes (41 cm×41 cm×30 cm) placed inside Digiscan activity animal monitors (AccuSan Instruments, Inc, Columbus, Ohio). The monitors were equipped with 16 infrared light beams spaced 2.5 cm apart along 2 horizontal planes perpendicular to one another (front-back and left-right of testing box). The total horizontal activity counts, defined as the total number of beam interruptions that occurred in the sensors located along the horizontal axes, during the first 10 minutes of testing (i.e., 30–40 minutes post s.c. dosing) was used as the dependent measure of locomotor activity. Data were analyzed using a priori planned analyses of variance where an effect was considered significant if p<0.05.

TABLE 4

| Group | Horizontal Activity Counts.* |
|---|---|
| Vehicle | 4,818.7 + 633.69 |
| d-amphetamine | 8,772.3 + 426.02 |
| Chlordiazepoxide + d-amphetamine | 11,250.0 + 820.02 |
| LiCl | 7,612.4 + 849.38 |
| Compound of Example 1 | 7,859.2 + 661.21 |

*Horizontal counts for the first 10 minutes of testing.

As depicted in Table 4, a significant increase [F(1,14)=28.8, p<0.001] in locomotor scores was observed following amphetamine treatment. When chlordiazepoxide was added to the amphetamine the result was a significant augmentation relative to the effect of amphetamine alone [F(1,16)=7.2, p=0.016]. Lithium (2 mEq/kg i.p. at 28 and 4 h pre-test), an efficacious medicament for the treatment of bipolar disorder, significantly prevented the augmentation produced by the combination treatment [F(1,17)=9.4, p=0.007]. In similar fashion, the cinnamide KCNQ opener, compound of Example 1 (5 mg/kg i.v. 45 minutes pre-test), significantly prevented the effect of the augmentation produced by the combination treatment [F(1,16)=10.4, p=0.005]. These results indicate that Compound of Example 1 as well as other modulators of the KCNQ channel will be useful for the treatment of mania and bipolar disorders.

Neuropathic Pain Methods and Results

Method A: Chung Model of Neuropathic Pain (Chung Surgery and von Frey Test)

To test agents for activity against peripheral mononeuropathy nerve injury-induced tactile allodynia, male Sprague Dawley rats (wt. 120–160 g) were surgically prepared with unilateral tight ligation of spinal nerves L5 and L6 following the method of Kim and Chung (Kim S. H., Chung J. M. (1992) *Pain*, September;50(3):355–63). After 3–4 weeks recovery, paw withdrawal to light touch was assessed as described by Chaplan et al. (Chaplan S. R., et al., (1994) *J. Neurosci Methods*, July;53(1):55–63). In brief, rats are placed in a plastic cage with a wire mesh bottom and allowed to acclimate for 15–30 minutes, until cage exploration and grooming stops. The plantar surface of each hind paw is touched with a series of von Frey hairs with varying stiffness requiring a known force to buckle to determine the nociceptive threshold. Adult male Sprague Dawley rats (avg. wt. 340 g) were tested in the present study. After acclimation, baseline von Frey thresholds were assessed for the injured hindpaw at −15 min. All test compounds were delivered at 0 min by the intravenous (i.v.) route in a volume of 0.5–2 ml/kg. The vehicle for test compounds was 100% PEG-400. For gabapentin the vehicle was deionized $H_2O$. Animals were tested in one of the following 4 treatment conditions: (a) PEG400, (b) gabapentin (Neurontin) 100 mg/kg, (c) test compounds 3 mg/kg and (d) test compounds 10 mg/kg. Following drug administration, von Frey thresholds are measured at 15, 30, 60 and 90 min. Data were analyzed by a 2-way repeated measures analysis of variance followed by Dunnett's test (p<0.05). Experimenters were kept blind to the treatment condition of rats they tested.

Reversal of neuropathic pain behavior may be expressed as a percentage (0–100%) of the maximum possible effect, over and above the vehicle effects. Specifically, drug effects can be described in terms Δ% MPE according to the following equation:

$$\Delta\%MPE = \left(\frac{(AUCdrug - AUCvehicle)}{((Time \times Max) - AUCvehicle)}\right) \times 100$$

where:

AUCdrug=area under the curve for von Frey thresholds of the drug-treated group;

AUCvehicle=area under the curve for von Frey thresholds in the vehicle group;

Time=duration of post-drug testing period (90 min); and

Max=maximum von Frey threshold (15 g).

For example, a compound which immediately reversed neuropathic pain behavior to normal levels, such that animals only responded to the highest von Frey filament (15 g), and maintained normal levels through out the post-drug testing period (90 min) would be calculated as Δ% MPE= 100%.

The results for representative compounds of Formula I are provided in Table 5.

TABLE 5

| Example Number | AUC (Δ% MPE)* |
|---|---|
| Gabapentin | 50 (100 mg/kg, i.v.) |
| 1 | 8 (3 mg/kg, i.v.) |
| 82 | 25 (10 mg/kg, i.v.) |
| 90 | 13 (3 mg/kg, i.v.) |
| 169 | 31 (10 mg/kg, i.v.) |

*Δ% MPE = % MPE (Drug AUC) − % MPE (Vehicle AUC)

Method B: Diabetic Model of Neuropathic Pain (Streptozoticin & von Frey Test)

To test agents for activity against systemic polyneuropathy nerve injury-induced tactile allodynia, animals were treated with streptozoticin (STZ) to create a diabetic condition by selective cytotoxic action upon pancreatic β-islet cells that produce insulin following the method of Courteix, et al. (Courteix C., et al., (1993) *Pain*, April;53(1):81–8). In brief, male Sprague Dawley rats (wt. 200–275 g) received an injection of STZ (75 mg/kg, i.p.) and diabetes was confirmed three weeks after STZ injection by measurement of tail vein blood glucose levels. After 3–4 weeks, paw withdrawal to light touch was assessed as described by Chaplan et al. (Chaplan S. R., et al., (1994) *J Neurosci Methods*, July;53(1):55–63). In brief, rats are placed in a plastic cage with a wire mesh bottom and allowed to acclimate for 15–30 minutes, until cage exploration and grooming stops. The plantar surface of each hind paw is touched with a series of von Frey hairs with varying stiffness requiring a known force to buckle to determine the nociceptive threshold. Adult male Sprague Dawley rats (avg. wt. 300 g) were tested in the present study. After acclimation, baseline von Frey thresholds were assessed for the injured hindpaw at −15 min. All test compounds were delivered at 0 min by the intravenous (i.v.) route in a volume of 0.5–2 ml/kg. The vehicle for the compounds of Formula I was 100% PEG-400. For gabapentin the vehicle was deionized H2O. Animals were tested in one of the following 4 treatment conditions: (a) PEG400, (b) gabapentin (Neurontin) 200 mg/kg, (c) test compounds 10 mg/kg and (d) test compounds 30 mg/kg. Following drug administration, von Frey thresholds are measured at 15, 30, 60 and 90 min. Data were analyzed by a 2-way repeated measures analysis of variance followed by Dunnett's test (p<0.05). Experimenters were kept blind to the treatment condition of rats they tested.

Reversal of neuropathic pain behavior may be expressed as a percentage (0–100%) of the maximum possible effect, over and above the vehicle effects. Specifically, drug effects can be described in terms Δ% MPE according to the following equation:

$$\Delta\%MPE = \left(\frac{(AUCdrug - AUCvehicle)}{((Time \times Max) - AUCvehicle)}\right) \times 100$$

where:
AUCdrug=area under the curve for von Frey thresholds of the drug-treated group;
AUCvehicle=area under the curve for von Frey thresholds in the vehicle group;
Time=duration of post-drug testing period (90 min); and
Max=maximum von Frey threshold (15 g).

For example, a compound which immediately reversed neuropathic pain behavior to normal levels, such that animals only responded to the highest von Frey filament (15 g), and maintained normal levels through out the post-drug testing period (90 min) would be calculated as Δ% MPE= 100%.

The results for representative compounds of Formula I are provided in Table 6.

TABLE 6

| Example Number | AUC (Δ% MPE)* |
|---|---|
| 82 | 23 (10 mg/kg, i.v.) |
| 90 | 56 (10 mg/kg, i.v.) |
| 169 | 12 (10 mg/kg, i.v.) |

*Δ% MPE = % MPE (Drug AUC) − % MPE (Vehicle AUC)

The results in Tables 5 and 6 suggest that compounds of Formula I are efficacious in reducing neuropathic pain including pain associated with diabetic neuropathy.

Anxiety Methods and Results

The purpose of the Canopy test is to investigate the potential of compounds of Formula I as effective treatments for anxiety by examining an integral component of the risk assessment repertoire of defensive behaviors, the stretched attend posture (SAPs). SAPs are characterized by a forward elongation of the body exhibited when the mouse is either standing still or moving slowly forward. This behavior is investigatory, and is considered an important behavioral indicator of anxiety in mice (Grewal et al., 1997). In brief, mice are placed on an elevated circular platform with a covered space in the middle, and an open space surrounding the covered zone. The number of SAPs the animals makes when exploring this environment are measured. Compounds that are effective in the clinic, such as diazepam (valium) will reduce the number of time the animals exhibits SAPs, and this is hypothesized to reflect clinical anxiolytic potential.

Subjects: Male BalbC/HSD mice (Harlan Sprague Dawley) weighing approximately 20–25 g at the beginning of the experiment, were used. Animals were group housed 4–5 per cage, in standard shoebox cages and maintained on a 12:12 h light-dark cycle (lights on at 0600). All animals were allowed food and water ad libitum throughout the procedure.

Apparatus: The test apparatus is comprised of a black plexiglas circular platform (70 cm diameter) elevated 60 cm above the floor. A clear red plexiglas (translucent) 'canopy' (38 cm diameter) is supported 4 cm directly above the platform by a central pillar, effectively dividing the platform into an inner, covered zone (beneath the canopy) and an outer, exposed zone. The apparatus is illuminated by normal room lighting.

Procedure: On test days mice are transported in their home cage to the testing room which is free of noise/distraction and the mice are injected with the compound of choice, prior to testing. For the KCNQ compounds, when administered IV, pretreatment time is 15 minutes. For oral administration, pretreatment time is 1 hour. Following the pretreatment, the animal is placed in the covered zone of the platform, always oriented in the same direction, facing the pillar. For 5 minutes the animals are allowed to freely explore the apparatus. The dependent variable is the number of Stretched Attend Postures, which are scored by an observer blind to treatment condition. Data were analyzed by an overall analysis of variance followed by Dunnett's post hoc tests. An effect was considered significant if p<0.05.

All test compounds are administered in a volume of 10 ml/kg. Vehicle and buspirone (as the positive control) treated mice were run with each experiment, and buspirone was dissolved in the same vehicle as used per each compound. Compounds of Formula I were administered IV, in a vehicle containing 10% PEG400/5% Tween/85% water, warmed on a hot plate.

Results: There was a significant reduction in stretched attend postures following administration of buspirone (0.5 mg/kg), as well compounds of Formula I. The effects of representative compounds of Formula I are listed in Table 7 and the data are presented as percent of vehicle controls.

TABLE 7

| Example Number | % Reduction SAPs |
|---|---|
| Buspirone | 71 (0.5 mg/kg. i.v.) |
| 1 | 44 (1.25 mg/kg, iv.) |
| 82 | 28 (30 mg/kg, i.v.) |
| 169 | 18 (10 mg/kg, i.v.) |

The compounds of Example 82 and 152 were run in separate experiments with a vehicle control in the canopy stretched attend postures test. Data are presented as percent of representative control, and significance was assess by Dunnett's post hoc comparing responses of drug treated animals to vehicle controls, for example, the compound of Example 82 was 75% and Example 152 was 80% of vehicle control.

In another embodiment, this invention includes pharmaceutical compositions comprising at least one compound of Formula I in combination with a pharmaceutical adjuvant, carrier or diluent.

In still another embodiment, this invention relates to a method of treatment or prevention of disorders responsive to opening of KCNQ potassium channels in a mammal in need thereof, which comprises administering to said mammal a therapeutically effective amount of a compound of Formula I. Preferably, the compounds of Formula I are useful in the treatment of treatment of migraine or a migraine attack, cluster headaches, bipolar disorder, convulsions, mania, acute mania, epilepsy, anxiety, depression, schizophrenia, functional bowel disorders, stroke, traumatic brain injury, multiple sclerosis, neurodegenerative disorders or alleviating pain such as musculoskeletal pain, post operative pain, surgical pain, inflammatory pain, neuropathic pain such as diabetic neuropathy and pain associated with cancer and fibromyalgia.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjutants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.01 $\mu$g/kg to 10 mg/kg body weight. For parenteral administration, the dose may be in the range of 0.1 $\mu$g/kg to 1 mg/kg body weight for intravenous administration. For oral administration, the dose may be in the range about 0.1 $\mu$g/kg to 5 mg/kg body weight. The active ingredient will preferably be administered in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the spirit of the invention.

DESCRIPTION OF SPECIFIC EMBODIMENTS

Unless otherwise stated, solvents and reagents were used directly as obtained from commercial sources, and reactions were performed under a nitrogen atmosphere. Flash chromatography was conducted on Silica gel 60 (0.040–0.063 particle size; EM Science supply). ¹H NMR spectra were recorded on a Bruker DRX-500f at 500 MHz; a Bruker DPX-300B at 300 MHz; or a Varian Gemini 300 at 300 MHz. The chemical shifts were reported in ppm on the δ scale relative to δTMS=0. The following internal references were used for the residual protons in the following solvents: CDCl₃ ($δ_H$ 7.26), CD₃OD ($δ_H$ 3.30) and DMSO-d₆ ($δ_H$ 2.50). Standard acronyms were employed to describe the multiplicity patterns: s (singlet), d (doublet), t (triplet), q (quartet), m (multiplet), b (broad), app (apparent). The coupling constant (J) is in hertz. LC/MS was performed on a Shimadzu LC-10AS liquid chromatograph using a SPD-10AV UV-VIS detector with Mass Spectrometry data determined using a Micromass LC Platform in positive electrospray ionization mode (ESI+). Mass Spectrometry (MS) data was obtained using a standard flow injection technique on a Micromass LC Platform in positive electrospray ionization mode (ESI+) unless otherwise noted. High resolution mass spectrometry (HRMS) data was obtained using a standard flow injection technique on a Finnigan MAT 900 mass spectrometer in electrospray ionization (ESI) mode. The analytical reverse phase HPLC method is as follows unless otherwise noted: Column YMC ODS-A C18 S7 (3.0×50 mm), Start % B=0, Final % B=100, Gradient Time=2 min, Flow rate 5 ml/minutes. Wavelength=220 nm, Solvent A=10% MeOH—90% H₂O—0.1% TFA, Solvent B=90% MeOH—10% H₂O—0.1% TFA; and $R_t$ in min. Preparative reverse phase HPLC was performed on a Shimadzu LC-8A automated preparative HPLC system with detector (SPD-10AV UV-VIS) wavelength and solvent systems (A and B) the same as above except where otherwise noted.

The following LCMS conditions were employed for the analysis of the compounds of Examples 1–301 and are as follows:

a) YMC C18 S5 4.6×50 mm; 0–100% gradient over 4 min; 4 mL/min flow rate
b) YMC ODS-A C18 S7 3.0×50 mm; 0–100% gradient over 2 min; 5 mL/min flow rate
c) YMC C18 S5 4.5×50 mm; 0–100% gradient over 8 min; 2.5 mL/min flow rate
d) YMC C18 S7 3.0×50 mm; 0–100% gradient over 3 min; 5 mL/min flow rate
e) YMC ODSA S3 6.0×150 mm; 0–100% gradient over 5 min; 1.5 mL/min flow rate
f) PHS-PRIMESPHERE C18 4.6×30 mm; 0–100% gradient over 2 min; 5 mL/min flow rate
g) YMC C18 S7 3.0×50 mm; 0–100% gradient over 4 min; 5 mL/min flow rate
h) YMC ODS-A C18 S7 3.0×50 mm; 0–100% gradient over 2 min; 5 mL/min flow rate
i) YMC ODS-A C18 S7 3.0×50 mm; 0–100% gradient over 1.5 min; 5 mL/min flow rate
j) YMC Xterra C18 S7 3.0×50 mm; 0–100% gradient over 2 min; 5 mL/min flow rate
k) YMC Pro-ODS C18 S5 4.6×33 mm; 0–100% gradient over 3 min; 4 mL/min flow rate
l) YMC ODS-A C18 S7 3.0×50 mm; 0–100% gradient over 4 min; 4 mL/min flow rate
m) Chiralpak AD column, 50×500 mm, 90% hexanes/10% ethanol, 75 mL/min flow rate
n) Chiralpak AD column, 50×500 mm, 75% hexanes/25% ethanol, 75 mL/min flow rate
o) Chiralpak AD column, 50×500 mm, 85% hexanes/15% ethanol, 75 mL/min flow rate
p) YMC C18 S5 4.6×50 mm; 0–100% gradient over 2 min; 5 mL/min flow rate
q) Phenomenex Luna C18 S10, 3.0×50 mm; 0–100% gradient over 2 min; 5 mL/min flow rate
r) YMC ODS S7 3.0×50 mm; 0–100% gradient over 2 min; 5 mL/min flow rate
s) YMC Combiscreen S5 4.6×50 mm; 0–100% gradient over 2 min; 5 mL/min flow rate.
t) YMC ODS-A C18 S5 4.6×33 mm, 01–100% gradient over 2 min, 5 mL/min flow rate
u) PRIMESPHERE SB C18, 4.6×30 mm; 0–100% gradient over 2 min; 4 ml/min flow rate
v) YMC Xterra C18 S5 4.6×50 mm; 0–100% gradient over 3 min; 4 mL/min flow rate.
w) Primeshere C18-HC 4.6×30 mm; (5 mM NH₄OAc) 0–100% gradient over 2 min; 4 mL/min flow rate
x) Chiralpak AD column, 50×500 mm, 75% hexanes/25% ethanol, 16 mL/min flow rate
SolventA=10% CH3CN-90% H₂O-5 mM NH4Oac
SolventB=90% CH3CN-10% H₂O-5 mM NH4Oac

PREPARATION OF INTERMEDIATES

Preparation 1

Preparation of 1-(1,3-benzodioxol-5-yl) acetaldehyde, oxime

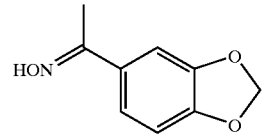

A mixture of 3,4-methylenedioxyacetophenone (8.2 g, 50 mmole), ammonium hydroxide hydrochloride (7 g, 600 mmole), and sodium hydroxide (5N) (20 mL, 100 mmole) in THF (60 mL) was stirred under reflux for 6 days. The reaction mixture was allowed to cool to room temperature then concentrated in vacuo. The residue obtained was extracted with CH₂Cl₂ (3×30 mL). The combined organic layers were dried over anhydrous magnesium sulfate, filtered and the filtrate was concentrated in vacuo to provide the oxime (crude product, 8.98 g, quantitative yield). The crude product was used without any further purification.

¹H NMR (CDCl₃): δ 2.239 (s, 3H), 2.53 (s, 3H), 5.97 (s, 1H), 6.039 (s, 1H), 6.814 (d, J=8.1 Hz, 1H), 6.857 (d, J=8.2 Hz, 0.5H), 7.108 (dd, J=8.1, 1.7 Hz, 0.5H), 7.16 (d, J=1.7 Hz, 0.5H), 7.436 (d, J=1.7 Hz, 0.5H), 7.566 (dd, J=8.1, 2.6 Hz, 0.5H).

Preparation 2

Preparation of (±)-1-benzo[1,3]dioxol-5-yl-ethylamine

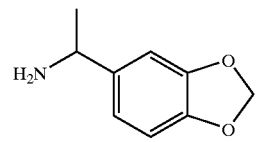

A suspension of Raney nickel (1 mL) in methanol (5 mL) and ammonium hydroxide (1 mL) was added to a solution of 1-(1,3-benzodioxol-5-yl)acetaldehyde, oxime (Preparation 1, 8.98 g, 50 mmole) in methanol (50 mL). The reaction mixture was hydrogenated (shaken on a Parr hydrogenator under H$_2$ atmosphere at 60 psi) for 24 hours. The reaction mixture was filtered, and the resultant filtrate was concentrated in vacuo to provide the title compound as an oil (3.68 g, 45%).

$^1$H NMR (CDCl$_3$): δ 1.35 (d, 3H), 4.079 (q, 1H), 5.92 (s, 2H), 6.77 (m, 2H), 6.863 (s, 1H); MS (M+H)$^+$ 166.08.

Preparation 3

Preparation of 5-acetyl-2,3-dihydrobenzo[b]furan, oxime

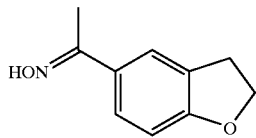

A mixture of 5-acetyl-2,3-dihydrobenzo[b]furan (2.5 g, 15 mmole) in ethanol (25 mL) and hydroxylamine hydrochloride (5.4 g, 77 mmole) was stirred under reflux for 8 hours. The reaction mixture was allowed to cool to room temperature and then concentrated in vacuo. The residue obtained was dissolved in CH$_2$Cl$_2$ (200 mL) and the solution was washed with brine (2×100 mL). The organic layer was then dried over anhydrous magnesium sulfate and filtered. The resultant filtrate was concentrated in vacuo to provide the titled product (2.7 g) as a solid. MS: 178.13 (M+H)$^+$.

Preparation 4

Preparation of (±)-1-(2,3-dihydro-benzofuran-5-yl)-ethylamine

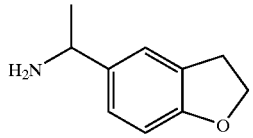

A mixture of 5-acetyl-2,3-dihydrobenzo[b]furan, oxime, (Preparation 3, 2.7 g, 16 mmole) in methanol (50 mL), ammonium hydroxide (5 mL) and Raney nickel (3 mL) was hydrogenated on a Parr hydrogenator (H$_2$, 50 psi) for 2 days. The reaction mixture was filtered through Celite and the resultant filtrate was concentrated in vacuo. The residue was purified by flash column chromatography on silica gel using methanol (100%) to give the title compound (1.74 g, 70%) as a brown oil.

MS: 164.10 (M+H)$^+$.

Preparation 5

Preparation of 1-(2,3-dihydro-1,4-benzodioxin-6-yl) acetaldehyde, oxime

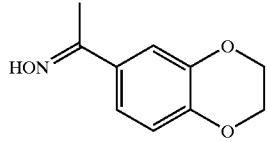

A mixture of 1,4-benzodioxan-6-yl methyl ketone (10.0 g, 0.056 mole), and ammonium hydroxide hydrochloride (19.4 g, 0.28 mole) in ethanol (100 mL) was stirred under reflux for 16 hours. The reaction mixture was allowed to cool to room temperature then concentrated in vacuo. The residue was dissolved in CH$_2$Cl$_2$ and the solution was washed with water (3×200 mL). The organic layer was dried over magnesium sulfate, filtered, and the filtrate was concentrated in vacuo to provide the title product (10.74 g, 70%) as a white solid. The product was carried on to the next step without any further purification.

MS: 194.11 (M+H)$^+$.

Preparation 6

Preparation of (±)-1-(2,3-dihydro-benzo[1,4]dioxin-6-yl)-ethylamine

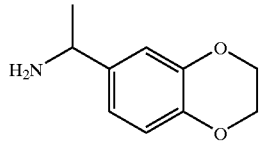

A mixture of 1-(2,3-dihydro-1,4-benzodioxin-6-yl) acetaldehyde, oxime, (Preparation 5, 10.74 g, 0.0556 mole), and Raney nickel (1 mL) in ammonium hydroxide/methanol (20 mL/200 mL) was hydrogenated (H$_2$, 50 psi) for 48 hours. The reaction mixture was filtered through Celite and the resultant filtrate was concentrated in vacuo. The residual oil obtained was diluted with HCl (1N). The aqueous layer was washed with EtOAc (1×250 mL). The aqueous layer was then made basic with NaOH (1N), and extracted with EtOAc (3×200 mL). The combined organic layers were dried over anhydrous magnesium sulfate, filtered and the resultant filtrate was concentrated in vacuo to provide the title product (7.1 g, 66%) as a clear oil.

$^1$H NMR (DMSO): δ 1.184 (d, J=6.56 mHz, 3H), 4.214 (s, 4H), 6.845 (m, 3H).

Preparation 7

Preparation of 3,4-dihydro-1H-isoquinoline-2-carboxylic acid methyl ester

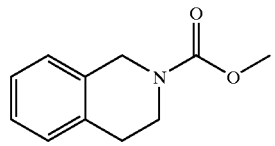

A solution of methyl chloroformate (15.45 mL, 200 mmol) in CH$_2$Cl$_2$ (50 mL) was added to a solution of 1,2,3,4-tetrahydroisoquinoline (13.3 g, 100 mmol) and triethylamine (57 mL, 400 mmol) in CH$_2$Cl$_2$ (200 mL) at 0° C. The reaction mixture was stirred for 3 hours then was quenched with water. The organic layer was separated and washed with water (2×50 mL). The organic layer was then dried over anhydrous magnesium sulfate, filtered and the resultant filtrate was concentrated in vacuo to provide the title compound (19.1 g). The crude material thus obtained was used without further purification.

$^1$H NMR (CDCl$_3$): δ 2.86 (t, 2H), 3.69 (b, 2H), 3.75 (s, 3H), 4.62 (s, 2H), 7.192 (m, 4H).

Preparation 8

Preparation of 7-acetyl-3,4-dihydro-1H-isoquinoline-2-carboxylic acid methyl ester

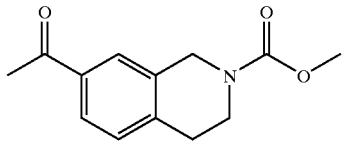

A solution of acetyl chloride (10.66 mL, 0.15 mol) in carbon disulfide (20 mL) was added dropwise to a suspension of 3,4-dihydro-1H-isoquinoline-2-carboxylic acid methyl ester, Preparation 7 (19 g, 0.1 mole) and aluminum chloride (40 g, 0.3 mol) in carbon disulfide (400 mL). The reaction mixture was stirred under reflux for 16 hours. The reaction mixture was then cooled to room temperature and quenched with ice-water. The aqueous layer was extracted with CH$_2$Cl$_2$ (3×75 mL). The organic layers were combined and passed through a silica gel plug. The resultant filtrate was concentrated in vacuo and the residue was purified by flash column chromatography on silica eluted with hexane/EtOAc (2:1). The product was obtained as an oil (16.3 g, 70%).

$^1$H NMR (CDCl$_3$): δ 2.57 (s, 3H), 2.89 (b, 2H), 3.709 (b, 2H), 3.75 (s, 3H), 4.665 (s, 2H), 7.26 (m, 1H), 7.76 (m, 2H).

Preparation 9

Preparation of 1,2,3,4-tetrahydro-7-[1-(hydroxyimino)ethyl]isoquinoline-2-carboxylic acid, methyl ester

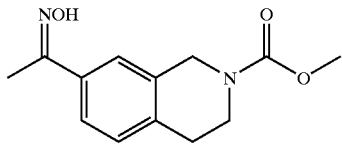

A mixture of 7-acetyl-3,4-dihydro-1H-isoquinoline-2-carboxylic acid methyl ester, Preparation 8 (11.65 g, 50 mmol), ammonium hydroxide hydrochloride (7 g, 100 mmol) and sodium hydroxide (10N) (10 mL, 100 mmol) in THF (50 mL) was heated under reflux for 24 hours. The reaction mixture was cooled to room temperature, concentrated in vacuo, and extracted with CH$_2$Cl$_2$ (3×50 mL). The combined organic layers were dried over anhydrous magnesium sulfate, filtered, and the resultant filtrate was concentrated in vacuo. The residue obtained was purified by flash column chromatography on silica eluted with hexane/EtOAc (1:1) to provide the title compound as an oil (11.7 g, 94%).

$^1$H NMR (CDCl$_3$): δ 2.26 (s, 3H), 2.857 (b, 2H), 3.7 (b, 2H), 3.753 (s, 3H), 4.63 (s, 2H), 7.15 (d, J=8.04 Hz, 1H), 7.446 (m, 2H), 8.14 (s, 1H).

Preparation 10

Preparation of (±)-7-(1-aminoethyl)-3,4-dihydro-1H-isoquinoline-2-carboxylic acid methyl ester

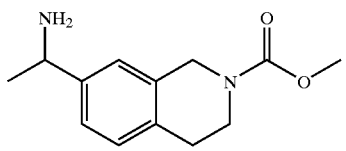

A suspension of 1,2,3,4-tetrahydro-7-[1-(hydroxyimino)ethyl]-isoquinoline-2-carboxylic acid, methyl ester, Preparation 9 (9.9 g, 40 mmol) and Raney nickel (1 mL) in methanol (50 mL) and ammonium hydroxide (15 mL) was hydrogenated (H$_2$, 50 psi) for 3 days. The reaction mixture was then filtered and the resultant filtrate was concentrated in vacuo. The residue was purified by flash column chromatography on silica using a gradient system of solvents: ethyl acetate (100%) to ammonium hydroxide/methanol (30%). The product was obtained as an oil (6.55 g, 70%).

$^1$H NMR (CDCl$_3$): δ 1.37 (d, 3H), 2.04 (m, 2H), 3.68 (b, 2H), 3.74 (s, 3H), 4.09 (q, 1H), 4.61 (b, 2H), 7.16 (m, 3H); MS: 235.16 (M+H)$^+$.

Preparation 11

Preparation of 1-(2H-3,4-dihydro-3-oxo-1,4-benzoxazin-6-yl)-acetaldehyde, oxime

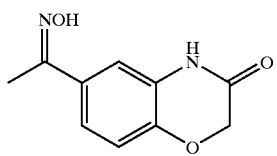

A mixture of 6-acetyl-2H-1,4-benzoxazin-3(4H)-one (19.1 g, 100 mmol), ammonium hydroxide hydrochloride (10 g, 200 mmol), and sodium hydroxide (10N) (20 mL, 200 mmol) in THF (80 mL) was heated under reflux for 1 hour. The reaction mixture was cooled to room temperature and concentrated in vacuo. The residue was washed with water (200 mL) and the resultant solid (18 g, 87%) was used without further purification.

$^1$H NMR (DMSO-d$_6$): δ 2.087 (s, 3H), 4.58 (s, 2H), 6.94 (d, J=8.4 mHz, 1H), 7.19 (dd, J=8.4, 2.1 mHz, 1H), 7.26 (d, J=2.04 mHz, 1H); MS: 207.10 (M+H)$^+$.

Preparation 12

Preparation of (±)-6-(1-aminoethyl)-4H-benzo[1,4]oxazin-3-one

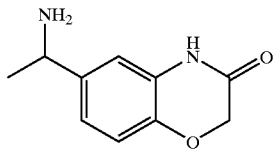

A mixture of 1-(2H-3,4-dihydro-3-oxo-1,4-benzoxazin-6-yl)acetaldehyde, oxime, Preparation 11 (8.24 g, 40 mmol) and Raney nickel (1 mL) in methanol (75 mL) and ammonium hydroxide (30 mL) was hydrogenated ($H_2$, 50 psi) for 2 days. The reaction mixture was filtered, and the resultant filtrate was concentrated in vacuo to afford the title compound (7.2 g, 94%) which was used without further purification.

$^1$H NMR (CDCl$_3$): δ 1.367 (d, 3H), 4.12 (q, 1H), 4.59 (s, 2H), 6.869 (s, 1H), 6.93 (s, 1H), 7.259 (s, 1H).

Preparation 13

Preparation of (±)-1-(3,4-dihydro-2H-benzo[1,4]oxazin-6-yl)ethylamine

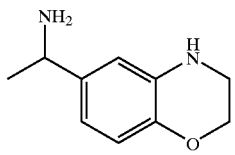

Lithium aluminum hydride (2.28 g, 60 mmol) was carefully added to a suspension of (±)-6-(1-aminoethyl)-4H-benzo[1,4]oxazin-3-one, Preparation 11 (3.84 g, 20 mmol) in THF (80 mL) at −78° C. The reaction mixture was stirred while warming to room temperature, then under reflux for 4 hours. The reaction mixture was then cooled to −78° C. and was quenched with water (2.3 mL), sodium hydroxide (10N) (2.3 mL), and water (4.6 mL). The resulting mixture was filtered and the resultant filtrate was concentrated in vacuo. The residual material was extracted with CH$_2$Cl$_2$ (3×50 mL). The combined organic layers were dried over sodium sulfate, filtered and the resultant filtrate was concentrated in vacuo to provide the title compound (3.38 g, 95%) as an oil.

$^1$H NMR (CDCl$_3$): δ 1.43 (d, 3H), 3.42 (t, 2H), 3.94 (q, 1H), 4.22 (t, 2H), 6.58 (m, 2H), 6.743 (m, 1H).

Preparation 14

Preparation of 3-trifluoromethoxyacetophenone, oxime

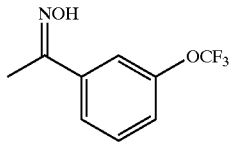

A mixture of 3-trifluoromethoxyacetophenone (3.0 g, 15 mmol), and ammonium hydroxide hydrochloride (2.08 g, 30 mmol), and sodium hydroxide (2N) (30 mmol) in THF (30 mL) was heated under reflux for 2 hours. The reaction mixture was cooled to room temperature, and concentrated in vacuo. The residual material was dissolved in diethyl ether (200 mL). The organic layer was washed with brine (2×50 mL), dried over anhydrous magnesium sulfate, filtered, and the resultant filtrate was concentrated in vacuo to provide the title compound (3.10 g, 98%) as an oil. The crude product thus obtained was used without further purification. MS: 270.08 (M+H)$^+$.

Preparation 15

Preparation of (±)-1-(3-trifluoromethoxy-phenyl)ethylamine

A mixture of 3-trifluoromethoxyacetophenone, oxime, Preparation 14 (3.08 g, 12.36 mmol), Raney nickel (1 mL) in methanol (50 mL) and ammonium hydroxide (5 mL) was hydrogenated (H$_2$, 50 psi) for 16 hours. The reaction mixture was filtered through Celite and the resultant filtrate was concentrated in vacuo. The suspension obtained was acidified with hydrochloric acid (6N) (100 mL). The aqueous layer was washed with diethyl ether (2×50 mL). The aqueous layer was then made basic with sodium hydroxide (10 N) (with cooling). The basic aqueous layer was then extracted with CH$_2$Cl$_2$ (2×100 mL). The combined organic layer was washed with brine (100 mL), dried over anhydrous magnesium sulfate, filtered, and the resultant filtrate was concentrated in vacuo to provide the title compound (1.82 g, 63%) as an oil.

MS: 206.06 (M+H)$^+$.

Preparation 16

Preparation of 3-pyridin-2-yl-acrylic acid

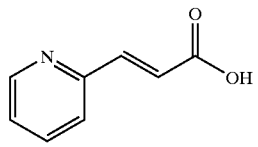

A mixture of pyridine-2-carboxaldehyde (32.1 g 0.30 mmol), malonic acid (62.4 g, 0.60 mmol) in pyridine (200 mL) and pyrrolidine (2 mL) was stirred under reflux for 16 hours. The reaction mixture was allowed to cool to room temperature and poured into ice water (200 mL). The aqueous layer was extracted with CH$_2$Cl$_2$ (2×100 mL). The combined organic layer was concentrated in vacuo and the crude material obtained was purified by flash column chromatography on silica using a gradient system of solvents: 1) ethyl acetate (100%); 2) methanol/ethyl acetate (10%). The title product was obtained (6.28 g, 14%) as a grayish-green solid.

$^1$H NMR (DMSO-d$_6$, 300 mHz) δ: 6.83 (1H, d, J=18 Hz), 7.40 (1H, m), 7.58 (1H, d, J=15 Hz), 7.74 (1H, d), 7.88 (1H, m), and 8.62 (1H, d, J=6.0 Hz);

MS: 149 [M+H]$^+$.

Preparation 17

Preparation of 2,3-dihydroindole-1-carboxylic acid methyl ester

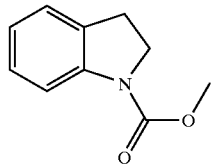

A mixture of indoline (11.97 g, 0.1 mol), methyl chloroformate (15.45 mL, 0.2 mol), triethylamine (40.4 g, 0.4 mol), and DMAP (0.5 g, 0.004 mol) in CH$_2$Cl$_2$ (100 mL) was stirred for 16 hours. The reaction mixture was quenched with water (10 mL). The reaction was extracted with CH$_2$Cl$_2$ (1×40 mL). The organic layer washed with water (1×50 mL), dried over anhydrous magnesium sulfate, filtered and the resultant filtrate was concentrated in vacuo to provide the title compound (17.6 g, 99%) which was used without further purification.

Preparation 18

Preparation of 5-acetyl-2,3-dihydroindole-1-carboxylic acid methyl ester

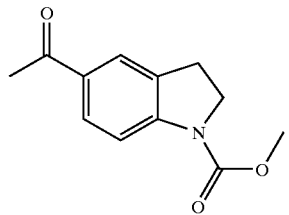

Acetyl chloride (10.66 mL, 0.15 mol) was added slowly to a mixture of 2,3-dihydro-indole-1-carboxylic acid methyl ester, Preparation 17 (17 g, 0.1 mol), and aluminum chloride (40 g, 0.3 mol) in carbon disulfide (150 mL) at 0° C. The reaction mixture was warmed to room temperature and heated under reflux for 16 hours. The reaction mixture was then cooled to room temperature and poured into ice water. The resulting mixture was extracted with CH$_2$Cl$_2$ (3×40 mL). The combined organic layers were dried over anhydrous magnesium sulfate, filtered, and the resultant filtrate was concentrated in vacuo. The residue was purified by flash column chromatography on silica using ethyl acetate/hexane (30%) to provide the title product (8.8 g, 40%) as a solid.

$^1$H NMR (CDCl$_3$): δ 2.55 (s, 3H), 3.195 (t, 2H), 3.865 (s, 3H), 4.105 (t, 2H), 7.835 (m, 3H).

Preparation 19

Preparation of 2,3-dihydro-5-[1-(hydroxyimino) ethyl]-1H-indole-1-carboxylic acid, methyl ester

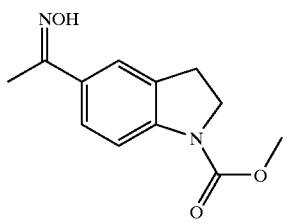

A mixture of 5-acetyl-2,3-dihydroindole-1-carboxylic acid methyl ester, Preparation 18 (6.57 g, 30 mmol), triethylamine (6.06 g, 60 mmol), and ammonium hydroxide hydrochloride (4.2 g, 60 mmol) in ethanol (80 mL) was stirred under reflux for 16 hours. The reaction mixture was cooled to room temperature and concentrated in vacuo. The residue was extracted with CH$_2$Cl$_2$ (1×60 mL), and the organic layer was dried over anhydrous magnesium sulfate, filtered, and the resultant filtrate was concentrated in vacuo. The crude material was purified by flash column chromatography on silica eluting with ethyl acetate/hexane (30%) to provide the title product (6.3 g, 90%) as a solid.

$^1$H NMR (CDCl$_3$): δ 1.426 (t, 3H), 3.152 (m, 3H), 3.83 (s, 3H), 4.05 (t, 2H), 7.46 (m, 2H), 7.6 (b, 1H), 8.2 (b, 1H); MS: 235.10 (M+H)$^+$.

Preparation 20

Preparation of (±)-5-(1-aminoethyl)-2,3-dihydroindole-1-carboxylic acid methyl ester

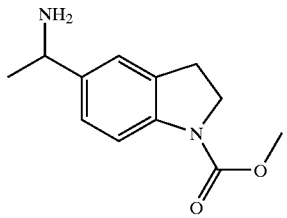

A mixture of 2,3-dihydro-5-[1-(hydroxyimino)ethyl]-1H-indole-1-carboxylic acid, methyl ester, Preparation 19 (6 g, 25.6 mmol), and Raney nickel (1 mL) in methanol/ ammonia/water (75 mL:15 mL) was hydrogenated (H$_2$, 50 psi) for 3 days. The reaction mixture was filtered, and the resultant filtrate was concentrated in vacuo. The residue was purified by flash column chromatography on silica eluting with a gradient system of solvents: ethyl acetate (100%) to ammonium hydroxide/methanol (30%) to provide the title compound (4.1 g, 73%) as a solid.

$^1$H NMR (CDCl$_3$): δ 1.39 (d, J=6.6 mHz, 3H), 2.276 (b, 2H), 3.124 (t, 2H), 3.993 (s, 3H), 4.09 (m, 2H), 7.26 (t, 3H).

Preparation 21

Preparation of (S)-1-(3-morpholin-4-yl-phenyl)ethylamine hydrochloride

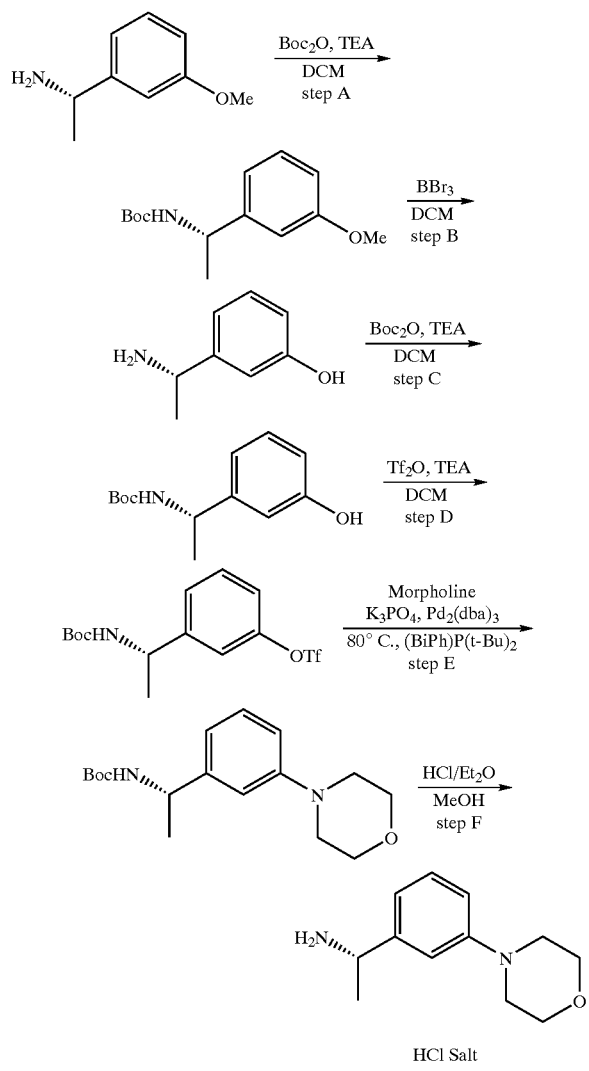

HCl Salt

Step A: [(S)-1-(3-Methoxyphenyl)ethyl]carbamic acid tert-butyl ester

A solution of (S)-3-methoxy-benzylmethylamine (2 g, 13.2 mmol), di-t-butyl-di-carbonate (3 g, 14.6 mmol), triethyl amine (7.37 mL, 53 mmol) in dichloromethane (66 mL) was stirred at room temperature for 5 hours. The reaction mixture was washed with saturated sodium bicarbonate solution (10 mL), and the aqueous layer was extracted with dichloromethane (2×15 mL). The combined organic layer was dried over magnesium sulfate, concentrated under vacuum to provide the title compound as colorless oil (3.15 g, 95% yield). The crude product was used without any further purification.

$^1$H NMR (CDCl$_3$): δ 1.27 (m, 12H), 3.80 (s, 3H), 4.78 (broad s, 2H), 6.84 (m, 3H), 7.24 (m, 1H). MS (M+H)$^+$ 252.

Step B: 3-[(S)-1-Aminoethyl]phenol

To a solution of [(S)-1-(3-methoxyphenyl)ethyl]carbamic acid tert-butyl ester (3 g, 12 mmol) in dichloromethane (25 mL) at −78° C. was added BBr$_3$ (1.0 M solution in dichloromethane) (26 mL, 26 mmol) dropwise. After the addition, the solution was warmed up to room temperature. The reaction mixture was quenched with methanol (100 mL) and concentrated under vacuum. This process was repeated until no white fumes were observed upon adding methanol. The title compound was obtained as pale yellow solid (2.6 g, quantitative yield). The crude product was used without any further purification $^1$H NMR (CD$_3$OD): δ 1.60 (d, 3H), 4.35 (q, 1H), 6.85 (m, 3H), 7.25 (m, 1H).

MS (M+H)$^+$ 152.

Step C: [(S)-1-(3-Hydroxyphenyl)ethyl]carbamic acid tert-butyl ester

A solution of 3-[(S)-1-aminoethyl]phenol (1.60 g, 11.7 mmol), di-t-butyl-di-carbonate (2.8 g, 12.8 mmol), triethylamine (6.48 mL, 47 mmol) in dichloromethane (30 mL) was stirred at room temperature for 0.5 hours. The reaction mixture was washed with saturated sodium bicarbonate solution (10 mL), and the aqueous layer was extracted with dichloromethane (2×15 mL). The combined organic layer was dried over magnesium sulfate, concentrated under vacuum to provide the title compound as pale yellow solid (2.73 g, quantitative yield). The crude product was used without any further purification.

$^1$H NMR (CDCl$_3$): δ 1.45 (m, 12H), 4.80 (broad s overlapping, 2H), 6.75 (m, 3H), 7.18 (m, 1H).

MS (M+H)$^+$ 238.

Step D: Trifluoromethanesulfonic acid 3-(1-tert-butoxycarbonylaminoethyl)-phenyl ester To a solution of [(S)-1-(3-hydroxyphenyl)ethyl]carbamic acid tert-butyl ester (2.73 g,in dichloromethane (30 mL) at 0° C. was added triethyl amine (3.20 mL, 23 mmol) followed by addition of trifluoromethylsulfonyl anhydride (2.13 mL, 12.7 mmol). After the addition, the solution was stirred at room temperature for 30 minutes. The reaction mixture was quenched with water (10 mL) and the aqueous layer was extracted with dichloromethane (2×15 mL). The combined organic layer was dried over magnesium sulfate and concentrated under vacuum. The crude product was purified by flash chromatography of Biotage with 20% ethyl acetate/hexanes to provide the title compound as a pale yellow solid (4.23 g).

$^1$H NMR (CD$_3$OD): δ 1.43 (m, 12H), 4.81 (broad s, 2H), 7.14 (m, 1H), 7.20 (s, 1H), 7.33 (m, 1H), 7.41 (m, 1H).

MS (M+H)$^+$ 369.

Step E: [1-(3-Morpholin-4-yl-phenyl)ethyl]carbamic acid tert-butyl ester

A mixture of trifluoro-methanesulfonic acid 3-(1-tert-butoxycarbonylaminoethyl)phenyl ester (1.5 g, 4.08 mmol), morpholine (8 mL) Pd$_2$(dba)$_3$ (187 mg, 5 mol %), di-t-butyl-biphenylphosphine (243 mg, 20 mol %), potassium phosphate (1.21 g, 5.71 mmol) was stirred at 80° C. in a sealed tube for 10 hours. After cooling down, the reaction mixture was diluted with dichloromethane (50 mL) and washed with water (10 mL). The aqueous layer was extracted with dichloromethane (2×15 mL) and the combined organic layer was dried over magnesium sulfate and concentrated under vacuum. The crude product was purified by flash chromatography of Biotage with 30% ethyl acetate/hexanes to provide the title compound as a pale yellow solid (1.01 g, 81% yield).

$^1$H NMR (CD$_3$OD): δ 1.42 (m, 12H), 3.16 (m, 4H), 3.86 (m, 4H), 4.78 (broad s, 2H), 6.81 (m, 3H), 7.24 (m, 1H).

MS (M+H)$^+$ 307.

Step F: 1-(3-Morpholin-4-yl-phenyl)ethylamine hydrochloride

To a solution of [1-(3-morpholin-4-yl-phenyl)ethyl]carbamic acid tert-butyl ester (1 g, 3.27 mmol) in methanol (3 mL) was added hydrochloric acid (1.0 M in ethyl ether)

(13.1 mL, 13.1 mmol) and the reaction mixture was stirred at room temperature for 10 hours. The reaction mixture was concentrated under vacuum to provide the title compound as pale yellow solid (0.67 g, quantitative yield) which was used for next step without any further purification.

$^1$H NMR (CD$_3$OD): δ 1.66 (d, 3H), 3.59 (m, 4H), 4.07 (m, 4H), 4.54 (m, 1H), 7.43 (m, 1H), 7.60 (m, 2H), 7.70 (s, 1H).

MS (M+H)$^+$ 207.

Preparation 22

Preparation of (±)-1-(3-morpholin-4-yl-phenyl)propylamine

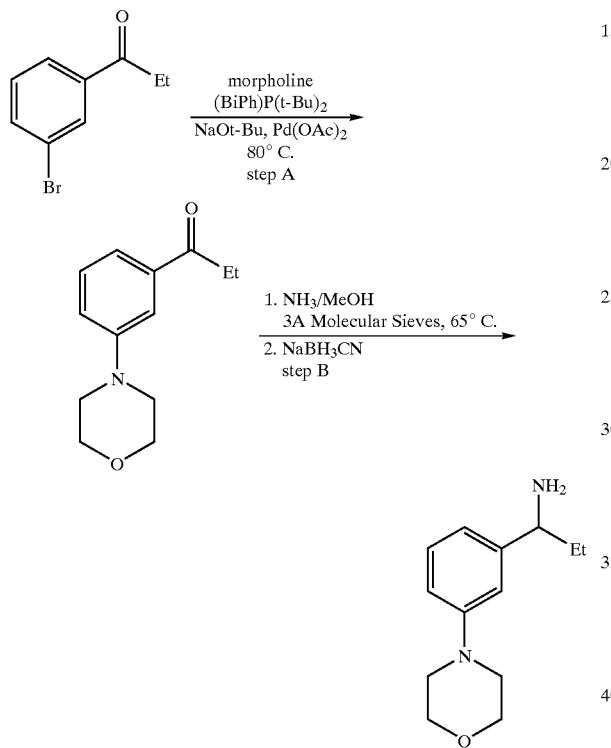

Step A: 1-(3-Morpholin-4-yl-phenyl)propan-1-one

A mixture of 3'-bromopropiophenone (11.4 g, 53 mmol), morpholine (60 mL), palladium acetate (300 mg, 2.5 mol %), di-t-butyl-biphenylphosphine (800 mg, 5 mol %), sodium t-butyloxide (6.1 g, 64 mmol) was stirred at 80° C. in a sealed tube for 24 hours. After cooling down, the reaction mixture was diluted with dichloromethane (150 mL) and washed with water (50 mL). The aqueous layer was extracted with dichloromethane (2×75 mL) and the combined organic layer was dried over magnesium sulfate and concentrated under vacuum. The crude product was purified by flash chromatography of Biotage with 25% ethyl acetate/hexanes to provide the title compound as pale yellow clear oil (4.23 g,).

$^1$H NMR (CDCl$_3$): δ 1.21 (t, 3H), 2.98 (q, 2H), 3.21 (m, 4H), 3.87 (m, 4H), 7.09 (m, 1H), 7.35 (m, 1H), 7.45 (m, 1H), 7.51 (m, 1H).

MS (M+H.

Step B: 1-(3-Morpholin-4-yl-phenyl)propylamine

A mixture of 1-(3-morpholin-4-yl-phenyl)propan-1-one (4.06 g, 18.5 mmol), powdered 3A molecular sieves (4 g), in ammonia (2.0 M solution in methanol) (61.2 mL) was stirred in sealed vessel at 65° C. for 2 hours, at which time sodium cyanoborohydride (2.33 g, 37 mmol) and glacial acetic acid (8.47 mL) was added and the mixture was stirred at 65° C. for another 2 hours. After cooling down, the reaction mixture was filtered to remove molecular sieves and the filtrate was concentrated under vacuum. Solids was re-dissolved in dichloromethane (100 mL) and washed with saturated sodium bicarbonate solution (15 mL). The aqueous layer was extracted with dichloromethane (2×25 mL) and the combined organic layer was dried over magnesium sulfate, and concentrated under vacuum. The crude pale yellow oil was purified by Biotage flash chromatography with 90:10:10 dichloromethane:methanol:triethylamine to afford the title compound as a pale yellow clear oil (2.56 g).

$^1$H NMR (CDCl$_3$): δ 0.86 (t, 3H), 1.71 (m, 2H), 3.16 (m, 4H), 3.85 (m, 4H), 6.80 (m, 2H), 6.89 (s, 1H), 7.23 (m, 1H).

MS (M+H)$^+$ 221.

Preparation 23

Preparation of (±)-2,2,2-trifluoro-1-(3-morpholin-4-yl-phenyl)ethylamine

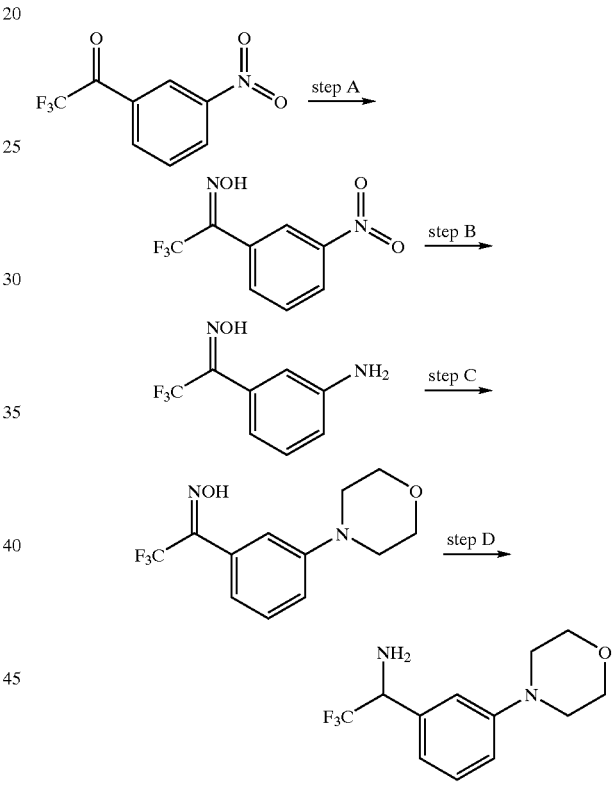

Step A: 2,2,2-Trifluoro-1-(3-nitro-phenyl)ethanone oxime

A mixture of 2,2,2-trifluoro-1-(3-nitro-phenyl)ethanone (4 g), NH$_2$OH.HCl (5.037 g), and Et$_3$N (20.44 g) in EtOH (80 mL) was refluxed for 4 days. After concentration, the residue was extracted with CH$_2$Cl$_2$. The organic layer was washed with water and dried over MgSO$_4$. The crude product was purified by silica gel flash chromatography (30% ethyl acetate in hexanes) to give the title compound (3.4 g) as a solid.

$^1$H NMR (300 MHz, CDCl$_3$): δ 8.91 (s, 1H), 8.56 (d, J=8.1 Hz, 1H), 8.33 (d, J=7.7 Hz, 1H), 7.81 (t, J=8.1 Hz, 1H).

MS: 233 (M−H)$^+$.

Step B: 1-(3-Aminophenyl)-2,2,2-trifluoroethanone oxime

A mixture of 2,2,2-trifluoro-1-(3-nitrophenyl)ethanone oxime (2.34 g) and 5% Pt(S)/C (2340 mg) in ethanol (530 mL) was hydrogenated at 50 psi for 2 hours. The crude reaction mixture was filtered, and the filtrate was concentrated in vacuo to give the title compound (2 g) as an oil which was used in the next step without purification.

¹H NMR (300 MHz, CDCl₃): δ 8.50(s, 1H), 7.28–7.19 (m, 1H), 6.87–6.77 (m, 3H).

Step C: 2,2,2-Trifluoro-1-(3-morpholin-4-yl-phenyl) ethanone oxime

A mixture of 1-(3-aminophenyl)-2,2,2-trifluoroethanone oxime (1.7 g), bromoethyl ether (2.246 g), and i-Pr₂NEt (2.57 g) in toluene (20 mL) was refluxed for 4 hours. After cooling, the reaction mixture was quenched with water. The aqueous layer was extracted with dichloromethane, and the combined organic layers were dried over magnesium sulphate, filtered and concentrated in vacuo. The crude product was purified by silica gel flash chromatography (50% ethyl acetate in hexane) to give the title compound as an oil (2.04 g).

¹H NMR (300 MHz, CDCl₃): δ 9.50(s, 1H), 7.39 (dd, J=5.7, 3.6 Hz, 1H), 7.05–6.98 (m, 3H), 3.89 (t, J=4.7, 4H), 3.20 (d, J=4.7 Hz, 4H).

Step D: (±)-2,2,2-Trifluoro-1-(3-morpholin-4-yl-phenyl) ethylamine

A suspension of 2,2,2-trifluoro-1-(3-morpholin-4-yl-phenyl)-ethanone oxime (1.37 g) and Ra—Ni (1 mL) in a mixture of 3 ml of 30% ammonium hydroxide and 15 mL of MeOH was hydrogenated at 60 psi for 16 hours. The crude reaction mixture was filtered through Celite and the filtrate was concentrated in vacuo to give the title compound as an oil (1.3 g).

MS: 261 (M+H)⁺.

Preparation 24

Preparation of (±)-1-(3-fluoro-5-morpholin-4-yl-phenyl)ethylamine

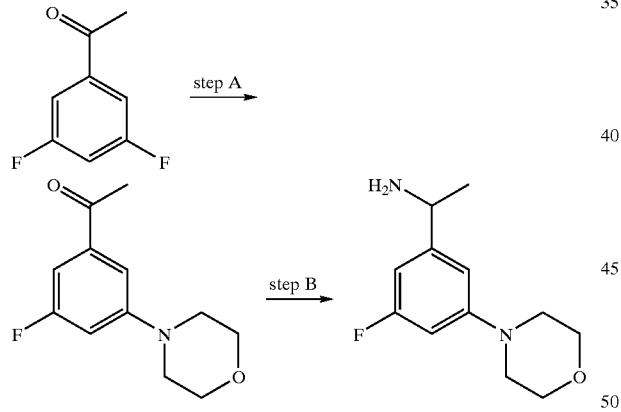

Step A: 1-(3-Fluoro-5-molpholin-4-yl-phenyl)ethanone

A mixture of 3,5-difluoroacetophenone (7.8 g) and K₂CO₃ (13.8 g) in morpholine (10 mL) was stirred at 150° C. for 3 days. After cooling, the reaction mixture was quenched with water and extracted with CH₂Cl₂. The organic layer was washed with water and dried over MgSO₄ Purification by silica gel flash chromatography (25% ethyl acetate in hexane) gave 5.4 g of the title compound as an oil.

¹H NMR (300 MHz, CDCl₃): δ 7.26 (dd, J=3.7, 2.0 Hz, 1H), 7.08 (dt, J=8.7, 2.0 Hz, 1H), 6.76 (dt, J=11.4, 2.2 Hz, 1H), 3.86 (t, J=4.8, 4H), 3.21 (d, J=4.8 Hz, 4H), 2.56 (s, 3H).

MS: 224 (M+H)⁺.

Step B: (±)-1-(3-Fluoro-5-morpholin-4-yl-phenyl) ethylamine

A mixture of 1-(3-fluoro-5-morpholin-4-yl-phenyl) ethanone (2.23 g), NH₂OH.HCl (1.4 g), and Et₃N (2.8 mL) in EtOH (20 mL) was refluxed for 3 hours. After concentration, the residue was extracted with CH₂Cl₂. The organic layer was washed with water, dried over MgSO4 and concentrated in vacuo. A suspension of the resulting residue (2.23 g) and Ra—Ni (1 mL) in a mixture of 3 mL of 30% ammonium hydroxide and 15 mL of MeOH was hydrogenated at 50 psi for 16 hours. The crude reaction mixture was filtered through Celite, and the filtrate was concentrated in vacuo. The crude product was purified by silica gel flash chromatography (10% ammonium hydroxide in methanol) to give 1.665 g of the title compound as an oil.

¹H NMR (300 MHz, CDCl₃): δ 7.00–6.92 (m, 2H), 6.74–6.69 (m, 1H), 4.38 (q, J=6.6 Hz, 1H), 3.86 (t, J=4.7, 4H), 3.09 (d, J=4.8 Hz, 4H), 1.40 (d, J=4.7 Hz, 3H). MS: 225 (M+H)⁺.

Preparation 25

Preparation of (±)-1-(2-fluoro-5-morpholin-4-yl-phenyl)ethylamine

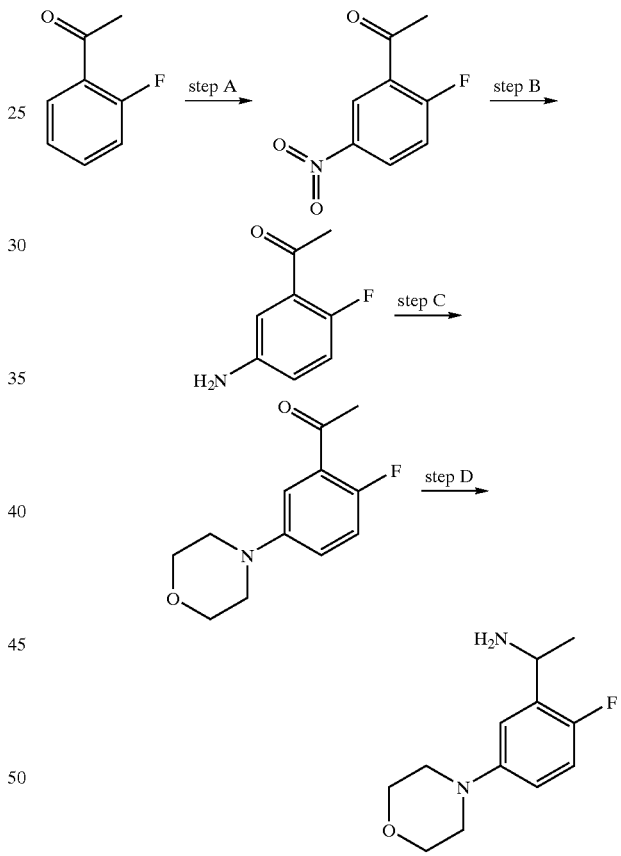

Step A: 1-(2-Fluoro-5-nitro-phenyl)ethanone

2'-Fluoroacetophenone (11.04 g) was dropwise added to concentrated H₂SO₄ (46 mL) at −20° C. After the addition was complete, a thoroughly mixed solution of fuming nitric acid (6.4 mL) and concentrated H₂SO₄ (18 mL) was added dropwise at −15° C. The reaction mixture was stirred at −15° C. for 15 minutes and then poured into 500 g of ice. The resulting solid was collected, washed with and dissolved in CH₂Cl₂. The organic layer was washed with water, dried over MgSO₄, and concentrated in vacuo. The residue was purified by silica gel flash chromatography (25% ethyl acetate in hexane) to give 8 g of the title compound as a solid.

$^1$H NMR (300 MHz, CDCl$_3$): δ 8.78 (dd, J=6, 3 Hz, 1H), 8.43–8.38 (m, 1H), 7.37 (t, J=9.4 Hz, 1H), 2.71 (d, J=4.8 Hz, 3H).

Step B: 1-(5-Amino-2-fluoro-phenyl)ethanone

A mixture of 1-(2-fluoro-5-nitro-phenyl)ethanone (7.3 g) and 5% Pt(S)/C (730 mg) in ethanol (50 mL) was hydrogenated at 50 psi for 20 hours. The reaction mixture was filtered through Celite and the filtrate was concentrated in vacuo. The residue was purified by silica gel flash chromatography (33% ethyl acetate in hexane) to give the title compound as a solid (3.56 g).

$^1$H NMR (300 MHz, CDCl$_3$): δ 7.12 (dd, J=5.9, 3 Hz, 1H), 6.93 (dd, J=10.5, 8.7 Hz, 1H), 6.82–6.77 (m, 1H), 2.60 (d, J=5 Hz, 3H).

MS: 154 (M+H)$^+$.

Step C: 1-(2-Fluoro-5-morpholin-4-yl-phenyl)ethanone

A mixture of 1-(5-amino-2-fluoro-phenyl)-ethanone (3.5 g), bromoethyl ether (5.929 g), and i-Pr$_2$NEt (7.121 g) in toluene (20 mL) was refluxed for 16 hours. After cooling, the reaction mixture was quenched with water. The aqueous layer was extracted with dichloromethane, and the combined organic layers were dried over magnesium sulphate, filtered, and concentrated in vacuo. The residue was purified by silica gel flash chromatography (25% ethyl acetate in hexane) to give 3.74 g of the title compound as an oil.

$^1$H NMR (300 MHz, CDCl$_3$): δ 7.36–7.33 (m, 1H), 7.08–7.03 (m, 2H), 3.86–3.83 (m, 4H), 3.13–3.10 (m, 4H), 2.6 (d, J=5.1 Hz, 3H).

MS: 224 (M+H)$^+$.

Step D: (±)-1-(2-Fluoro-5-morpholin-4-yl-phenyl)ethylamine

A mixture of 1-(2-fluoro-5-morpholin-4-yl-phenyl)ethanone (3.702 g), NH$_2$OH.HCl (2.3 g), and Et$_3$N (4.7 mL) in EtOH (50 mL) was refluxed for 3 hours. After concentration, the residue was extracted with CH$_2$Cl$_2$. The organic layer was washed with water, dried over MgSO4, and concentrated in vacuo to give 3.78 g of crude oxime. A suspension of the crude oxime (2.23 g) and Ra—Ni (1 mL) in a mixture of 18 ml of 30% ammonium hydroxide and 54 mL of MeOH was hydrogenated at 50 psi for 3 hours. After filtration and concentration, the residue was purified by silica gel flash chromatography (50% ethyl acetate in hexanes and then 10% ammonium hydroxide in methanol) to give 3.1 g of the title compound as an oil.

$^1$H NMR (300 MHz, CDCl$_3$): δ 7.09 (dd, J=6.3, 3 Hz, 1H), 6.84 (t, J=9.0 Hz, 1H), 6.39–6.33 (m, 1H), 4.36 (q, J=6.5 Hz, 1H), 3.56–3.53 (m, 4H), 2.72–2.69 (m, 4H), 1.28 (d, J=6.5 Hz, 3H).

MS: 225 (M+H)$^+$.

Preparation 26

Preparation of (±)-1-(4-fluoro-3-morpholin-4-yl-phenyl)ethylamine

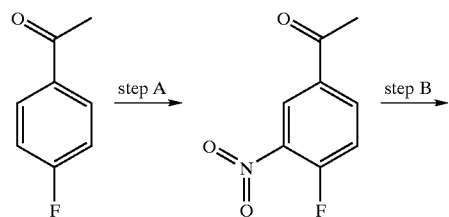

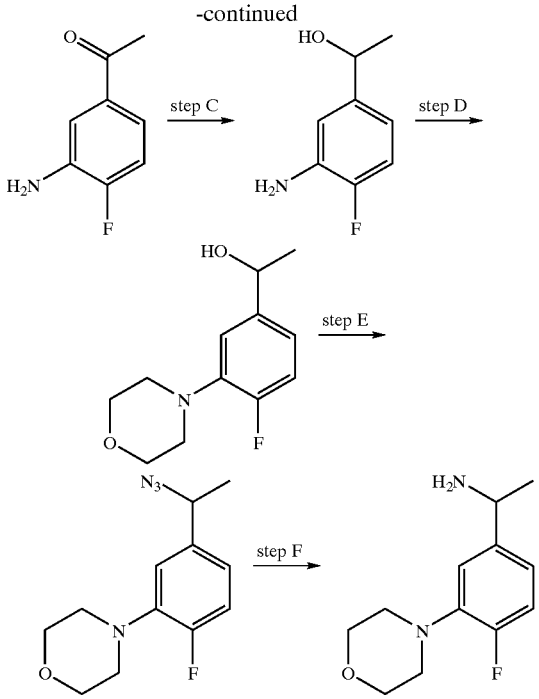

Step A: 1-(4-Fluoro-3-nitrophenyl)ethanone

To a solution of 4'-fluoroacetophenone (111.04 g) in concentrated H$_2$SO$_4$ (46 mL) was dropwise added a thoroughly mixed solution of fuming nitric acid (6.4 mL) and concentrated H$_2$SO$_4$ (118 mL) at 15° C. After the addition was complete, the reaction mixture was stirred at −15° C. for 30 min and then poured into ice-water. The resulting mixture was extracted with CH$_2$Cl$_2$, and the organic layer was washed with water, dried over MgSO$_4$ and concentrated in vacuo. The resulting residue was Purified by silica gel flash chromatography (30% ethyl acetate in hexane) to give 5.6 g of the title compound as a solid.

$^1$H NMR (300 MHz, CDCl$_3$): δ 8.64 (dd, J=7.1, 2.2 Hz, 1H), 8.27–8.22 (m, 1H), 7.41 (dd, J=10.1, 8.7 Hz, 1H), 2.66 (s, 3H).

Step B: 1-(3-Amino-4-fluorophenyl)-ethanone

A mixture of 1-(4-fluoro-3-nitrophenyl)-ethanone (4.94 g) and 5% Pt(S)/C (500 mg) in ethanol (50 mL) was hydrogenated at 50 psi for 3 hours. After filtration and concentration, the residue was purified by silica gel flash chromatography over silica gel (elution with 30% ethyl acetate in hexane) to give 3.3 g of the title compound as a solid.

$^1$H NMR (300 MHz, CDCl$_3$): δ 7.41 (dd, J=8.7, 2.1 Hz, 1H), 7.33–7.29 (m, 1H), 7.04 (dd, J=10.6, 8.4 Hz, 1H), 2.53 (s, 3H).

Step C: (±)-1-(3-Amino-4-fluorophenyl)-ethanol

To a solution of 1-(3-amino-4-fluorophenyl)-ethanone (3 g) in a mixture of MeOH (20 mL) and CH$_2$Cl$_2$ (20 mL) was added in portions NaBH$_4$ (1520 mg) at 0° C. After stirring for 0.5 hours, the reaction mixture was quenched with saturated NH$_4$Cl solution and most of the solvent was removed in vacuo. The residue was extracted with CH$_2$Cl$_2$, and the combined organic layer was washed with water, dried over MgSO$_4$ and concentrated in vacuo. The residue was purified by silica gel flash chromatography (33% ethyl acetate in hexane) to give 2.9 g of the title compound as an oil.

$^1$H NMR (300 MHz, CDCl$_3$): δ 6.93 (dd, J=10.8, 8.3 Hz, 1H), 6.81 (dd, J=8.6, 2.1 Hz, 1H), 6.69–6.64 (m, 1H), 4.78 (q, J=6.4 Hz, 1H), 1.44 (d, J=6.4 Hz, 3H).

MS: 156 (M+H)$^+$.

Step D: (±)-1-(4-Fluoro-3-morpholin-4-yl-phenyl)ethanol

A mixture of 1-(3-amino-4-fluoro-phenyl)ethanol (3.1 g), bromoethyl ether (5.413 g), and i-Pr$_2$NEt (6.1921 g) in toluene (15 mL) was refluxed for 4 hours. After cooling, the reaction mixture was quenched with water. The aqueous layer was extracted with dichloromethane, and the combined organic layers were dried over magnesium sulphate, filtered and concentrated in vacuo. The residue was purified by silica gel flash chromatography (33% ethyl acetate in hexane) to give 3.98 g of the title compound as an oil.

$^1$H NMR (300 MHz, CDCl$_3$): δ 7.03–6.90 (m, 3H), 4.85 (q, J=6.3 Hz, 1H), 0.8–3.85 (m, 4H), 3.11–3.08 (m, 4H), 1.45 (d, J=6.3 Hz, 3H).

MS: 226 (M+H)$^+$.

Step E: (±)-4-[5-(1-Azido-ethyl)-2-fluorophenyl] morpholine

To a solution of 1-(4-fluoro-3-morpholin-4-yl-phenyl) ethanol (3.7 g) and diphenylphosphory azide (6.765) in toluene (24 mL) at 0° C. was added a solution of DBU (3.74 g) in toluene (2 mL) and the resulting solution was stirred at 0° C. for 2 hours. The reaction mixture was warmed to room temperature and then stirred for 16 hours. The reaction was diluted with ethyl acetate and quenched with water. The organic layer was washed with water, dried over MgSO$_4$, and concentrated in vacuo. The residue was purified by silica gel flash chromatography (10% ethyl acetate in hexane) to give 3.71 g of the title compound as an oil.

$^1$H NMR (300 MHz, CDCl$_3$): δ 7.05–6.98 (m, 1H), 6.92–6.81 (m, 2H), 4.56 (q, J=6.8 Hz, 1H), 3.89–3.86 (m, 4H), 3.12–3.09 (m, 4H), 1.50 (d, J=6.8 Hz, 3H).

MS: 251 (M+H)$^+$.

Step F: (±)-1-(4-Fluoro-3-morpholin-4-yl-phenyl) ethylamine

To a solution of 4-[5-(1-azido-ethyl)-2-fluoro-phenyl]-morpholine (1 g) in THF (20 mL) at 40° C. was added LiAlH$_4$ (500 mg). The reaction mixture was warmed to room temperature and then stirred for 1 hour. The reaction was quenched with water, 10 N sodium hydroxide followed again by water. The resulting mixture was filtered through Celite and the filtrate was concentrated in vacuo. The residue was extracted with CH$_2$Cl$_2$, and the organic layer was washed with water, dried over Na$_2$SO$_4$, filtered and concentrated in vacuo to give 890 mg of the title compound as an oil.

$^1$H NMR (300 MHz, CDCl$_3$): δ 6.91–6.84 (m, 2H), 6.73–6.68 (m, 1H), 3.78 (q, J=6.5 Hz, 1H), 3.61–3.57 (m, 4H), 2.83–2.80 (m, 4H), 1.17 (d, J=6.5 Hz, 3H).

MS: 225 (M+H)$^+$.

Preparation 27

Preparation of (S)-{4-[3-(1-Amino-ethyl)-phenyl]-morpholin-2-yl}-methanol

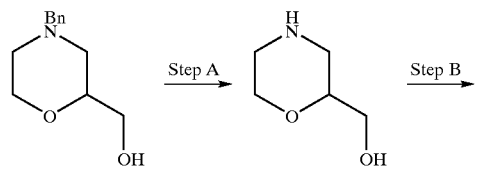

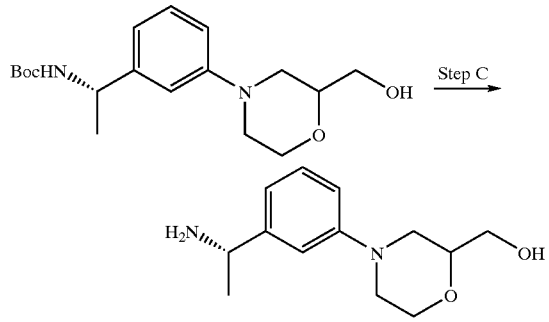

Step A. Preparation of morpholin-2-yl-methanol

The mixture of (4-benzyl-morpholin-2-yl)methanol (2 g, 9.7 mmol), palladium on C (10 wt %) (2.5 g), and methanol (48 ml) was put onto hydrogenator and shaken at 50 psi of hydrogen for 3 days. The mixture was filtered through Celite pad and washed with methanol. The filtrate was concentrated under vacuum. The sticky colorless oil (quantitative yield) was used for next step without purification.

$^1$H NMR (400 MHz, CD$_3$OD): δ 3.85 (m, 1H), 3.59 (m, 1H), 3.48 (m, 3H), 2.88 (m, 1H), 2.76 (m, 2H), 2.55 (m, 1H).

Step B. Preparation of (S)-{1-[3-(2-Hydroxymethyl-morpholin-4-yl)-phenyl]-ethyl}-carbamic acid tert-butyl ester The solution of (S)-[1-(3-bromo-phenyl)ethyl]carbamic acid tert-butyl ester (2.6 g, 8.8 mmol), morpholin-2-yl-methanol (1.1 mg, 9.7 mmol), palladium acetate (10 mol %, 197 mg), 2-(di-t-butylphosphino) biphenyl (20 mol %, 523 mg), and sodium tert-butoxide (1.1 g, 1.3eq) in toluene (28 ml) was stirred in sealed tube at 80° C. for 4 days. The reaction mixture was filtered through Celite pad and washed with 10% methanol/dichloromethane. The filtrate was concentrated under vacuum and purified by flash chromatography with 40% acetone/hexane. Yellow solid was obtained as the title compound (1.0 g, 39% yield).

$^1$H NMR (400 MHz, CDCl$_3$): δ 7.23 (m, 1H), 6.81 (m, 3H), 4.75 (s, 2H), 4.06 (m, 1H), 3.65–3.85 (m, 4H), 3.44 (t, J=10, 2H), 2.84 (m, 1H), 2.67 (t, J=10, 1H), 1.90 (t, J=6, 1H), 1.42 (m, 12H).

MS: 337 (M+H)$^+$.

Step C. Preparation of (S)-{4-[3-(1-Amino-ethyl)phenyl] morpholin-2-yl}-methanol The mixture of (S)-{1-[3-(2-hydroxymethyl-morpholin-4-yl)phenyl]-ethyl}-carbamic acid tert-butyl ester (1.0 g, 3.4 mmol) and hydrochloric acid (1.0M solution in diethyl ether) (10.2 mmol, 3eq) was stirred at room temperature overnight. Concentrated under vacuum and the title compound was obtained as pale red solid (quantitative yield) ready for use for next step without purification.

$^1$H NMR (400 MHz, CD$_3$OD): δ 7.54 (m, 2H), 7.45 (m, 1H), 7.33 (m, 1H), 4.49 (q, J=7, 1H), 4.13 (m, 1H), 3.89–4.04 (m, 2H), 3.55–3.70 (m, 4H), 3.34 (m, 1H), 3.16 (t, J=10, 1H), 1.63 (d, J=7, 3H).

MS: 237 (M+H)$^+$.

Preparation 28

Preparation of (S)-{4-[3-(1-Amino-ethyl)-phenyl]-morpholin-2-ylmethyl}-carbamic acid tert-butyl ester

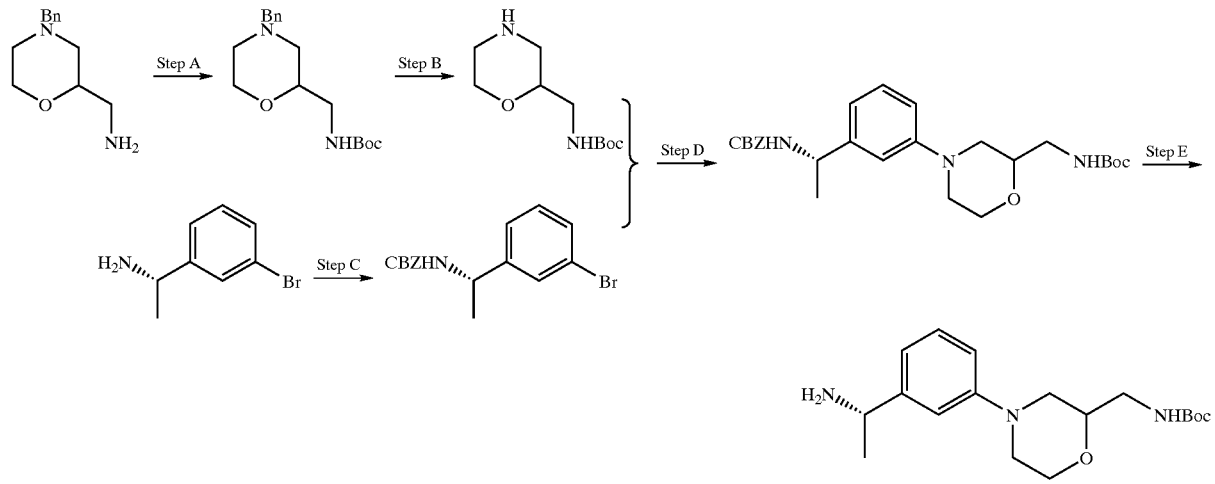

Step A. Preparation of (4-Benzyl-morpholin-2-ylmethyl) carbamic acid tert-butyl ester The solution of (4-benzyl-morpholin-2-yl)methylamine (1.4 g, 6.8 mmol), di-tert-butyl dicarbonate (1.5 g, 6.9 mmol) and triethyl amine (1.4 ml, 10.2 mmol) in dichloromethane (14 ml) was stirred at room temperature for 4.5 hr. The solution was washed with saturated sodium bicarbonate solution and organic layer was separated. The aqueous layer was extracted with dichloromethane three times. The combined organic layer was dried over magnesium sulfate and concentrated under vacuum. The pale yellow clear sticky oil was gradually converted to pale yellow solid upon exposure to the atmosphere. The crude product (2.2 g, quantitative yield) was used for next step without purification.

$^1$H NMR (400 MHz, CDCl$_3$): δ 7.30 (m, 5H), 4.86 (s, 1H), 3.80 (m, 1H), 3.55–3.64 (m, 2H), 3.48 (s, 1H), 3.28 (m, 1H), 3.04 (m, 1H), 2.60–2.81 (m, 2H), 2.13 (m, 1H), 1.88 (t, J=8, 1H), 1.42 (s, 9H).

MS: 307 (M+H)$^+$.

Step B. Preparation of Morpholin-2-ylmethyl-carbamic acid tert-butyl ester

The mixture of (4-benzyl-morpholin-2-ylmethyl) carbamic acid tert-butyl ester (1.09 g, 3.6 mmol), palladium on C (10 wt %) (300 mg), and methanol (17 ml) was put onto hydrogenator and shaken at 50 psi of hydrogen for 5 days. The mixture was filtered through Celite pad and washed with methanol. The filtrate was concentrated under vacuum. The greenish sticky oil was gradually converted to pale green solid upon exposure to the atmosphere. The crude product (quantitative yield) was used for next step without purification.

$^1$H NMR (400 MHz, CD$_3$OD): δ 3.79 (m, 1H), 3.40–3.57 (m, 2H), 3.03 (m, 2H), 2.83 (m, 1H), 2.74 (m, 2H), 2.43 (t, J=4, 1H), 1.41 (s, 9H).

Step C. Preparation of (S)-[1-(3-Bromo-phenyl)ethyl] carbamic acid benzyl ester At 0° C., the solution of (S)-3-bromo-benzylmethylamine (10 g, 50 mmol) and Hunig Base (18.3 ml, 105 mmol) in dichloromethane (100 ml) was added slowly CBZ-chloride (9.6 ml, 67.5 mmol). After addition, reaction mixture was warmed up to room temperature and stirred at room temperature for 8 hr. The solution was washed with saturated sodium bicarbonate solution and organic layer was separated. The aqueous layer was extracted with dichloromethane three times. The combined organic layer was dried over magnesium sulfate and concentrated under vacuum. The crude product was purified by flash chromatography with 20% acetone/hexanes. 14.7 g of the title product was obtained as white solid (88% yield).

$^1$H NMR (400 MHz, CDCl$_3$): δ 7.44 (s, 1H), 7.26–7.36 (m, 6H), 7.15–7.26 (m, 2H), 5.07 (q, J=12, 2H), 5.00 (s, 1H), 4.81 (s, 1H), 1.45 (d, J=7, 3H).

Step D. Preparation of (S)-(1-{3-[2-(tert-Butoxycarbonylamino-methyl)-morpholin-4-yl]-phenyl}ethyl)carbam acid benzyl ester The solution of (S)-[1-(3-bromo-phenyl)ethyl]carbamic acid benzyl ester (1.1 g, 3.23 mmol), morpholin-2-ylmethyl-carbamic acid tert-butyl ester (767 mg, 3.6 mmol), palladium acetate (20 mol %, 145 mg), 2-(di-t-butylphosphino)biphenyl (40 mol %, 385 mg), sodium tert-butoxide (408 mg, 1.3 eq), and TEA (1.2 ml, 3 eq) in toluene (6.5 ml) was stirred in sealed tube at 80° C. for 2 days. The solution was filtered through Celite Pad and washed with ethyl acetate. The filtrate was concentrated under vacuum and purified by flash chromatography with gradient of 20% ethyl acetate/hexane to 30% ethyl acetate/hexane over 20 minutes. Pale yellow solid was obtained as the product (600 mg, 40% yield).

$^1$H NMR (400 MHz, CDCl$_3$): δ 7.20–7.37 (m, 6H), 6.81 (m, 3H), 5.08 (q, J=10, 2H), 5.01 (s, 1H), 4.91 (s, 1H), 4.80 (s, 1H), 3.99 (m, 1H), 3.65–3.79 (m, 2H), 3.33–3.47 (m, 3H), 3.17 (m, 1H), 2.80 (t, J=8, 1H), 2.53 (t, J=8, 1H), 1.45 (m, 12H).

MS: 470 (M+H)$^+$.

Step E. Preparation of (S)-{4-[3-(1-Aminoethyl)phenyl]morpholin-2-ylmethyl}-carbamic acid tert-butyl ester The mixture of (S)-(1-{3-[2-(tert-butoxycarbonylaminomethyl)-morpholin-4-yl]-phenyl}-ethyl)-carbamic acid benzyl ester (600 mg, 1.3 mmol), palladium on C (10 wt %) (300 mg), and methanol (10 ml) was put onto hydrogenator and shaken at 50 psi of hydrogen for 2 days and one night. The mixture was filtered through Celite Pad and washed with methanol. The filtrate was concentrated under vacuum. The sticky oil (89% yield) was used for next step without purification.

$^1$H NMR (400 MHz, CD$_3$OD): δ 7.20 (t, J=8, 1H), 6.95 (s, 1H), 6.83 (m, 2H), 3.99 (m, 2H), 3.71 (t, J=11, 1H), 3.64

(m, 1H), 3.52 (d, J=12, 1H), 3.44 (d, J=12, 1H), 3.18 (m, 2H), 2.73 (t, J=12, 1H), 2.44 (t, J=12, 1H), 1.43 (s, 9H), 1.38 (d, J=7, 3H).

MS: 336 (M+H)$^+$.

Preparation 29

Preparation of (±)-7-(1-Aminoethyl)-3,4-dihydro-2H-quinoline-1-carboxylic acid tert-butyl ester Step A: 7-Acetyl-3,4-dihydro-2H-quinoline-1-carboxylic acid tert-butyl ester

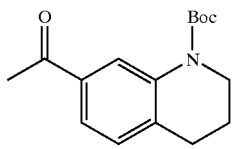

A mixture of 1-(1,2,3,4-tetrahydro-quinolin-7-yl)-ethanone (840 mg, 4.8 mmol) ((Y. Ishihara, T. Tanaka and G. Goto, *J. Chem. Soc. Perkins Trans.* 3401 (1992)) and di-t-butyl dicarbonate (1.36 g, 6.24 mmol) and DMAP (60 mg) was heated at 85° C. for 30 minutes. Additional di-t-butyl dicarbonate (680 mg, 3.12 mmol) was added and the reaction was complete after 60 min at 85° C. The mixture was evaporated and chromatographed (SiO$_2$, 10% EtOAc in hexane) yielding 1.2 g (91%) of the title compound as a white solid (m.p:125–27° C.).

$^1$H NMR 400 MHz (CDCl$_3$) δ (ppm): 8.00 (1H, br s), 7.33 (1H, d, J=7.95 Hz), 7.15 (1H, d, J=8.18 Hz), 3.74 (2H, t, J=6.11 Hz), 2.81 (2H, t, J=6.55 Hz), 2.39 (3H, s), 1.98–1.94 (2H, m), 1.55 (9H, s).

MS [M+H]$^+$ 276.

Step B: 7-(1-Hydroxyiminoethyl)-3,4-dihydro-2H-quinoline-1-carboxylic acid tert-butyl ester

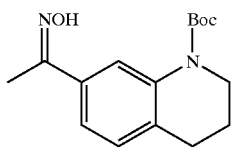

A solution of 7-acetyl-3,4-dihydro-2H-quinoline-1-carboxylic acid tert-butyl ester (1.2 g, 4.35 mmol) in EtOH was treated with NH$_2$OH.HCl (0.57 g, 8 mmol). The resulting solution was stirred at 23° C. for 3 h in presence of Amberlist A-21 (2.0 g). The mixture was filtered and the solvent was evaporated. The residue was dissolved in EtOAc, washed with aqueous NaHCO$_3$ and then brine. After drying (MgSO$_4$), the organic layer was evaporated and the crude oxime was purified by chromatography (SiO$_2$, 10–25% EtOAc in hexane) to give 1.08 g (86%) of the title compound as a white solid (m.p: 134–37° C.).

IR (Nujol) $\nu_{max}$(cm$^{-1}$): 3230, 1691.

$^1$H NMR 400 MHz (CDCl$_3$) δ (ppm): 7.98 (1H, s), 7.32 (1H, dd, J=1.53 Hz and J=8.07 Hz), 7.11 (1H, d, J=8.07 Hz), 3.74 (2H, t, J=6.05 Hz), 2.80 (2H, t, J=6.55 Hz), 2.33 (3H, s), 1.97 (2H, m), 1.56 (9H, s).

MS [M+H]$^+$ 291.

Step C: (±)-7-(1-Aminoethyl)-3,4-dihydro-2H-quinoline-1-carboxylic acid tert-butyl ester

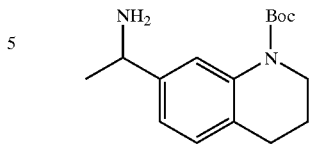

A solution of 7-(1-hydroxyiminoethyl)-3,4-dihydro-2H-quinoline-1-carboxylic acid tert-butyl ester (1.0 g, 3.44 mmol) in MeOH (50 ml) was hydrogenated for 1 h under a pressure of 44 psi, in presence of 50% RaNi/H$_2$O (2 mL). Additional catalyst was added (1 mL) and the hydrogenation proceeded for 3 hours. The catalyst was filtered off and filtrate evaporated. The crude product was chromatographed (SiO$_2$, 15% of 2.0M NH$_3$/MeOH in CH$_3$CN) to provide 0.72 g (76%) of the title compound as a white solid. m.p: 61–64° C.

IR (Nujol) $\nu_{max}$ (cm$^{-1}$): 1694.

$^1$H NMR 400 MHz (CDCl$_3$) δ (ppm): 7.66 (1H, s), 7.06 (1H, d, J=7.90 Hz), 7.02 (1H, dd, J=1.57 Hz and J=8.03 Hz), 4.11 (1H, q, J=6.57 Hz), 3.72 (2H, t, J=6.03 Hz), 2.77 (2H, t, J=6.59 Hz), 2.34 (2H, br s), 1.95 (2H, m), 1.55 (9H, s), 1.43 (3H, d, J=6.51 Hz).

MS [M+CH$_3$CN]$^+$ 318.

Preparation 30

Preparation of (±)-6-(1-Aminoethyl)-3,4-dihydro-2H-quinoline-1-carboxylic acid tert-butyl ester Step A: 6-Acetyl-3,4-dihydro-2H-quinoline-1-carboxylic acid tert-butyl ester

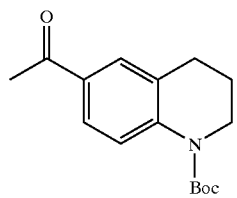

A mixture of 1-(1,2,3,4-tetrahydroquinolin-6-yl)ethanone (1.0 g, 5.71 mmol), di-t-butyl dicarbonate (1.62 g, 7.42 mmol) and DMAP (70 mg, 0.5 mmol) was heated at 85° C. for 30 minutes. An additional amount of di-t-butyl dicarbonate (1.62 g) was added and heating maintained for 1 hour. The resulting reaction mixture was chromatographed (SiO$_2$, 10% EtOAc in hexane to give 1.48 g (94%) of title compound as a yellowish solid. m.p: 80–82° C.

IR (Nujol) $\nu_{max}$(cm$^{-1}$): 1701, 1673, 1601.

$^1$H NMR 400 MHz (CDCl$_3$) δ (ppm): 7.84 (1H, d, J=7.84 Hz), 7.75 (1H, dd, J=8.57 Hz and J=2.02 Hz), 7.73 (1H, unresolved d), 3.76 (2H, t, J=6.06 Hz), 2.83 (2H, t, J=6.53 Hz), 2.58 (3H, s), 1.96 (2H, m), 1.56 (9H, s).

MS [M+H]$^+$ 276.

Step B: 6-(1-Hydroxyiminoethyl)-3,4-dihydro-2H-quinoline-1-carboxylic acid tert-butyl ester

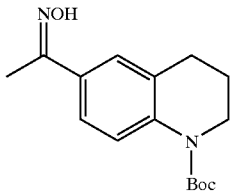

A solution of 6-acetyl-3,4-dihydro-2H-quinoline-1-carboxylic acid tert-butyl ester (1.38 g, 5 mmol) in EtOH (20 mL) was treated with NH$_2$OH.HCl (695 mg, 10 mmol). The resulting solution was stirred at 23° C. for 3 hours in the presence of Amberlist A-21 (2.0). Then the mixture was filtered and the solvent evaporated. The residue was dissolved in EtOAc, washed with aqueous NaHCO$_3$ and then brine. After drying (MgSO$_4$), the organic layer was concentrated and the crude oxime purified by chromatography (SiO$_2$, 10–25% EtOAc in hexane) to give 1.4 g (90%) of the title compound as a white solid. m.p: 127–129° C.

IR (Nujol) $v_{max}$ (cm$^{-1}$): 3309, 1669.

$^1$H NMR 400 MHz (CDCl$_3$) δ (ppm): 7.80 (1H, d, J=8.58 Hz), 7.49 (1H, unresolved d), 7.46 (1H, dd, J=8.69 Hz and J=2.10 Hz), 3.75 (2H, t, J=6.06 Hz), 2.82 (2H, t, J=6.49 Hz), 2.38 (3H, s), 1.95 (2H, m), 1.56 (9H, s).

MS [M+H]$^+$ 291.

Step C: (±)-6-(1-Aminoethyl)-3,4-dihydro-2H-quinoline-1-carboxylic acid tert-butyl ester

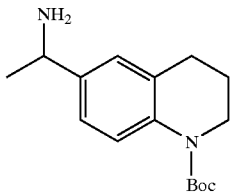

A solution of 6-(1-hydroxyimino-ethyl)-3,4-dihydro-2H-quinoline-1-carboxylic acid tert-butyl ester (1.0 g, 3.44 mmol), dissolved in MeOH (50 mL), was hydrogenated under a pressure of 40 psi in the presence of 50% RaNi/H$_2$O (3 mL) for 5 hours. The catalyst was filtered off and the solvent evaporated. The crude amine was purified by chromatography (SiO$_2$, 15% of 2.0M NH$_3$/MeOH in CH$_3$CN) to give 0.57 g (60%) of the title compound as a white solid. m.p: 73–75° C.

IR (Nujol) $v_{max}$ (cm$^{-1}$): 1695.

$^1$H NMR 400 MHz (CDCl$_3$) δ (ppm): 7.64 (1H, d, J=8.73 Hz), 7.14 (1H, dd, 8.39 Hz and J=2.17 Hz), 7.11 (1H, unresolved d), 4.11 (1H, q, J=6.57 Hz), 3.72 (2H, t, J=6.14 Hz), 2.78 (2H, t, J=6.55 Hz), 2.5 (2H, br s), 1.95 (2H, m), 1.54 (9H, s), 1.43 (3H, d, J=6.50 Hz).

MS [M+CH$_3$CN]$^+$ 318.

Preparation 31

Preparation of (S)-{1-[3-(cis-2,6-dimethylmorpholin-4-yl)phenyl]ethyl-carbamic acid tert-butyl ester

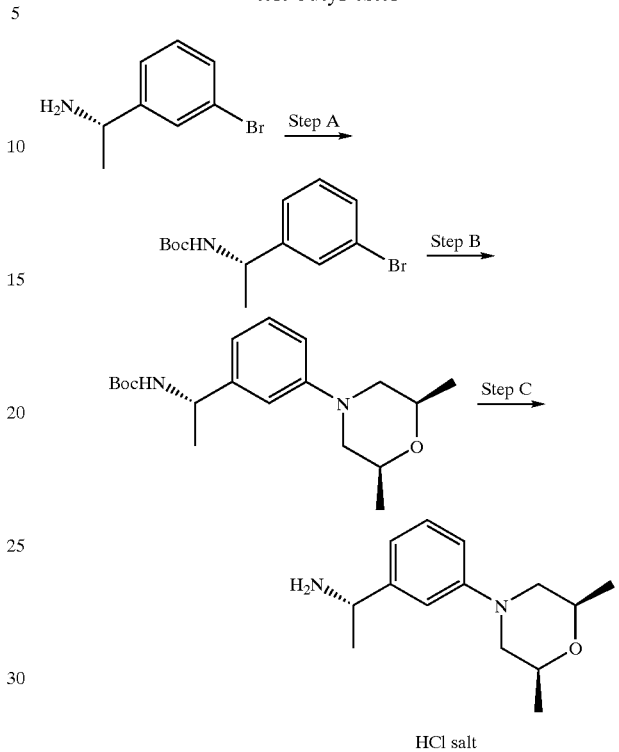

Step A: (S)-[1-(3-Bromophenyl)ethyl]-carbamic acid tert-butyl ester

A solution of (S)-3-bromo-ethylphenylamine (20 g, 0.1 mol), di-tert-butyl dicarbonate (21.8 g, 0.1 mol) and triethylamine (27.8 ml, 0.2 mol) in dichloromethane (100 ml) was stirred at room temperature overnight. The solution was washed with saturated sodium bicarbonate solution and organic layer was separated. The aqueous layer was extracted with dichloromethane three times. The combined organic layer was dried over magnesium sulfate and concentrated under vacuum. The white solid (36 g, 87%) was used for next step without purification.

$^1$H NMR (400 MHz, CDCl$_3$): δ 7.44 (m, 1H), 7.37 (m, 1H), 7.21 (m, 2H), 4.75 (s, 2H), 1.42 (s, 9H).

MS: 301 (M+H)$^+$.

Step B: (S)-{1-[3-(cis-2,6-Dimethylmorpholin-4-yl)phenyl]ethyl}-carbamic acid tert-butyl ester A solution of (S)-[1-(3-bromophenyl)ethyl]carbamic acid tert-butyl ester (5 g, 16.7 mmol), cis-2,6-dimethylmorpholine (5.75 g, 3eq.), palladium acetate (5 mol %, 187 mg), 2-(di-t-butylphosphino) biphenyl (10 mol %, 498 mg), and sodium tert-butoxide (1.68 g, 1.05eq) in toluene (33 ml) was stirred at 80° C. for 1.5 hours. The solution was filtered through Celite Pad and washed with ethyl acetate. The filtrate was concentrated under vacuum and purified by flash chromatography with gradient of 20% ethyl acetate/hexane to 30% ethyl acetate/hexane over 20 minutes. The product was obtained as a yellow solid (2.12 g, 38% yield).

$^1$H NMR (400 MHz, CDCl$_3$): δ 7.23 (t, J=8 Hz, 1H), 6.83 (s, 1H), 6.77 (m, 2H), 4.75 (s, 2H), 3.78 (m, 2H), 3.43(d, J=12 Hz, 2H), 2.40 (t, J=10 Hz, 2H), 1.41 (s, 9H), 1.25 (d, J=4 Hz, 3H).

MS: 335 (M+H)$^+$.

Step C: (S)-1-[3-(cis-2,6-Dimethylmorpholin-4-yl)phenyl]ethylamine hydrochloric acid salt A solution of {1-[3-(cis-2,6-dimethylmorpholin-4-yl)phenyl]-ethyl}carbamic acid tert-butyl ester (2.12 g, 6.35 mmol), and hydrochloric acid (1.0M solution in diethyl ether) (15.9 mmol, 2.5eq) in methanol (5 ml) was stirred at room temperature overnight. Concentrated under vacuum and 2 g of hydrochloric acid salt of (S)-1-[3-(cis-2,6-dimethylmorpholin-4-yl)phenyl]-ethylamine was obtained as yellow solid (quantitative yield).

MS: 235 (M+H)$^+$.

Preparation 32

Preparation of [(S)-1-(3-bromophenyl)ethyl]carbamic acid tert-butyl ester

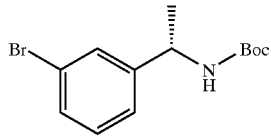

(S)-1-(3-Bromophenyl)ethylamine (8 g, 40 mmol) and Et$_3$N (8.4 mL, 60 mmol) were added in CH$_2$Cl$_2$ (200 mL), di-tert-butyl dicarbonate (8.7 g, 40 mmol) was added and the reaction mixture was stirred at room temperature for 4 hours, HCl 0.25N (100 mL) was added and the resulting solution was washed, the organic layer was dried over anhydrous magnesium sulfate, filtered and the filtrate was concentrated in vacuo to provide the title compound (12 g, quantitative yield) as white solid. The crude product was used without any further purification.

$^1$H NMR (CDCl$_3$, 400 MHz): δ 1.42 (m, 12H), 4.76 (m, 3H), 7.1–7.3 (m, 2H), 7.36 (d, J=7.1 Hz, 1H). 7.46 (s, 1H).

Preparation 33

Preparation of [(S)-1-(phenyl 3-boronic acid)ethyl]carbamic acid tert-butyl ester

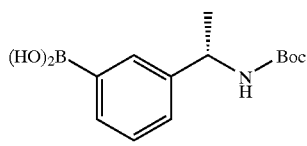

(S)-1-(3-Bromophenyl)ethyl]carbamic acid tert-butyl ester (5 g, 16.6 mmol) were added in THF (100 mL)and cooled to –78° C., methyllithium (11.8 mL, 1.4M/Et$_2$O, 16.6 mmol) was added and the reaction mixture was stirred for 5 minutes, tert-butyllithium (19.6 mL, 1.7M/pentane, 33.4 mmol) was added and the reaction mixture was stirred for 5 minutes, trimethylborate (2.82 mL, 24.9 mmol) was added rapidly and the reaction mixture was agitated for 1 hour. NH$_4$Cl (sat.) (100 mL) was added and the resulting solution was allowed to reach 23° C. The resulting mixture was extracted with ethyl acetate (3×100 mL), the organic layer was dried over anhydrous magnesium sulfate, filtered and the filtrate was concentrated in vacuo, the crude product was purified by flash chromatography (30% EtOAC/Hex.) to provide the title compound (2.7 g, 61% yield) as white solid.

$^1$H NMR (DMSO d$_6$, 400 MHz): δ 1.2–1.4 (m, 12H), 4.6–4.7 (m, 3H), 7.2–7.4 (m, 2H), 7.6–7.8 (m, 2H).

Preparation 34

Preparation of (S)-1-[3-(6-chloro-pyridin-3-yl)phenyl]ethylamine

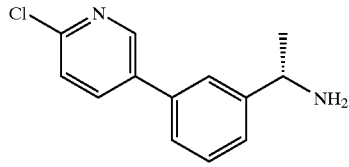

(S)-1-(Phenyl-3-boronic acid)ethyl]carbamic acid tert-butyl ester (1.29 g, 4.86 mmol) and 2-chloro-5-iodo-pyridine (1.4 g, 11.4 mmol) was diluted in ethyleneglycol dimethylether (25 mL) in a sealed tube, cesium carbonate (4.75 g, 14.6 mmol), and water (5 mL) was added and argon was bubbled for 10 minutes. Pd(PPh$_3$)$_4$ (280 mg, 0.24 mmol) is added. The reaction mixture was stirred at 100° C. for 18 hours. The reaction mixture was cooled down and ethyl acetate (100 mL) was added and the resulting solution was washed with NH$_4$Cl (sat.) (2×100 mL), the organic layer was dried over anhydrous magnesium sulfate, filtered and the filtrate was concentrated in vacuo. The crude product was diluted in CH$_2$Cl$_2$ (30 mL) and trifluoroacetic acid (10 mL). The reaction mixture was agitated for 1 hour and concentrated in vacuo. The residue was purified by solid phase extraction (SCX cartridge, silca gel benzene sulfonic acid linked) to give the title product (785 mg, 69% yield) as yellow oil.

$^1$H NMR (DMSO d$_6$, 400 MHz): δ 1.28 (d, 3H, J=6.8 Hz), 4.04 (q, 1H, J=6.8 Hz), 7.4–7.45 (m, 2H), 7.5–7.55 (m, 1H), 7.61 (d, 1H J=7.8 Hz,), 7.72 (s, 1H), 8.15 (dd, 1H J=8.3, 2.5 Hz,), 8.73 (d, 1H J=3.3 Hz,).

Preparation 35

Preparation of (S)-1-[3-(6-fluoro-pyridin-3-yl)phenyl]ethylamine

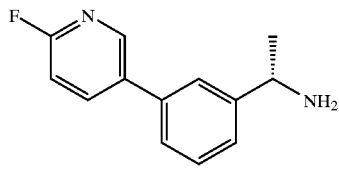

(S)-1-(3-Bromophenyl)ethyl]carbamic acid tert-butyl ester (2.3 g, 7.6 mmol) and 2-fluoropyridine-3-boronic acid (1 g, 7.09 mmol) was diluted in ethyleneglycol dimethylether (30 mL), cesium carbonate (6.3 g, 19.3 mmol), and water (5 mL) was added and argon was bubbled for 10 minutes. Pd(PPh$_3$)$_4$ (372 mg, 0.32 mmol) is added. The reaction mixture was stirred at 100° C. for 18 hours. The reaction mixture was cooled down and ethyl acetate (100 mL) was added and the resulting solution was washed with NH$_4$Cl (sat.) (2×100 mL), the organic layer was dried over anhydrous magnesium sulfate, filtered and the filtrate was concentrated in vacuo. The crude product was diluted in CH$_2$Cl$_2$ (30 mL) and trifluoroacetic acid (10 mL). The reaction mixture was agitated for 1 hour and concentrated in vacuo. The residue was purified by solid phase extraction (SCX cartridge, silca gel benzene sulfonic acid linked) to give the title product (1.18 g, 85% yield) as brown oil.

$^1$H NMR (DMSO d$_6$, 400 MHz): δ 1.26 (d, 3H, J=6.6 Hz), 4.06 (q, 1H, J=6.6 Hz), 7.28 (dd, 1H J=8.6, 3.3 Hz,), 7.4–7.45 (m, 2H), 7.5–7.55 (m, 1H), 7.71 (s, 1H), 8.27 (dd, 1H J=8.6, 2.8 Hz,), 8.54 (d, 1H J=2.5 Hz,).

Preparation 36

Preparation of (S)-1-(3-pyridin-4-yl-phenyl) ethylamine

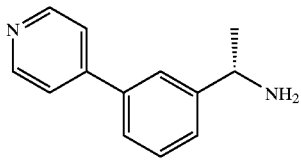

(S)-1-(3-Bromophenyl)ethyl]carbamic acid tert-butyl ester (1.5 g, 5 mmol) and pyridine-3boronic acid (921 mg, 7.5 mmol) was diluted in ethyleneglycol dimethylether (25 mL) in a sealed tube, cesium carbonate (3.25 g, 10 mmol), and water (10 mL) was added and argon was bubbled for 10 minutes. Pd(PPh$_3$)$_4$ (289 mg, 0.25 mmol) is added. The reaction mixture was stirred at 100° C. for 18 hours. The reaction mixture was cooled down and ethyl acetate (100 mL) was added and the resulting solution was washed with NH$_4$Cl (sat.) (2×100 mL), the organic layer was dried over anhydrous magnesium sulfate, filtered and the filtrate was concentrated in vacuo. The crude product was diluted in CH$_2$Cl$_2$ (30 mL) and trifluoroacetic acid (10 mL). The reaction mixture was agitated for 1 hour and concentrated in vacuo. The residue was purified by solid phase extraction (SCX cartridge, silca gel benzene sulfonic acid linked) to give the title product (424 mg, 43% yield) as yellow oil.

$^1$H NMR (DMSO d$_6$, 400 MHz): δ 1.28 (d, 3H, J=6.6 Hz), 4.05 (q, 1H, J=6.6 Hz), 7.4–7.45 (m, 2H), 7.55–7.65 (m, 2H), 7.67–7.72 (m, 2H), 7.79 (s, 1H), 8.60–8.65 (m, 1H).

Preparation 37

Preparation of (S)-1-(3-pyridin-2-yl-phenyl) ethylamine

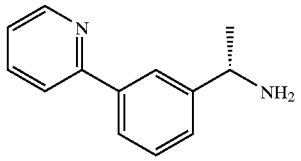

[(S)-1-(Phenyl 3-boronic acid)ethyl]carbamic acid tert-butyl ester (500 mg, 1.89 mmol) and 2-bromopyridine (2.7 mL, 2.83 mmol) was diluted in ethyleneglycol dimethylether (10 mL) in a sealed tube, Cesium carbonate (1.23 g, 3.78 mmol), and water (5 mL) was added and Argon was bubbled for 10 minutes. Pd(PPh$_3$)$_4$ (109 mg, 0.1 mmol) is added. The reaction mixture was stirred at 100° C. for 18 hours. The reaction mixture was cooled down and ethyl acetate (100 mL) was added and the resulting solution was washed with water (2×100 mL), the organic layer was dried over anhydrous magnesium sulfate, filtered and the filtrate was concentrated in vacuo. The crude product was diluted in CH$_2$Cl$_2$ (15 mL) and trifluoroacetic acid (7 mL). The reaction mixture was agitated for 1 hour and concentrated in vacuo. The residue was purified by solid phase extraction (SCX cartridge, silca gel benzene sulfonic acid linked) to give the title product (173 mg, 46% yield) as brown oil.

$^1$H NMR (DMSO d$_6$, 400 MHz): δ 1.29 (d, 3H, J=6.6 Hz), 4.08 (q, 1H, J=6.8 Hz), 7.34 (dd, 1H, J=4.8, 7.3 Hz), 7.4–7.45 (m, 2H), 7.8–7.9 (m, 2H), 7.9–8.0 (m, 1H), 8.08 (s, 1H), 8.66 (d, 1H, J=4.8 Hz).

Preparation 38

Preparation of (S)-1-(3-pyrimidin-5-yl-phenyl) ethylamine

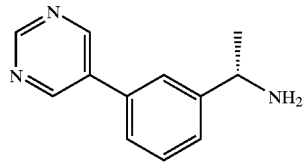

[(S)-1-(Phenyl 3-boronic acid)ethyl]carbamic acid tert-butyl ester (350 mg, 1.32 mmol) and 5-bromopyrimidine (314 mg, 1.98 mmol) was diluted in ethyleneglycol dimethylether (10 mL) in a sealed tube, cesium carbonate (2.15 g, 6.6 mmol), and water (2 mL) was added and argon was bubbled for 10 minutes. Pd(PPh$_3$)$_4$ (76 mg, 0.066 mmol) is added. The reaction mixture was stirred at 100° C. for 18 hours. The reaction mixture was cooled down and ethyl acetate (100 mL) was added and the resulting solution was washed with water (2×100 mL), the organic layer was dried over anhydrous magnesium sulfate, filtered and the filtrate was concentrated in vacuo. The crude product was diluted in CH$_2$Cl$_2$ (15 mL) and trifluoroacetic acid (7 mL). The reaction mixture was agitated for 1 hour and concentrated in vacuo. The residue was purified by solid phase extraction (SCX cartridge, silca gel benzene sulfonic acid linked) to give the title product (150 mg, 57% yield) as brown oil.

$^1$H NMR (DMSO d$_6$, 400 MHz): δ 1.28 (d, 3H, J=6.6 Hz), 4.05 (q, 1H, J=6.6 Hz), 7.4–7.5 (m, 2H), 7.62 (m, 1H), 7.79 (s, 1H), 9.14 (s, 2H), 9.18 (s, 1H).

Preparation 39

Preparation of (S)-1-(3-pyrazin-2-yl-phenyl) ethylamine

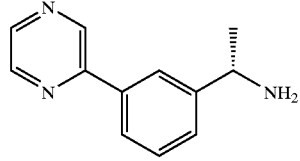

[(S)-1-(Phenyl 3-boronic acid)ethyl]carbamic acid tert-butyl ester (350 mg, 1.32 mmol) and chloropyrazine (166 mg, 1.45 mmol) was diluted in ethyleneglycol dimethylether (6 mL) in a sealed tube, cesium carbonate (1.29 g, 3.96 mmol), and water (1 mL) was added and argon was bubbled for 10 minutes. Pd(PPh$_3$)$_4$ (76 mg, 0.066 mmol) is added. The reaction mixture was stirred at 100° C. for 18 hours. The reaction mixture was cooled down and ethyl acetate (100 mL) was added and the resulting solution was washed with water (2×100 mL), the organic layer was dried over anhydrous magnesium sulfate, filtered and the filtrate was concentrated in vacuo. The crude product was diluted in CH$_2$Cl$_2$ (15 mL) and trifluoroacetic acid (7 mL). The reaction mixture was agitated for 1 hour and concentrated in vacuo. The residue was purified by solid phase extraction (SCX cartridge, silca gel benzene sulfonic acid linked) to give the title product (134 mg, 51% yield) as brown oil.

¹H NMR (acetone d₆, 400 MHz): δ 1.62 (d, 3H, J=6.8 Hz), 4.44 (q, 1H, J=6.6 Hz), 7.7–7.8 (m, 2H), 8.25 (dt, 1H, J=7.3, 1.8), 8.42 (s, 1H), 8.83 (d, 1H, J=2.5 Hz), 8.94 (dd, 1H J=2.5, 1.5 Hz) 9.47 (d, 1H, J=1.5 Hz).

Preparation 40

Preparation of (S)-1-[3-(4-methyl-pyridin-3-yl) phenyl]ethylamine

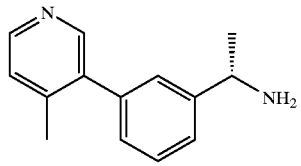

[(S)-1-(Phenyl 3-boronic acid)ethyl]carbamic acid tert-butyl ester (100 mg, 0.38 mmol) and 3-bromo-4-methylpyridine (97 mg, 0.57 mmol) was diluted in ethyleneglycol dimethylether (5 mL) in a sealed tube, 2M sodium bicarbonate (0.5 mL) was added and argon was bubbled for 10 minutes. Pd(PPh₃)₄ (22 mg, 0.02 mmol) is added. The reaction mixture was stirred at 100° C. for 18 hours. The reaction mixture was cooled down and purified on preparative HPLC (NH₄OAc).The product was diluted in CH₂Cl₂ (3 mL) and trifluoroacetic acid (1 mL). The reaction mixture was agitated for 30 minutes and concentrated in vacuo. The product is directly use in the next step as 2TFA salt. the title product (95 mg, 57% yield).

Preparation 41

Preparation of (S)-1-[3-(2-methyl-morpholin-4-yl)-phenyl]-ethylamine hydrochloric acid salt

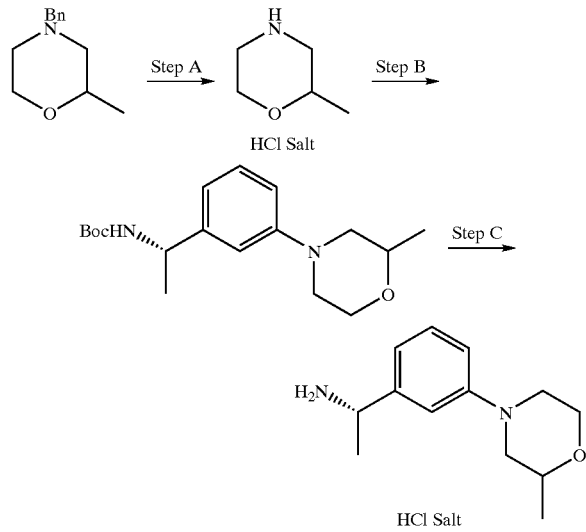

Step A: Preparation of 2-methyl-morpholine hydrochloric acid salt

The mixture of 4-benzyl-2-methyl-morpholine (8.78 g, 46 mmol), palladium on C (10%, 1 g), and hydrochloric acid (1.0M in diethyl ether) (46.4 ml, 1.01eq.) in methanol (100 ml) was put on hydrogenator at 50 psi for 4 days. Filtered through Celite pad and washed with methanol and concentrated under vacuum. The pale green solid was used for next step without further purification (6.24 g, 99% yield).

¹H NMR (400 MHz, CD₃OD): δ 4.00 (m, 1H), 3.77 (m, 2H), 3.28 (t, J=2 Hz, 2H), 3.19(m, 1H), 3.77 (t, J=1 Hz, 1H), 1.18 (d, J=6 Hz, 3H).

Step B: Preparation of (S)-{1-[3-(2-methyl-morpholin-4-yl) phenyl]-ethyl}carbamic acid tert-butyl ester The solution of (S)-[1-(3-bromo-phenyl)-ethyl]-carbamic acid tert-butyl ester (4.36 g, 14.5 mmol), 2-Methyl-morpholine hydrochloric acid salt (4 g. 2eq.), palladium acetate (20 mol %, 652 mg), 2-(di-t-butylphosphino) biphenyl (40 mol %, 1.73 g), triethylamine (4.45 ml, 2.2eq.), and sodium tert-butoxide (1.54 g, 1.1eq) in toluene (26 ml) was stirred at 80° C. for 2 days. The solution was filtered through Celite Pad and washed with ethyl acetate. The filtrate was washed with saturated sodium bicarbonate solution and the organic layer was separated. The aqueous layer was extracted with ethyl acetate three times. The combined organic layer was dried over magnesium sulfate and concentrated under vacuum. The crude product was purified by flash chromatography with 25% ethyl acetate/hexane. Yellow sticky oil was obtained as the product (2.7 g, 58% yield).

¹H NMR (400 MHz, CDCl₃): δ 7.22 (t, J=6 Hz, 1H), 6.84 (s, 1H), 6.78 (m, 2H), 4.75 (s, 2H), 3.9 8 (m, 1H), 3.79–3.75 (m, 2H), 3.42 (dd, J=9 Hz, 23 Hz, 2H), 2.81 (m. 1H), 2.47 (t, 1H), 1.41 (s, 9H), 1.25 (d, J=4 Hz, 3H).

MS: 321 (M+H)⁺.

Step C: Preparation of (S)-1-[3-(2-methyl-morpholin-4-yl)-phenyl]-ethylamine Hydrochloric acid Salt The solution of (S)-{1-[3-(2-methyl-morpholin-4-yl)-phenyl]-ethyl}-carbamic acid tert-butyl ester (2.62 g, 8.19 mmol), and hydrochloric acid (1.0M solution in diethyl ether) (12.3 ml, 3eq) in methanol (25 ml) was stirred at room temperature overnight. Concentrated under vacuum and 2.43 g of hydrochloric acid salt of (S)-1-[3-(2-methyl-morpholin-4-yl)-phenyl]-ethylamine was obtained as yellow solid (quantitative yield).

¹H NMR (400 MHz, CD₃OD): δ 7.89 (s, 1H), 7.75 (m, 1H), 7.73 (t, J=1 Hz, 1H), 7.68 (m, 1H), 4.57 (q, J=7 Hz, 1H), 4.15 (m, 3H), 3.64 (m, 3H), 3.36(m, 1H), 1.66 (d, J=7 Hz, 3H), 1.27 (d, J=6 Hz, 3H).

MS: 221 (M+H)⁺.

Preparation 42

Preparation of (S)-1-[3-(4-methylpiperazin-1-yl) phenyl]ethylamine

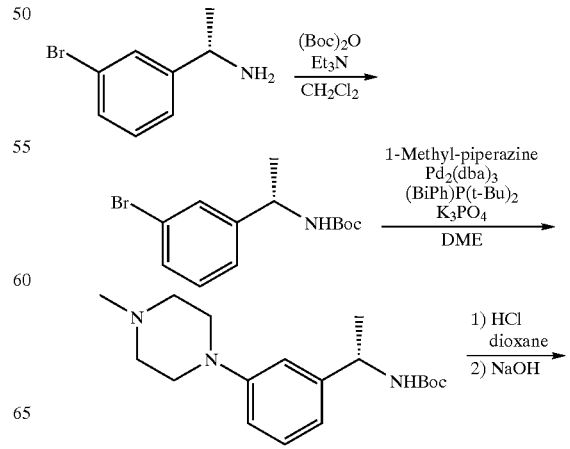

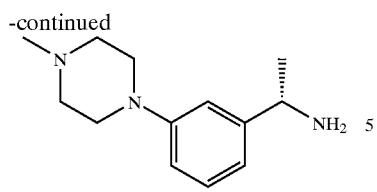

Step A: (S)-[1-(3-Bromophenyl)ethyl]carbamic acid tert-butyl ester

Step A: To a mixture of (S)-1-(3-bromophenyl)ethylamine (40.0 g, 200 mmol) and triethylamine (40.5 g, 400 mmol) in dichloromethane (400 mL) was added a solution of di-t-butyl-di-carbonate (52.4 g, 240 mmol) in dichloromethane (100 mL). The solution was stirred at room temperature for 2 hours. The reaction was quenched with water (100 ml). The organic layer was washed with brine (2×250 ml), dried over magnesium sulfate and concentrated under vacuum to provide (S)-[1-(3-Bromophenyl)ethyl]carbamic acid tert-butyl ester as white solid in quantitative yield (61 g). The crude product was used without further purification.

$^1$H NMR (300 MHz, CDCl$_3$): δ 1.41 (m, 12H), 4.75 (m, 2H), 7.15–7.22 (m, 2H), 7.34–7.38 (m, 1H), 7.42 (s, 1H).

Step B: (S)-{1-[3-(4-Methylpiperazin-1-yl)phenyl] ethyl}carbamic acid tert-butyl ester A mixture of (S)-[1-(3-bromophenyl)ethyl]carbamic acid tert-butyl ester (5.0 g, 16.7 mmol), 1-methylpiperazine (6.7 g, 67 mmol), Pd$_2$(dba)$_3$ (1.55 g, 10 mol %), di-t-butyl-biphenylphosphine (0.51 g, 10 mol %), potassium phosphate (7.2 g, 34 mmol) in ethylene glycol dimethyl ether (40 ml) was refluxed for 4 hours. After cooling to room temperature, the reaction mixture was diluted with dichloromethane (100 mL) and the precipitate was filtered off. The filtrate was concentrated under vacuum. The crude product was purified by flash chromatography over silica with ethyl acetate/hexanes (1:1) to provide (S)-{1-[3-(4-methylpiperazin-1-yl) phenyl]ethyl}carbamic acid tert-butyl ester as an oil (3.4 g, 64% yield).

MS (M+H)$^+$ 320.

Step C: (S)-1-[3-(4-methylpiperazin-1-yl)phenyl] ethylamine

A solution of (S)-{1-[3-(4-methylpiperazin-1-yl)phenyl] ethyl}carbamic acid tert-butyl ester (3.4 g, 10.7 mmol) and hydrochloric acid (4N, 11 ml) in dioxane (40 ml) was stirred at 40° C. for 5 hours. The reaction mixture was concentrated under vacuum, dissolved into dichloromethane (100 mL), and based with 5N NaOH. The organic layer was washed with brine (2×100 ml), dried over sodium sulfate and concentrated under vacuum to afford the title compound as an oil (1.90 g, 81% yield) which was used for next step without further purification.

$^1$H NMR (300 MHz, CDCl$_3$): δ 1.36 (d, 3H), 2.05 (br, s, 2H), 2.35 (s, 3H), 2.55 (t, 4H), 3.21 (t, 4H), 4.05 (q, 1H), 6.76–6.82 (m, 2H), 6.93 (s, 1H), 7.17–7.2 (m, 1H).

MS (M+H)$^+$ 220.

EXAMPLES

Example 1

Preparation of (S)-3-(4-Fluoro-phenyl)-N-(1-naphthalen-2-yl-ethyl)acrylamide

Example of the general method described below used for the preparation of Examples 2–21:

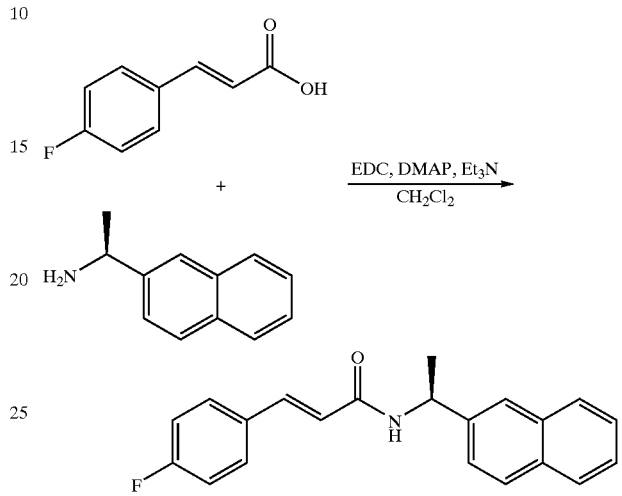

To a solution of 4-fluorocinnamic acid (0.2 g, 1.2 mmol) in CH$_2$Cl$_2$ (5 mL) at room temperature was added (S)-1-(2-naphthyl)ethylamine (0.21 g, 1.2 mmol), EDC hydrochloride (0.46 g, 2.4 mmol), DMAP (0.15 g, 1.2 mmol), and triethylamine (0.67 mL, 4.8 mmol), and the resulting solution was stirred at room temperature for 12 hours. Water was added, and the mixture was extracted with CH$_2$Cl$_2$ (three times). The combined organic layers were washed with brine, dried over anhydrous sodium sulfate, and concentrated in vacuo. The residue was purified by silica gel chromatography eluting with 6% methanol/94% CH$_2$Cl$_2$ to afford the title compound as a white solid (270 mg).

$^1$H NMR (CDCl$_3$, 400 mHz) δ: 1.65 (3H, d, J=6.9 Hz), 5.45 (1H, m), 5.91 (1H, d, J=7.5 Hz), 6.33 (1H, d, J=15.6 Hz), 7.04 (2H, t, J=8.6 Hz), 7.48 (5H, m), 7.61 (1H, d, J=15.6 Hz), 7.83 (4H, m).

MS (ESI+): 320.25 [M+H]$^+$.

Examples 2–22

Examples 2–22 were prepared as depicted in the following general reaction scheme and according to the following general procedure and analogous to the preparation of Example 1 as described above:

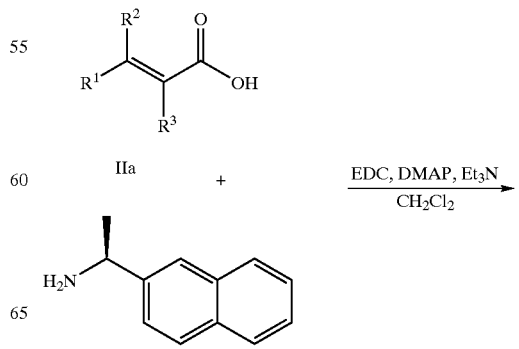

-continued

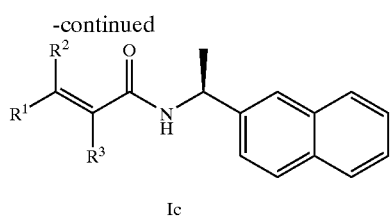

Ic

General Procedure

To a solution of an appropriately substituted cinnamic acid derivative, IIa (1.2 mmol) in CH$_2$Cl$_2$ (5 mL) at room temperature was added (S)-1-(2-naphthyl)ethylamine (0.21 g, 1.2 mmol), EDC hydrochloride (0.46 g, 2.4 mmol), DMAP (0.15 g, 1.2 mmol), and triethylamine (0.67 mL, 4.8 mmol), and the resulting solution was stirred at room temperature for 12 hours. Water was added, and the mixture was extracted with CH$_2$Cl$_2$ (three times). The combined organic layers were washed with brine, dried over anhydrous sodium sulfate, filtered and the filtrate was concentrated in vacuo. The residue was purified by silica gel chromatography, typically eluting with 6% methanol/94% CH$_2$Cl$_2$, to afford the compound of general Formula Ic. Examples 2–22 were prepared by this general method and analogous to the preparation of Example 1 as described above.

| Example No. | Structure | Chemical Name | HPLC rt (min), method | Mass (M + H)$^+$ m/z |
|---|---|---|---|---|
| 2 | 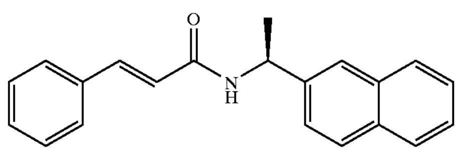 | (S)-N-(1-Naphthalen-2-yl-ethyl)-3-phenyl-acrylamide | | 301 |
| 3 | 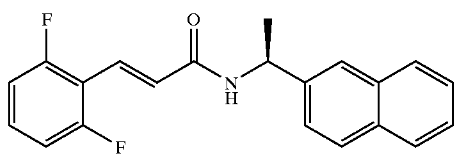 | (S)-3-(2,6-Difluoro-phenyl)-N-(1-naphthalen-2-yl-ethyl)-acrylamide | 1.69 (b) | 338 |
| 4 | 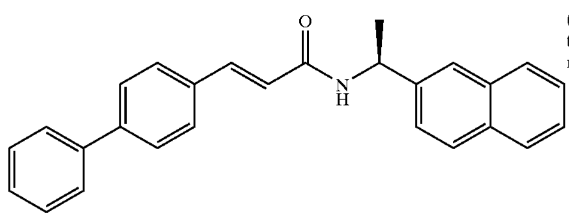 | (S)-3-Biphenyl-4-yl-N-(1-naphthalen-2-yl-ethyl)-acrylamide | 1.88 (b) | 378 |
| 5 | 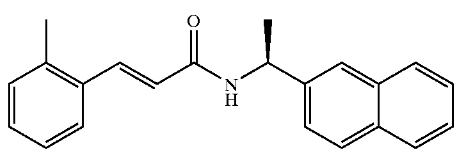 | (S)-N-(1-Naphthalen-2-yl-ethyl)-3-o-tolyl-acrylamide | 1.71 (b) | 316 |
| 6 | 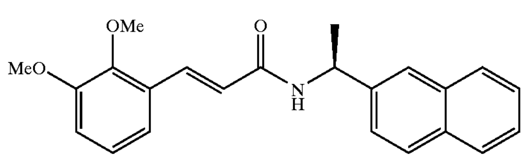 | (S)-3-(2,3-Dimethoxy-phenyl)-N-(1-naphthalen-2-ylethyl)-acrylamide | 1.55 (b) | 362 |
| 7 | 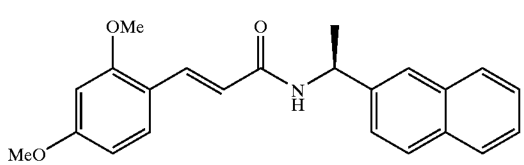 | (S)-3-(2,4-Dimethoxy-phenyl)-N-(1-naphthalen-2-yl-ethyl)-acrylamide | 1.69 (b) | 362 |

-continued

| Example No. | Structure | Chemical Name | HPLC rt (min), method | Mass (M + H)+ m/z |
| --- | --- | --- | --- | --- |
| 8 | 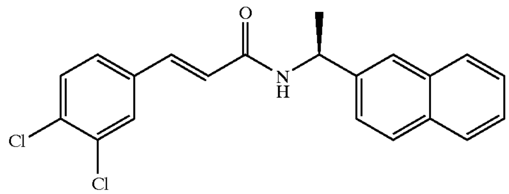 | (S)-3-(3,4-Dichloro-phenyl)-N-(1-naphthalen-2-yl-ethyl)-acrylamide | 1.87 (b) | 370 |
| 9 | 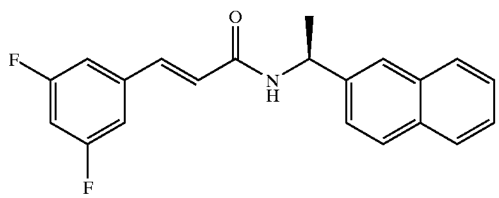 | (S)-3-(3,5-Difluoro-phenyl)-N-(1-naphthalen-2-yl-ethyl)-acrylamide | 1.69 (b) | 338 |
| 10 | 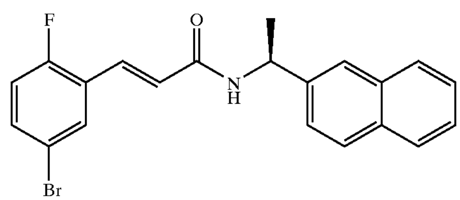 | (S)-3-(5-Bromo-2-fluoro-phenyl)-N-(1-naphthalen-2-yl-ethyl)-acrylamide | 1.77 (b) | 398 |
| 11 | 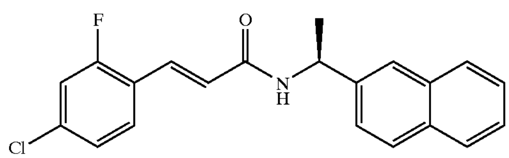 | (S)-3-(4-Chloro-2-fluoro-phenyl)-N-(1-naphthalen-2-yl-ethyl)-acrylamide | 1.77 (b) | 354 |
| 12 | 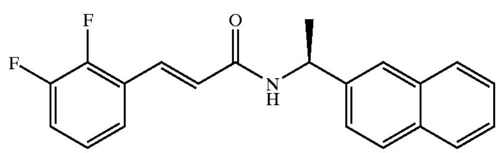 | (S)-3-(2,3-Difluoro-phenyl)-N-(1-naphthalen-2-yl-ethyl)-acrylamide | 1.67 (b) | 338 |
| 13 | 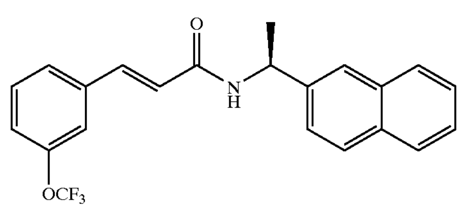 | (S)-N-(1-Naphthalen-2-yl-ethyl)-3-(3-trifluoromethoxy-phenyl)-acrylamide | 1.79 (b) | 386 |
| 14 | 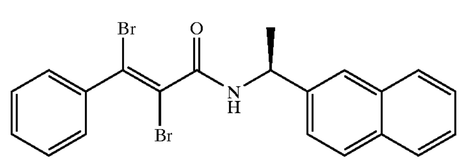 | (S)-2,3-Dibromo-N-(1-naphthalen-2-yl-ethyl)-3-phenyl-acrylamide | 1.62 (b) | 460 |
| 15 | 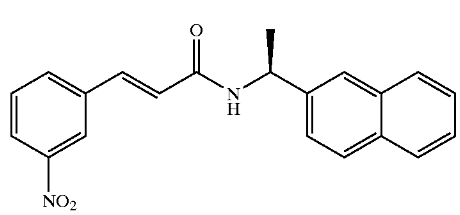 | (S)-N-(1-Naphthalen-2-yl-ethyl)-3-(3-nitro-phenyl)-acrylamide | 1.57 (b) | 346 |

-continued

| Example No. | Structure | Chemical Name | HPLC rt (min), method | Mass (M + H)+ m/z |
|---|---|---|---|---|
| 16 | 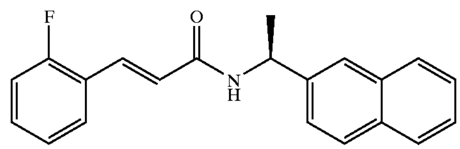 | (S)-3-(2-Fluoro-phenyl)-N-(1-naphthalen-2-yl-ethyl)-acrylamide | 1.61 (b) | 320 |
| 17 | 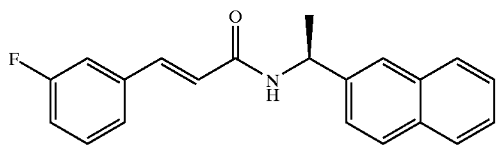 | (S)-3-(3-Fluoro-phenyl)-N-(1-naphthalen-2-yl-ethyl)-acrylamide | 1.62 (b) | 320 |
| 18 | 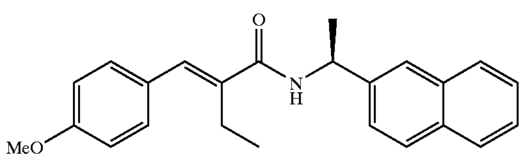 | (S)-2-(4-Methoxy-benzylidene)-N-(1-naphthalen-2-ylethyl)-butyramide | 1.86 (m) | 360 |
| 19 | 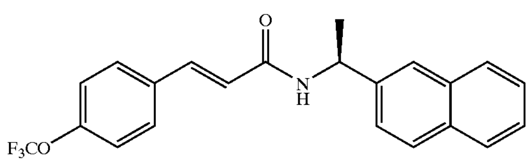 | (S)-N-(1-Naphthalen-2-yl-ethyl)-3-(4-trifluoromethoxy-phenyl)-acrylamide | 1.93 (m) | 386 |
| 20 | 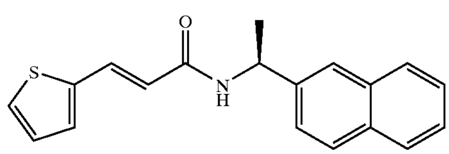 | (S)-N-(1-Naphthalen-2-yl-ethyl)-3-thiophen-2-yl-acrylamide | 1.48 (b) | 308 |
| 21 | 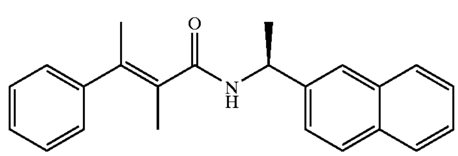 | (S)-2-Methyl-3-phenyl-but-2-enoic acid(1-naph-thalen-2-yl-ethyl)-amide | 1.81 (b) | 330 |
| 22 | 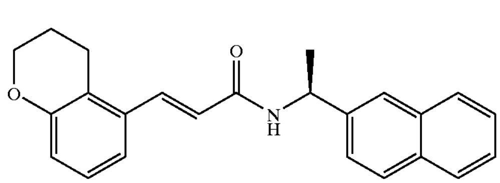 | (S)-3-Chroman-5-yl-N-(1-naphthalen-2-yl-ethyl)-acrylamide | 1.84 (m) | 357 |

Example 23

Preparation of N-(1-Benzo 11,3dioxol-5-yl-ethyl)-3-(3-methoxy-phenyl)-acrylamide (Enantiomer of Undetermined Chirality)

Example of the general method described below used for the preparation of Examples 24–54.

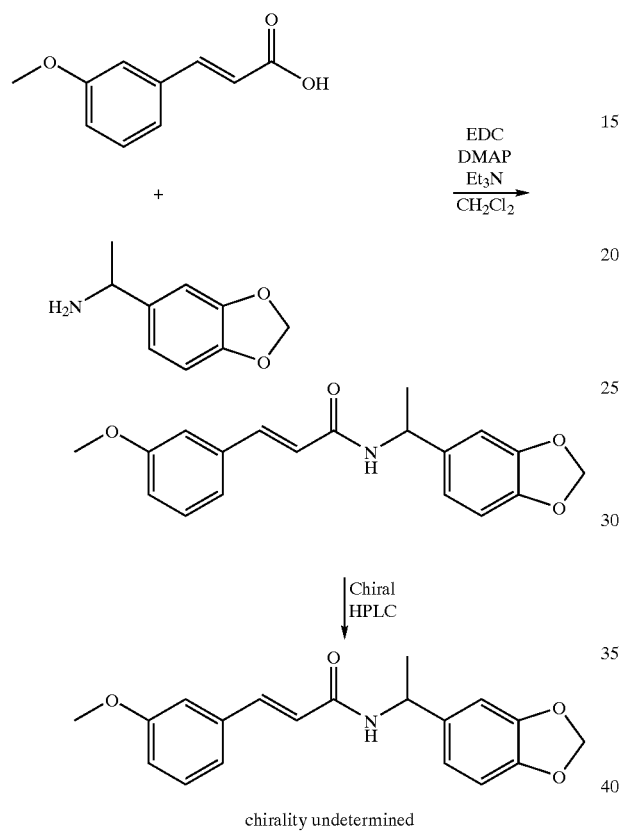

Step A: (±)-N-(1-Benzo[1,3]dioxol-5-yl-ethyl)-3-(3-methoxy-phenyl)acrylamide

A mixture of 3-methoxycinnamic acid (2 mmole), (±)-1-benzo[1,3]dioxol-5-yl-ethylamine, Preparation 2 (396 mg, 2.4 mmole), EDC hydrochloride (768 mg, 4 mmole), DMAP (244 mg, 2 mmole), and triethylamine (404 mg, 4 mmole) in $CH_2Cl_2$ (5 mL) was stirred at room temperature for 16 hours. Water was added, and the mixture was extracted with $CH_2Cl_2$ (three times). The combined organic layers were washed with brine, dried over anhydrous sodium sulfate, filtered and the filtrate was concentrated in vacuo. The crude product was subjected to purification by flash column chromatography on silica gel eluted with EtOAc/hexane (2:1) to provide the racemic titled compound (510 mg, 78%).

MS (M+H)+ 326.27.

Step B: Separation of N-(1-benzo[1,3]dioxol-5-yl-ethyl)-3-(3-methoxy-phenyl) acrylamide (Enantiomer of Undetermined Chirality)

(±)-N-(1-Benzo[1,3]dioxol-5-yl-ethyl)-3-(3-methoxy-phenyl)-acrylamide, prepared as described above in Step A, was purified by HPLC using a chiral OD column eluted with ethanol/hexane (75%) to provide the title compound (39 mg).

$^1$H NMR (CDCl$_3$): δ 7.59 (d, J=15.6 Hz, 1H), 7.30–7.24 (m, 1H), 7.08 (d, J=7.7 Hz, 1H), 7.00 (s, 1H), 6.91–6.76 (m, 4H), 6.35 (d, J=15.5 Hz, 1H), 5.94 (s, 2H), 5.78 (d, J=7.5 Hz, 1H), 5.26–5.16 (m, 1H), 3.81 (s, 3H), 1.52 (d, J=6.9 Hz, 3H); Retention time: 15.14 (minutes).

MS: 326.27 (M+H)+.

$[\alpha]^{22}_D$=+1.29 (CH$_2$Cl$_2$, 3.87 mg/mL).

Examples 24–54

Examples 24–54 prepared as depicted in the following general reaction scheme and according to the following general procedure and analogous to the preparation of Example 23 as described above:

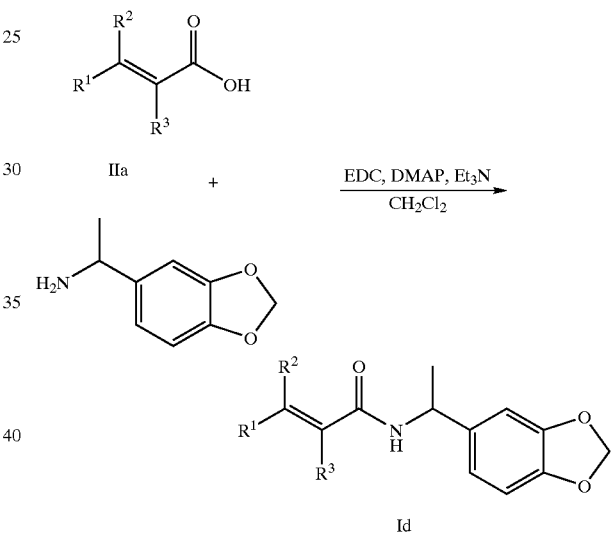

General Procedure

A mixture of an appropriate cinnamic acid derivative of Formula IIa (2 mmole), (±)-1-benzo[1,3]dioxol-5-yl-ethylamine, Preparation 2 (396 mg, 2.4 mmole), EDC hydrochloride (768 mg, 4 mmole), DMAP (244 mg, 2 mmole), and triethylamine (404 mg, 4 mmole) in $CH_2Cl_2$ (5 mL) was stirred at room temperature for 16 hours. Water was added, and the mixture was extracted with $CH_2Cl_2$ (three times). The combined organic layers were washed with brine, dried over anhydrous sodium sulfate, filtered and the filtrate was concentrated in vacuo. The crude product was subjected to purification by flash column chromatography on silica gel, typically eluting with EtOAc/hexane (2:1) to provide the compound of general Formula Id. Examples 24–54 were prepared by this general method with the following exception. For Examples 53–54, the racemic product was then subjected to chiral HPLC using a chiral OD column eluted with ethanol/hexane (75%) to provide the product as a single enantiomer of undetermined chirality.

| Example No. | Structure | Chemical Name | HPLC rt (min), method | Mass (M + H)+ m/z |
|---|---|---|---|---|
| 24 | 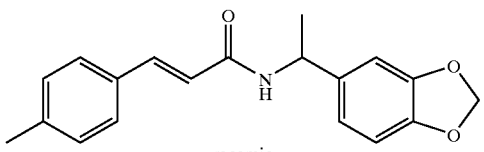 racemic | (±)-3-Benzo[1,3]dioxol-5-yl-N-(1-p-to-lyl-ethyl)-acrylamide | 1.54 (b) | 310 |
| 25 | 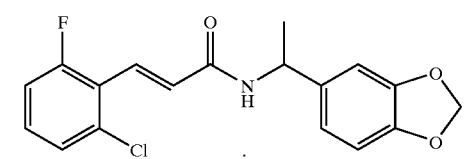 racemic | (±)-N-(1-Benzo[1,3]-diox-ol-5-yl-ethyl)-3-(2,6-di-fluoro-phenyl)-acrylamide | 1.38 (b) | 332 |
| 26 | 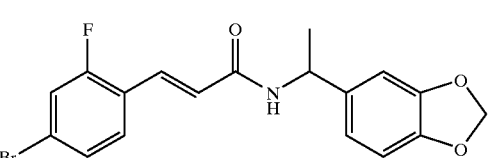 racemic | (±)-N-(1-Benzo[1,3]-diox-ol-5-yl-ethyl)-3-(4-bro-mo-2-fluoro-phenyl)-acrylamide | 1.55 (b) | 393 |
| 27 | 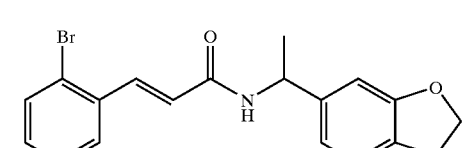 racemic | (±)-N-(1-Benzo[1,3]-diox-ol-5-yl-ethyl)-3-(2-bro-mo-phenyl)-acrylamide | 1.44 (b) | 375 |
| 28 | 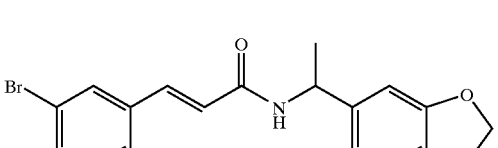 racemic | (±)-N-(1-Benzo[1,3]-diox-ol-5-yl-ethyl)-3-(3-bro-mo-phenyl)-acrylamide | 1.49 (b) | 375 |
| 29 | 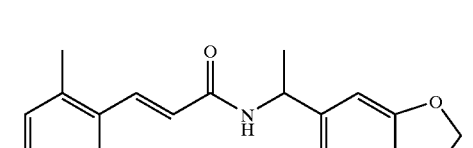 racemic | (±)-N-(1-Benzo[1,3]-diox-ol-5-yl-ethyl)-3-o-to-lyl-acrylamide | 1.40 (b) | 310 |
| 30 | 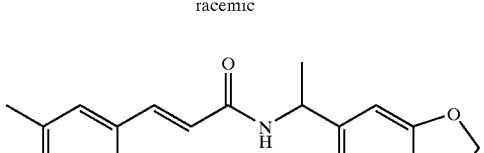 racemic | (±)-N-(1-Benzo[1,3]-diox-ol-5-yl-ethyl)-3-m-to-lyl-acrylamide | | 310 |
| 31 | 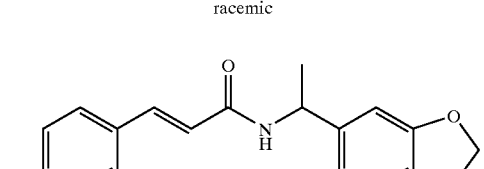 racemic | (±)-N-(1-Benzo[1,3]-diox-ol-5-yl-ethyl)-3-p-to-lyl-acrylamide | | 310 |

-continued

| Example No. | Structure | Chemical Name | HPLC rt (min), method | Mass (M + H)+ m/z |
|---|---|---|---|---|
| 32 | racemic | (±)-N-(1-Benzo[1,3]-diox-ol-5-yl-ethyl)-3-(2-chlor-o-6-fluoro-phenyl)-acrylamide | | 389 |
| 33 | racemic | (±)-3-Benzo[1,3]-dioxol-5-yl-N-(1-ben-zo[1,3]-diox-ol-5-yl-ethyl)-acrylamide | | 340 |
| 34 | racemic | (±)-N-(1-Benzo[1,3]-diox-ol-5-yl-ethyl)-3-(3,4-di-methoxy-phenyl)-acrylamide | | 356 |
| 35 | racemic | (±)-N-(1-Benzo[1,3]-diox-ol-5-yl-ethyl)-3-(2,3-di-methoxy-phenyl)-acrylamide | | 356 |
| 36 | racemic | (±)-N-(1-Benzo[1,3]-diox-ol-5-yl-ethyl)-3-(3,5-di-methoxy-phenyl)-acrylamide | | 397 |
| 37 | racemic | (±)-N-(1-Benzo[1,3]-diox-ol-5-yl-ethyl)-3-(2,4-di-chloro-phenyl-acrylamide | | 364 |
| 38 | racemic | (±)-N-(1-Benzo[1,3]-diox-ol-5-yl-ethyl)-3-(2,5-di-fluoro-phenyl)-acrylamide | | 332 |
| 39 | racemic | (±)-N-(1-Benzo[1,3]-diox-ol-5-yl-ethyl)-3-(3,5-di-fluoro-phenyl)-acrylamide | | 332 |

-continued

| Example No. | Structure | Chemical Name | HPLC rt (min), method | Mass (M + H)+ m/z |
|---|---|---|---|---|
| 40 | 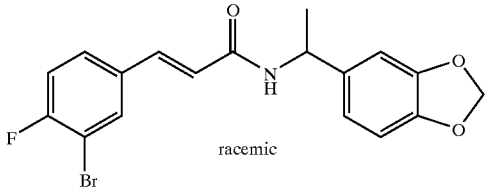 racemic | (±)-N-(1-Benzo[1,3]-diox-ol-5-yl-ethyl)-3-(3-bromo-4-fluoro-phenyl)-acrylamide | | 392 |
| 41 | 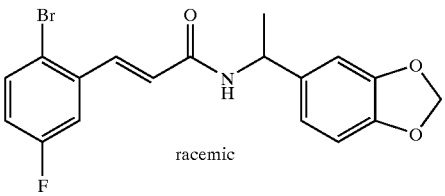 racemic | (±)-N-(1-Benzo[1,3]-diox-ol-5-yl-ethyl)-3-(5-bromo-2-fluoro-phenyl)-acrylamide | | 392 |
| 42 | 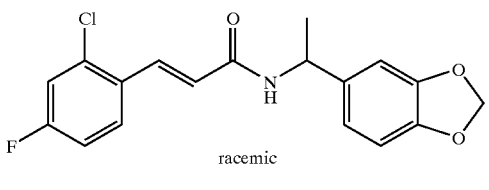 racemic | (±)-N-(1-Benzo[1,3]-diox-ol-5-yl-ethyl)-3-(2-chloro-4-fluoro-phenyl)-acrylamide | | 348 |
| 43 | 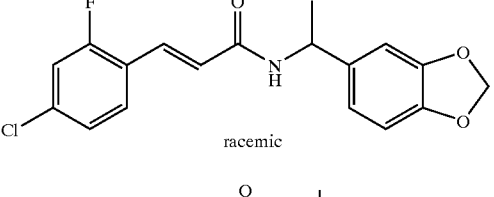 racemic | (±)-N-(1-Benzo[1,3]-diox-ol-5-yl-ethyl)-3-(4-chloro-2-fluoro-phenyl)-acrylamide | | 348 |
| 44 | 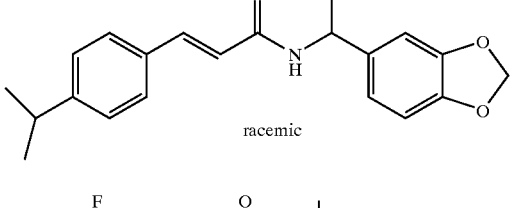 racemic | (±)-N-(1-Benzo[1,3]-diox-ol-5-yl-ethyl)-3-(4-iso-propyl-phenyl)-acrylamide | | 338 |
| 45 | 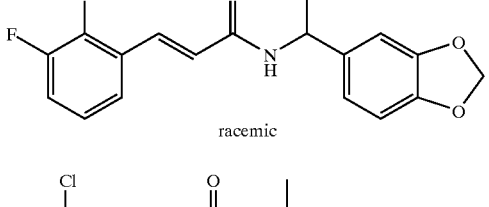 racemic | (±)-N-(1-Benzo[1,3]-diox-ol-5-yl-ethyl)-3-(2,3-di-fluoro-phenyl)-acrylamide | | 332 |
| 46 | 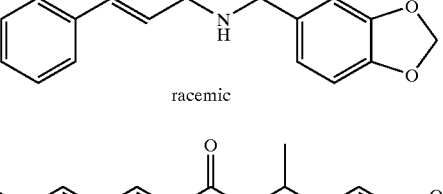 racemic | (±)-N-(1-Benzo[1,3]-diox-ol-5-yl-ethyl)-3-(2-chloro-phenyl)-acrylamide | | 330 |
| 47 | 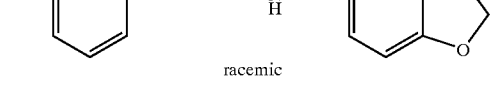 racemic | (±)-N-(1-Benzo[1,3]-diox-ol-5-yl-ethyl)-3-(3-chloro-phenyl)-acrylamide | | 330 |

-continued

| Example No. | Structure | Chemical Name | HPLC rt (min), method | Mass (M + H)+ m/z |
|---|---|---|---|---|
| 48 | 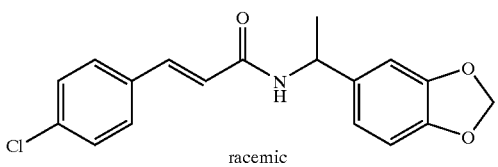 racemic | (±)-N-(1-Benzo[1,3]-diox-ol-5-yl-ethyl)-3-(4-chloro-phenyl)-acrylamide | | 330 |
| 49 | 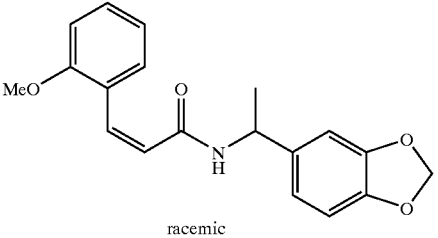 racemic | (±)-N-(1-Benzo[1,3]-diox-ol-5-yl-ethyl)-3-(2-methoxy-phenyl)-acrylamide | | 326 |
| 50 | 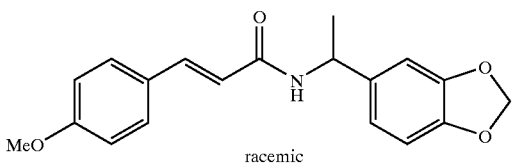 racemic | (±)-N-(1-Benzo[1,3]-diox-ol-5-yl-ethyl)-3-(4-methoxy-phenyl)-acrylamide | | 326 |
| 51 | 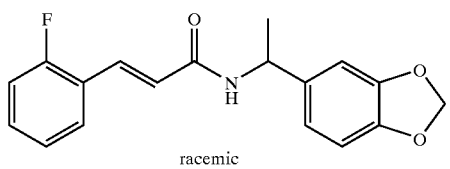 racemic | (±)-N-(1-Benzo[1,3]-diox-ol-5-yl-ethyl)-3-(2-fluoro-phenyl)-acrylamide | | 314 |
| 52 | 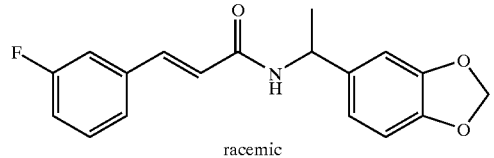 racemic | (±)-N-(1-Benzo[1,3]-diox-ol-5-yl-ethyl)-3-(3-fluoro-phenyl)-acrylamide | | 314 |
| 53 | 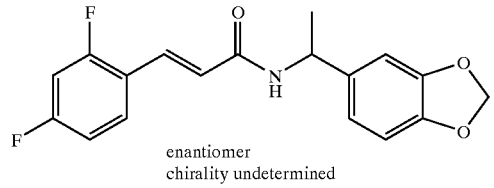 enantiomer chirality undetermined | (N-(1-Benzo[1,3]dioxol-5-yl-ethyl)-3-(2,4-di-fluoro-phenyl)-acrylamide | 1.49 (b) | 332 |
| 54 | 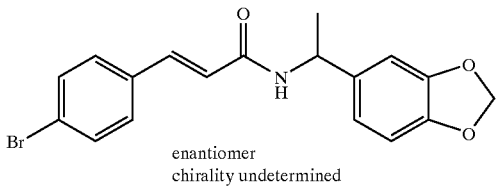 enantiomer chirality undetermined | (N-(1-Benzo[1,3]dioxol-5-yl-ethyl)-3-(4-bromo-phennyl)-acrylamide | 1.45 (b) | 376 |

Example 55

Preparation of N-[1-(2,3-Dihydrobenzofuran-5-yl)ethyl]-3-(3-methoxyphenyl)-acrylamide (Enantiomer of Undetermined Chirality)

Example of the general method described below used for the preparation of Examples 56–81:

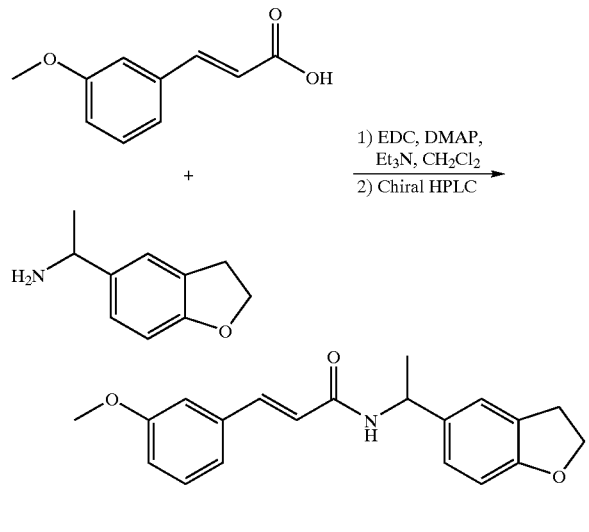

A mixture of 3-(3-methoxyphenyl)acrylic acid (178 mg, 1.0 mmole), 1-(2,3-dihydrobenzofuran-5-yl)ethylamine, Preparation 4 (163 mg, 1.0 mmole), EDC hydrochloride (384 mg, 2.0 mmole), DMAP (122 mg, 1.0 mmole), and triethylamine (0.6 mL, 4.0 mmole) in $CH_2Cl_2$ (5 mL) was stirred at room temperature for 16 hours. The reaction mixture was then purified by flash column chromatography on silica gel using Hexane/EtOAc (2:1) to provide the desired racemic product (279 mg, 86%). The racemic product was resolved by HPLC using chiral OD column to provide the product as an enantiomer of undetermined chirality (110 mg, 34%). Retention time: 33.5 minutes (method n).

$^1$H NMR (CDCl$_3$): δ 1.64 (d, J=6.6 mHz, 3H), 3.21 (t, 2H), 3.8 (s, 3H), 4.58 (t, 2H), 5.29 (m, 1H), 5.83 (bd, 1H), 6.38 (d, J=15.57 mHz, 1H), 6.75 (d, J=8.19 mHz, 1H), 6.90 (dd, J=6.99, 1.11 mHz, 1H), 6.99 (bs, 1H), 7.05 (t, 2H), 7.23 (m, 2H), 7.609 (d, J=15.57 mHz, 1H).

MS: 324.20 (M+H)$^+$.

Examples 56–81

Examples 56–81 were prepared as depicted in the following general reaction scheme and according to the following general procedure and analogous to the preparation of Example 55 as described above:

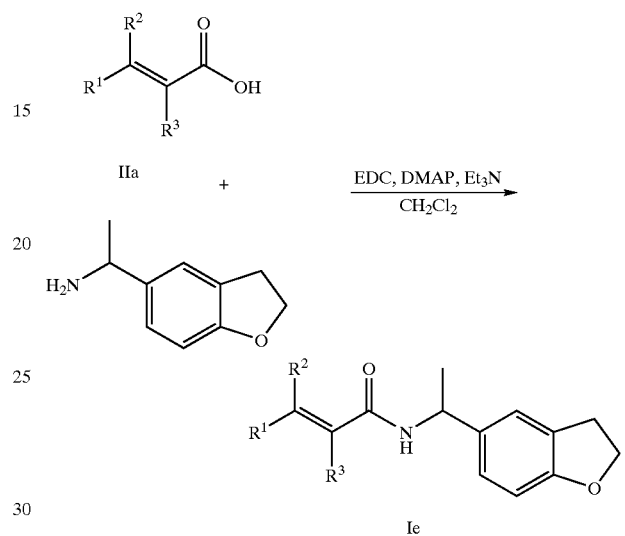

General Procedure

A mixture of an appropriate cinnamic acid derivative of Formula IIa (1.0 mmole), 1-(2,3-dihydrobenzofuran-5-yl)ethylamine, Preparation 4 (163 mg, 1.0 mmole), EDC hydrochloride (384 mg, 2.0 mmole), and DMAP (122 mg, 1.0 mmole), and triethylamine (0.6 mL, 4.0 mmole) in $CH_2Cl_2$ (5 mL) was stirred at room temperature for 16 hours. The reaction mixture was then purified by flash column chromatography on silica gel, typically eluted with Hexane/EtOAc (2:1) to provide the product of general Formula Ie. For Example 80, the racemic product was resolved by HPLC using a chiral OD column to provide the product as a single enantiomer of undetermined chirality.

| Example No. | Structure | Chemical Name | HPLC rt (min), method | Mass (M + H)$^+$ m/z |
|---|---|---|---|---|
| 56 | racemic | (±)-3-(2,6-Difluoro-phenyl)-N-[1-(2,3-dihydro-benzofuran-5-yl)-ethyl]-acrylamide | 1.38 (b) | 330 |
| 57 | racemic | (±)-3-(4-Bromo-2-fluoro-phenyl)-N-[1-(2,3-dihydro-benzofuran-5-yl)-ethyl]-acrylamide | 1.55 (b) | 390 |

-continued

| Example No. | Structure | Chemical Name | HPLC rt (min), method | Mass (M + H)+ m/z |
|---|---|---|---|---|
| 58 | 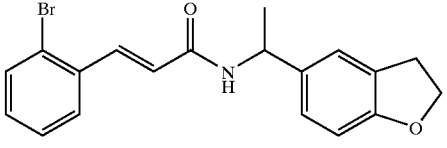 racemic | (±)-3-(2-Bromo-phenyl)-N-[1-(2,3-di-hydro-benzo-furan-5-yl)-ethyl]-acrylamide | 1.44 (b) | 373 |
| 59 | 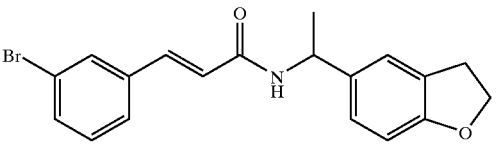 racemic | (±)-3-(3-Bromo-phenyl)-N-[1-(2,3-di-hydro-benzo-furan-5-yl)-ethyl]-acrylamide | 1.50 (b) | 373 |
| 60 | 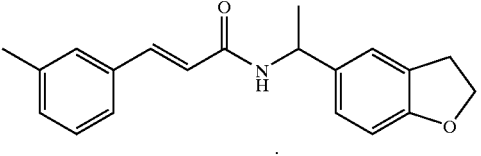 racemic | (±)-N-[1-(2,3-Dihydro-benzo-furan-5-yl)-ethyl]-3-m-tol-yl-acrylamide | | 308 |
| 61 | 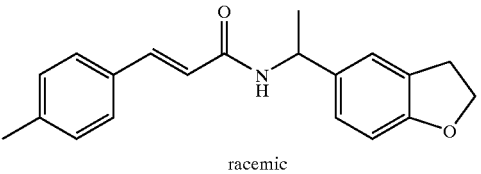 racemic | (±)-N-[1-(2,3-Dihydro-benzo-furan-5-yl)-ethyl]-3-p-tol-yl-acrylamide | | 308 |
| 62 | 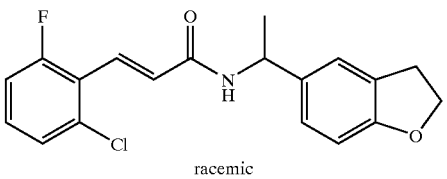 racemic | (±)-3-(2-Chloro-6-fluor-o-phenyl)-N-[1-(2,3-di-hydro-benzofuran-5-yl)-eth-yl]-acrylamide | | 346 |
| 63 | 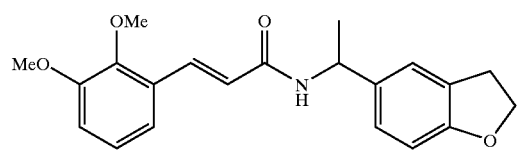 racemic | (±)-N-[1-(2,3-Dihydro-benzo-furan-5-yl)-ethyl]-3-(2,3-di-methoxy-phen-yl)-acrylamide | | 354 |
| 64 | 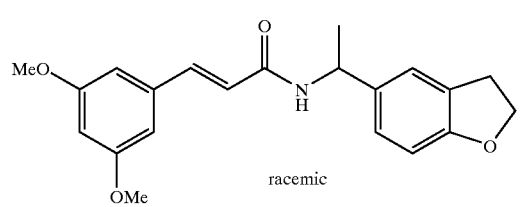 racemic | (±)-N-[1-(2,3-Dihydro-benzo-furan-5-yl)-ethyl]-3-(3,5-di-methoxy-phen-yl)-acrylamide | | 354 |

-continued

| Example No. | Chemical Name | HPLC rt (min), method | Mass (M + H)+ m/z |
|---|---|---|---|
| 65 | (±)-3-(2,4-Dichloro-phenyl)-N-[1-(2,3-dihydro-benzofuran-5-yl)-ethyl]-acrylamide | | 362 |
| 66 | (±)-3-(5-Bromo-2-fluoro-phenyl)-N-[1-(2,3-dihydro-benzofuran-5-yl)-ethyl]-acrylamide | | 390 |
| 67 | (±)-3-(2-Chloro-4-fluoro-phenyl)-N-[1-(2,3-dihydro-benzofuran-5-yl)-ethyl]-acrylamide | | 346 |
| 68 | (±)-3-(4-Chloro-2-fluoro-phenyl)-N-[1-(2,3-dihydro-benzofuran-5-yl)-ethyl]-acryalmide | | 346 |
| 69 | (±)-3-(2,3-Difluoro-phenyl)-N-[1-(2,3-dihydro-benzofuran-5-yl)-ethyl]-acrylamide | 1.40 (b) | 330 |
| 70 | (±)-N-[1-(2,3-Dihydro-benzofuran-5-yl)-ethyl]-3-(3-trifluoromethoxy-phenyl)-acrylamide | 1.55 (b) | 377 |
| 71 | (±)-3-(2-Chloro-phenyl)-N-[1-(2,3-dihydro-benzofuran-5-yl)-ethyl]-acrylamide | | 328 |

-continued

| Example No. | Structure | Chemical Name | HPLC rt (min), method | Mass (M + H)+ m/z |
|---|---|---|---|---|
| 72 | racemic | (±)-3-(3-Chloro-phenyl)-N-[1-(2,3-dihydro-benzo-furan-5-yl)-ethyl]-acrylamide | | 328 |
| 73 | racemic | (±)-N-[1-(2,3-Dihydro-benzo-furan-5-yl)-ethyl]-3-(4-methoxy-phenyl)-acrylamide | | 324 |
| 74 | racemic | (±)-N-[1-(2,3-Dihydro-benzo-furan-5-yl)-ethyl]-3-(4-trifluoromethyl-phenyl)-acrylamide | | 362 |
| 75 | racemic | (±)-N-[1-(2,3-Dihydro-benzo-furan-5-yl)-ethyl]-3-(2-fluoro-phenyl)-acrylamide | | 312 |
| 76 | racemic | (±)-N-[1-(2,3-Dihydro-benzo-furan-5-yl)-ethyl]-3-(3-fluoro-phenyl)-acrylamide | | 312 |
| 77 | racemic | (±)-N-[1-(2,3-Dihydro-benzo-furan-5-yl)-ethyl]-3-indan-5-yl-acrylamide | | 334 |
| 78 | enantiomer chirality undetermined | 3-(3,5-Difluoro-phenyl)-N-[1-(2,3-dihydro-benzo-furan-5-yl)-ethyl]-acrylamide | 62.2 (m) | 330 |

| Example No. | Structure | Chemical Name | HPLC rt (min), method | Mass (M + H)+ m/z |
|---|---|---|---|---|
| 79 | ![structure] enantiomer chirality undetermined | 3-(4-Chloro-phenyl)-N-[1-(2,3-di-hydro-benzo-furan-5-yl)-ethyl]-acrylamide | 45.6 (n) | 328 |
| 80 | ![structure] enantiomer chirality undetermined | 3-(2,4-Difluoro-phenyl)-N-[1-(2,3-di-hydro-benzo-furan-5-yl)-ethyl]-acrylamide | 35.7 (n) | 330 |
| 81 | ![structure] racemic | 3-Benzo[1,3]-dioxol-5-yl-N-[1-(2,3-di-hydro-benzo-furan-5-yl)-ethyl]-acrylamide | | 337 |

Example 82

Preparation of (S)-3-Phenyl-N-[1-(3-morpholin-4-yl-phenyl)ethyl]acrylamide

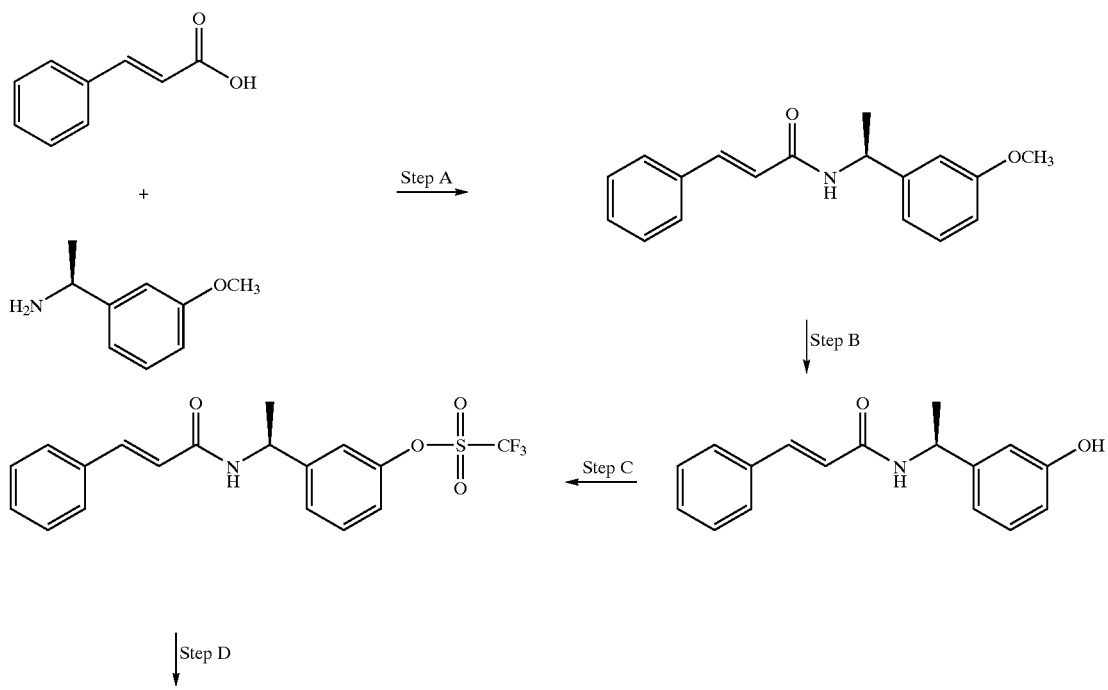

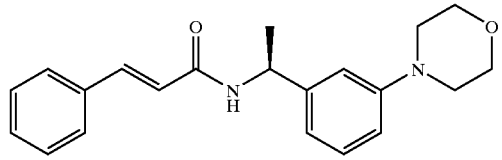

Step A: (S)-3-Phenyl-N-[1-(3-methoxyphenyl)ethyl] acrylamide

To a solution of cinnamic acid (1.62 g) in CH$_2$Cl$_2$ (40 mL) at room temperature was added (S)-1-(2-phenyl)ethylamine (1.5 g), EDC hydrochloride (3.81 g), DMAP (1.21 g), and triethylamine (5.53 mL), and the resulting solution was stirred at room temperature for 12 hours. Water was added, and the mixture was extracted with CH$_2$Cl$_2$ (three times). The combined organic layers were washed with brine, dried over anhydrous sodium sulfate, and concentrated in vacuo. The residue was purified by silica gel chromatography eluting with 6% methanol/94% CH$_2$Cl$_2$ to afford the titled compound as a white solid(1.3 g).

$^1$H NMR (CDCl$_3$, 400 mHz) δ 1.57 (3H, d, J=6.9 Hz), 5.25 (1H, m), 5.81 (1H, d), 6.38 (1H, d, J=15.6 Hz), 6.82 (1H, d), 6.83 (1H, m), 6.97 (1H, m), 7.27 (2H, m), 7.36 (2H, m), 7.49 (2H, m), 7.63 (1H, d, J=15.6 Hz).

MS: 282.30 (M+H)$^+$.

Step B: (S)-3-Phenyl-N-[1-(3-hydroxyphenyl)ethyl] acrylamide

To a solution of (S)-3-phenyl-N-[1-(3-methoxyphenyl) ethyl]acrylamide (100 mg) in CH$_2$Cl$_2$ (0.5 mL) at −78° C. was added boron tribromide (1.0 M solution in CH$_2$Cl$_2$, 2.14 mL). The resulting solution was warmed to room temperature and stirred at room temperature for 3 hours. Water was added, and the mixture was extracted with CH$_2$Cl$_2$ (three times). The combined organic layers were washed with brine, dried over anhydrous sodium sulfate, and concentrated in vacuo to provide the title compound.

$^1$H NMR (CDCl$_3$, 400 mHz) δ 1.52 (3H, d, J=6.9 Hz), 5.20 (1H, m), 6.15(1H, d, J=7.5 Hz), 6.38 (1H, d, J=15.6 Hz), 6.77 (1H, m), 6.87 (2H, m), 7.17 (2H, t, J=8.0 Hz), 7.32 (2H, m), 7.51 (2H, m), 7.61 (2H, d, J=15.6 Hz).

MS: 268.31 (M+H)$^+$.

Step C: (S)-3-Phenyl-N-[1-(3-trifluoromethanesulfonyloxy-phenyl)ethyl]-acrylamide To a solution of (S)-3-phenyl-N-[1-(3-hydroxyphenyl) ethyl]acrylamide (0.7 g) in CH$_2$Cl$_2$ (15 mL) at-78° C. was added pyridine (1.1 mL) followed by triflic anhydride (0.49 mL). The resulting solution was warmed to room temperature and stirred at room temperature for 12 hours. Water was added, and the mixture was extracted with CH$_2$Cl$_2$ (three times). The combined organic layers were washed with brine, dried over anhydrous sodium sulfate, and concentrated in vacuo. The crude product was purified by silica gel chromatography eluting with 40% EtOAc/60% hexane to provide the title compound.

$^1$H NMR (CDCl$_3$, 400 mHz) δ 1.57 (3H, d, J=6.9 Hz), 5.29 (1H, m), 5.92 (1H, d, J=7.6 Hz), 6.42 (1H, d, J=15.6 Hz), 7.16–7.50 (9H, m), 7.64 (1H, d, J=15.6 Hz).

MS: 400.33 (M+H)$^+$.

Step D: (S)-3-Phenyl-N-[1-(3-morpholin-4-yl-phenyl) ethyl]-acrylamide

To a solution of (S)-3-phenyl-N-[1-(3-trifluoromethanesulfonyloxy-phenyl)-ethyl]acrylamide (50 mg) in DME (0.5 mL) at room temperature was added Pd$_2$(dba)$_3$ (29 mg), potassium phosphate (37 mg), morpholine (0.02 mL), and the resulting suspension was heated at 80° C. for 15 hours. The solvent was removed in vacuo, and the residue was purified by preparative HPLC to afford the title compound as the trifluoacetic acid salt.

$^1$H NMR (CD$_3$OD, 400 mHz) δ 1.42 (3H, d, J=5.6 Hz), 3.32 (4H, m), 3.86 (4H, m), 5.02 (1H, q, J=5.6 Hz), 6.56 (1H, d, J=12.6 Hz), 7.1–7.5 (10 h, m).

MS: 337.39 (M+H)$^+$.

Examples 83–84

Examples 83–84 were prepared by the same method used to prepare Example 82 (above) with the exception of using trans-2,4-difluorocinnamic acid in place of trans-cinnamic acid in Step A. Example 84 was prepared by the same method used to prepare Example 82 (above) with the exception of using 2,6-dimethylmorpholine in place of morpholine in Step D.

| Example No. | Structure | Chemical Name | HPLC rt (min), method | Mass (M + H)$^+$ m/z |
|---|---|---|---|---|
| 83 | 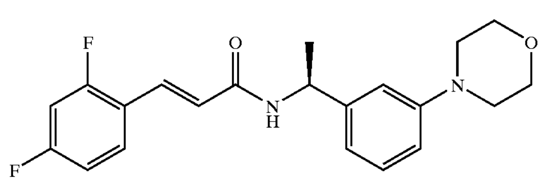 | (S)-3-(2,4-Difluoro-phenyl)-N-[1-(3-morpholin-4-yl-phenyl)-ethyl]-acrylamide | 1.37 (b) | 372 |

-continued

| Example No. | Structure | Chemical Name | HPLC rt (min), method | Mass (M + H)+ m/z |
|---|---|---|---|---|
| 84 | 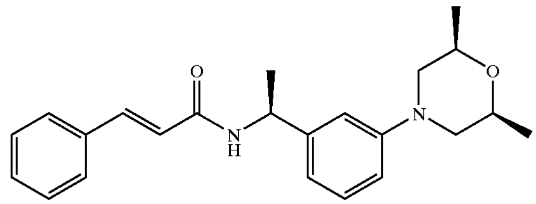 | (S)-N-[1-(3-(2,6-di-methyl-Morpholin)-4-yl-phenyl)-ethyl]-3-phenyl-acrylamide | 1.45 (b) | 336 |

Example 85

Preparation of [(S)-3-(2-fluoro-phenyl)-N-[1-(3-morpholin-4-yl-phenyl)-ethyl]-acrylamide

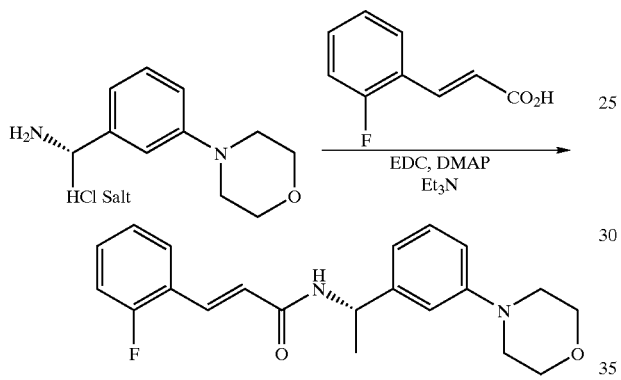

Mixture of (S)-1-(3-morpholin-4-yl-phenyl)-ethylamine hydrochloride, Preparation 21 (50 mg, 0.21 mmol), 2-fluorocinnamic acid (37 mg, 0.23 mmol), EDC (79 mg, 0.41 mmol), DMAP (25 mg, 0.21 mmol), triethylamine (0.11 ml, 0.82 mmol) in dichloromethane (1 mL) was stirred at room temperature for 10 hours. The reaction mixture was concentrated under vacuum and purified by filtering through 2 g silica-gel syringe with 80% ethyl acetate/hexanes. The filtrate was concentrated under vacuum to provide the title compound as a white solid.

$^1$H NMR (CDCl$_3$): δ 1.56 (d, 3H), 3.17 (m, 4H), 3.86(m, 4H), 5.24(m, 1H), 6.52 (d, J=16 Hz, 1H), 6.84 (m, 3H), 7.13 (m, 2H), 7.28 (m, 2H), 7.46 (t, 1H), 7.69 (d, J=16 Hz, 1H).

MS (M+H)+ 355.

Examples 86–98

Example 86–98 were prepared from appropriate acids by the same method used to prepare Example 85.

| Example No. | Structure | Chemical Name | HPLC rt (min), method | Mass (M + H)+ m/z |
|---|---|---|---|---|
| 86 | 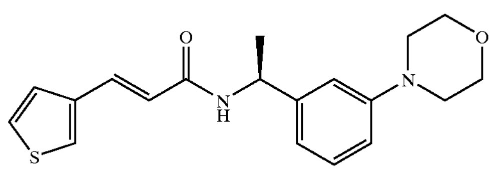 | (S)-N-[1-(3-Morpholin-4-yl-phenyl-ethyl]-3-thio-phen-3-yl-acrylamide | 1.25 (p) | 343 |
| 87 | 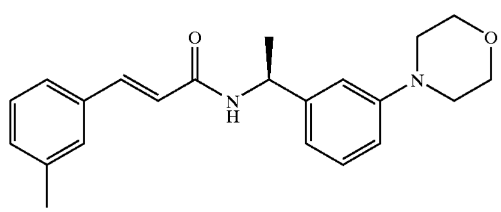 | (S)-3-(3-Methyl-phenyl)-N-[1-(3-morpholin-4-yl-phenyl)-ethyl]-acrylamide | 1.40 (q) | 351 |
| 88 | 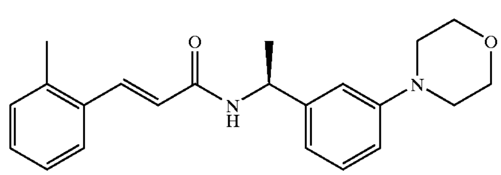 | (S)-3-(2-Methyl-phenyl)-N-[1-(3-morpholin-4-yl-phenyl)-ethyl]-acrylamide | 1.39 (q) | 351 |

| Example No. | Structure | Chemical Name | HPLC rt (min), method | Mass (M + H)+ m/z |
|---|---|---|---|---|
| 89 | 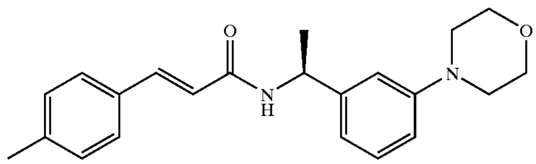 | (S)-3-(4-Methyl-phenyl)-N-[1-(3-morpholin-4-yl-phenyl)-ethyl]-acrylamide | 1.40 (q) | 351 |
| 90 | 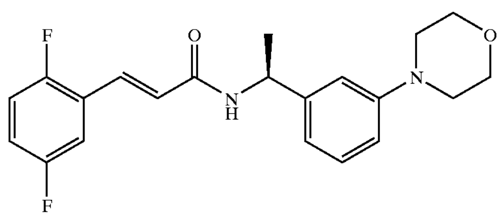 | (S)-3-(2,5-Difluoro-phenyl)-N-[1-(3-morpholin-4-yl-phenyl)-ethyl]-acrylamide | 1.40 (b) | 373 |
| 91 | 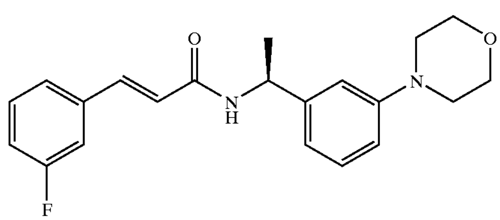 | (S)-3-(4-Fluoro-phenyl)-N-[1-(3-morpholin-4-yl-phenyl)-ethyl]-acrylamide | | |
| 92 | 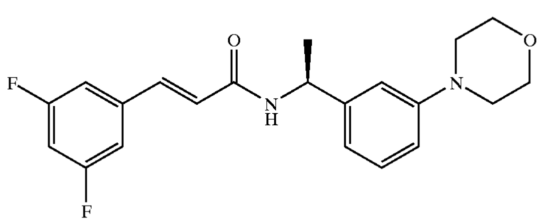 | (S)-3-(3,5-Difluoro-phenyl)-N-[1-(3-morpholin-4-yl-phenyl)-ethyl]-acrylamide | 1.44 (b) | 373 |
| 93 | 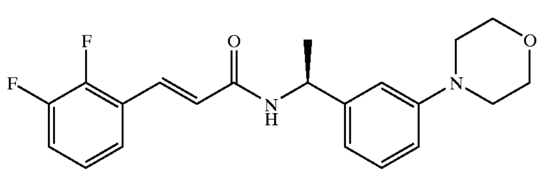 | (S)-3-(2,3-Difluoro-phenyl)-N-[1-(3-morpholin-4-yl-phenyl)-ethyl]-acrylamide | 1.41 (b) | 373 |
| 94 | 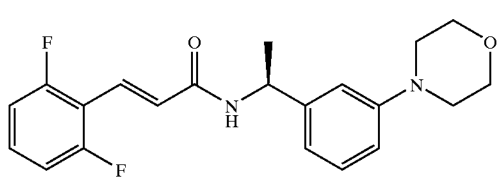 | (S)-3-(2,6-Difluoro-phenyl)-N-[1-(3-morpholin-4-yl-phenyl)-ethyl]-acrylamide | 1.37 (b) | 373 |

-continued

| Example No. | Structure | Chemical Name | HPLC rt (min), method | Mass (M + H)+ m/z |
|---|---|---|---|---|
| 95 | 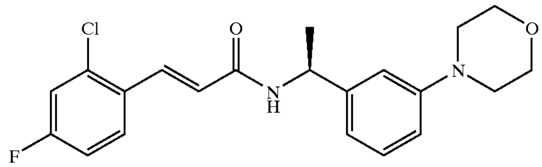 | (S)-3-(2-Chloro-4-fluoro-phenyl)-N-[1-(3-morpholin-4-yl-phenyl)-ethyl]-acrylamide | 1.62 (b) | 389 |
| 96 | 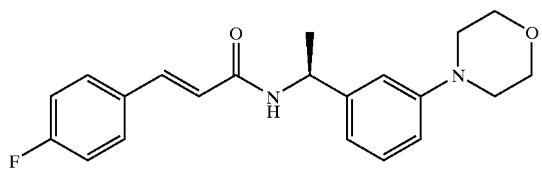 | (S)-3-(4-Fluoro-phenyl)-N-[1-(3-morpholin-4-yl-phenyl)-ethyl]-acrylamide | 1.29 (b) | 355 |
| 97 | 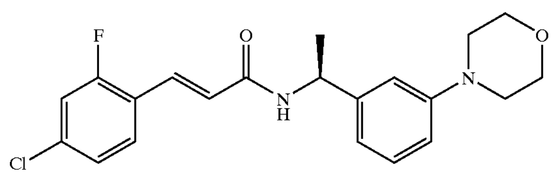 | (S)-3-(4-Chloro-2-fluoro-phenyl)-N-[1-(3-morpholin-4-yl-phenyl)-ethyl]-acrylamide | 1.53 (q) | 389 |
| 98 | 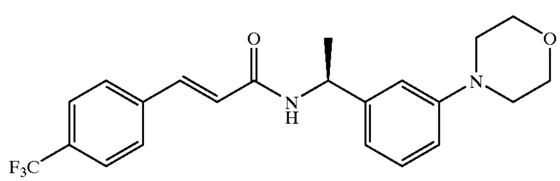 | (S)-3-(4-Trifluoromethyl-phenyl)-N-[1-(3-morpholin-4-yl-phenyl)-ethyl]-acrylamide | 1.57 (q) | 405 |

Example 99

Preparation of (S)-N-{1-[3-(cis-2,6-Dimethyl-morpholin-4-yl)-phenyl]ethyl}-3-(2-fluoro-phenyl)-acrylamide

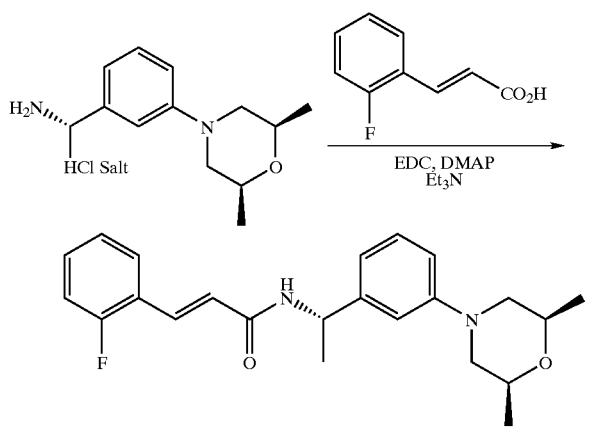

Mixture of (S)-1-[3-(cis-2,6-dimethyl-morpholin-4-yl)-phenyl]-ethylamine hydrochloric acid salt, Preparation 31 (50 mg, 0.16 mmol), 2-fluorocinnamic acid (30 mg, 0.18 mmol), EDC (65 mg, 0.33 mmol), DMAP (20 mg, 0.16 mmol), triethylamine (0.09 ml, 0.65 mmol) in dichloromethane (0.7 mL) was stirred at room temperature overnight. The reaction mixture was purified by filtering through 2 g silica-gel syringe with 70% ethyl acetate/hexanes. The filtrate was concentrated under vacuum to provide the title compound as a white solid.

$^1$H NMR (CDCl$_3$): δ 7.68 (d, J=16 Hz, 1H), 7.45 (m, 1H), 7.30 (m, 1H), 7.23 (m, 1H), 7.14 (m, 1H), 7.08 (m, 1H), 6.89–6.80 (m, 3H), 6.49 (d, J=16 Hz, 1H), 5.79 (d, 1H), 5.22 (m, 1H), 3.79 (m, 2H), 3.45 (d, J=11 Hz, 2H), 2.41 (t, J=11 Hz, 2H), 1.54 (d, J=2 Hz, 3H), 1.25 (d, J=7 Hz, 6H).

MS (M+H)+ 383.

Examples 100–109

Examples 100–109 were prepared from appropriate acids by the same method used to prepare Example 99.

| Example No. | Structure | Chemical Name | HPLC rt (min), method | Mass (M + H)+ m/z |
|---|---|---|---|---|
| 100 | 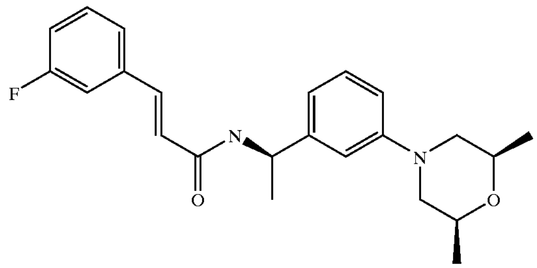 | (S)-N-{1-[3-(cis-2,6-Dimethyl-morpholin-4-yl)-phenyl]-ethyl}-3-(3-fluoro-phenyl)-acrylamide | 1.67 (p) | 383 |
| 101 | 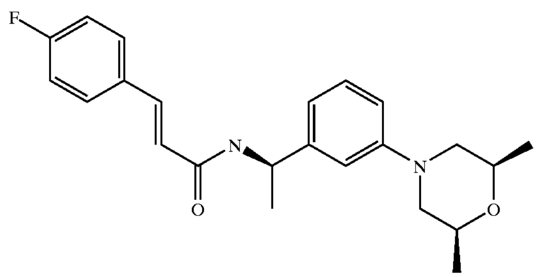 | (S)-N-{1-[3-(cis-2,6-Dimethyl-morpholin-4-yl)-phenyl]-ethyl}-3-(4-fluoro-phenyl)-acrylamide | 1.66 (p) | 383 |
| 102 | 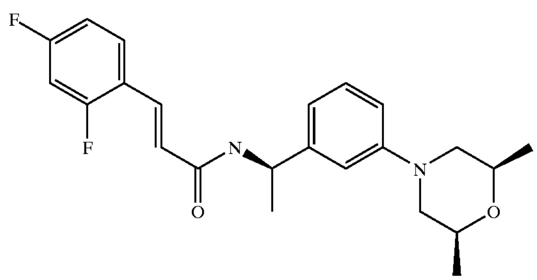 | (S)-3-(2,4-Difluoro-phenyl)-N-{1-[3-(cis-2,6-dimethyl-morpholin-4-yl)-phenyl]-ethyl}-acrylamide | 1.72 (p) | 401 |
| 103 | 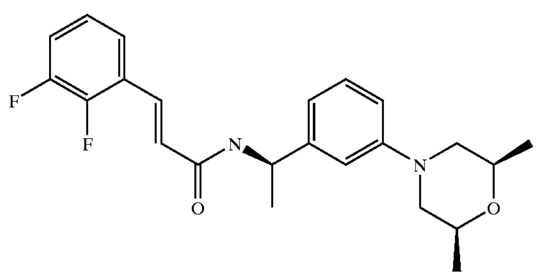 | (S)-3-(2,3-Difluoro-phenyl)-N-{1-[3-(cis-2,6-dimethyl-morpholin-4-yl)-phenyl]-ethyl}-acrylamide | 1.73 (p) | 401 |
| 104 | 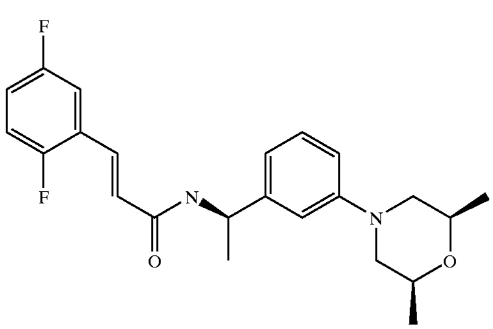 | (S)-3-(2,5-Difluoro-phenyl)-N-{1-[3-(cis-2,6-dimethyl-morpholin-4-yl)-phenyl]-ethyl}-acrylamide | 1.71 (p) | 401 |

-continued

| Example No. | Structure | Chemical Name | HPLC rt (min), method | Mass (M + H)+ m/z |
|---|---|---|---|---|
| 105 | 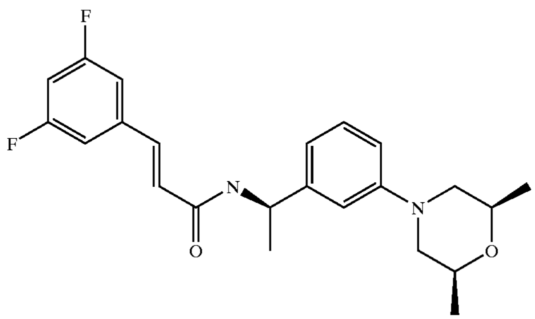 | (S)-3-(3,5-Difluoro-phenyl)-N-{1-[3-(cis-2,6-dimethyl-morpholin-4-yl)-phenyl]-ethyl}-acrylamide | 1.75 (p) | 401 |
| 106 | 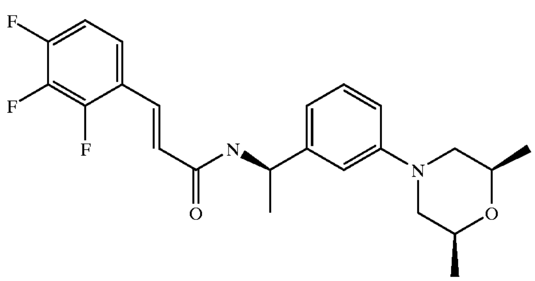 | (S)-N-{1-[3-(cis-2,6-Dimethyl-morpholin-4-yl)-phenyl]-ethyl}-3-(2,3,4-trifluoro-phenyl)-acrylamide | 1.82 (p) | 419 |
| 107 | 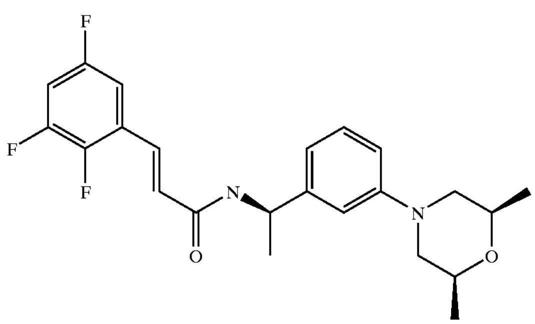 | (S)-N-{1-[3-(cis-2,6-Dimethyl-morpholin-4-yl)-phenyl]-ethyl}-3-(2,3,5-trifluoro-phenyl)-acrylamide | 1.79 (p) | 419 |
| 108 | 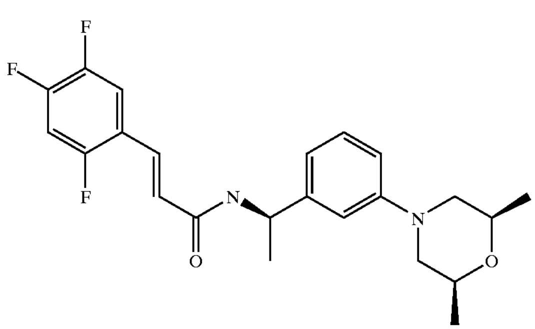 | (S)-N-{1-[3-(cis-2,6-Dimethyl-morpholin-4-yl)-phenyl]-ethyl}-3-(2,4,5-trifluoro-phenyl)-acrylamide | 1.77 (p) | 419 |

-continued

| Example No. | Structure | Chemical Name | HPLC rt (min), method | Mass (M + H)+ m/z |
|---|---|---|---|---|
| 109 | 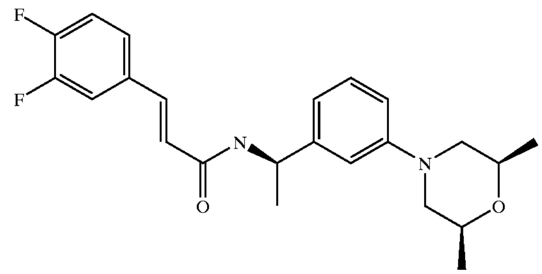 | (S)-3-(3,4-Difluoro-phen-yl)-N-{1-[3-(cis-2,6-di-methyl-morpholin-4-yl)-phen-yl]-ethyl}-acrylamide | 1.72 (p) | 401 |

Example 110

Preparation of (S)-N-{1-[3-(2-Methyl-morpholin-4-yl)-phenyl]ethyl}-3-phenyl-acrylamide

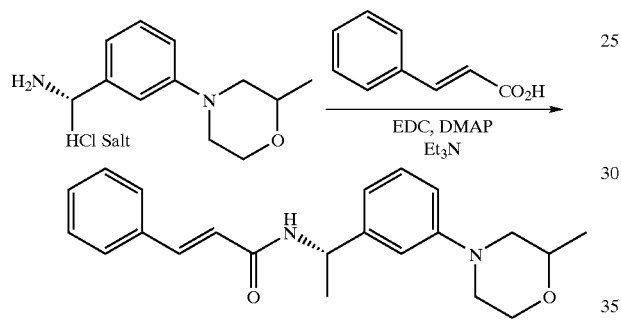

Mixture of (S)-1-[3-(2-methyl-morpholin-4-yl)-phenyl]-ethylamine hydrochloric acid salt, Preparation 41(30 mg, 0.10 mmol), cinnamic acid (17 mg, 0.11 mmol), EDC (40 mg, 0.20 mmol), DMAP (13 mg, 0.10 mmol), triethylamine (0.06 ml, 0.40 mmol) in dichloromethane (0.5 mL) was stirred at room temperature overnight. The reaction mixture was purified by filtering through 2 g silica-gel syringe with 70% ethyl acetate/hexanes. The filtrate was concentrated under vacuum to provide the title compound as a yellow solid.

$^1$H NMR (CDCl$_3$): δ 7.62(d, J=16 Hz, 1H), 7.47 (m, 2H), 7.34 (m, 3H), 7.25 (m, 1H), 6.91–6.81 (m, 3H), 6.35 (d, J=16 Hz, 1H), 5.74 (d, 1H), 5.28(m, 1H), 3.98 (m, 1H), 3.77 (m, 2H), 3.45 (m, 2H), 2.81 (m, 1H), 2.49 (m, 1H), 1.54 (d, J=2 Hz, 3H), 1.25 (d, J=6 Hz, 3H).

MS (M+H)+ 351.

Examples 111–119

Examples 111–119 were prepared from appropriate acids by the same method used to prepare Example 110.

| Example No. | Structure | Chemical Name | HPLC rt (min), method | Mass (M + H)+ m/z |
|---|---|---|---|---|
| 111 | 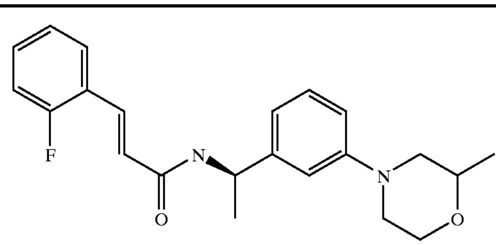 | (S)-3-(2-Fluoro-phenyl)-N-{1-[3-(2-methyl-morpholin-4-yl)-phenyl]-ethyl}-acrylamide | 1.59 (p) | 369 |
| 112 | 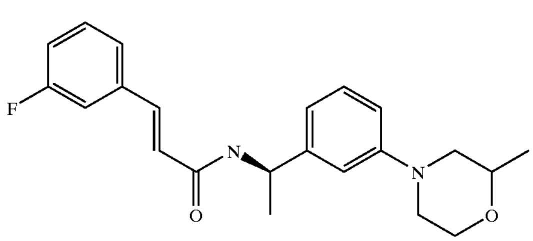 | (S)-3-(3-Fluoro-phenyl)-N-{1-[3-(2-methyl-morpholin-4-yl)-phenyl]-ethyl}-acrylamide | 1.61 (p) | 369 |

| Example No. | Structure | Chemical Name | HPLC rt (min), method | Mass (M + H)+ m/z |
|---|---|---|---|---|
| 113 | 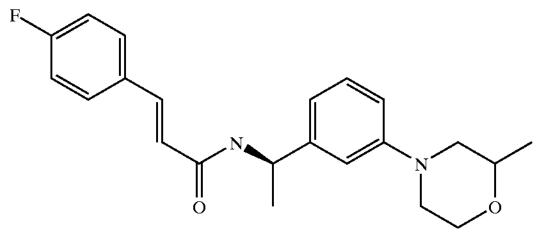 | (S)-3-(4-Fluoro-phenyl)-N-{1-[3-(2-methyl-morpholin-4-yl)-phenyl]-ethyl}-acrylamide | 1.57 (p) | 369 |
| 114 | 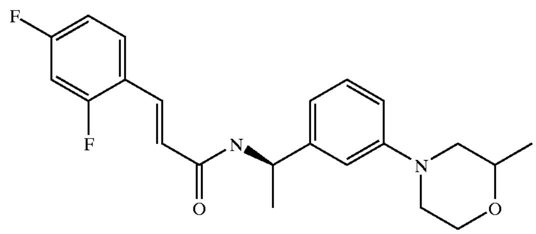 | (S)-3-(2,4-Difluoro-phenyl)-N-{1-[3-(2-methyl-morpholin-4-yl)-phenyl]-ethyl}-acrylamide | 1.63 (p) | 387 |
| 115 | 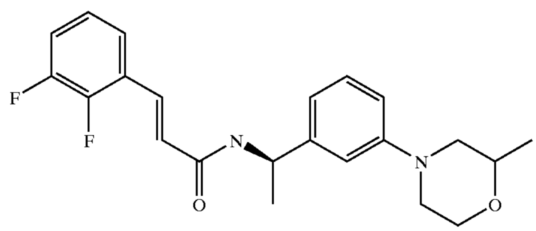 | (S)-3-(2,3-Difluoro-phenyl)-N-{1-[3-(2-methyl-morpholin-4-yl)-phenyl]-ethyl}-acrylamide | 1.64 (p) | 387 |
| 116 | 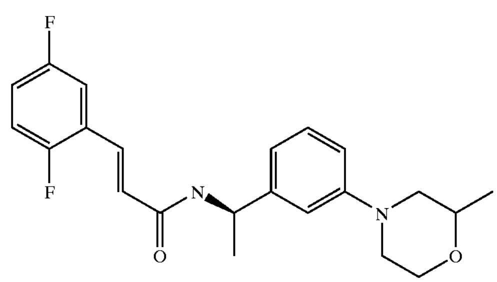 | (S)-3-(2,5-Difluoro-phenyl)-N-{1-[3-(2-methyl-morpholin-4-yl)-phenyl]-ethyl}-acrylamide | 1.62 (p) | 387 |
| 117 | 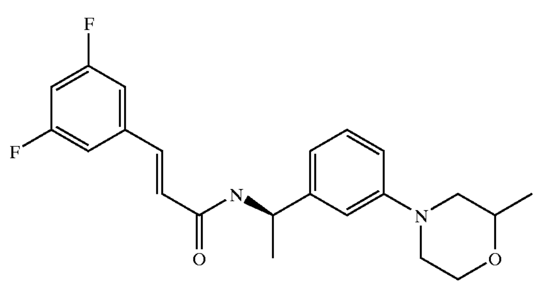 | (S)-3-(3,5-Difluoro-phenyl)-N-{1-[3-(2-methyl-morpholin-4-yl)-phenyl]-ethyl}-acrylamide | 1.67 (p) | 387 |
| 118 | 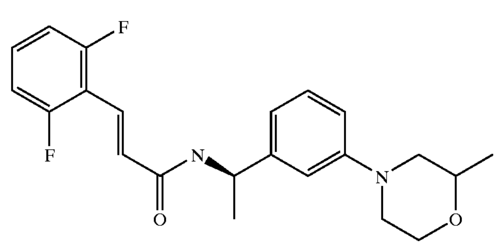 | (S)-3-(2,6-Difluoro-phenyl)-N-{1-[3-(2-methyl-morpholin-4-yl)-phenyl]-ethyl}-acrylamide | 1.60 (p) | 387 |

| Example No. | Structure | Chemical Name | HPLC rt (min), method | Mass (M + H)+ m/z |
|---|---|---|---|---|
| 119 | 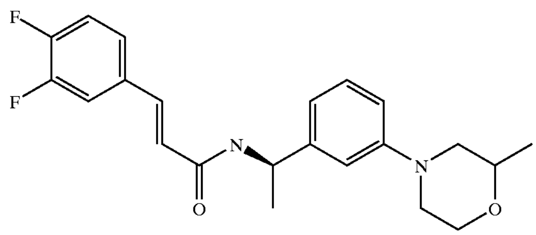 | (S)-3-(3,4-Difluoro-phenyl)-N-{1-[3-(2-methyl-morpholin-4-yl)-phenyl]-ethyl}-acrylamide | 1.65 (p) | 387 |

Example 120

Preparation of (S)-N-{1-[3-(2-Oxa-5-aza-bicyclo[2.2.1]hept-5-yl)phenyl]ethyl}-3-phenyl-acrylamide

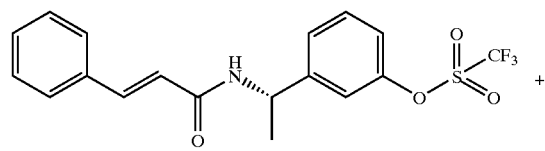

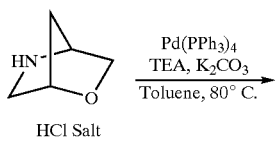

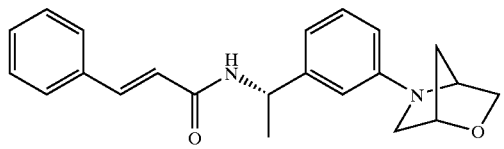

Mixture of (S)-trifluoro-methanesulfonic acid 3-[1-(3-phenyl-acryloylamino)ethyl]phenyl ester (Step C in Example 82) (100 mg, 0.25 mmol), 2-oxa-5-aza-bicyclo[2.2.1]heptane (68 mg, 2eq), tetrakis (triphenylphosphine) palladium (0) (10 mol %, 29 mg), potassium carbonate (104 mg, 3eq), and triethylamine (0.2 ml) in toluene (1 ml) was stirred at 80° C. for 15 hours. Reaction mixture was diluted with 20 ml dichloromethane, washed with saturated sodium bicarbonate solution. The organic layer was separated and the aqueous layer was extracted with dichloromethane three times. The combined organic layer was dried over magnesium sulfate and concentrated under vacuum. The crude product was purified by flash chromatography with 40% acetone/hexane to obtain the title compound as a pale yellow solid (14 mg, 16% yield).

$^1$H NMR (CDCl$_3$): δ 7.61 (d, 1H), 7.48 (m, 2H), 7.34 (m, 3H), 7.21 (t, 1H), 6.71 (d, 1H), 6.56 (s, 1H), 6.51 (d, 1H), 6.35 (d, 1H), 5.77 (d, 1H), 5.21 (m, 1H), 4.65 (s, 1H), 4.41 (s, 1H), 3.88 (m, 2H), 3.44 (d, 1H), 3.16 (d, 1H), 1.95 (m, 2H), 1.54 (d, 3H).

MS (M+H)+ 349.

Example 121

Preparation of (S)-N-{1-[3-(2-Hydroxymethyl-morpholin-4-yl)-phenyl]-ethyl}-3-phenyl-acrylamide

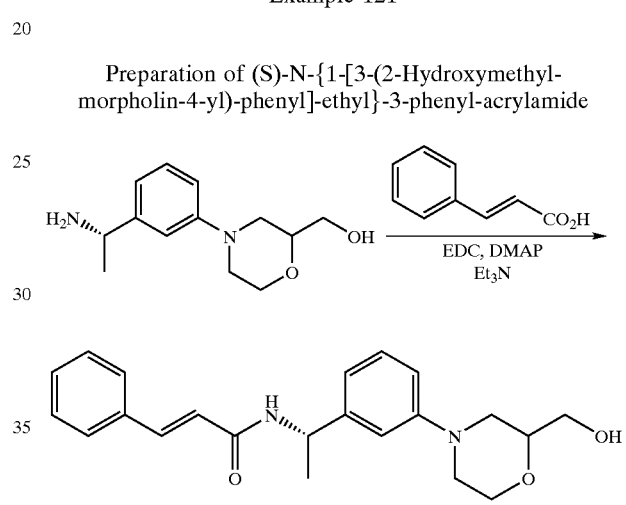

Mixture of (S)-{4-[3-(1-amino-ethyl)-phenyl]-morpholin-2-yl}-methanol (27 mg, 0.09 mmol), cinnamic acid, Preparation 27 (12.8 mg, 0.09 mmol), EDC (34 mg, 0.18 mmol), DMAP (11 mg, 0.09 mmol), triethylamine (0.05 ml, 0.36 mmol) in dichloromethane (0.6 ml) was stirred at room temperature overnight. The reaction mixture was purified by filtering through 2 g silica-gel syringe with 60:40:1 acetone:hexanes:methanol. The filtrate was concentrated under vacuum to provide the title compound as a white solid.

$^1$H NMR (CDCl$_3$): δ 7.62 (d, J=16, 1H), 7.47 (m, 2H), 7.34 (m, 3H), 7.26 (m, 1H), 6.80–6.90 (m, 3H), 6.35 (d, J=16, 1H), 5.78 (d, J=10, 1H), 5.22 (m, 1H), 4.05 (m, 1H), 3.63–3.84 (m, 4H), 3.45 (m, 2H), 2.83 (m, 1H), 2.68 (t, J=11, 1H), 2.56 (m, 1H), 1.55 (d, J=8, 3H).

MS (M+H)+ 367.

Examples 122–124

Examples 122–124 were prepared from appropriate acids by the same method used to prepare Example 121.

| Example No. | Structure | Chemical Name | HPLC rt (min), method | Mass (M + H)+ m/z |
|---|---|---|---|---|
| 122 | 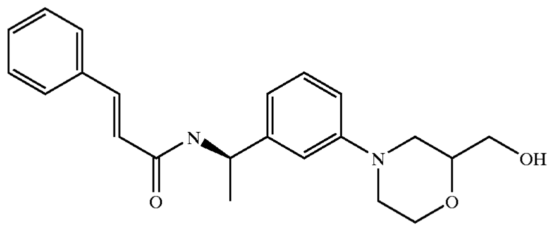 | (S)-N-{1-[3-(2-Hydroxymethyl-morpholin-4-yl)-phenyl]-ethyl}-3-phenyl-acrylamide | 1.37 (p) | 367 |
| 123 | 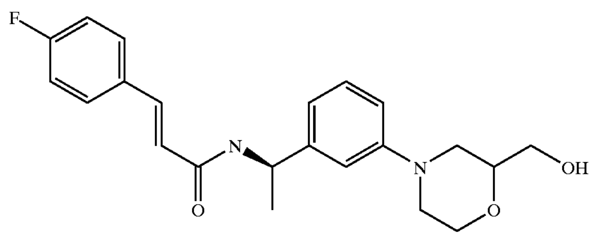 | (S)-3-(4-Fluoro-phenyl)-N-{1-[3-(2-hydroxymethyl-morpholin-4-yl)-phenyl]-ethyl}-acrylamide | 1.44 (p) | 385 |
| 124 | 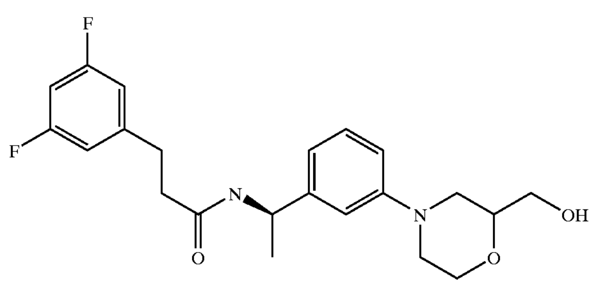 | (S)-3-(3,5-Difluoro-phenyl)-N-{1-[3-(2-hydroxymethyl-morpholin-4-yl)-phenyl]-ethyl}-propionamide | 1.54 (p) | 403 |

Example 125

Preparation of (S)-[4-(3-{1-[3-(3,4-Difluoro-phenyl)-acryloylamino]-ethyl}-phenyl)-morpholin-2-ylmethyl]-carbamic acid tert-butyl ester

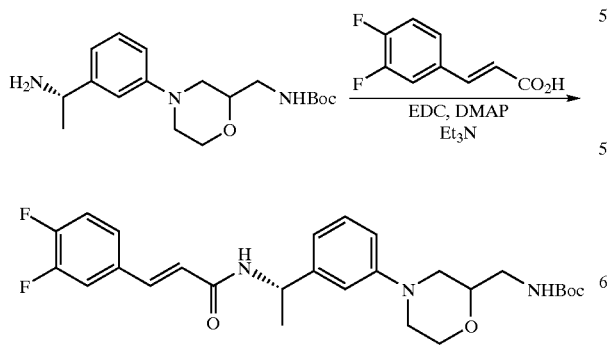

Mixture of (S)-{4-[3-(1-amino-ethyl)-phenyl]-morpholin-2-ylmethyl}-carbamic acid tert-butyl ester, Preparation 28 (20 mg, 0.06 mmol), 3,4-difluorocinnamic acid (12.1 mg, 0.07 mmol), EDC (23 mg, 0.12 mmol), DMAP (7.3 mg, 0.06 mmol), triethylamine (0.03 ml, 0.24 mmol) in dichloromethane (0.6 ml) was stirred at room temperature overnight. The reaction mixture was purified by filtering through 2 g silica-gel syringe with 80% ethyl acetate/hexanes. The filtrate was concentrated under vacuum to provide the title compound as a white solid.

$^1$H NMR (CDCl$_3$): δ 7.51 (d, J=15, 1H), 7.20–7.31 (m, 4H), 6.85 (m, 2H), 6.80 (m, 1H), 6.27 (d, J=15, 1H), 5.82 (m, 1H), 5.25 (m, 1H), 4.93 (s, 1H), 4.00 (m, 1H), 3.62–3.78 (m, 2H), 3.36–3.47 (m, 3H), 3.15 (m, 1H), 2.82 (t, J=12, 1H), 2.56 (t, J=12, 1H), 1.53 (d, 3H), 1.44 (s, 9H).

MS (M+H)$^+$ 502.

Example 126

Example 126 was prepared from appropriate acids by the same method used to prepare Example 125.

| Example No. | Structure | Chemical Name | HPLC rt (min), method | Mass (M + H)+ m/z |
|---|---|---|---|---|
| 126 | 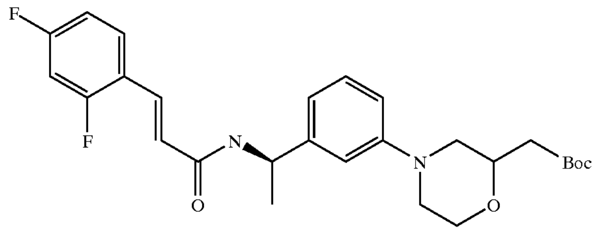 | (S)-[4-(3-{1-[3-(2,4-Difluoro-phenyl)-acryloylamino]-ethyl}-phenyl)-morpholin-2-ylmethyl]-carbamic acid tert-butyl ester | 1.88 (p) | 502 |

Example 127

Preparation of (S)-N-{1-[3-(2-Aminomethyl-morpholin-4-yl)-phenyl]-ethyl}-3-(3,4-difluoro-phenyl)-acrylamide

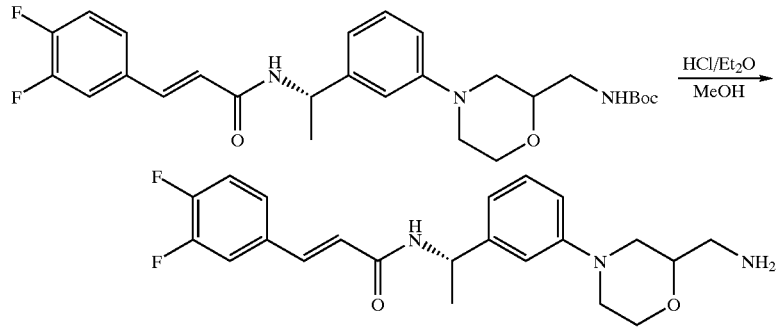

The solution of (S)-[4-(3-{1-[3-(3,4-difluoro-phenyl)-acryloylamino]-ethyl}-phenyl)-morpholin-2-ylmethyl]-carbamic acid tert-butyl ester, Example 125 (about 24 mg), and hydrochloric acid (1.0M solution in diethyl ether) (0.3 ml) in methanol (0.3 ml) was stirred at room temperature overnight. Concentrated under vacuum and sticky oil was filtered through 2 g anion-exchange cartridge with methanol. Filtrate was concentrated under vacuum and the title compound was obtained as pale yellow solid (quantitative yield).
$^1$H NMR (400 MHz, CD$_3$OD): δ 7.42–7.51 (m, 2H), 7.19–7.39 (m, 3H), 6.95 (s, 1H), 6.87 (m, 1H), 6.58 (d, J=16, 1H), 5.04 (q, J=8, 1H), 4.03 (m, 1H), 3.76 (m, 2H), 3.56 (d, J=12, 1H), 3.46 (d, J=12, 1H), 2.98 (m, 1H), 2.96 (m, 1H), 2.77 (m, 1H), 2.48 (t, J=12, 1H), 1.47 (d, J=7, 3H).

MS: 402 (M+H)+.

Examples 128–129

Examples 128–129 were prepared from appropriate amides by the same method used to prepare Example 127.

| Example No. | Structure | Chemical Name | HPLC rt (min), method | Mass (M + H)+ m/z |
|---|---|---|---|---|
| 128 | 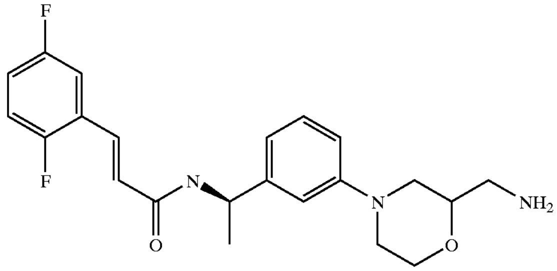 | (S)-N-{1-[3-(2-Aminomethyl-morpholin-4-yl)-phenyl]-ethyl}-3-(2,5-difluoro-phenyl)-acrylamide | 1.23 (j) | 402 |

-continued

| Example No. | Structure | Chemical Name | HPLC rt (min), method | Mass (M + H)+ m/z |
|---|---|---|---|---|
| 129 | ![structure] | (S)-N-{1-[3-(2-Amino-methyl-morpholin-4-yl)-phenyl]-ethyl}-3-(3,5-difluoro-phenyl)-acrylamide | 1.25 (j) | 402 |

Example 130

Preparation of (±)-N-1-(3-morpholin-4-yl-phenyl)-propyl]-3-phenyl-acrylamide

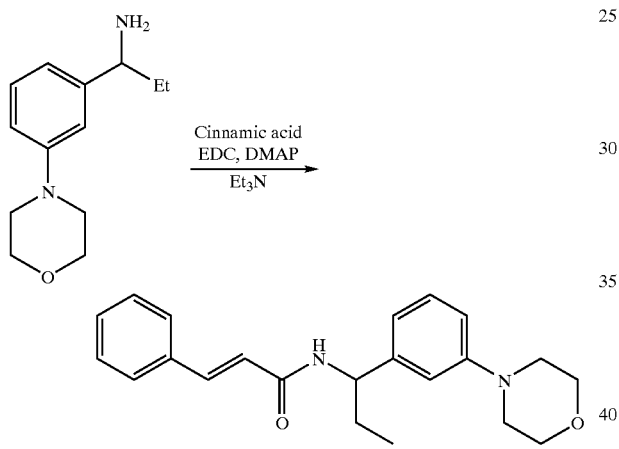

Mixture of 1-(3-morpholin-4-yl-phenyl)propylamine (70 mg, 0.32 mmol), cinnamic acid, Preparation 22 (52 mg, 0.35 mmol), EDC (122 mg, 0.64 mmol), DMAP (39 mg, 0.32 mmol), triethylamine (0.18 ml, 1.27 mmol) in dichloromethane (1 mL) was stirred at room temperature for 10 hours. The reaction mixture was concentrated under vacuum and purified by filtering through 5 g silica-gel syringe with 50% ethyl acetate/hexanes. The filtrate was concentrated under vacuum to provide the title compound as a white solid.

$^1$H NMR (CDCl$_3$): δ 0.94 (t, 3H), 1.91 (m, 2H), 3.18 (m, 4H), 3.87(m, 4H), 4.99(m, 1H), 5.80 (m, 1H), 6.38 (d, J=16 Hz, 1H), 6.88 (m, 3H), 7.26 (m, 1H), 7.34 (m, 3H), 7.47 (m, 2H), 7.62 (d, J=16 Hz, 1H).

MS (M+H)+ 351.

Examples 131–142

Examples 131–142 were made from appropriate acids by the same method used to prepare Example 130.

| Example No. | Structure | Chemical Name | HPLC rt (min), method | Mass (M + H)+ m/z |
|---|---|---|---|---|
| 131 | 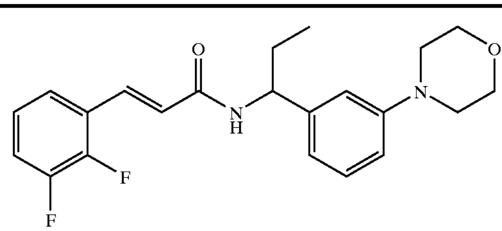 | (±)-3-(2,3-Difluoro-phenyl)-N-[1-(3-morpholin-4-yl-phenyl)-propyl]-acrylamide | 1.50 (b) | 387 |
| 132 | 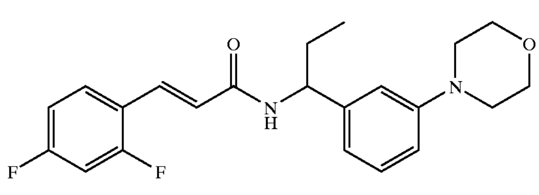 | (±)-3-(2,4-Difluoro-phenyl)-N-[1-(3-morpholin-4-yl-phenyl)-propyl]-acrylamide | 1.47 (b) | 387 |

-continued

| Example No. | Structure | Chemical Name | HPLC rt (min), method | Mass (M + H)+ m/z |
|---|---|---|---|---|
| 133 | 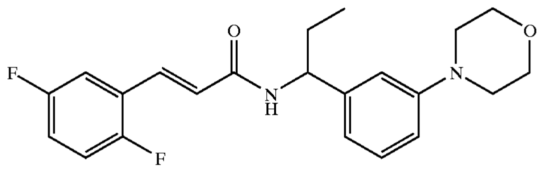 | (±)-3-(2,5-Difluoro-phenyl)-N-[1-(3-morpholin-4-yl-phenyl)-propyl]-acrylamide | 1.47 (b) | 377 |
| 134 | 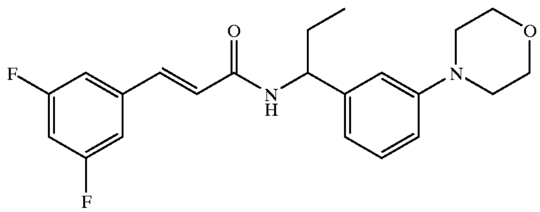 | (±)-3-(3,5-Difluoro-phenyl)-N-[1-(3-morpholin-4-yl-phenyl)-propyl]-acrylamide | 1.53 (b) | 387 |
| 135 | 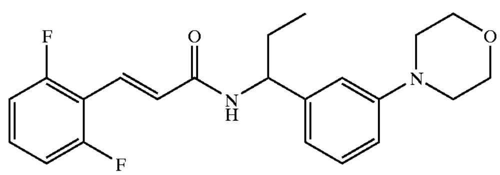 | (±)-3-(2,6-Difluoro-phenyl)-N-[1-(3-morpholin-4-yl-phenyl)-propyl]-acrylamide | 1.45 (b) | 387 |
| 136 | 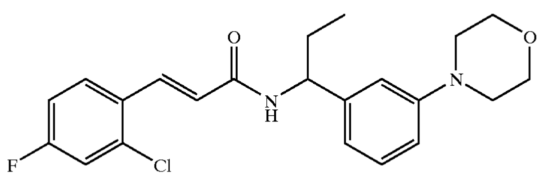 | (±)-3-(2-Chloro-4-fluoro-phenyl)-N-[1-(3-morpholin-4-yl-phenyl)-propyl]-acrylamide | 1.60 (r) | 403 |
| 137 | 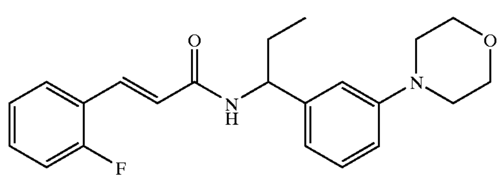 | (±)-3-(2-Fluoro-phenyl)-N-[1-(3-morpholin-4-yl-phenyl)-propyl]-acrylamide | 1.43 (r) | 369 |
| 138 | 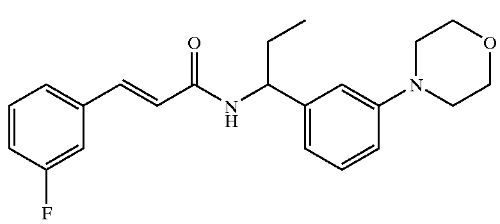 | (±)-3-(3-Fluoro-phenyl)-N-[1-(3-morpholin-4-yl-phenyl)-propyl]-acrylamide | 1.46 (r) | 369 |

-continued

| Example No. | Structure | Chemical Name | HPLC rt (min), method | Mass (M + H)+ m/z |
|---|---|---|---|---|
| 139 | 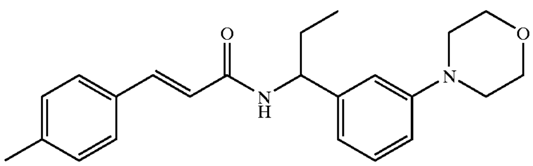 | (±)-3-(4-Methyl-phenyl)-N-[1-(3-morpholin-4-yl-phenyl)-propyl]-acrylamide | 1.49 (r) | 365 |
| 140 | 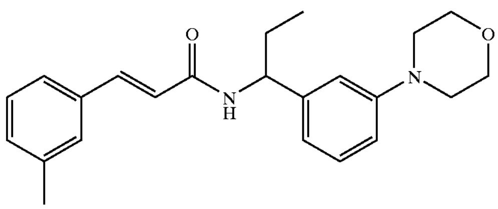 | (±)-3-(3-Methyl-phenyl)-N-[1-(3-morpholin-4-yl-phenyl)-propyl]-acrylamide | 1.53 (r) | 365 |
| 141 | 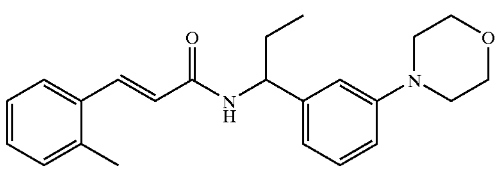 | (±)-3-(2-Methyl-phenyl)-N-[1-(3-morpholin-4-yl-phenyl)-propyl]-acrylamide | 1.51 (r) | 365 |
| 142 | 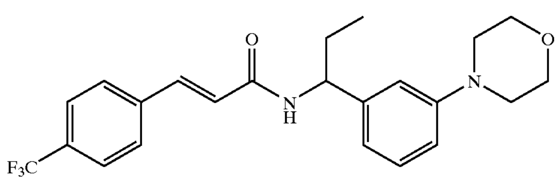 | (±)-3-(4-Trifluoromethyl-phenyl)-N-[1-(3-morpholin-4-yl-phenyl)-propyl]-acrylamide | 1.66 (r) | 419 |

Example 143

Preparation of (±)-3-(2-fluoro-phenyl)-N-[2,2,2-trifluoro-1-(3-morpholin-4-yl-phenyl)ethyl]acrylamide

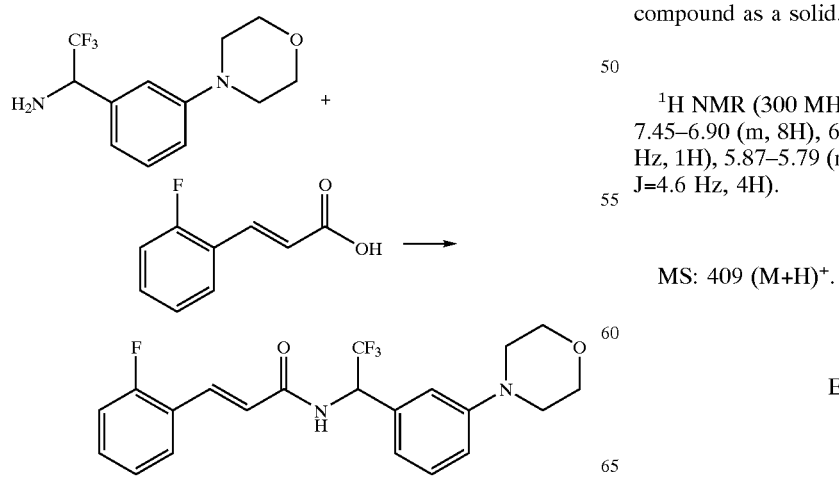

A mixture of 2-fluorocinnamic acid (33 mg), 2,2,2-trifluoro-1-(3-morpholin-4-yl-phenyl)-ethylamine, Preparation 23 (52 mg), DMAP (24 mg), EDC.HCl (80 mg), and Et₃N (80 mg) in CH₂Cl₂ (4 mL) was stirred for 16 hours. Purification by flash chromatography over silica gel (elution with 50% ethyl acetate in hexane) gave 65 mg of the title compound as a solid.

¹H NMR (300 MHz, CDCl₃): δ 7.75 (d, J=15.7 Hz, 1H), 7.45–6.90 (m, 8H), 6.63 (d, J=15.7 Hz, 1H), 6.45 (d, J=9.4 Hz, 1H), 5.87–5.79 (m, 1H), 3.84 (t, J=4.6 Hz, 4H), 3.16 (t, J=4.6 Hz, 4H).

MS: 409 (M+H)+.

Examples 144–148

Examples 144–148 were made from appropriate acid using the same method used to prepare Example 143.

| Example No. | Structure | Chemical Name | HPLC rt (min), method | Mass (M + H)+ m/z |
|---|---|---|---|---|
| 144 | 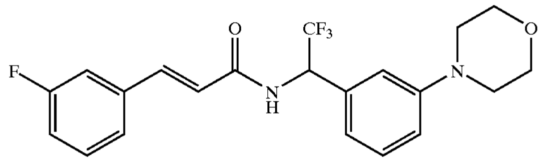 | (±)-3-(3-Fluoro-phenyl)-N-[2,2,2-trifluoro-1-(3-morpholin-4-yl-phenyl)-ethyl]-acrylamide | 1.59 (j) | 409 |
| 145 | 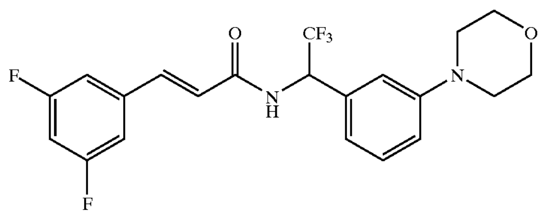 | (±)-3-(3,5-Difluoro-phenyl)-N-[2,2,2-trifluoro-1-(3-morpholin-4-yl-phenyl)-ethyl]-acrylamide | 1.64 (j) | 427 |
| 146 | 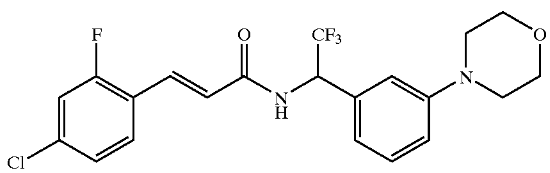 | (±)-3-(4-Chloro-2-fluoro-phenyl)-N-[2,2,2-trifluoro-1-(3-morpholin-4-yl-phenyl)-ethyl]-acrylamide | 1.73 (j) | 443 |
| 147 | 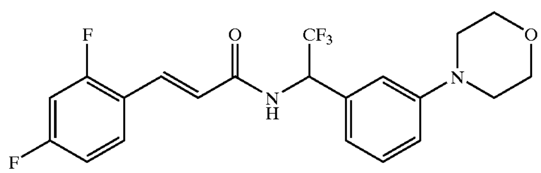 | (±)-3-(2,4-Difluoro-phenyl)-N-[2,2,2-trifuoro-1-(3-morpholin-4-yl-phenyl)-ethyl]-acrylamide | 1.61 (j) | 427 |
| 148 | 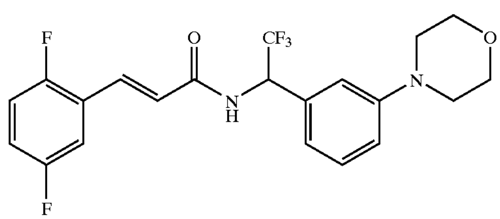 | (±)-3-(2,5-Difluoro-phenyl)-N-[2,2,2-trifluoro-1-(3-morpholin-4-yl-phenyl)-ethyl]-acrylamide | 1.62 (j) | 427 |

Example 149

Preparation of N-[1-(4-Fluoro-3-morpholin-4-yl-phenyl)ethyl]-3-phenyl-acrylamide

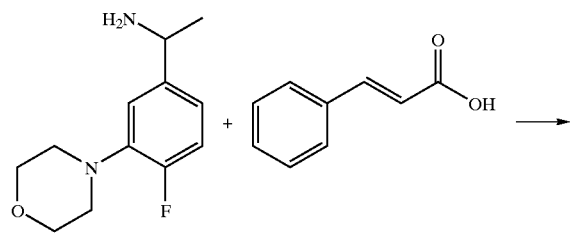

-continued

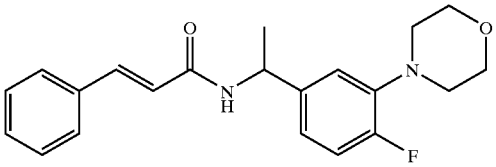

A mixture of cinnamic acid (23 mg), 1-(4-fluoro-3-morpholin-4-yl-phenyl)-ethylamine, Preparation 26 (34 mg), DMAP (18 mg), EDC.HCl (27 mg), and Et$_3$N (66 mg) in CH$_2$Cl$_2$ (4 mL) was stirred for 16 hours. Purification by fresh chromatography over silica gel (elution with 50% ethyl acetate in hexane) gave 51 mg of the title compound as a solid.

$^1$H NMR (300 MHz, CDCl$_3$): δ 7.69 (d, J=15.6 Hz, 1H), 7.49–7.34 (m, 5H), 6.99–6.92 (m, 3H), 6.38 (d, J=15.6 Hz,

1H), 5.85 (d, J=7.9 Hz, 1H), 5.25–5.19 (m, 1H), 3.86 (t, J=4.6 Hz, 4H), 3.09 (t, J=4.6 Hz, 4H), 1.53 (d, J=6.9 Hz, 3H).

MS: 355 (M+H)+.

Examples 150–169

Examples 150–169 were made from appropriate acide using the same procedures to prepare Example 149.

| Example No. | Structure | Chemical Name | HPLC rt (min), method | Mass (M + H)+ m/z |
|---|---|---|---|---|
| 150 | 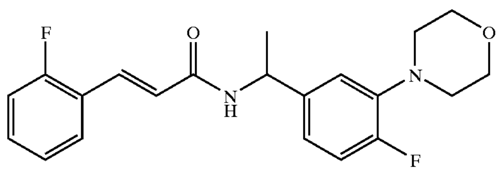 | (±)-N-[1-(4-Fluoro-3-morpholin-4-yl-phenyl)-ethyl]-3-(2-fluoro-phenyl)-acrylamide | 1.46 (j) | 373 |
| 151 | 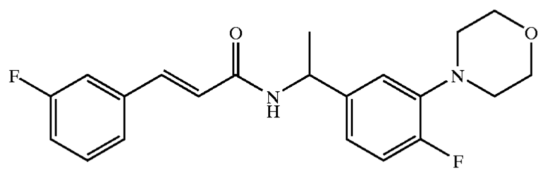 | (±)-N-[1-(4-Fluoro-3-morpholin-4-yl-phenyl)-ethyl]-3-(3-fluoro-phenyl)-acrylamide | 1.48 (j) | 373 |
| 152 | 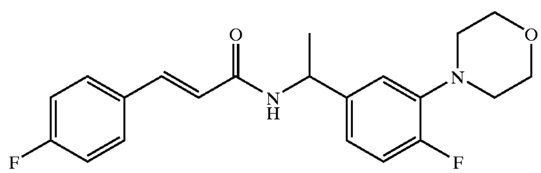 | (±)-N-[1-(4-Fluoro-3-morpholin-4-yl-phenyl)-ethyl]-3-(4-fluoro-phenyl)-acrylamide | 1.51 (j) | 373 |
| 153 | 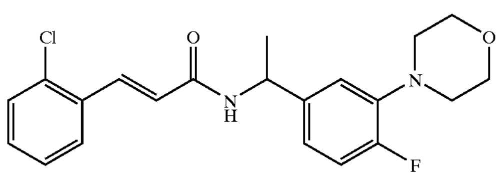 | (±)-N-[1-(4-Fluoro-3-morpholin-4-yl-phenyl)-ethyl]-3-(2-chloro-phenyl)-acrylamide | 1.54 (j) | 389 |
| 154 | 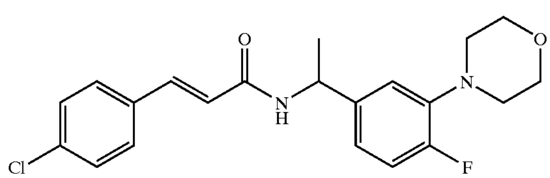 | (±)-N-[1-(4-Fluoro-3-morpholin-4-yl-phenyl)-ethyl]-3-(4-chloro-phenyl)-acrylamide | 1.60 (j) | 389 |
| 155 | 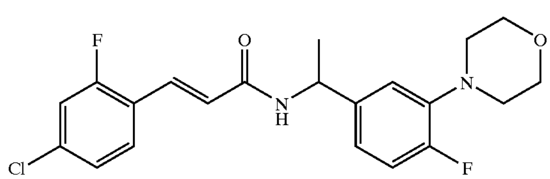 | (±)-N-[1-(4-Fluoro-3-morpholin-4-yl-phenyl)-ethyl]-3-(4-chloro-2-fluoro-phenyl)-acrylamide | 1.63 (j) | 407 |
| 156 | 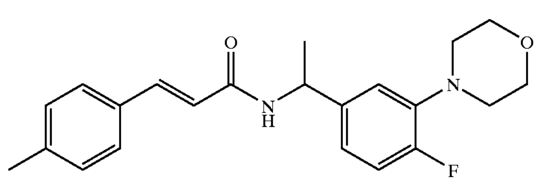 | (±)-N-[1-(4-Fluoro-3-morpholin-4-yl-phenyl)-ethyl]-3-(4-methyl-phenyl)-acrylamide | 1.54 (j) | 369 |

-continued

| Example No. | Structure | Chemical Name | HPLC rt (min), method | Mass (M + H)+ m/z |
|---|---|---|---|---|
| 157 | 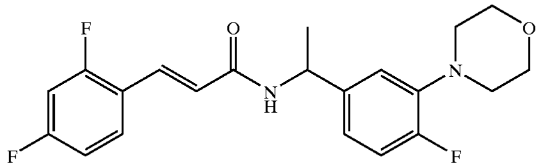 | (±)-N-[1-(4-Fluoro-3-morpholin-4-yl-phenyl)-ethyl]-3-(2,4-difluoro-phenyl)-acrylamide | 1.51 (j) | 391 |
| 158 | 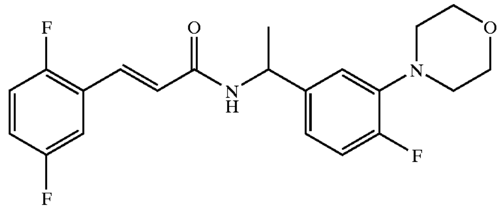 | N-[1-(4-Fluoro-3-morpholin-4-yl-phenyl)-ethyl]-3-(2,5-difluoro-phenyl)-acrylamide | 1.50 (j) | 391 |
| 159 | 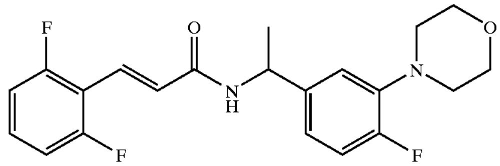 | (±)-N-[1-(4-Fluoro-3-morpholin-4-yl-phenyl)-ethyl]-3-(2,6-difluoro-phenyl)-acryalmide | 1.49 (j) | 391 |
| 160 | 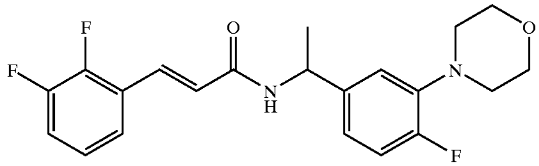 | (±)-N-[1-(4-Fluoro-3-morpholin-4-yl-phenyl)-ethyl]-3-(2,3-difluoro-phenyl)-acrylamide | 1.50 (j) | 391 |
| 161 | 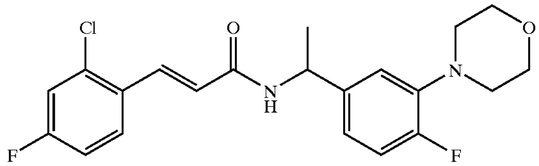 | (±)-N-[1-(4-Fluoro-3-morpholin-4-yl-phenyl)-ethyl]-3-(2-chloro-4-fluoro-phenyl)-acrylamide | 1.58 (j) | 407 |
| 162 | enantiomer chirality undetermined | 3-(2,4-Difluoro-phenyl)-N-[1-(4-fluoro-3-morpholin-4-yl-phenyl)-ethyl]-acrylamide | 46.4 (n) | 391 |
| 163 | enantiomer chirality undetermined | 3-(3,5-Difluoro-phenyl)-N-[1-(4-fluoro-3-morpholin-4-yl-phenyl)-ethyl]-acrylamide | 26.7 (n) | 391 |

-continued

| Example No. | Structure | Chemical Name | HPLC rt (min), method | Mass (M + H)+ m/z |
|---|---|---|---|---|
| 164 | enantiomer chirality undetermined | 3-(3,4-Difluoro-phenyl)-N-[1-(4-fluoro-3-morpholin-4-yl-phenyl)-ethyl]-acrylamide | 43.6 (n) | 391 |
| 165 | enantiomer chirality undetermined | 3-(2,5-Difluoro-phenyl)-N-[1-(4-fluoro-3-morpholin-4-yl-phenyl)-ethyl]-acrylamide | 31.6 (n) | 391 |
| 166 | enantiomer chirality undetermined | 3-(2,3-Difluoro-phenyl)-N-[1-(4-fluoro-3-morpholin-4-yl-phenyl)-ethyl]-acrylamide | 28.2 (n) | 391 |
| 167 | enantiomer chirality undetermined | N-[1-(4-Fluoro-3-morpholin-4-yl-phenyl)-ethyl]-3-(3-fluoro-phenyl)-acrylamide | 37.1 (n) | 371 |
| 168 | enantiomer chirality undetermined | N-[1-(4-Fluoro-3-morpholin-4-yl-phenyl)-ethyl]-3-(2-fluoro-phenyl)-acrylamide | 42.9 (n) | 371 |

Example 169

Preparation of (S)-N-[1-(4-Fluoro-3-morpholin-4-yl-phenyl)-ethyl]-3-(4-fluoro-phenyl)-acrylamide

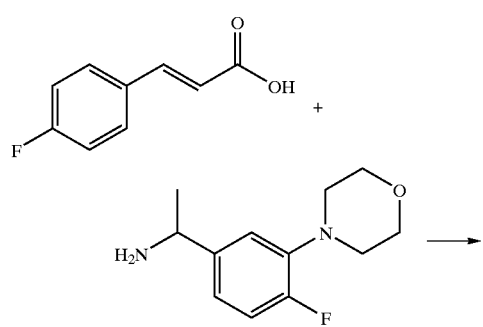

→

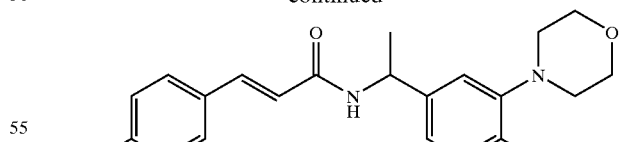

A mixture of 4-fluorocinnamic acid (3.16 g, 19.6 mmol), 1-(4-Fluoro-3-morpholin-4-yl-phenyl)-ethylamine (4.39 g, 19.1 mmol), EDC.HCl (7.53 g, 39.2 mmol), DMAP (2.39 g, 19.6 mmol) and Et$_3$N (8.23 ml, 58.8 mmol) in CH$_2$Cl$_2$ (60 ml) was stirred at room temperature for 16 hours. Purification by flesh chromatography over silica gel (elution with 50% ethyl acetate in hexane) gave 6.9 g of the title compound. The enantiomer was separated by Chiralpak AD column (50×500 mm, 20um) eluted with 45% EtOH in hexane, RT=36.1 min.

$^1$H NMR (300 MHz, CDCl$_3$): δ 7.58 (d, 1H), 7.56–7.41 (m, 2H), 7.05–6.89 (m, 5H), 6.30 (d, 1H), 5.92 (d, 1H), 5.19 (m, 1H), 3.84 (t, 4H), 3.06 (t, 4H), 1.52 (d, 3H).

MS: 373 (M+H)$^+$.

$[α]_D^{25}$=+23.21 (EtOH).

Example 170

Preparation of (±)-N-[1-(2-Fluoro-5-morpholin-4-yl-phenyl)ethyl]-3-(2-fluoro-phenyl)acrylamide

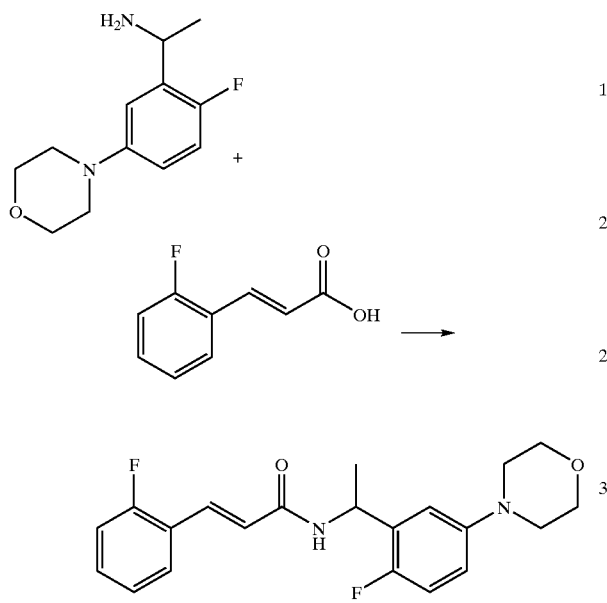

A mixture of 2-fluoro-cinnamic acid (83 mg), 1-(2-fluoro-5-morpholin-4-yl-phenyl)ethylamine, Preparation 25(112 mg), DMAP (61 mg), EDC.HCl (190 mg), and Et$_3$N (202 mg) in CH$_2$Cl$_2$ (4 mL) was stirred for 16 hours. The crude product was purified by flash chromatography over silica gel (elution with 50% ethyl acetate in hexane) to give 150 mg of the title compound as a solid.

$^1$H NMR (300 MHz, CDCl$_3$): δ 7.69 (d, J=15.8 Hz, 1H), 7.40–6.78 (m, 8H), 6.53 (d, J=15.8 Hz, 1H), 6.16 (d, J=8.3 Hz, 1H), 5.37–5.27 (m, 1H), 3.84 (t, J=4.7 Hz, 4H), 3.09 (t, J=4.9 Hz, 4H), 1.56 (d, J=7.0 Hz, 3H).

MS: 373 (M+H)$^+$.

Example 171

Preparation of (±)-N-[1-(3-fluoro-5-morpholin-4-yl-phenyl)ethyl]-3-phenyl-acrylamide

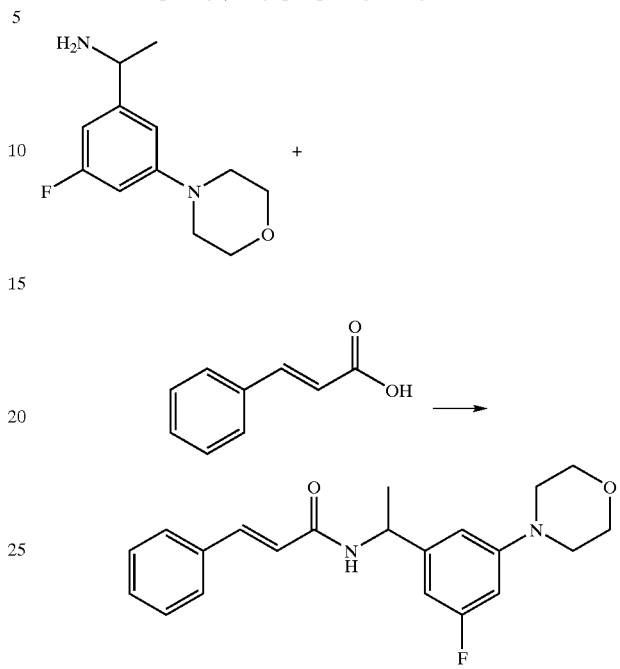

A mixture of cinnamic acid (44 mg), 1-(3-fluoro-5-morpholin-4-yl-phenyl)ethylamine, Preparation 24 (66 mg), DMAP (36 mg), EDC.HCl (120 mg), and Et$_3$N (120 mg) in CH$_2$Cl$_2$ (4 mL) was stirred for 16 hours. Purification of the crude product by flash chromatography over silica gel (elution with 50% ethyl acetate in hexane) gave 78 mg of the title compound as a solid.

$^1$H NMR (300 MHz, CDCl$_3$): δ 7.75 (d, J=15.6 Hz, 1H), 7.48–7.33 (m, 5H), 6.61–6.26 (m, 5H), 5.25–5.14 (m, 1H), 3.84 (t, J=4.7 Hz, 4H), 3.16 (t, J=4.7 Hz, 4H), 1.51 (d, J=6.9 Hz, 3H).

MS: 355 (M+H)$^+$.

Examples 172–182

Examples 172–182 were made from appropriate acids using the same procedures used to prepare Example 171.

| Example No. | Structure | Chemical Name | HPLC rt (min), method | Mass (M + H)$^+$ m/z |
|---|---|---|---|---|
| 172 | ![structure] | (±)-N-[1-(3-Fluoro-5-morpholin-4-yl-phenyl)-ethyl]-3-(3-fluoro-phenyl)-acrylamide | 1.57 (j) | 373 |

-continued

| Example No. | Structure | Chemical Name | HPLC rt (min), method | Mass (M + H)+ m/z |
|---|---|---|---|---|
| 173 | 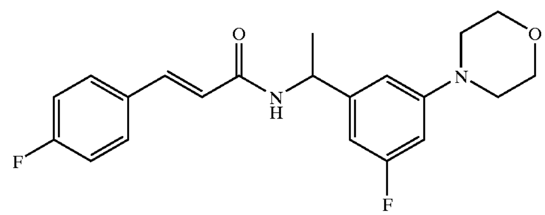 | (±)-N-[1-(3-Fluoro-5-morpholin-4-yl-phenyl)-ethyl]-3-(4-fluoro-phenyl)-acrylamide | 1.55 (j) | 373 |
| 174 | 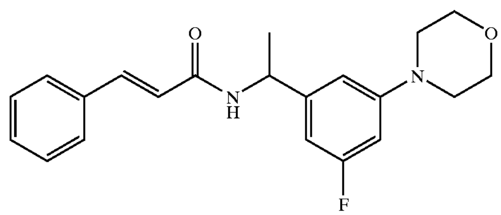 | (±)-N-[1-(3-Fluoro-5-morpholin-4-yl-phenyl)-ethyl]-3-(phenyl)-acrylamide | 1.52 (j) | 355 |
| 175 | 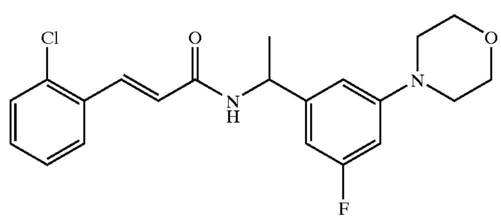 | (±)-N-[1-(3-Fluoro-5-morpholin-4-yl-phenyl)-ethyl]-3-(2-chloro-phenyl)-acrylamide | 1.63 (j) | 389 |
| 176 | 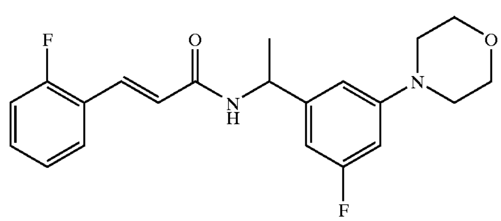 | (±)-N-[1-(3-Fluoro-5-morpholin-4-yl-phenyl)-ethyl]-3-(2-fluoro-phenyl)-acrylamide | 1.55 (j) | 373 |
| 177 | 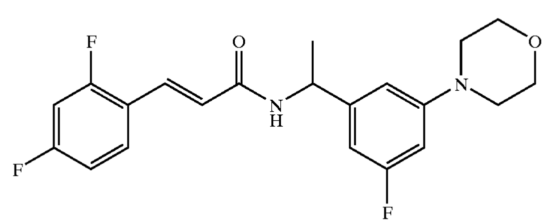 | (±)-N-[1-(3-Fluoro-5-morpholin-4-yl-phenyl)-ethyl]-3-(2,4-difluoro-phenyl)-acrylamide | 1.59 (j) | 391 |
| 178 | 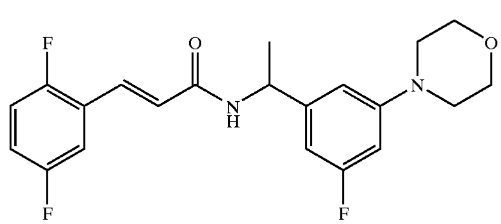 | (±)-N-[1-(3-Fluoro-5-morpholin-4-yl-phenyl)-ethyl]-3-(2,5-difluoro-phenyl)-acrylamide | 1.59 (j) | 391 |

-continued

| Example No. | Structure | Chemical Name | HPLC rt (min), method | Mass (M + H)+ m/z |
|---|---|---|---|---|
| 179 | 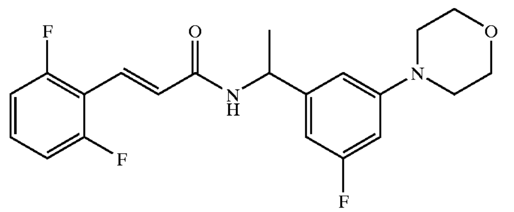 | (±)-N-[1-(3-Fluoro-5-morpholin-4-yl-phenyl)-ethyl]-3-(2,6-difluoro-phenyl)-acrylamide | 1.58 (j) | 391 |
| 180 | 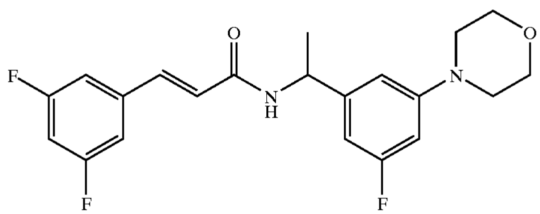 | (±)-N-[1-(3-Fluoro-5-morpholin-4-yl-phenyl)-ethyl]-3-(3,5-difluoro-phenyl)-acrylamide | 1.63 (j) | 391 |
| 181 | 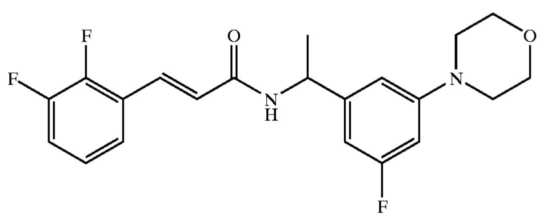 | (±)-N-[1-(3-Fluoro-5-morpholin-4-yl-phenyl)-ethyl]-3-(2,3-difluoro-phenyl)-acrylamide | 1.61 (j) | 391 |
| 182 | 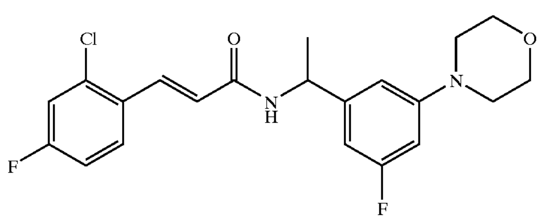 | (±)-N-[1-(3-Fluoro-5-morpholin-4-yl-phenyl)-ethyl]-3-(2-chloro-4-fluoro-phenyl)-acrylamide | 1.69 (j) | 407 |

Example 183

Preparation of (±)-3-(3-Fluorophenyl)-N-[1-(2,3-dihydrobenzo[1,4]dioxin-6-yl)-ethyl]acrylamide (Enantiomer of Undetermined Chirality)

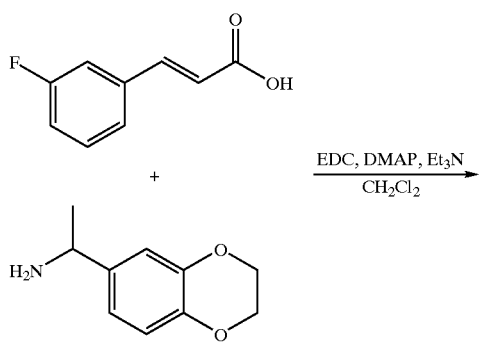

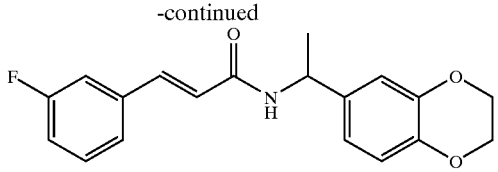

Triethylamine (1 mL, 7 mmole) was added to a solution of 3-fluoro cinnamic acid (0.3 g, 1.8 mmole), (±)-1-(2,3-dhydrobenzo[1,4]dioxin-6-yl)ethylamine, Preparation 6 (0.32 g, 2 mmole), EDC (0.7 g, 4 mole), and DMAP (0.21 g, 1.8 mmole) in CH$_2$Cl$_2$ (25 mL). The reaction mixture was stirred at room temperature for 16 hours. The reaction mixture was then washed with water (2×10 mL). The organic layer was dried over anhydrous magnesium sulfate, filtered, and the resultant filtrate was concentrated in vacuo. The residue was purified by the following methods: 1) flash column chromatography using Ethyl Acetate (100%); 2) chiral HPLC using an OD column (Hexane/Ethanol (7.5:2.5). The title compound was obtained as a white solid. Retention time: 105.9 min (Chiralpak AD column, 50×500 mm, 85% hexanes/15% ethanol, 75 mL/min flow rate)

$^1$H NMR (DMSO-d$_6$): δ 1.36 (d, J=7 Hz, 3H), 4.21 (m, 4H), 4.93 (m, 1H), 6.69 (H, d, J=16 Hz), 6.79 (1H, s), 6.81 (1H, d, J=16 Hz), 7.23 (broad t, J=8.1 Hz, 1H), 7.43 (m, 4H), 8.47 (d, J=8.1 Hz, 1H).

MS: 341 (M+H)$^+$.

Examples 184–195

Examples 184–195 were prepared as depicted in the following general reaction scheme, according to the following general procedure, and substantially in the same fashion as Example 183:

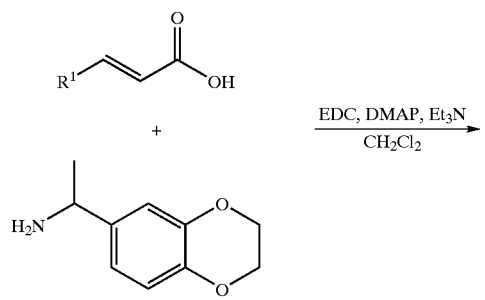

-continued

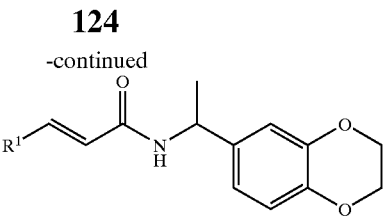

General Procedure

A mixture of an appropriate cinnamic acid derivative (1.8 mmol), (±)-1-(2,3-dihydrobenzo[1,4]dioxin-6-yl)ethylamine, Preparation 6 (0.32 g, 2.0 mmol), EDC hydrochloride (0.7 g, 4.0 mmol), and DMAP (0.21 g, 1.8 mmol), and triethylamine (1.0 mL, 7.0 mmol) in CH$_2$Cl$_2$ (25 mL) was stirred at room temperature for 16 hours. The reaction mixture was then washed with water (2×10 mL). The organic layer was dried over anhydrous magnesium sulfate, filtered and the resultant filtrate was concentrated in vacuo. The residue was purified by: 1) flash column chromatography on silica typically eluted with EtOAc (100%) and (for Examples 191–194) a second purification as follows: 2) chiral HPLC using an OD column (Hexane/Ethanol (7.5:2.5)).

| Example No. | Structure | Chemical Name | HPLC rt (min), method | Mass (M + H)$^+$ m/z |
|---|---|---|---|---|
| 184 | 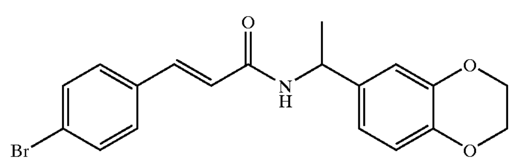 | (±)-3-(4-Bromo-phenyl)-N-[1-(2,3-dihydro-benzo[1,4]diox-in-6-yl)-eth-yl]-acrylamide | 1.48 (b) | 388 |
| 185 | 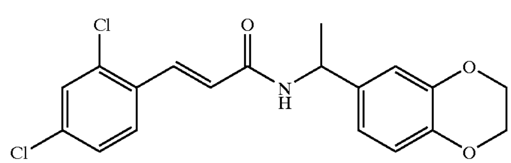 | (±)-3-(2,4-Dichloro-phen-yl)-N-[1-(2,3-di-hydro-benzo[1,4]-diox-in-6-yl)-ethyl]-acryla-mide | 1.59 (b) | 378 |
| 186 | 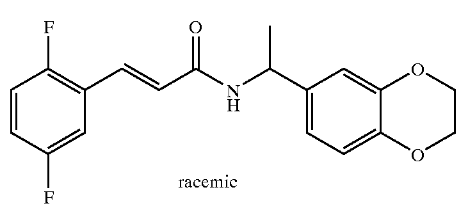 | (±)-3-(2,5-Difluoro-phen-yl)-N-[1-(2,3-di-hydro-benzo[1,4]-diox-in-6-yl)-ethyl]-acryla-mide | | 346 |
| 187 | 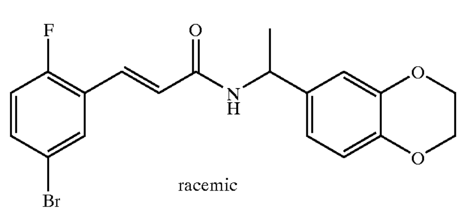 | (±)-3-(5-Bromo-2-fluoro-phen-yl)-N-[1-(2,3-di-hydro-benzo[1,4]-diox-in-6-yl)-ethyl]-acryla-mide | | 408 |

-continued

| Example No. | Structure | Chemical Name | HPLC rt (min), method | Mass (M + H)+ m/z |
|---|---|---|---|---|
| 188 | racemic | (±)-3-(2-Chloro-4-fluoro-phenyl)-N-[1-(2,3-dihydro-benzo[1,4]-dioxin-6-yl)-ethyl]-acrylamide | | 362 |
| 189 | racemic | (±)-3-(2,3-Difluoro-phenyl)-N-[1-(2,3-dihydro-benzo[1,4]-dioxin-6-yl)-ethyl]-acrylamide | | 346 |
| 190 | racemic | 3-(2-Chloro-phenyl)-N-[1-(2,3-dihydro-benzo[1,4]dioxin-6-yl)-ethyl]-acrylamide | | 344 |
| 191 | enantiomer chirality undetermined | N-[1-(2,3-Dihydro-benzo[1,4]dioxin-6-yl)-ethyl]-3-(4-isopropyl-phenyl)-acrylamide | 66.0 (n) | 352 |
| 192 | enantiomer chirality undetermined | 3-(2-Bromo-phenyl)-N-[1-(2,3-dihydro-benzo[1,4]dioxin-6-yl)-ethyl]-acrylamide | 89.9 (o) | 390 |
| 193 | enantiomer chirality undetermined | N-[1-(2,3-Dihydro-benzo[1,4]dioxin-6-yl)-ethyl]-3-m-tolyl-acrylamide | 48.7 (n) | 324 |

-continued

| Example No. | Structure | Chemical Name | HPLC rt (min), method | Mass (M + H)+ m/z |
|---|---|---|---|---|
| 194 | 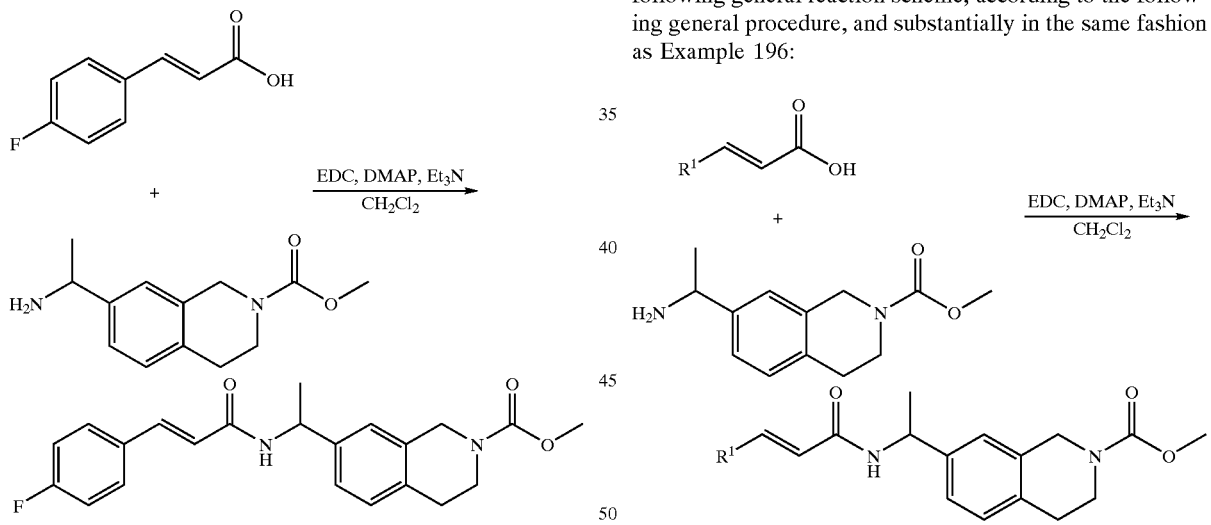  enantiomer chirality undetermined | 3-(2,4-Difluoro-phenyl)-N-[1-(2,3-di-hydro-benz-o[1,4]dioxin-6-yl)-eth-yl]-acrylamide | 57.9 (n) | 346 |
| 195 | racemic | (±)-3-Benzo[1,3]dioxol-5-yl-N-[1-(2,3-di-hydro-benz-o[1,4]dioxin-6-yl)-eth-yl]-acrylamide | | 354 |

Example 196

Preparation of (±)-7-{1-[3-(4-Fluorophenyl) acryloylamino]ethyl}3,4-dihydro-1H-isoquinoline-2-carboxylic acid methyl ester A mixture of 4-fluorocinnamic acid (1 mmol), (±)-7-(1-aminoethyl)-3,4-dihydro-1H-isoquinoline-2-carboxylic acid methyl ester, Preparation 10 (280 mg, 1.2 mmol), EDC hydrochloride (387 mg, 2 mmol), DMAP (122 mg, 1 mmol), and triethylamine (404 mg, 4 mmol) in CH$_2$Cl$_2$ (8 mL) was stirred at room temperature for 16 hours. The reaction mixture was directly subjected to purification by flash column chromatography on silica gel eluted with EtOAc/hexane (50%) to provide the title compound (295 mg).

$^1$H NMR (CDCl$_3$): δ 7.59 (d, J=15.5 Hz, 1H), 7.49–7.44 (m, 2H), 7.17–7.02 (m, 5H), 6.30 (d, J=15.5 Hz, 1H), 5.79 (d, J=7.7 Hz, 1H), 5.21–5.13 (m, 1H), 4.51 (s, 2H), 3.78–3.68 (m, 2H), 3.74 (s, 3H), 2.84–2.82 (m, 2H), 1.54 (d, J=6.9 Hz, 3H).

MS: 382 (M+H)+.

Examples 197–201

Examples 197–201 were prepared as depicted in the following general reaction scheme, according to the following general procedure, and substantially in the same fashion as Example 196:

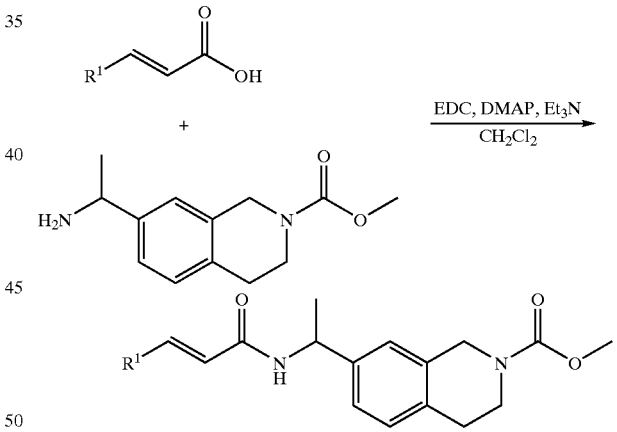

General Procedure

A mixture of an appropriate cinnamic acid derivative (1 mmol), (±)-7-(1-aminoethyl)-3,4-dihydro-1H-isoquinoline-2-carboxylic acid methyl ester, Preparation 10 (280 mg, 1.2 mmol), EDC hydrochloride (387 mg, 2 mmol), DMAP (122 mg, 1 mmol), and triethylamine (404 mg, 4 mmol) in CH$_2$Cl$_2$ (8 mL) was stirred at room temperature for 16 hours. The reaction mixture was directly subjected to purification by flash column chromatography on silica gel typically eluted with EtOAc/hexane (50%) to provide the compound of Examples 197–201.

| Example No. | Structure | Chemical Name | HPLC rt (min), method | Mass (M + H)+ m/z |
|---|---|---|---|---|
| 197 | racemic | (±)-7-[1-(3-Phenyl-acryloyl-amino)-ethyl]-3,4-di-hydro-1H-iso-quinoline-2-carboxylic acid methyl ester | 1.52 (b) | 365 |
| 198 | racemic | (±)-7-{1-[3-(2-Fluoro-phen-yl)-acryloylamino]-eth-yl}-3,4-dihydro-1H-iso-quinoline-2-carboxylic acid methyl ester | 1.41 (b) | 382 |
| 199 | racemic | (±)-7-{1-[3-(4-Chloro-phen-yl)-acryloylamino]-eth-yl}-3,4-dihydro-1H-iso-quinoline-2-carboxylic acid methyl ester | 1.69 (b) | 399 |
| 200 | racemic | (±)-7-[1-(3-o-Tolyl-acryloyl-amino)-ethyl]-3,4-di-hydro-1H-iso-quinoline-2-carboxylic acid methyl ester | 1.62 (b) | 379 |
| 201 | racemic | (±)-7-{1-[3-(2-Chloro-phen-yl)-acryloylamino]-eth-yl}-3,4-dihydro-1H-iso-quinoline-2-carboxylic acid methyl ester | 1.63 (b) | 399 |

Example 202

Preparation of 3-(2-Fluorophenyl)-N-[1-(4-methyl-3,4-dihydro-2H-benzo[1,4]oxazin-6-yl)ethyl] acrylamide

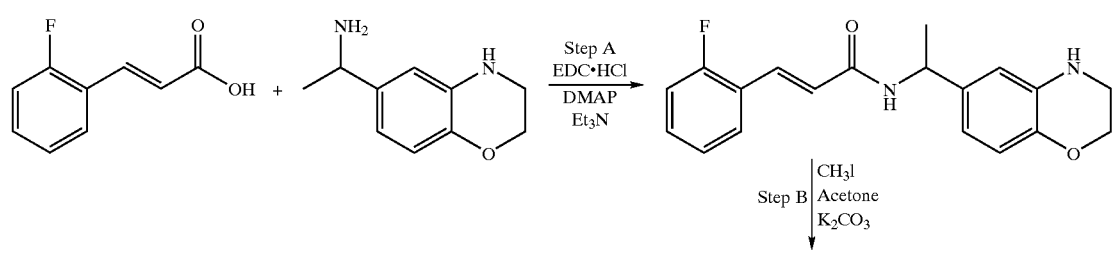

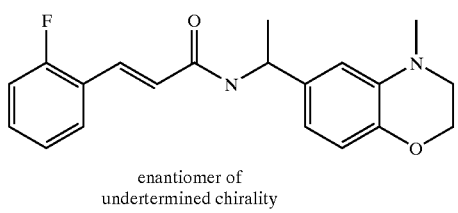

enantiomer of
undetermined chirality

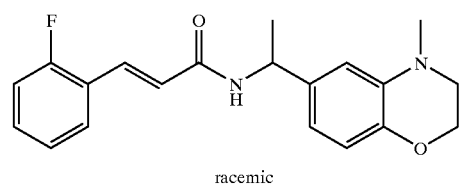

racemic

Step C
chiral HPLC

Step A: (±)-N-[1-(3,4-dihydro-2H-benzo[1,4]oxazin-6-yl)-ethyl]-3-(2-fluorophenyl)acrylamide A mixture of 2-fluorocinnamic acid (0.5 mmol), (±)-1-(3,4-dihydro-2H-benzo[1,4]oxazin-6-yl)ethylamine, Preparation 13 (28.5 mg, 0.16 mmol), EDC hydrochloride (192 mg, 1 mmol), DMAP (61 mg, 0.5 mmol), and triethylamine (202 mg, 2 mmol) in $CH_2Cl_2$ was stirred for 3 days. The reaction mixture was directly subjected to purification by flash column chromatography on silica using EtOAc/Hexane (8:1) to provide the desired product (149 mg).
$^1$H NMR (CDCl$_3$): δ 7.68 (d, J=15.8 Hz, 1H), 7.48–7.43 (m, 1H), 7.34–7.25 (m, 1H), 7.15–7.04 (m, 2H), 6.75 (d, J=8.2 Hz, 1H), 6.66–6.59 (m, 2H), 6.50 (d, 15.8 Hz, 1H), 5.90 (d, J=7.6 Hz, 1H), 5.17–5.07 (m, 1H), 4.23 (t, J=4.2 Hz, 2H), 3.40 (t, J=4.2 Hz, 2H), 1.50 (d, J=6.8 Hz, 3H).
MS: 326 (M+H)$^+$.

Step B: (±)-3-(2-fluorophenyl)-N-[1-(4-methyl-3,4-dihydro-2H-benzo[1,4]oxazin-6-yl)ethyl]acrylamide A mixture of (±)-N-[1-(3,4-dihydro-2H-benzo[1,4]oxazin-6-yl)ethyl]-3-(2-fluoro-phenyl)acrylamide [Product of Step A, (0.3 mmol)], methyl iodide (2 mL), and potassium carbonate (138 mg) in acetone (8 mL) was heated under reflux for 2 hours. The reaction mixture was cooled to room temperature and concentrated in vacuo. The residual material was taken up in $CH_2Cl_2$ (10 mL) and the insoluble material was filtered off. The resultant filtrate was concentrated in vacuo and the resultant crude material was purified by flash column chromatography on silica using EtOAc/hexane (2:1) to provide the title compound (64.5 mg) of Example 202.

$^1$H NMR (CDCl$_3$): δ 7.69 (d, J=15.8 Hz, 1H), 7.48–7.43 (m, 1H), 7.34–7.27 (m, 1H), 7.15–7.04 (m, 1H), 6.74 (d, J=8.3 Hz, 1H), 6.66–6.63 (m, 2H), 6.50 (d, J=15.8 Hz, 1H), 5.88 (b, 1H), 5.22–5.12 (m, 1H), 4.27 (t, J=4.4 Hz, 2H), 3.26 (t, J=4.4 Hz, 2H), 2.89 (s, 3H), 1.54 (d, J=6.8 Hz, 3H).
MS: 341 (M+H)$^+$.

Step C: Separation of 3-(2-fluorophenyl)-N-[1-(4-methyl-3,4-dihydro-2H-benzo[1,4]oxazin-6-yl)ethyl]acrylamide (chirality undetermined)

(±)-3-(2-Fluorophenyl)-N-[1-(4-methyl-3,4-dihydro-2H benzo[1,4]oxazin-6-yl)ethyl]-acrylamide was separated by HPLC using chiral OD column to give the title compound as a single enantiomer of undetermined chirality of Example 203 in the following table.

Examples 203–213

Examples 203–211 were prepared in substantially the same fashion as described for Steps A and B of Example 202 starting from the appropriate cinnamic acid derivative. Example-213 was prepared in substantially the same fashion as described for Step A of Example 202, starting from the appropriate cinnamic acid derivative and Example 212 was prepared in substantially the same fashion as described for Steps A and C of Example 202.

| Example No. | Structure | Chemical Name | HPLC rt (min), method | Mass (M + H)$^+$ m/z |
|---|---|---|---|---|
| 203 | (structure shown, racemic) | (±)-3-(3-Chloro-phenyl)-N-[1-(4-methyl-3,4-dihydro-2H-benzo[1,4]oxazin-6-yl)-ethyl]-acrylamide | 1.35 (b) | 358 |
| 204 | (structure shown, racemic) | (±)-3-(2-Chloro-4-fluoro-phenyl)-N-[1-(4-methyl-3,4-dihydro-2H-benzo[1,4]oxazin-6yl)ethyl-acrylamide | 1.33 (b) | 375 |

-continued

| Example No. | Structure | Chemical Name | HPLC rt (min), method | Mass (M + H)+ m/z |
|---|---|---|---|---|
| 205 | racemic | (±)-3-(4-Chloro-2-fluoro-phenyl)-N-[1-(4-methyl-3,4-dihydro-2H-benzo-[1,4]oxazin-6-yl)-ethyl]-acrylamide | 1.35 (b) | 375 |
| 206 | racemic | (±)-3-(2,4-Dichloro-phenyl)-N-[1-(4-methyl-3,4-dihydro-2H-benzo-[1,4]oxazin-6-yl)-ethyl]-acrylamide | 1.42 (b) | 391 |
| 207 | racemic | (±)-3-(2,5-Difluoro-phenyl)-N-[1-(4-methyl-3,4-dihydro-2H-benzo-[1,4]oxazin-6-yl)-ethyl]-acrylamide | 1.27 (b) | 359 |
| 208 | racemic | (±)-3-(2,4-Difluoro-phenyl)-N-[1-(4-methyl-3,4-dihydro-2H-benzo-[1,4]oxazin-6-yl)-ethyl]-acrylamide | 1.28 (b) | 359 |
| 209 | racemic | (±)-3-(2-Chloro-phenyl)-N-[1-(4-methyl-3,4-dihydro-2H-benzo[1,4]-oxazin-6-yl)-ethyl]-acrylamide | 1.32 (b) | 357 |
| 210 | racemic | (±)-3-(3-Fluoro-phenyl)-N-[1-(4-methyl-3,4-dihydro-2H-benzo[1,4]-oxazin-6-yl)-ethyl]-acrylamide | 1.26 (b) | 341 |
| 211 | racemic | (±)-3-(4-Fluoro-phenyl)-N-[1-(4-methyl-3,4-dihydro-2H-benzo[1,4]-oxazin-6-yl)-ethyl]-acrylamide | 1.26 (b) | 341 |

-continued

| Example No. | Structure | Chemical Name | HPLC rt (min), method | Mass (M + H)+ m/z |
|---|---|---|---|---|
| 212 | 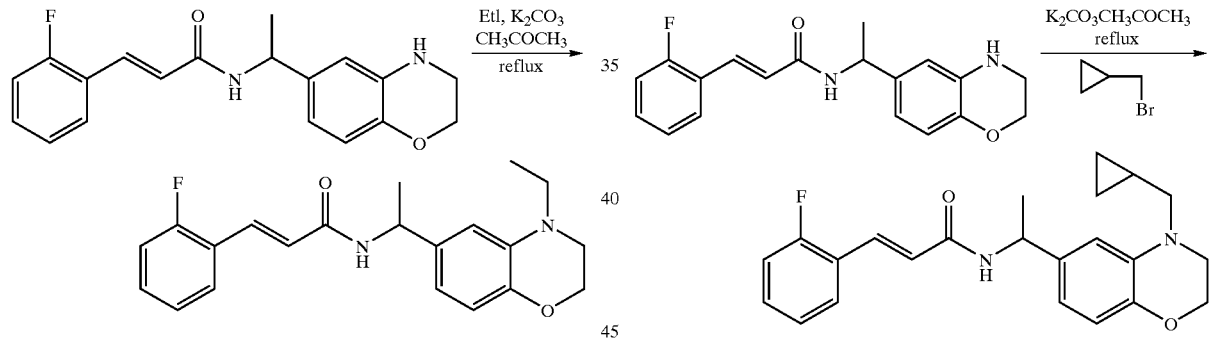 enantiomer chirality undetermined | 3-(2-Chloro-4-fluoro-phenyl)-N-[1-(3,4-di-hydro-2H-benzo-[1,4]oxa-zin-6-yl)-ethyl]-acrylamide | 1.21 (b) | 361 |
| 213 | racemic | (±)-3-(2-Chloro-phenyl)-N-[1-(3,4-di-hydro-2H-benz-o[1,4]oxazin-6-yl)-ethyl]-acrylamide | 1.16 (b) | 343 |

Example 214

Preparation of 3-(2-fluoro-phenyl)-N-[1-(4-ethyl-3,4-dihydro-2H-benzo[1,4]oxazin-6-yl)ethyl]-acrylamide To a solution of N-[1-(3,4-dihydro-2H-benzo[1,4]oxazin-6-yl)-ethyl]-3-(2-fluoro-phenyl)-acrylamide, separated from its racemate (Step A in Example 202) by chiral HPLC (method o), rt 85.73/min) (30 mg) in acetone (5 ml) were added potassium carbonate (38 mg) and ethyl iodide (1 ml). The mixture was refluxed for 2 hours and cooled to room temperature. The solvent was evaporated in vacuo. The crude product was extracted with CH$_2$Cl$_2$ and purified by silica gel chromatography eluting with hexane/ethyl acetate (1:1) to give the title compound (27 mg, 86%).

MS: 355 [M+H]+.

HPLC rt: 1.47 min. (method t).

Example 215

Preparation of 3-(2-fluoro-phenyl)-N-[1-(4-cyclopropylmethyl-3,4-dihydro-2H-benzo[1,4]oxazin-6-yl)ethyl]-acrylamide To a solution of N-[1-(3,4-dihydro-2H-benzo[1,4]oxazin-6-yl)-ethyl]-3-(2-fluoro-phenyl)-acrylamide, separated from its racemate (Step A in Example 202) by chiral HPLC (method o, rt 85.73/min) (30 mg) in acetone (5 ml) were added potassium carbonate (38 mg) and cyclopropylmethyl iodide (1 ml). The mixture was refluxed for 2 hours and cooled to room temperature. The solvent was evaporated in vacuo. The crude product was extracted with CH$_2$Cl$_2$ and purified by silica gel chromatography eluting with hexane/ethyl acetate (1:1) to give the title compound (27 mg, 86%).

MS: 381 [M+H]+.

HPLC rt: 1.58 min. (method t).

Example 216

Preparation of 3-(2-fluoro-phenyl)-N-[1-(4-isopropyl-3,4-dihydro-2H-benzo[1,4]oxazin-6-yl)ethyl]-acrylamide

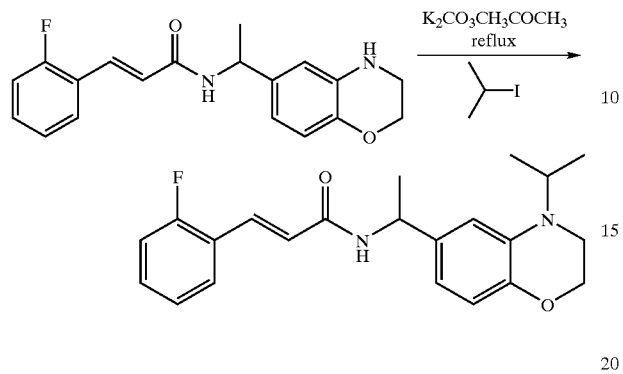

To a solution of N-[1-(3,4-dihydro-2H-benzo[1,4]oxazin-6-yl)-ethyl]-3-(2-fluoro-phenyl)-acrylamide, separated from its racemate (Step A in Example 202) by chiral HPLC (method o, rt 85.73/min) (30 mg) in acetone (5 ml) were added potassium carbonate (38 mg) and iso-propyl iodide (1 ml). The mixture was refluxed for 2 hours and cooled to room temperature. The solvent was evaporated in vacuo. The crude product was extracted with $CH_2Cl_2$ and purified by silica gel chromatography eluting with hexane/ethyl acetate (1:1) to give the title compound (27 mg, 86%).

MS: 369 [M+H]$^+$.

HPLC rt: 1.54 min. (method t).

Example 217

Preparation of 3-(2-fluoro-phenyl)-N-[1-(4-n-propyl-3,4-dihydro-2H-benzo[1,4]oxazin-6-yl)ethyl]acrylamide

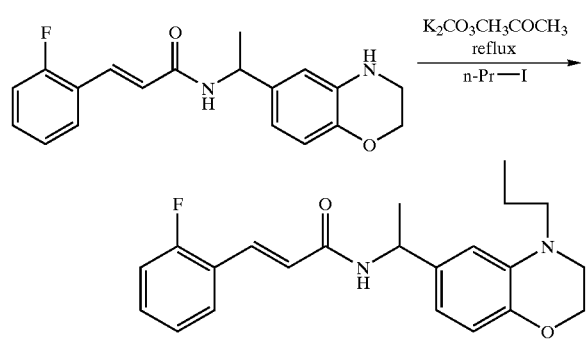

To a solution of N-[1-(3,4-dihydro-2H-benzo[1,4]oxazin-6-yl)-ethyl]-3-(2-fluoro-phenyl)-acrylamide, separated from its racemate (Step A in Example 202) by chiral HPLC (method o, rt 85.73/min) (30 mg) in acetone (5 ml) were added potassium carbonate (38 mg) and n-propyl iodide (1 ml). The mixture was refluxed for 2 hours and cooled to room temperature. The solvent was evaporated in vacuo. The crude product was extracted with $CH_2Cl_2$ and purified by silica gel chromatography eluting with hexane/ethyl acetate (1:1) to give the title compound (27 mg, 86%).

MS: 369 [M+H]$^+$.

HPLC rt: 1.64 min. (method t).

Example 218

Preparation of (±)-3-Pyridin-2-yl-N-[1-(3-trifluoromethoxyphenyl)ethyl]acrylamide

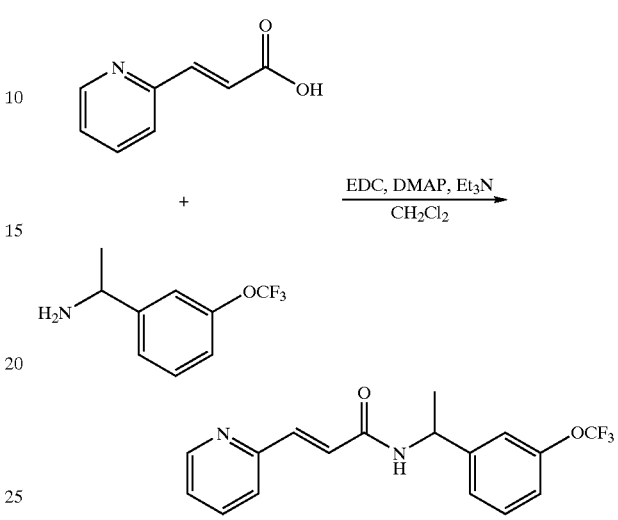

To a solution of 3-(pyridin-2-yl)acrylic acid, Preparation 16 (50 mg) in $CH_2Cl_2$ (2 mL) at room temperature were added (±)-1-(3-trifluoromethoxy phenyl)ethylamine, Preparation 15 (76 mg), EDC hydrochloride (129 mg), DMAP (41 mg), and triethylamine (0.2 mL), and the resulting solution was stirred at room temperature for 12 hours. The crude product was purified by silica gel chromatography eluting with ethyl acetate to provide the title compound as the racemate (96 mg). This racemate was separated by HPLC using AD column eluting with hexanes/ethanol (9:1) to give the title compound as an enantiomer of undetermined chirality.

$^1$H NMR (CDCl$_3$, 300 mHz) δ: 1.55 (3H, d, J=6.9 Hz), 5.28 (1H, quintet, J=7.1 Hz), 6.08 (1H, d, J=7.6 Hz), 7.02 (1H, d, J=15.1 Hz), 7.10–7.45 (6H, m), 7.62 (1H, d, J=15.1 Hz), 7.69 (1H, m), 8.59 (1H, d, J=4.4 Hz).

MS: 337 [M+H]$^+$.

Retention time: 46.5 min (chiralpak AD column, 5×50 cm, 20 um, 90% hexanes/10% ethanol, flow rate: 75 mL/min).

Examples 219–221

The compounds of Examples 219–221 were prepared in substantially the same fashion as Example 218 by coupling the appropriate acid with (±)-1-(3-trifluoromethoxy phenyl)ethylamine, Preparation 15, followed by purification and separation as previously described. For Examples 219–221, 3-(quinolin-3-yl)acrylic acid, 3-(pyridin-4-yl)acrylic acid, and 3-(pyridin-3-yl)acrylic acid were used, respectively.

| Example No. | Structure | Chemical Name | HPLC rt (min), method | Mass (M + H)+ m/z |
|---|---|---|---|---|
| 219 | ![structure] enantiomer chirality undetermined | 3-Quinolin-3-yl-N-[1-(3-tri-fluoromethoxy-phen-yl)-ethyl]-acrylamide | 53.8 (m) | 387 |
| 220 | ![structure] enantiomer chirality undetermined | 3-Pyridin-4-yl-N-[1-(3-tri-fluoromethoxy-phen-yl)-ethyl]-acrylamide | 35.1 (m) | 337 |
| 221 | ![structure] enantiomer chirality undetermined | 3-Pyridin-3-yl-N-[1-(3-tri-fluoromethoxy-phen-yl)-ethyl]-acrylamide | 44.3 (m) | 337 |

Example 222

Preparation of (±)-5-{1-[3-(2,4-Difluorophenyl)acryloylamino]ethyl}-2,3-dihydroindole-1-carboxylic acid, methyl ester

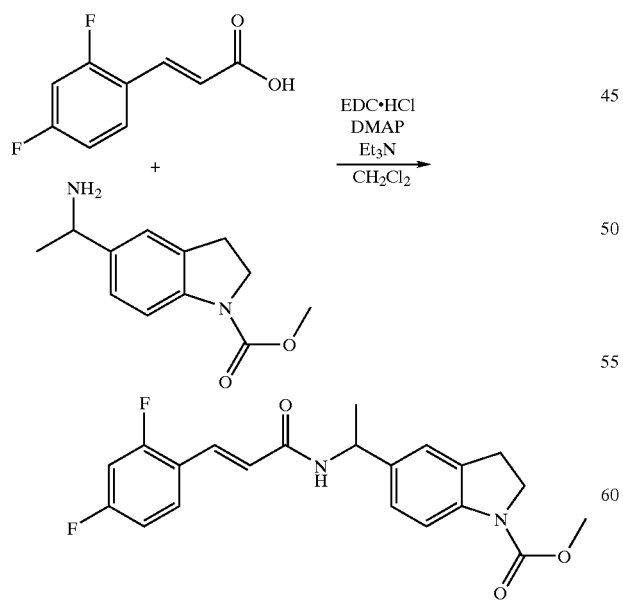

A mixture of 2,4-difluorocinnamic acid (0.5 mmol), (±)-5-(1-aminoethyl)-2,3-dihydro-indole-1-carboxylic acid, methyl ester, Preparation 20 (132 mg, 0.6 mmole), EDC hydrochloride (192 mg, 1.0 mmole), DMAP (61 mg, 0.5 mmole), and triethylamine (202 mg, 2 mmole) in CH₂Cl₂ (8 mL) was stirred at room temperature for 16 hours. Water was added, the aqueous layer was extracted with dichloromethane, and the combined organic layers were washed with brine, dried over magnesium sulfate, and evaporated in vacuo. The crude product was purified by flash column chromatography on silica eluting with EtOAc/hexane (7:3) to give the title compound (125 mg) as a solid.

$^1$H NMR (CDCl$_3$): δ 7.63 (d, J=15.8 Hz, 1H), 7.48–7.40 (m, 1H), 7.17 (b, 2H), 6.91–6.80 (m, 2H), 6.45 (d, J=14.4 Hz, 1H), 5.80 (d, J=7.6 Hz, 1H), 5.26–5.16 (m, 1H), 4.01 (t, J=8.8 Hz, 2H), 3.83 (s, 3H), 3.11 (t, J=8.7 Hz, 2H), 1.54 (d, J=206.9 Hz, 3H).

MS: 387.14 (M+H)⁺.

Examples 223–230

The compounds of Examples 223–230 were prepared in substantially the same fashion as Example 222 by coupling the appropriate acid with (±)-5-(1-aminoethyl)-2,3-dihydro-indole-1-carboxylic acid, methyl ester, Preparation 20, followed by purification as previously described.

| Example No. | Structure | Chemical Name | HPLC rt (min), method | Mass (M + H)+ m/z |
|---|---|---|---|---|
| 223 | racemic | (±)-5-{1-[3-(3-Fluoro-phenyl)-acryloylamino]-ethyl}-2,3-dihydro-indole-1-carboxylic acid methyl ester | | 369 |
| 224 | racemic | (±)-5-{1-[3-(2-Chloro-phenyl)-acryloylamino]-ethyl}-2,3-dihydro-indole-1-carboxylic acid methyl ester | 1.57 (b) | 385 |
| 225 | racemic | (±)-5-{1-[3-(4-Chloro-phenyl)-acryloylamino]-ethyl}-2,3-dihydro-indole-1-carboxylic acid methyl ester | 1.68 (b) | 385 |
| 226 | racemic | (±)-5-[1-(3-o-Tolyl-acryloylamino)-ethyl]-2,3-dihydro-indole-1-carboxylic acid methyl ester | 1.63 (b) | 365 |
| 227 | racemic | (±)-5-{1-[3-(2,5-Difluoro-phenyl)-acryloylamino]-ethyl}-2,3-dihydro-indole-1-carboxylic acid methyl ester | 1.25 (i) | 387 |
| 228 | racemic | (±)-5-{1-[3-(2,4-Dichloro-phenyl)-acryloylamino]-ethyl}-2,3-dihydro-indole-1-carboxylic acid methyl ester | 1.40 (I) | 419 |

-continued

| Example No. | Structure | Chemical Name | HPLC rt (min), method | Mass (M + H)+ m/z |
|---|---|---|---|---|
| 229 | ![structure] racemic | (±)-5-{1-[3-(4-Chloro-2-fluoro-phenyl)-acryloyl-amino]-ethyl}-2,3-dihydro-indole-1-carboxylic acid methyl ester | 1.34 (I) | 403 |
| 230 | ![structure] racemic | (±)-5-{1-[3-(2-Chloro-4-fluoro-phenyl)-acryloyl-amino]-ethyl}-2,3-dihydro-indole-1-carboxylic acid methyl ester | | 403 |

Example 231

Preparation of (±)-3-(2-fluoro-phenyl)-N-[1-(1,2,3,4-tetrahydro-quinolin-7-yl)ethyl]-acrylamide

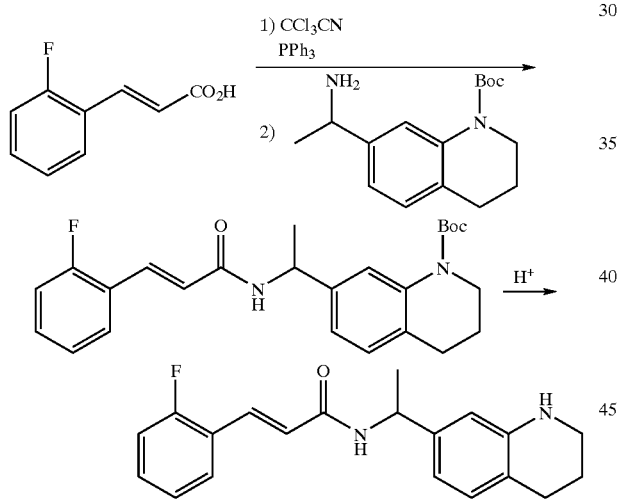

A solution of 3-(2-fluoro-phenyl)-acrylic acid (166 mg, 1 mmol), CCl$_3$CN (289 mg, 2 mmol) and PPh$_3$ (52 mg, 2 mmol) in CH$_2$Cl$_2$ (10 mL) was stirred at 23° C. for 1.5 hours. Then 7-(1-amino-ethyl)-3,4-dihydro-2H-quinoline-1-carboxylic acid tert-butyl ester, Preparation 29 (276 mg, 1 mmol) was introduced followed by triethylamine (304 mg, 3 mmol). After stirring for 1 hour, the solvent was evaporated, the residue was re-dissolved in a mixture of MeOH (5 mL) and 1M HCl in Et$_2$O (5 mL), and stirred at 23° C. for 24 hours. The solvent was evaporated and the residual material was partitioned between EtOAc and aqueous NaHCO$_3$. The organic phase was washed with water, dried (MgSO$_4$) and evaporated. The crude product was purified by chromatography (SiO$_2$, 10–50% EtOAc in hexane) to give 267 mg (82%) of the title compound as a tan solid.

m.p.: 171–173° C.

IR (Nujol) $v_{max}$ (cm$^{-1}$): 3396, 3260, 1656, 1621.

$^1$H NMR 400 MHz (DMSO-d$_6$) δ (ppm): 8.48 (1H, d, J=8.07 Hz), 7.63 (1H, t, J=6.64 Hz), 7.47 (1H, d, J=16.18 Hz), 7.44–7.40 (1H, m), 7.30–7.25 (2H, m), 6.80 (1H, d, J=16.18 Hz), 6.77 (1H, partially resolved d), 6.40 (1H, partially resolved dd), 6.39 (1H, s), 5.82 (1H, bras), 4.85 (1H, m), 3.15 (2H, t, J=5.54 Hz), 2.61 (2H, t, J=2.61 Hz), 1.80–1.74 (2H, m). 1.35 (3H, d, J=7.18 Hz).

MS [M+H]$^+$ 325.

Examples 232–235

Examples 232–235 were made using substantially the same method used to prepare Example 231.

Example 232

Preparation of (±)-3-(3-Fluoro-phenyl)-N-[1-(1,2,3,4-tetrahydro-quinolin-7-yl)ethyl]-acrylamide

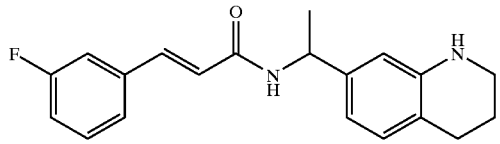

m.p.: 130–132° C. (dec).

IR (Nujol) $v_{max}$ (cm$^{-1}$): 3310, 1661, 1615.

$^1$H NMR 400 MHz (DMSO-d$_6$) δ (ppm): 8.38 (1H, d, J=8.07 Hz), 7.50–7.35 (4H, m), 7.24–7.17 (1H, m), 6.77 (1H, d, J=7.74 Hz), 6.73 (1H, d, J=15.72 Hz), 6.42–6.37 (2H, m), 5.59 (1H, br s), 4.90–4.80 (1H, m), 3.15 (2H, t, J=5.40 Hz), 2.61 (2H, t, J=6.35 Hz), 1.81–1.72 (2H, m), 1.35 (3H, d, J=7.1 Hz).

MS [M+H]$^+$ 325.

Example 233

Preparation of (±)-3-phenyl-N-[1-(1,2,3,4-tetrahydro-quinolin-7-yl)ethyl]-acrylamide

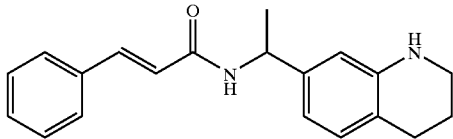

m.p.: 144–146° C.
IR (Nujol) $v_{max}$ (cm$^{-1}$): 3231, 1652, 1615.
$^1$H NMR 400 MHz (DMSO-d$_6$) δ (ppm): 8.36 (1H, d, J=8.11 Hz), 7.57–7.52 (2H, m), 7.45–7.34 (4H, m), 6.77 (1H, d, J=7.69 Hz), 6.70 (1H, d, J=15.77 Hz), 6.43–6.37 (2H, m), 5.60 (1H, s), 4.89–4.81 (1H, m), 3.15 (2H, t, J=5.56 Hz), 2.62 (2H, t, J=6.35 Hz), 1.82–1.72 (2H, m), 1.35 (3H, d, J=7.11 Hz).
MS [M+H]$^+$ 307.

Example 234

Preparation of (±)-3-(2,5-difluoro-phenyl)-N-[1-(1,2,3,4-tetrahydro-quinolin-7-yl)ethyl]-acrylamide

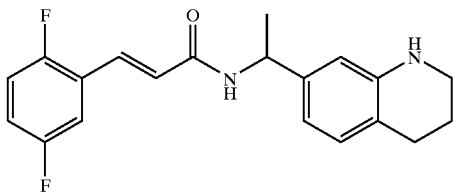

m.p.: 139–141° C.
IR (Nujol) $v_{max}$ (cm$^{-1}$): 3226, 1653, 1615.
$^1$H NMR 400 MHz (DMSO-d$_6$) δ (ppm): 8.50 (1H, d, J=8.08 Hz), 7.51–7.44 (1H, m), 7.41 (1H, d, J=16.67 Hz), 7.39–7.24 (2H, m), 6.83 (1H, d, J=15.56 Hz), 6.77 (1H, d, J=7.63 Hz), 6.42–6.36 (2H, m), 5.60 (1H, s), 4.89–4.80 (1H, m), 3.15 (2H, t, J=5.58 Hz), 2.61 (2H, t, J=6.34 Hz), 1.81–1.72 (2H, m), 1.35 (3H, d, J=6.98 Hz).
MS [M+H]$^+$ 343.

Example 235

Preparation of (±)-3-(4-fluoro-phenyl)-N-[1-(1,2,3,4-tetrahydro-quinolin-7-yl)ethyl]-acrylamide

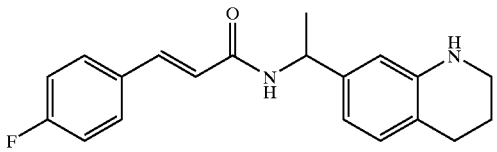

m.p.: 125–127° C. (dec)
IR (Nujol) $v_{max}$ (cm$^{-1}$): 3368, 3326, 1652, 1615.
$^1$H NMR 400 MHz (DMSO-d$_6$) δ (ppm): 8.34 (1H, d, J=8.12 Hz), 7.65–7.57 (2H, m), 7.40 (1H, d, J=15.82 Hz), 7.25 (2H, t, J=8.85 Hz), 6.77 (1H, d, J=7.51 Hz), 6.64 (1H, d, J=15.78 Hz), 6.42–6.37 (2H, m), 5.6 (1H, s), 4.89–4.80 (1H, m), 3.15 (2H, t, J=5.42 Hz), 2.61 (2H, t, J=6.39 Hz), 1.81–1.73 (2H, m), 1.34 (3H, d, J=7.19 Hz).
MS [M+H]$^+$ 325.

Example 236

Preparation of (±)-3-(2-fluoro-phenyl)-N-[1-(1-methyl-1,2,3,4-tetrahydro-quinolin-7-yl)ethyl]acrylamide

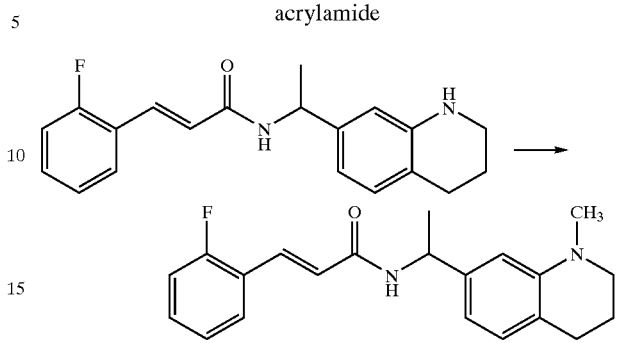

A solution of 3-(2-fluoro-phenyl)-N-[1-(1,2,3,4-tetrahydro-quinolin-7-yl)-ethyl]-acrylamide (39 mg, 0.12 mmol) in formic acid (3 mL) was treated at 23° C. with small portions of NaBH$_4$ (136 mg, 3.6 mmol). The reaction mixture was stirred for 16 hours, then MeOH was added and the solvent evaporated. The residue was partitioned between EtOAc and aqueous NaHCO$_3$. The organic phase was washed with water, dried (MgSO$_4$) and evaporated. The crude material was purified by chromatography (SiO$_2$, 5% CH$_3$CN in CH$_2$Cl$_2$) yielding 37 mg (91%) of the title compound as a tan solid.

m.p: 60–63° C.
IR (Nujol) $v_{max}$ (cm$^{-1}$): 3255, 1653, 1610.
$^1$H NMR 400 MHz (DMSO-d$_6$) δ (ppm): 8.52 (1H, d, J=8.07 Hz), 7.64 (1H, dt, J=7.75 and 1.76 Hz), 7.48 (1H, d, J=16.00 Hz), 7.44–7.41 (1H, m), 7.30–7.25 (2H, m), 6.83 (1H, d, J=7.54 Hz), 6.81 (1H, d, J=16.00 Hz), 6.55 (1H, d, J=1.34 Hz), 6.51 (1H, dd, J=7.55 and 1.34 Hz), 4.93 (1H, m), 3.17 (2H, t, J=5.51 Hz), 2.84 (3H, s), 2.65 (2H, t, J=6.26 Hz), 1.86 (2H, m), 1.38 (3H, d, J=7.07 Hz).
MS [M+H]$^+$ 339.

Examples 237–240

Examples 237–240 were made using substantially the same method used to prepare Example 236 following the procedures of Gribble et. al. (J. Amer. Chem. Soc., 1974, 7812).

Example 237

Preparation of (±)-3-(2,5-difluoro-phenyl)-N-[1-(1-methyl-1,2,3,4-tetrahydro-quinolin-7-yl)ethyl]acrylamide

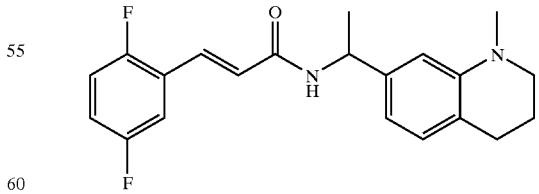

m.p.: 52–55° C.
IR (Nujol) $v_{max}$ (cm$^{-1}$): 3250, 1655, 1610.
$^1$H NMR 400 MHz (DMSO-d$_6$)) δ (ppm): 8.54 (1H, d, J=8.64 Hz), 7.53–7.47 (1H, m), 7.42 (1H, d, J=15.89 Hz), 7.4–7.2 (2H, m), 6.84 (1H, d, J=16.21 Hz), 6.83 (1H, d, J=7.70 Hz), 6.55 (1H, d, J=1.52 Hz), 6.51 (1H, dd, J=0.58 and 1.52 Hz), 4.98–4.88 (1H, m), 3.17 (2H, t, J=5.56 Hz), 2.84 (3H, s), 2.67 (2H, t, J=6.57 Hz), 1.91–1.82 (2H, m), 1.37 (3H, d, J=7.1 Hz).

MS [M+H]$^+$ 357.

Example 238

Preparation of (±)-N-[1-(1-methyl-1,2,3,4-tetrahydro-quinolin-7-yl)-ethyl]-3-phenyl-acrylamide

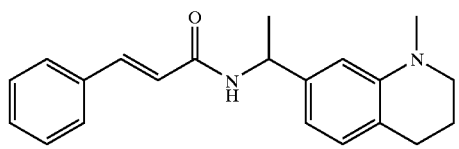

m.p.: 166° C. (dec)

IR (Nujol) $v_{max}$ (cm$^{-1}$): 3254, 1652, 1606.

$^1$H NMR 400 MHz (CDCl$_3$) δ (ppm): 7.64 (1H, d, J=15.61 Hz), 7.53–7.48 (2H, m), 7.41–7.34 (3H, m), 6.96 (1H, d, J=7.54 Hz), 6.63 (1H, dd, J=7.54 and 1.75 Hz), 6.59 (1H, d, J=1.68 Hz), 6.37 (1H, d, J=15.26 Hz), 5.81 (1H, d, J=6.98 Hz), 5.25–5.15 (1H, m), 3.25 (2H, t, J=5.49 Hz), 2.92 (3H, s), 2.77 (2H, t, J=6.26 Hz), 2.05–1.95 (2H, m), 1.58 (3H, d, J=5.57 Hz).

MS [M+H]$^+$ 321.

Example 239

Preparation of (±)-3-(3-fluoro-phenyl)-N-[1-(1-methyl-1,2,3,4-tetrahydro-quinolin-7-yl)ethyl]acrylamide

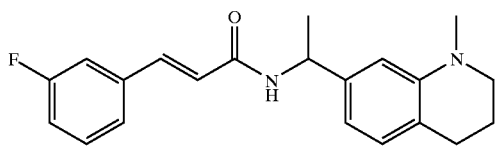

m.p.: 60–63° C.

IR (Nujol) $v_{max}$ (cm$^{-1}$): 3255, 1653, 1610.

$^1$H NMR 400 MHz (DMSO-d$_6$) δ (ppm): 8.42 (1H, d, J=7.95 Hz), 7.50–7.36 (4H, m), 7.21 (1H, m), 6.82 (1H, d, J=7.58 Hz), 6.74 (1H, d, J=15.83 Hz), 6.55 (1H, d, J=1.52 Hz), 6.51 (1H, dd, J=7.58 and 1.52 Hz), 4.98–4.88 (1H, m), 3.17 (2H, t, J=5.56 Hz), 2.84 (3H, s), 2.65 (2H, t, J=6.57 Hz), 2.53–2.49 (2H, m), 1.37 (3H, d, J=7.07 Hz).

MS [M+H]$^+$ 339.

Example 240

Preparation of (±)-3-(4-fluoro-phenyl)-N-[1-(1-methyl-1,2,3,4-tetrahydro-quinolin-7-yl)ethyl]acrylamide

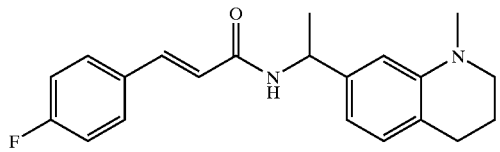

m.p: 183–185° C.

IR (Nujol) $v_{max}$ (cm$^{-1}$): 3266, 1669, 1653.

$^1$H NMR 400 MHz (DMSO-d$_6$) δ (ppm):8.39 (1H, d, J=8.08 Hz), 7.65–7.58 (2H, m), 7.41 (1H, d, J=16.05 Hz), 7.29–7.22 (2H, m), 6.82 (1H, d, J=7.58 Hz), 6.65 (1H, d, J=15.81 Hz), 6.55 (1H, d, J=1.52 Hz), 6.51 (1H, dd, J=1.52 and 7.58 Hz), 4.98–4.88 (1H, m), 3.16 (2H, t, J=5.47 Hz), 2.84 (3H, s), 2.65 (2H, t, J=6.40 Hz), 1.91–1.82 (2H, m), 1.37 (3H, d, J=6.93 Hz). MS [M+H]+339.

Examples 241–242

Examples 241–242 were made using substantially the same method used to prepare Example 236 with the exception that acetic acid was used instead of formic acid.

Example 241

Preparation of (±)-N-[1-(1-ethyl-1,2,3,4-tetrahydro-quinolin-7-yl)-ethyl]-3-phenyl-acrylamide

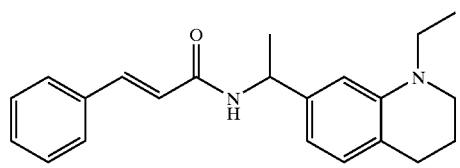

m.p.: 50–52° C.

IR (Nujol) $v_{max}$ (cm$^{-1}$): 3260, 1653, 1610.

$^1$H NMR 400 MHz (DMSO-d$_6$) δ (ppm): 8.41 (1H, d, J=8.21 Hz), 7.59–7.52 (2H, m), 7.45–7.35 (4H, m), 6.81 (1H, d, J=7.58 Hz), 6.70 (1H, d, J=16.22 Hz), 6.57 (1H, s), 6.47 (1H, d, J=7.52 Hz), 4.96–4.87 (1H, m), 3.3 (2H, partially resolved q), 3.21 (2H, t, J=5.57 Hz), 2.63 (2H, t, J=6.31 Hz), 1.89–1.79 (2H, m), 1.37 (3H, d, J=6.48 Hz), 1.06 (3H, t, J=6.99 Hz).

MS [M+H]$^+$ 335.

Example 242

Preparation of (±)-3-(2,5-difluoro-phenyl)-N-[1-(1-ethyl-1,2,3,4-tetrahydro-quinolin-7-yl)ethyl]acrylamide

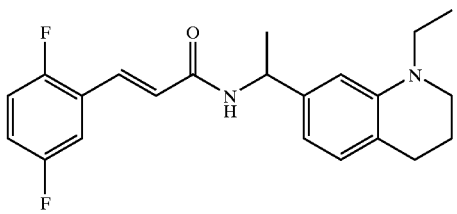

m.p.: 50–53° C.

IR (Nujol) $v_{max}$ (cm$^{-1}$): 3259, 1656, 1610.

$^1$H NMR 400 MHz (DMSO-d$_6$) δ (ppm): 8.54 (1H, d, J=8.16 Hz), 7.53–7.45 (1H, m), 7.41 (1H, d, J=15.79 Hz), 7.39–7.23 (2H, m), 6.83 (1H, d, J=15.66 Hz), 6.80 (1H, d, J=7.58 Hz), 6.56 (1H, s), 6.44 (1H, dd, J=7.58 and 1.52 Hz), 4.96–4.86 (1H, m), 3.3 (2H, partially resolved q), 3.20 (2H, t, J=5.56 Hz), 2.63 (2H, t, J=6.06 Hz), 1.88–1.79 (2H, m), 1.37 (3H, d, J=7.18 Hz), 1.06 (3H, t, J=6.57 Hz).

MS [M+H]$^+$ 371.

Example 243

Preparation of (±)-N-[1-(1-acetyl-1,2,3,4-tetrahydro-quinolin-7-yl)-ethyl]-3-phenyl-acrylamide

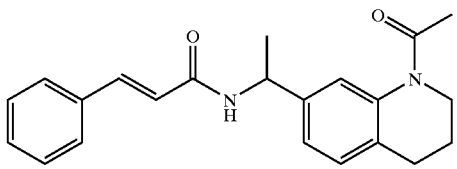

To a solution of 3-phenyl-N-[1-(1,2,3,4-tetrahydro-quinolin-7-yl)-ethyl]-acrylamide (Example 233) in CH$_2$Cl$_2$ at 0° C. was added triethylamine followed by acetyl chloride. Work up and flash chromatography provided the title compound.

m.p.: 65–68° C.

IR (Nujol) $v_{max}$ (cm$^{-1}$):3269, 1653, 1616.

$^1$H NMR 400 MHz (CDCl$_3$) δ (ppm): 7.65 (1H, d, J=15.61 Hz), 7.54–7.48 (3H, m), 7.46–7.35 (3H, m), 7.18–7.10 (2H, m), 6.42 (1H, d, J=15.17 Hz), 5.88 (1H, br d, J=3.57 Hz), 5.30–5.20 (1H, m), 3.80 (2H, t, J=6.33 Hz), 2.74 (2H, t, J=6.37 Hz), 2.27 (3H, s), 2.04–1.93 (2H, m), 1.58 (3H, d, J=7.12 Hz).

MS [M]$^+$ 348.

Example 244

Preparation of (±)-N-[1-(1[2-methoxyethyl]-1,2,3,4-tetrahydro-quinolin-7-yl)-ethyl]-3-phenyl-acrylamide

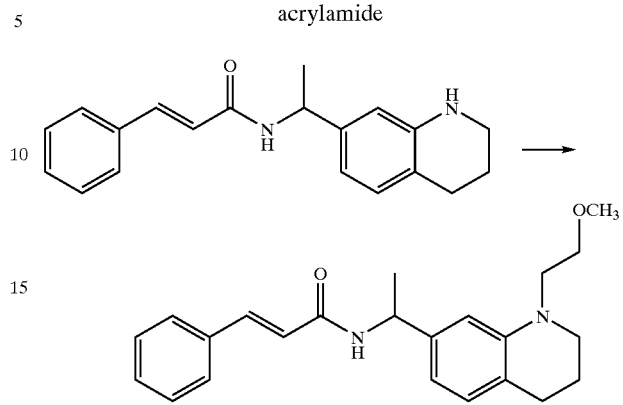

To a stirred solution of 3-phenyl-N-[1-(1,2,3,4-tetrahydro-quinolin-7-yl)ethyl]acrylamide (Example 233) (75 mg, 0.245 mmol) in methoxyacetic acid (5 ml) was added, in small portions, NaBH$_4$ (232 mg) over 30 minutes. The mixture was stirred at 23° C. for an additional 2 hours and then the excess hydride destroyed by adding MeOH. That solution was diluted with EtOAc and washed several times with water. The organic phase was dried (MgSO$_4$) and evaporated. The crude material was purified by chromatography (SiO$_2$, 25% EtOAc in hexane) yielding 59 mg (66%) of the desired compound as a thick oil.

IR (Nujol) $v_{max}$ (cm$^{-1}$): 3271, 1654, 1609.

$^1$H NMR 400 MHz (CDCl$_3$) δ (ppm):7.65 (1H, d, J=15.6 Hz), 7.52–7.48 (2H, m,), 7.41–7.35 (3H, m), 6.96 (1H, d, J=7.63 Hz), 6.66–6.57 (2H, broad m), 6.37 (1H, d, J=15.6 Hz), 5.84 (1H, broad d, J=7.12 Hz), 5.22–5.13 (1H, m), 3.60 (2H, t, J=5.81 Hz), 3.53–3.47 (3H, m), 3.38 (4H, s and m), 2.76 (2H, t, J=6.31 Hz), 1.99–1.91 (2H, m), 1.57 (3H, d, J=6.52 Hz).

MS [M+H]$^+$ 365.

Example 245

Preparation of N-[1-(1-hydroxyethyl)-1,2,3,4-tetrahydro-quinolin-7-yl)-ethyl]-3-phenyl-acrylamide

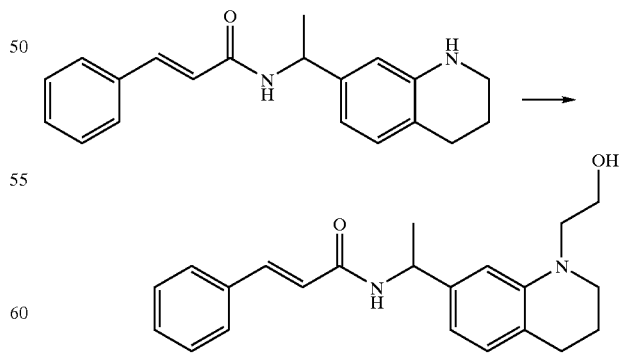

Ethylene oxide was bubbled, for a few minutes, into a cooled (5° C.) solution of 3-phenyl-N-[1-(1,2,3,4-tetrahydro-quinolin-7-yl)-ethyl]-acrylamide (50 mg, 0.163 mmol) in MeOH. The solution was stirred at 23° C., in a pressure tube, for 24 hours to bring the reaction to completion. The solvent was evaporated and the product chromatographed (SiO₂, 25% EtOAc in hexane) to yield 55 mg (96%) of a foam.

m.p.: 135° C.

IR (Nujol) $v_{max}$ (cm$^{-1}$): 3263, 1654, 1609.

$^1$H NMR 400 MHz (CDCl₃) δ (ppm): 7.64 (1H, d, J=15.72 Hz), 7.53–7.47 (2H, m), 7.41–7.33 (3H, m), 6.97 (1H, d, J=7.65 Hz), 6.73 (1H, s), 6.65 (1H, d, J=7.78 Hz), 6.38 (1H, d, J=15.62 Hz), 5.89 (1H, d, J=7.51 Hz), 5.17 (1H, m), 3.85 (2H, t, J=5.56 Hz), 3.48 (2H, t, J=5.63 Hz), 3.35 (2H, t, J=5.31 Hz), 2.78 (2H, t, J=5.06 Hz), 1.97 (2H, m), 1.56 (3H, d, J=6.88 Hz).

MS [M+H]⁺ 351.

Example 246

Preparation of 3-(2,5-difluoro-phenyl)-N-[1-(1-hydroxyethyl-1,2,3,4-tetrahydro-quinolin-7-yl)ethyl]-acrylamide

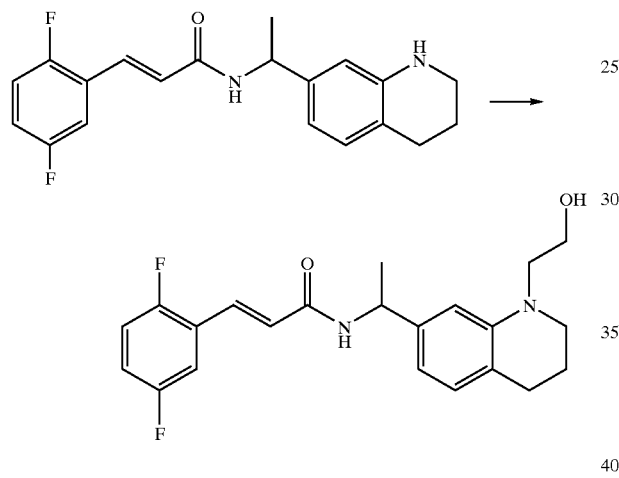

m.p.: 72–73° C.

IR (Nujol) $v_{max}$ (cm$^{-1}$): 3263, 1656, 1608.

$^1$H NMR 400 MHz (CDCl₃) δ (ppm): 7.65 (1H, d, J=15.75 Hz), 7.20–7.14 (1H, m), 7.10–6.99 (2H, m), 6.98 (1H, d, J=6.88 Hz), 6.73 (1H, s), 6.65 (1H, d, J=6.62 Hz), 6.49 (1H, d, J=16.30 Hz), 5.94 (1H, d, J=7.09 Hz), 5.16 (1H, m), 3.85 (2H, t, J=5.28 Hz), 3.48 (2H, t, J=5.27 Hz), 3.36 (2H, t, J=4.80 Hz), 2.78 (2H, t, J=5.81 Hz), 1.98 (2H, m), 1.56 (3H, d, J=6.55 Hz).

MS [M+H]⁺ 387.

Example 247

Preparation of 3-(3,5-difluoro-phenyl)-N-[1-(1-hydroxyethyl-1,2,3,4-tetrahydro-quinolin-6-yl)-ethyl]acrylamide

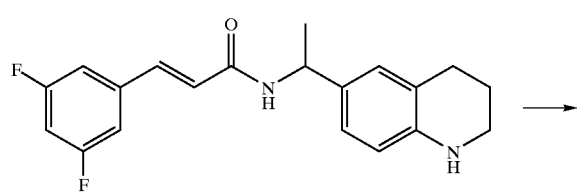

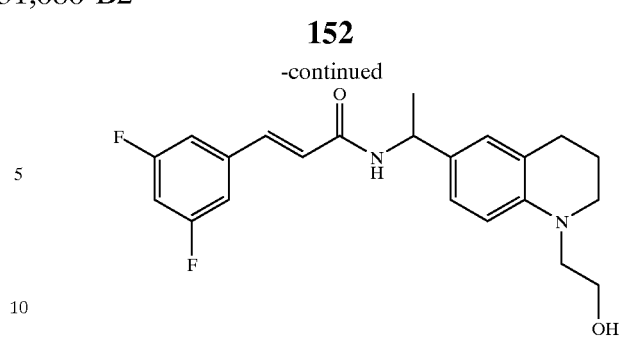

m.p.: 58–60° C.

IR (Nujol) $v_{max}$ (cm$^{-1}$): 3259, 1659, 1616.

$^1$H NMR 400 MHz (CDCl₃) δ (ppm): 7.54 (1H, d, J=15.19 Hz), 7.07 (1H, dd, 1=8.34 and 2.02 Hz), 7.03–6.96 (3H, m), 6.84–6.78 (1H, m), 6.70 (1H, unresolved d), 6.34 (1H, d, J=15.59 Hz), 5.80 (1H, d, 128.0 Hz), 5.15 (1H, m), 3.85 (2H, unresolved t), 3.45 (2H, t, J=5.85 Hz), 3.35 (2H, t, J=5.44 Hz), 2.80 (2H, t, J=6.35 Hz), 2.00 (2H, m), 1.55 (3H, d, J=7.08 Hz).

MS [M+H]⁺ 387.

Example 248

Preparation of 3-(3,5-difluoro-phenyl)-N-[1-(1,2,3,4-tetrahydro-quinolin-6-yl)-ethyl]acrylamide

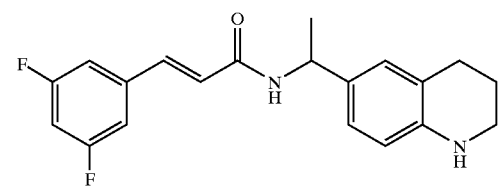

Example 0.248 was prepared by the same method used to prepare Example 231 with the exception of (1) using trans-3,5-difluorocinnamic acid in place of trans-2-fluorocinnamic acid, (2) using 6-(11-aminoethyl)-3,4-dihydro-2H-quinoline-1-carboxylic acid tert-butyl ester in place of 7-(1-amino-ethyl)-3,4-dihydro-2H-quinoline-1-carboxylic acid tert-butyl ester.

m.p.: 180° C. (dec).

IR (Nujol) $v_{max}$ (cm$^{-1}$): 3315, 1619.

$^1$H NMR 400 MHz (CDCl₃) δ (ppm): 7.53 (1H, d, J=15.69 Hz), 7.04–6.95 (4H, m), 6.84–6.77 (1H, m), 6.55 (1H, d, J=8.01 Hz), 6.37 (1H, d, J=15.66 Hz), 5.91 (1H, d, J=7.48 Hz), 5.19–5.10 (1H, m), 3.33 (2H, t, J=5.28 Hz), 2.78 (2H, t, J=6.57 Hz), 2.02–1.94 (2H, m), 1.54 (3H, d, J=6.51 Hz). MS [M+H]+343.

Examples 249–255

Examples 249–255 were made using substantially the same procedures used to prepare Example 248.

Example 249

Preparation of 3-phenyl-N-[1-(1,2,3,4-tetrahydro-quinolin-6-yl)ethyl]acrylamide

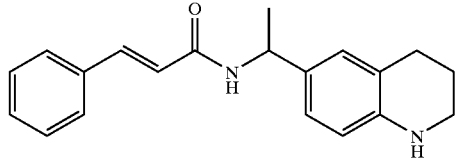

m.p.: 64–67° C.

IR (Nujol) $v_{max}$ (cm$^{-1}$): 3263, 1653, 1614.

$^1$H NMR 400 MHz (CDCl$_3$) δ (ppm): 7.63 (1H, d, J=15.62 Hz), 7.53–7.32 (6H, 2m), 7.04–6.98 (2H, m), 6.58 (1H, d, J=6.58 Hz), 6.39 (1H, d, J=15.70 Hz), 5.89 (1H, d, J=7.61 Hz), 5.21–5.11 (1H, m), 3.33 (2H, t, J=5.95 Hz), 2.78 (2H, t, J=6.35 Hz), 2.02–1.84 (2H, m), 1.54(3H, d, J=6.83 Hz).

MS [M+H]$^+$ 307.

Example 250

Preparation of 3-(3,4-difluoro-phenyl)-N-[1-(1,2,3,4-tetrahydro-quinolin-6-yl)-ethyl]acrylamide

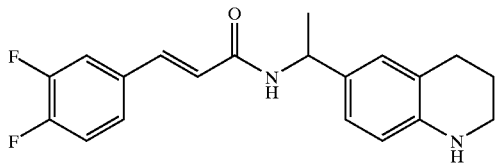

m.p: 156° C. (dec)

IR (Nujol) $v_{max}$ (cm$^{-1}$):3342, 1654, 1614.

$^1$H NMR 400 MHz (CDCl$_3$) δ (ppm): 7.54 (1H, d, J=15.7 Hz), 7.34–7.26 (1H, m), 7.24–7.12 (2H, m), 7.03–6.96 (2H, m), 6.56 (1H, d, J=7.56 Hz), 6.29 (1H, d, J=15.55 Hz), 5.88 (1H, d, J=7.47 Hz), 5.14–5.10 (1H, m), 3.33 (2H, d, J=5.59 Hz), 2.78 (2H, t, J=6.61 Hz), 2.02–1.94 (2H, m), 1.54 (3H, d, J=7.0 Hz). MS [M+H]+343.

Example 251

Preparation of 3-(2-fluoro-phenyl)-N-[1-(1,2,3,4-tetrahydro-quinolin-6-yl)ethyl]acrylamide

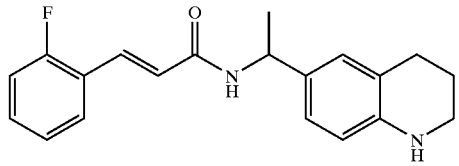

m.p.: 149–151° C. (dec).

IR (Nujol) $v_{max}$ (cm$^{-1}$): 3349, 1652, 1611.

$^1$H NMR 400 MHz (DMSO-d$_6$) δ (ppm): 8.41 (1H, d, J=8.46 Hz), 7.63 (1H, dt, J=7.74 and 1.55 Hz), 7.47 (1H, d, J=16.13 Hz), 7.45–7.39(1H, m), 7.32–7.24 (2H, m), 6.85–6.84 (2H, m), 6.78 (1H, d, J=15.45 Hz), 6.38 (1H, d, J=7.94 Hz), 5.55 (1H, br s), 4.92–4.82 (1H, m), 3.15 (2H, t, J=5.30 Hz), 2.65 (2H, t, J=6.25 Hz), 2.52–2.49 (2H, m), 1.34 (3H, d, J=7.19 Hz).

MS [M+H]$^+$ 325.

Example 252

Preparation of 3-(2,5-difluoro-phenyl)-N-[1-(1,2,3,4-tetrahydro-quinolin-6-yl)-ethyl]acrylamide

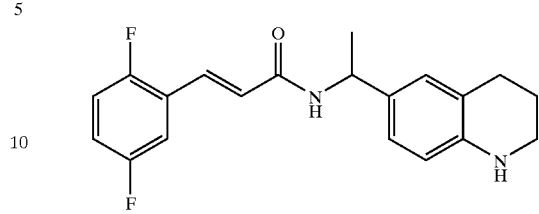

m.p.: 55–58° C.

IR (Nujol) $v_{max}$ (cm$^{-1}$): 3267, 1656, 1616.

$^1$H NMR 400 MHz (CDCl$_3$) δ (ppm): 7.65 (1H, d, J=16.18 Hz), 7.20–7.14 (1H, m), 7.10–6.97 (4H, m), 6.58 (1H, d, J=8.01 Hz), 6.50 (1H, d, J=16.11 Hz), 5.92 (1H, d, J=7.51 Hz), 5.21–5.10 (1H, m), 3.34 (2H, t, J=5.59 Hz), 2.79 (2H, t, J=6.26 Hz), 2.04–1.93 (2H, m), 1.54 (3H, d, J=6.41 Hz).

MS [M+H]$^+$ 343.

Example 253

Preparation of 3-(2,6-difluoro-phenyl)-N-[1-(1,2,3,4-tetrahydro-quinolin-6-yl)ethyl]acrylamide

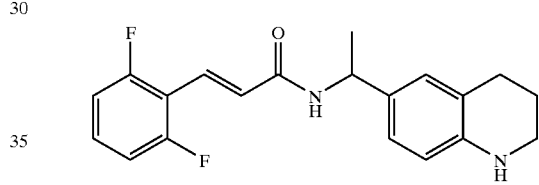

m.p.: 77–80° C.

IR (Nujol) $v_{max}$ (cm$^{-1}$): 3263, 1653, 1620.

$^1$H NMR 400 MHz (CDCl$_3$) δ (ppm): 7.75 (1H, d, J=16.0 Hz), 7.31–7.23 (2H, m), 7.01–6.89 (4H, m), 6.67 (1H, d, J=16.26 Hz), 6.48 (1H, d, J=7.91 Hz), 5.77 (1H, d, J=7.67 Hz), 5.2–5.11 (1H, m), 3.32 (2H, t, J=5.62 Hz), 2.78 (2H, t, J=6.40 Hz), 2.0–1.92 (2H, m), 1.55 (3H, d, J=7.06 Hz).

MS [M+H]$^+$ 343.

Example 254

Preparation of 3-(3-fluoro-phenyl)-N-[1-(1,2,3,4-tetrahydro-quinolin-6-yl)ethyl]acrylamide

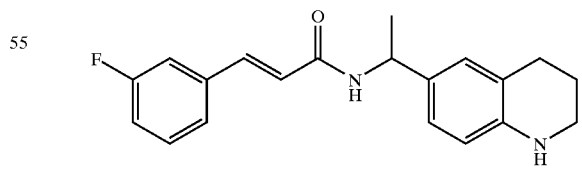

m.p.: 172–174° C.

IR (Nujol) $v_{max}$ (cm$^{-1}$): 3335, 1653, 1614.

$^1$H NMR 400 MHz (DMSO-d$_6$) δ (ppm): 8.30 (1H, d, J=8.18 Hz), 7.50–7.34 (4H, m), 7.24–7.17 (1H, m), 6.86–6.79 (2H, m), 6.72 (1H, d, J=15.88 Hz), 6.39 (1H, d, J=7.77 Hz), 5.53 (1H, s), 4.91–4.82 (1H, m), 3.15 (2H, t, J=5.62 Hz), 2.65 (2H, t, J=6.33 Hz), 1.83–1.73 (2H, m), 1.34 (3H, d, J=6.96 Hz).
MS [M+H]+ 325.

Example 255

Preparation of 3-(4-fluoro-phenyl)-N-[1-(1,2,3,4-tetrahydro-quinolin-6-yl)ethyl]acrylamide

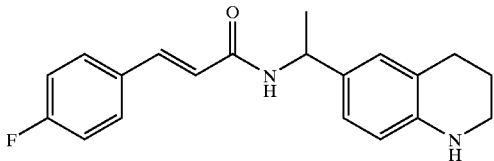

m.p.: 140–143° C.
IR (Nujol) $v_{max}$ (cm$^{-1}$): 3336, 1652, 1615.
$^1$H NMR 400 MHz (DMSO-d$_6$) δ (ppm): 8.26 (1H, d, J=7.95 Hz), 7.65–7.57 (2H, m), 7.39 (1H, d, J=15.76 Hz), 7.28–7.21 (2H, m), 6.85–6.79 (2H, m), 6.62 (1H, d, J=15.65 Hz), 6.38 (1H, d, J=8.22 Hz), 5.53 (1H, s), 4.91 (1H, m), 3.15 (2H, t, J=5.37 Hz), 2.65 (2H, t, J=6.57 Hz), 1.82–1.74 (2H, m), 1.34 (3H, d, J=7.21 Hz).
MS [M+H]+ 325.

Example 256

Preparation of N-[1-(1-methyl-1,2,3,4-tetrahydro-quinolin-6-yl)-ethyl]-3-phenyl-acrylamide

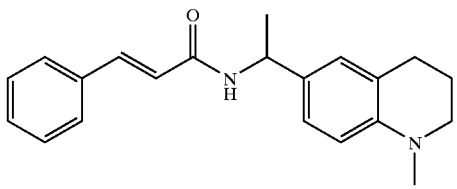

Example 256 was prepared from 3-phenyl-N-[1-(1,2,3,4-tetrahydro-quinolin-6-yl)-ethyl]-acrylamide by treatment with formic acid and sodium borohydride following the general procedures described by Gribble et. al. (J. Amer. Chem. Soc., 1974, 7812).
m.p.: 65–68° C.
IR (Nujol) $v_{max}$ (cm$^{-1}$): 3253, 1653, 1614.
$^1$H NMR 400 MHz (DMSO-d$_6$) δ (ppm): 8.32 (1H, d, J=8.04 Hz), 7.57–7.52 (2H, m), 7.45–7.34 (4H, m), 6.97 (1H, dd, J=8.59 and 2.02 Hz), 6.88 (1H, d, J=2.02 Hz), 6.68 (1H, d, J=15.7 Hz), 6.53 (1H, d, J=8.07 Hz), 4.96–4.86 (1H, m), 3.14 (2H, t, J=5.56 Hz), 2.80 (3H, s), 2.69 (2H, t, J=6.43 Hz), 1.92–1.85 (2H, m), 1.36 (3H, d, J=6.43 Hz).
MS [M+H]+ 321.

Example 257

Preparation of 3-(2,5-difluoro-phenyl)-N-[1-(1-methyl-1,2,3,4-tetrahydro-quinolin-6-yl)ethyl] acrylamide

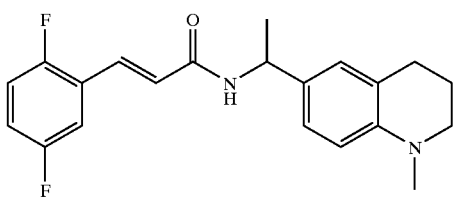

Example 257 was made using the same method used to prepare Example 256.
m.p.: 51–55° C.
IR (Nujol) $v_{max}$ (cm$^{-1}$): 3254, 1655, 1615.
$^1$H NMR 400 MHz (DMSO-d$_6$) δ (ppm): 8.47 (1H, d, J=8.7 Hz), 7.51–7.45 (1H, m), 7.41 (1H, d, J=16.22 Hz), 7.38–7.24 (2H, m), 6.97 (1H, dd, J=8.59 and 2.02 Hz), 6.88 (1H, d, J=2.02 Hz), 6.81 (1H, d, J=15.66 Hz), 6.53 (1H, d, J=8.59 Hz), 4.95–4.84 (1H, m), 3.14 (2H, t, J=5.56 Hz), 2.80 (3H, s), 2.68 (2H, t, J=6.57 Hz), 1.92–1.84 (2H, m), 1.36 (3H, d, J=7.07 Hz).
MS [M+H]+ 357.

Example 258

Preparation of (S)-3-phenyl-N-[1-(3-pyridyl-phenyl)-ethyl]acrylamide

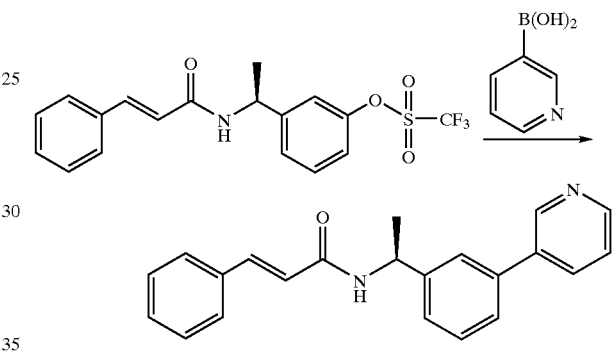

To a solution of (S)-3-phenyl-N-[1-(3-trifluoromethanesulfonyloxy-phenyl)ethyl]acrylamide [Product of Step C, Example 82, (55 mg)] in dioxane (0.6 mL) at room temperature was added Pd(PPh$_3$)$_4$ (15 mg), potassium carbonate (35 mg), and pyridine-3-boronic acid (17 mg). The resulting suspension was heated at 80° C. for 15 hours. The solvent was removed in vacuo, and the residue was purified by preparative HPLC to afford the title compound as the trifluoroacetic acid salt.
$^1$H NMR (CD$_3$OD, 400 mHz) δ 1.58 (3H, d, J=7.1 Hz), 5.22 (1H, q, J=7.1 Hz), 6.68 (1H, d, J=15.8 Hz), 7.3–7.8 (10 h, m), 8.12 (1H, m), 8.84 (1H, m), 8.87 (1H, m), 9.15 (1H, s); MS: 329.34 (M+H)+.

Examples 259–261

The compounds of examples 259–261 were made in substantially the same fashion as Example 258 by using the appropriate triflate derivative and boronic acid. Example 261 was prepared by reacting (S)-3-phenyl-N-[1-(3-trifluoromethanesulfonyloxyphenyl)ethyl]acrylamide with 4-pyridine boronic acid. Examples 259 and 261 were prepared by reacting (S)-3-(2,4-difluorophenyl)-N-[1-(3-trifluoromethanesulfonyloxyphenyl)ethyl]acrylamide (Prepared according to the method of Steps A-C in Example 82 using 2,4-difluorocinnamic acid instead of cinnamic acid) with 4-pyridine boronic acid and 4-pyridine boronic acid, respectively.

| Example No. | Structure | Chemical Name | HPLC rt (min), method | Mass (M + H)+ m/z |
|---|---|---|---|---|
| 259 | 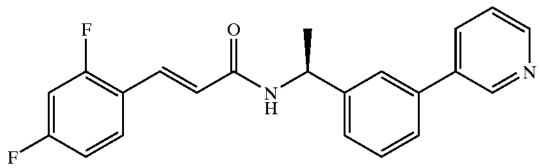 | (S)-(2,4-Difluoro-phenyl)-N-[1-(3-pyridin-3-yl-phenyl)-ethyl]-acrylamide | 1.30 (b) | 364 |
| 260 | 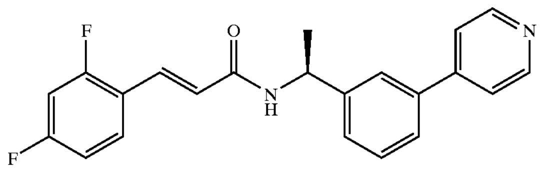 | (S)-3-(2,4-Difluoro-phenyl)-N-[1-(3-pyridin-4-yl-phenyl)-ethyl]-acrylamide | 1.30 (b) | 364 |
| 261 | 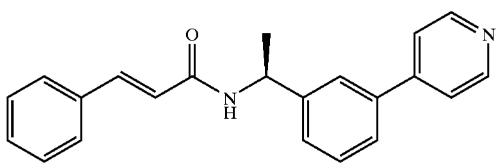 | (S)-3-Phenyl-N-[1-(3-pyridin-4-yl-phenyl)-ethyl]-acrylamide | 1.19 (b) | 329 |

Example 262–290

The compounds of Examples 262–290 were made in substantially the same fashion as Example 258 by using the appropriate triflate derivative and boronic acid.

| Example No. | Structure | Chemical name | HPLC rt (min), method | Mass (M + H)+ m/z |
|---|---|---|---|---|
| 262 | 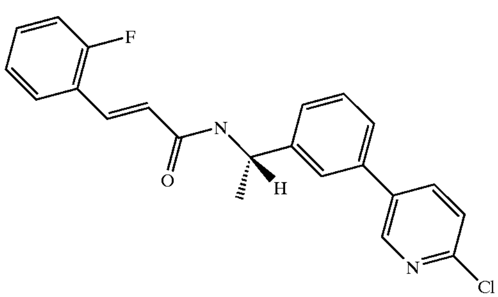 | (S)-N-{1-[3-(6-Chloro-pyridin-3-yl)-phenyl]-ethyl}-3-(2-fluoro-phenyl)-acrylamide | 1.84 (w) | 381 |
| 263 | 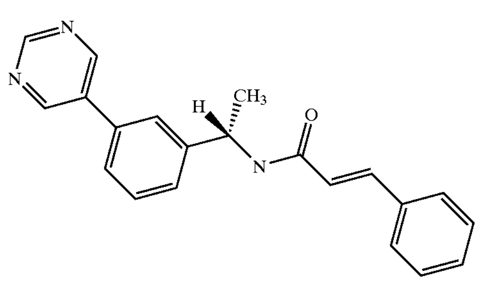 | (S)-3-Phenyl-N-[1-(3-pyrimidin-5-yl-phenyl)-ethyl]-acrylamide | 1.51 (w) | 330 |

-continued

| Example No. | Structure | Chemical name | HPLC rt (min), method | Mass (M + H)+ m/z |
|---|---|---|---|---|
| 264 | 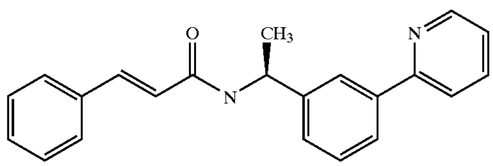 | (S)-3-Phenyl-N-[1-(3-pyridin-2-yl-phenyl)-ethyl]-acrylamide | 1.67 (w) | 329 |
| 265 | 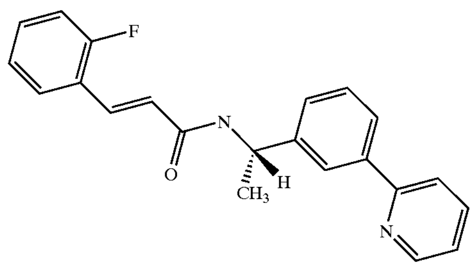 | (S)-3-(2-Fluoro-phenyl)-N-[1-(3-pyridin-2-yl-phenyl)-ethyl]-acrylamide | 1.70 (w) | 347 |
| 266 | 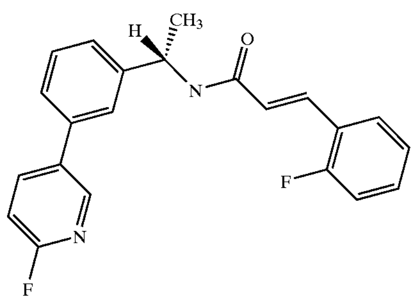 | (S)-3-(2-Fluoro-phenyl)-N-{1-[3-(6-fluoro-pyridin-3-yl)-phenyl]-ethyl}-acrylamide | 1.78 (w) | 365 |
| 267 | 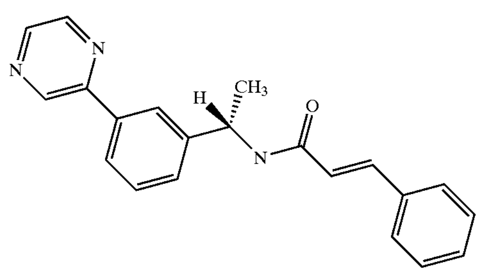 | (S)-3-Phenyl-N-[1-(3-pyrazin-2-yl-phenyl)-ethyl]-acrylamide | 1.57 (w) | 330 |
| 268 | 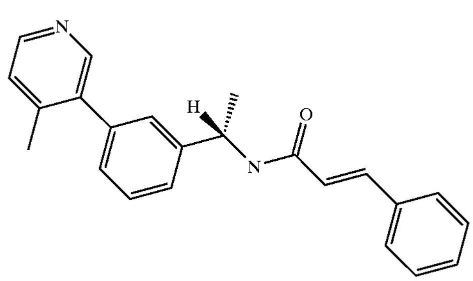 | (S)-N-{1-[3-(4-Methyl-pyridin-3-yl)-phenyl]-ethyl}-3-phenyl-acrylamide | 1.67 (w) | 361 |

-continued

| Example No. | Structure | Chemical name | HPLC rt (min), method | Mass (M + H)+ m/z |
|---|---|---|---|---|
| 269 | 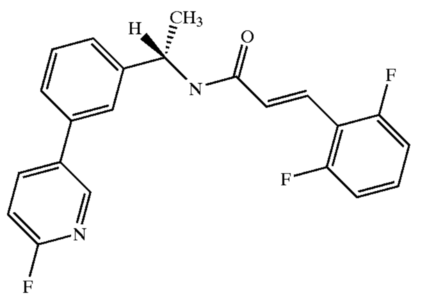 | (S)-3-(2,6-Difluoro-phenyl)-N-{1-[3-(6-fluoro-pyridin-3-yl)-phenyl]-ethyl}-acrylamide | 1.92 (w) | 383 |
| 270 | 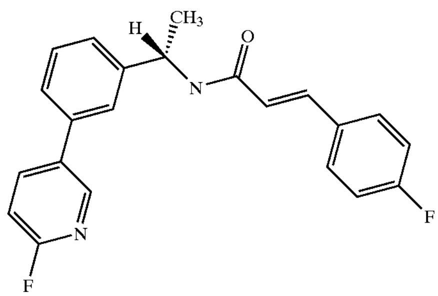 | (S)-3-(4-Fluoro-phenyl)-N-{1-[3-(6-fluoro-pyridin-3-yl)-phenyl]-ethyl}-acrylamide | 1.86 (w) | 365 |
| 271 | 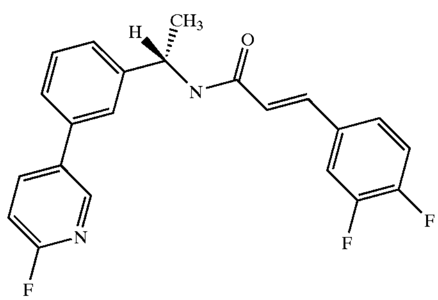 | (S)-3-(3,4-Difluoro-phenyl)-N-{1-[3-(6-fluoro-pyridin-3-yl)-phenyl]-ethyl}-acrylamide | 1.91 (w) | 383 |
| 272 | 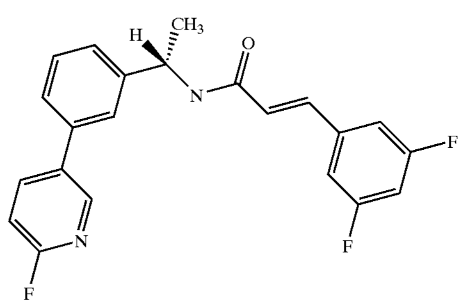 | (S)-3-(3,5-Difluoro-phenyl)-N-{1-[3-(6-fluoro-pyridin-3-yl)-phenyl]-ethyl}-acrylamide | 1.93 (w) | 383 |
| 273 | 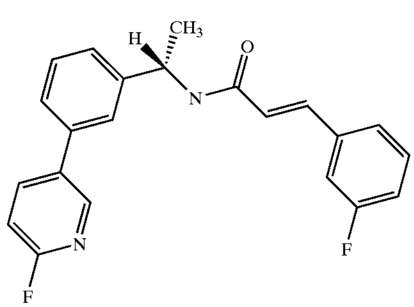 | (S)-3-(3-Fluoro-phenyl)-N-{1-[3-(6-fluoro-pyridin-3-yl)-phenyl]-ethyl}-acrylamide | 1.88 (w) | 365 |

-continued

| Example No. | Structure | Chemical name | HPLC rt (min), method | Mass (M + H)+ m/z |
|---|---|---|---|---|
| 274 | 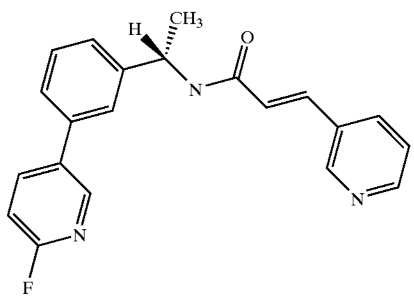 | (S)-N-{1-[3-(6-Fluoro-pyridin-3-yl)-phenyl]-ethyl}-3-pyridin-3-yl-acrylamide | 1.53 (w) | 348 |
| 275 | 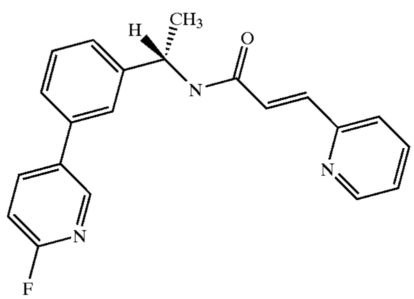 | (S)-N-{1-[3-(6-Fluoro-pyridin-3-yl)-phenyl]-ethyl}-3-pyridin-2-yl-acrylamide | 1.57 (w) | 348 |
| 276 | 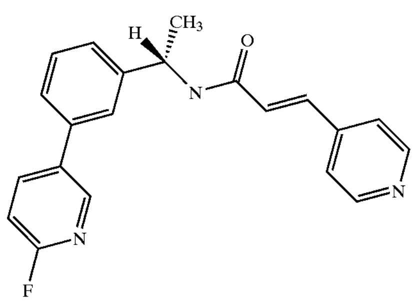 | (S)-N-{1-[3-(6-Fluoro-pyridin-3-yl)-phenyl]-ethyl}-3-pyridin-4-yl-acrylamide | 1.52 (w) | 348 |
| 277 | 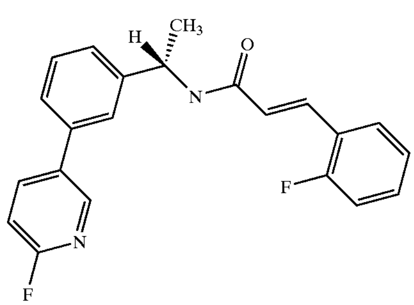 | (S)-3-(2-Fluoro-phenyl)-N-{1-[3-(6-fluoro-pyridin-3-yl)-phenyl]-ethyl}-acrylamide | 1.88 (w) | 365 |
| 278 | 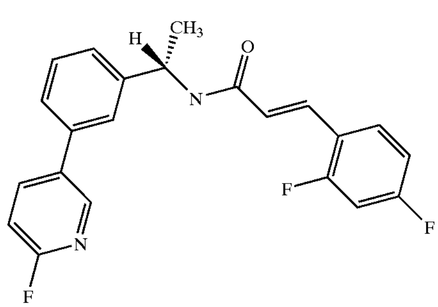 | (S)-3-(2,4-Difluoro-phenyl)-N-{1-[3-(6-fluoro-pyridin-3-yl)-phenyl]-ethyl}-acrylamide | 1.92 (w) | 383 |

-continued

| Example No. | Structure | Chemical name | HPLC rt (min), method | Mass (M + H)+ m/z |
|---|---|---|---|---|
| 279 | 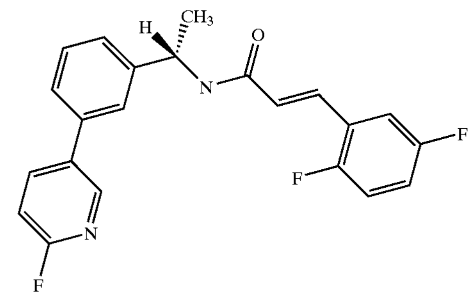 | (S)-3-(2,5-Difluoro-phenyl)-N-{1-[3-(6-fluoro-pyridin-3-yl)-phenyl]-ethyl}-acrylamide | 1.92 (w) | 383 |
| 280 | 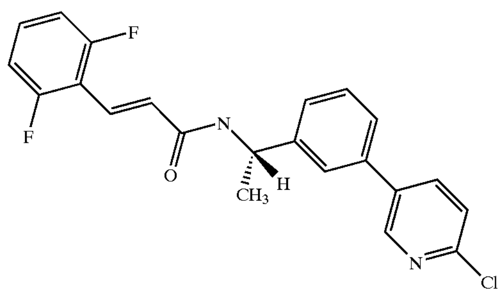 | (S)-N-{1-[3-(6-Chloro-pyridin-3-yl)-phenyl]-ethyl}-3-(2,6-difluoro-phenyl)-acrylamide | 1.99 (w) | 399 |
| 281 | 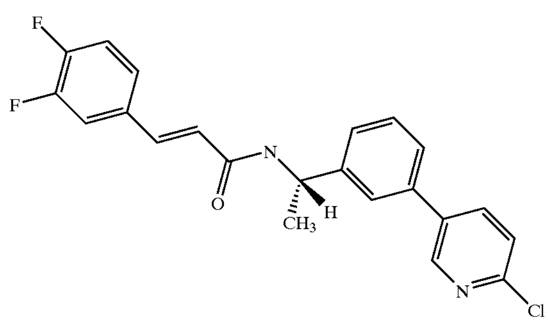 | (S)-N-{1-[3-(6-Chloro-pyridin-3-yl)-phenyl]-ethyl}-3-(3,4-difluoro-phenyl)-acrylamide | 1.97 (w) | 399 |
| 282 | 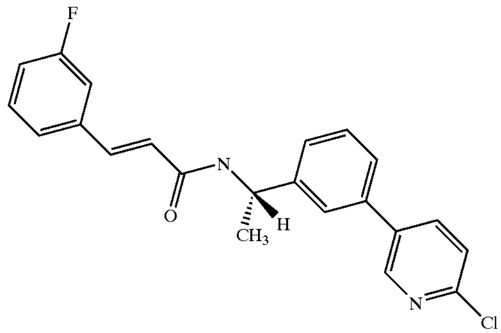 | (S)-N-{1-[3-(6-Chloro-pyridin-3-yl)-phenyl]-ethyl}-3-(3-fluoro-phenyl)-acrylamide | 1.95 (w) | 381 |

-continued

| Example No. | Structure | Chemical name | HPLC rt (min), method | Mass (M + H)+ m/z |
| --- | --- | --- | --- | --- |
| 283 | 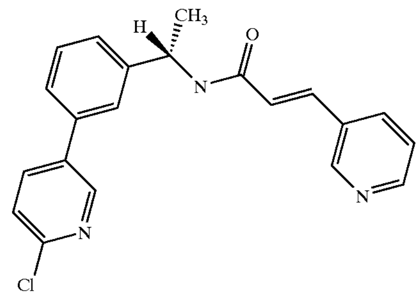 | (S)-N-{1-[3-(6-Chloro-pyridin-3-yl)-phenyl]-ethyl}-3-pyridin-3-yl-acrylamide | 1.59 (w) | 364 |
| 284 | 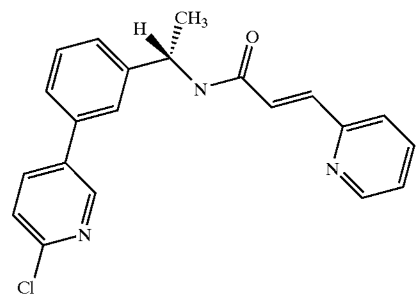 | (S)-N-{1-[3-(6-Chloro-pyridin-3-yl)-phenyl]-ethyl}-3-pyridin-2-yl-acrylamide | 1.64 (w) | 364 |
| 285 | 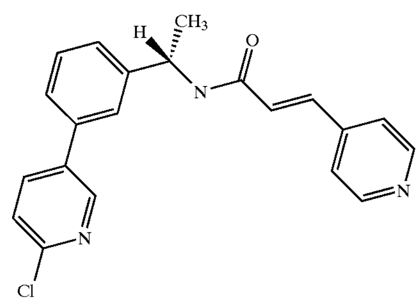 | (S)-N-{1-[3-(6-Chloro-pyridin-3-yl)-phenyl]-ethyl}-3-pyridin-4-yl-acrylamide | 1.59 (w) | 364 |
| 286 | 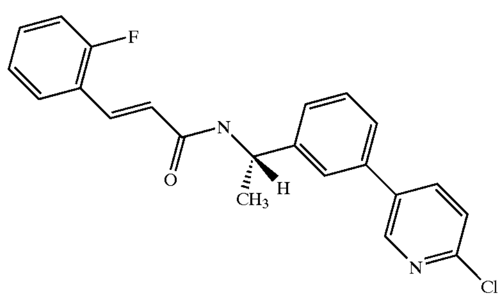 | (S)-N-{1-[3-(6-Chloro-pyridin-3-yl)-phenyl]-ethyl}-3-(2-fluoro-phenyl)-acrylamide | 1.95 (w) | 381 |
| 287 | 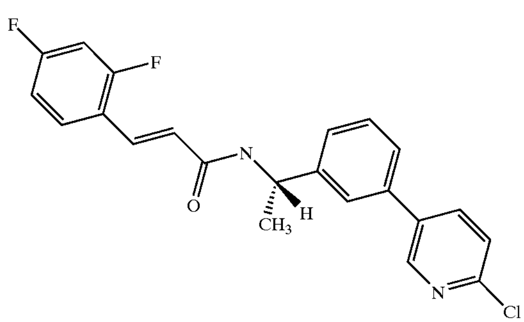 | (S)-N-{1-[3-(6-Chloro-pyridin-3-yl)-phenyl]-ethyl}-3-(2,4-difluoro-phenyl)-acrylamide | 1.98 (w) | 399 |

| Example No. | Structure | Chemical name | HPLC rt (min), method | Mass (M + H)+ m/z |
|---|---|---|---|---|
| 288 | 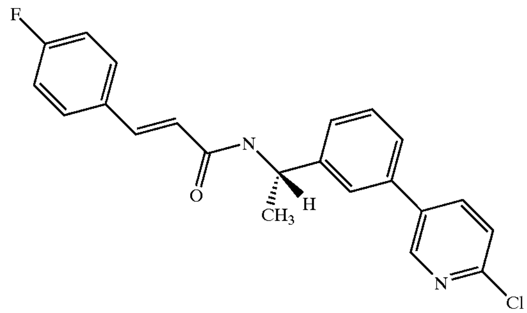 | (S)-N-{1-[3-(6-Chloro-pyridin-3-yl)-phenyl]-ethyl}-3-(4-fluoro-phenyl)-acrylamide | 1.92 (w) | 381 |
| 289 | 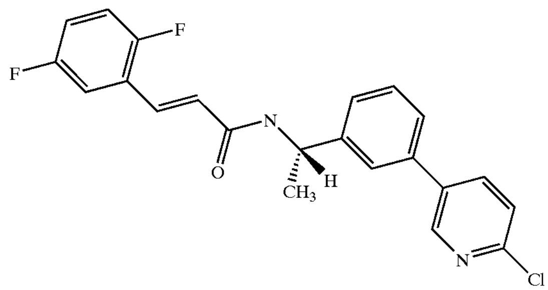 | (S)-N-{1-[3-(6-Chloro-pyridin-3-yl)-phenyl]-ethyl}-3-(2,5-difluoro-phenyl)-acrylamide | 1.98 (w) | 399 |
| 290 | 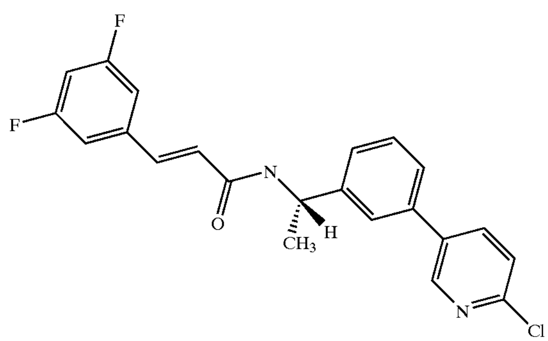 | (S)-N-{1-[3-(6-Chloro-pyridin-3-yl)-phenyl]-ethyl}-3-(3,5-difluoro-phenyl)-acrylamide | 2.00 (w) | 399 |

Example 291

Preparation of (S)-3-(2-fluoro-phenyl)-N-[1-(3-pyridin-3-yl-phenyl)ethyl]acrylamide

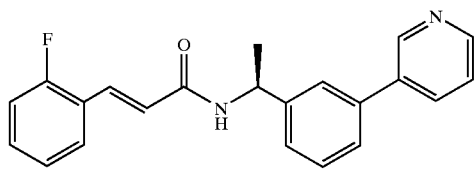

A mixture of 3-(2-fluoro-phenyl)-acrylic acid (0.083 mmol), (S)-1-(3-pyridin-3-yl-phenyl)ethylamine (12.7 mg, 0.064 mmol), EDC (18.4 mg, 0.096 mmol), HOBT (13 mg, 0.096 mmol), DMF (2 mL) and diisopropylethylamine (33 μL, 0.192 mmol) was stirred at 23° C., 18 hours. The residue was purified by preparative HPLC (Primeshere C18-HC 21.2×100 mm; (5 mM NH$_4$OAc) 0–100% gradient over 5 minutes 20 mL/min flow rate) to afford the title product.

$^1$H NMR (CDCl$_3$, 400 MHz): δ 1.55 (d, 3H, J=6.8 Hz), 5.29 (q, 1H, J=7.1 Hz), 6.20 (s, 1H), 6.55 (d, 1H, J=15.7 Hz), 6.9–7.1 (m, 2H), 7.2–7.3 (m, 2H), 7.3–7.5 (m, 3H) 7.64 (d, 1H J=15.9 Hz), 707–7.85 (m, 3H), 8.10 (s, 1H), 8.65 (d, 1H J=5 Hz,).

Example 292

Preparation of (S)-N-{1-[3-(6-fluoro-pyridin-3-yl)-phenyl]-ethyl}-3-phenyl-acrylamide

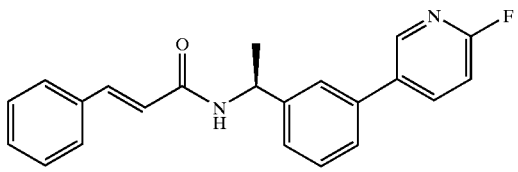

$^1$H NMR (CDCl$_3$, 400 MHz): δ 1.61 (d, 3H, J=6.8 Hz), 5.33 (q, 1H, J=7.1 Hz), 5.84 (d, 1H J=7.8 Hz), 6.40 (d, 1H, J=15.7 Hz), 7.0 (dd, 1H, J=2.5, 7.8), 7.3–7.55 (m, 9H), 7.64 (d, 1H J=15.7 Hz), 7.96 (dt, 1H, J=2.5, 7.8), 8.40 (d, 1H J=2.5 Hz,).

Example 293

Preparation of (S)-N-{1-[3-(6-chloro-pyridin-3-yl)-phenyl]-ethyl}-3-phenyl-acrylamide

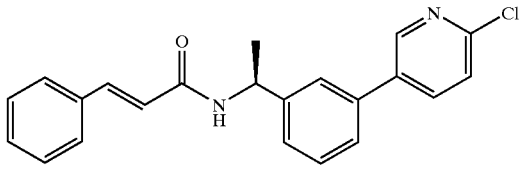

¹H NMR (CDCl₃, 400 MHz): δ 1.60 (d, 3H, J=7.1 Hz), 5.33 (q, 1H, J=7.3 Hz), 5.85 (d, 1H J=7.6 Hz), 6.40 (d, 1H, J=15.4 Hz), 7.3–7.55 (m, 1H), 7.64 (d, 1H J=15.7 Hz), 7.83 (dd, 1H, J=2.5, 8.3), 8.59 (d, 1H J=2.0 Hz,).

Example 294

Preparation of (S)-3-(2-fluoro-phenyl)-N-[1-(3-pyridin-4-yl-phenyl)ethyl]acrylamide

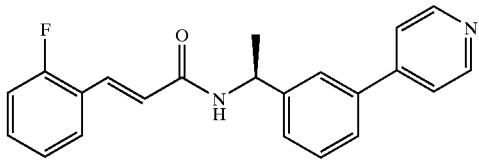

¹H NMR (CDCl₃, 400 MHz): δ 1.62 (d, 3H, J=7.1 Hz), 5.34 (q, 1H, J=7.1 Hz), 5.94 (d, 1H, J=8.1 Hz), 6.57 (d, 1H, J=15.9 Hz), 7.0–7.7 (m, 9H), 7.77 (s, 2H), 8.69 (d, 1H J=6.1 Hz).

Example 295

Preparation of (S)-3-(2-fluoro-phenyl)-N-[1-(3-pyrazin-2-yl-phenyl)ethyl]acrylamide

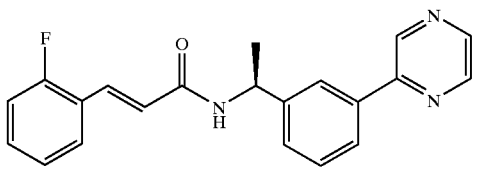

¹H NMR (CDCl₃, 400 MHz): δ 1.37 (d, 3H, J=7.1 Hz), 5.13 (q, 1H, J=7.3 Hz), 6.37 (d, 1H, J=8.1 Hz), 6.40 (d, 1H, J=15.9 Hz), 6.75–6.9 (m, 2H), 7.0–7.1 (m, 2H), 7.15–7.30 (m, 3H), 7.47 (d, 1H J=15.9 Hz), 7.64 (d, 1H, J=6.8), 7.82 (s, 1H), 8.28 (s, 1H) 8.39 (s, 1H), 8.78 (s, 1H).

Example 296

Preparation of (S)-3-(2-fluoro-phenyl)-N-[1-(3-pyrimidin-5-yl-phenyl)ethyl]acrylamide

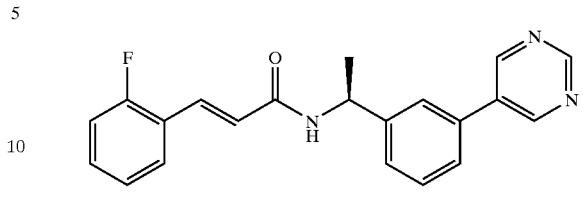

¹H NMR (CDCl₃, 400 MHz): δ 1.61 (d, 3H, J=7.1 Hz), 5.34 (q, 1H, J=7.1 Hz), 6.06 (d, 1H, J=7.1 Hz), 6.57 (d, 1H, J=15.7 Hz), 7.0–7.15 (m, 2H), 7.25–7.35 (m, 1H), 7.40–7.50 (m, 4H), 7.55 (s, 1H), 7.69 (d, 1H J=15.7 Hz), 8.93 (s, 1H), 8.20 (s, 1H).

Example 297

Preparation of (S)-3-(2-fluoro-phenyl)-N-{1-[3-(4-methyl-pyridin-3-yl)phenyl]ethyl}acrylamide

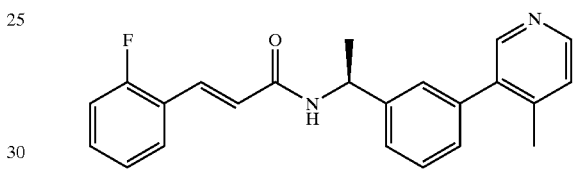

¹H NMR (CDCl₃, 400 MHz): δ 1.60 (d, 3H, J=6.8 Hz), 5.33 (q, 1H, J=7.1 Hz), 5.93 (d, 1H, J=7.8 Hz), 6.56 (d, 1H, J=15.7 Hz), 7.0–7.5 (m, 9H), 7.69 (d, 1H J=15.7 Hz), 8.45 (m, 2H).

Example 298

Preparation of (S)-3-(4-Fluorophenyl)-N-{1-[3-(4-methylpiperazin-1-yl)phenyl]ethyl}acrylamide

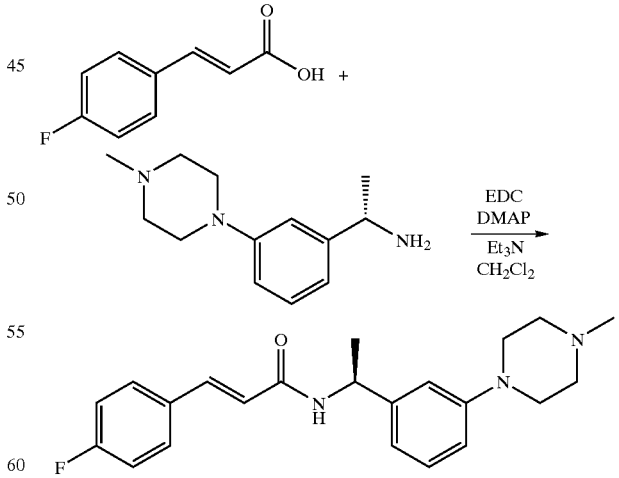

A solution of 4-fluorocinnamic acid (17 mg, 0.1 mmol), (S)-1-[3-(4-methylpiperazin-1-yl)-phenyl]ethylamine (preparation 42, 24 mg, 0.11 mmol), EDC (28 mg, 0.15 mmol), DMAP (12 mg, 0.1 mmol) and triethylamine (40 mg, 0.4 mmol) in dichloromethane (2 ml) was stirred overnight.

The reaction mixture was purified by fresh chromatography over silica gel with 5% methanol in dichloromethane to give the title compound as a solid (27 mg 74% yield).

$^1$H NMR (300 MHz, CDCl$_3$): δ 1.54 (d, 3H), 2.34 (s, 3H), 2.56 (t, 4H), 3.21 (t, 4H), 5.21 (m, 1H), 5.80 (d, 1H), 6.27 (d, 1H), 6.83–6.85 (m, 2H), 6.92 (s, 1H), 7.00–7.09 (m, 2H), 7.21–7.26 (m, 1H), 7.42–7.47 (m, 2H), 7.63 (d, 1H).

MS (M+H)$^+$ 368.

Examples 299–301

Examples 299–301 were made from appropriate acids using the same method used to prepare Example 298.

| Example No. | Structure | Chemical Name | HPLC rt (min) method | Mass (M + H)$^+$ m/z |
|---|---|---|---|---|
| 299 | 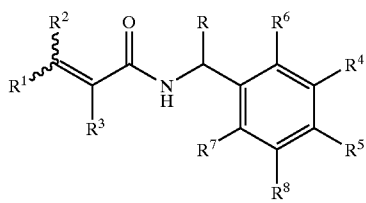 | (S)-3-(2-Fluorophenyl)-N-{1-[3-(4-methyl-piperazin-1-yl)-phenyl]-ethyl}-acrylamide | 1.26 (t) | 368 |
| 300 | 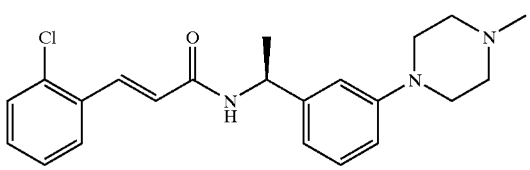 | (S)-3-(2-Chlorophenyl)-N-{1-[3-(4-methyl-piperazin-1-yl)-phenyl]-ethyl}-acrylamide | 1.34 (t) | 384 |
| 301 | 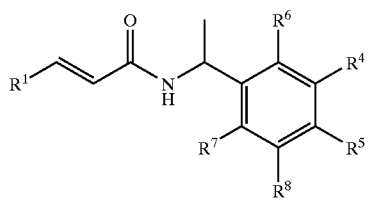 | (S)-3-(2,3-Difluoro-phenyl)-N-{1-[3-(4-methyl-piperazin-1-yl)-phenyl]-ethyl}-acrylamide | 1.31 (t) | 386 |

What is claimed is:

1. A compound of Formula I or a pharmaceutically acceptable salt thereof:

I wherein
R is C$_{1-4}$ alkyl or trifluoromethyl;
R$^1$ is selected from the group consisting of pyridinyl, quinolinyl, thienyl, furanyl, 1,4-benzodioxanyl, 1,3-benzodioxolyl, chromanyl, indanyl, biphenylyl, phenyl and substituted phenyl, in which said substituted phenyl is substituted with substituent independently selected from the group consisting of halogen, C$_{1-4}$ alkyl, C$_{1-4}$ alkoxy, trifluoromethyl, trifluoromethoxy and nitro;
R$^2$ and R$^3$ are each independently selected from the group consisting of hydrogen, C$_{1-4}$ alkyl and halogen;
R$^4$ is selected from the group consisting of di(C$_{1-4}$ alkyl) amino, trifluoromethoxy and optionally substituted morpholin-4-yl, pyridinyl, pyrimidinyl, piperazinyl, and pyrazinyl with one or two substituents in which said substituent is independently selected from the group consisting of C$_{1-4}$alkyl, aminomethyl, hydroxymethyl, chloro or fluoro;
R$^5$ is hydrogen, chloro or fluoro; or R$^4$ and R$^5$ taken together are —CH═CH—CH═CH— or —X(CH$_2$)$_m$Y— in which X and Y are each independently selected from the group consisting of CH$_2$, (CH$_2$)$_n$N(R$^9$)— and O, wherein m is 1 or 2; n is 0 or 1;
R$^6$, R$^7$, and R$^8$ are each independently selected from hydrogen, chloro and fluoro; and
R$^9$ is selected from the group consisting of hydrogen, C$_{1-4}$ alkyl, hydroxyethyl, C$_{1-4}$ alkoxyethyl, cyclopropylmethyl, —CO$_2$(C$_{1-4}$alkyl), and —CH$_2$CH$_2$NR$^{10}$R$^{11}$ in which R$^{10}$ and R$^{11}$ are each independently hydrogen or C$_{1-4}$ alkyl.

2. The compound of claim 1 having the Formula Ia or a pharmaceutically acceptable salt thereof:

Ia wherein
R$^1$ is selected from the group consisting of pyridinyl, 3-quinolinyl, 2-thienyl, benzodioxanyl, 1,3-benzodioxol-5-yl, chroman-5-yl, indan-5-yl, 4-biphenylyl, phenyl and substituted phenyl, in which said substituted phenyl is substituted with substituent independently selected from the group consisting of halogen, C$_{1-4}$ alkyl, C -4 alkoxy, trifluoromethyl, trifluoromethoxy and nitro;

R⁴ is selected from the group consisting of optionally substituted di($C_{1-4}$ alkyl)amino, trifluoromethoxy and optionally substituted morpholin-4-yl, pyridinyl, pyrimidinyl, piperazinyl, and pyrazinyl with one or two substituents in which said substituent is independently selected from the group consisting of $C_{1-4}$ alkyl, aminomethyl, hydroxymethyl, chloro or fluoro;

R⁵ is hydrogen or fluoro; or R⁴ and R⁵ taken together are —CH═CH—CH═CH— or —X(CH₂)ₘY—, in which X and Y are each independently selected from the group consisting of CH₂, (CH₂)ₙN(R⁹)— and O, wherein m is 1 or 2; n is 0 or 1;

R⁶, R⁷, and R⁸ are each independently selected from hydrogen, chloro and fluoro; and R⁹ is selected from the group consisting of hydrogen, $C_{1-4}$ alkyl, hydroxyethyl, $C_{1-4}$ alkoxyethyl, cyclopropylmethyl, —CO₂($C_{1-4}$alkyl), and —CH₂CH₂NR¹⁰R¹¹ in which R¹⁰ and R¹¹ are each independently hydrogen or $C_{1-4}$ alkyl.

3. The compound of claim 2 having the Formula Ib or a pharmaceutically acceptable salt thereof:

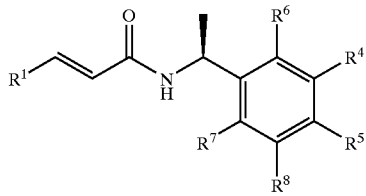

Ib wherein

R¹ is selected from the group consisting of pyridinyl, 3-quinolinyl, 2-thienyl, benzodioxanyl, 1,3-benzodioxol-5-yl, chroman-5-yl, indan-5-yl, 4-biphenylyl, phenyl and substituted phenyl, in which said substituted phenyl is substituted with substituent independently selected from the group consisting of halogen, $C_{1-4}$ alkyl, $C_{1-4}$ alkoxy, trifluoromethyl, trifluoromethoxy and nitro;

R⁴ is selected from the group consisting of optionally substituted di($C_{1-4}$ alkyl)amino, trifluoromethoxy and optionally substituted morpholin-4-yl, pyridinyl, pyrimidinyl, piperazinyl, and pyrazinyl with one or two substituents in which said substituent is independently selected from the group consisting of $C_{1-4}$ alkyl, aminomethyl, hydroxymethyl, chloro or fluoro;

R⁵ is hydrogen or fluoro; or R⁴ and R⁵ taken together are —CH═CH—CH═CH— or —X(CH₂)ₘY—, in which X and Y are each independently selected from the group consisting of CH₂, (CH₂)ₙN(R⁹)— and O, wherein m is 1 or 2; n is 0 or 1;

R⁶, R⁷, and R⁸ are each independently selected from hydrogen, chloro and fluoro; and R⁹ is selected from the group consisting of hydrogen, C₄ alkyl, hydroxyethyl, $C_{1-4}$ alkoxyethyl, cyclopropylmethyl, —CO₂($C_{1-4}$alkyl), and —CH₂CH₂NR¹⁰R¹¹ in which R¹⁰ and R¹¹ are each independently hydrogen or $C_{1-4}$ alkyl.

4. The compound of claim 3 wherein R¹ is selected from the group consisting of 2-thienyl, chroman-5-yl, 4-biphenylyl, phenyl and substituted phenyl in which said substituted phenyl is substituted with one or two substituents each independently selected from the group consisting of halogen, $C_{1-4}$ alkyl, $C_{1-4}$ alkoxy, trifluoromethoxy and nitro; and R⁴ and R⁵ taken together are —CH═CH—CH═CH—.

5. The compound of claim 2 wherein R¹ is substituted phenyl or 1,3-benzodioxol-5-yl in which said substituted phenyl is substituted with one or two substituents each independently selected from the group consisting of halogen, $C_{1-4}$ alkyl, and $C_{1-4}$ alkoxy; and R⁴ and R⁵ taken together are —X(CH₂)ₘY— in which X and Y are each O, and m is 1.

6. The compound of claim 2 wherein R¹ is selected from the group consisting of substituted phenyl, 1,3-benzodioxol-5-yl, and indan-5-yl in which said substituted phenyl is substituted with one or two substituents each independently selected from the group consisting of halogen, $C_{1-4}$ alkyl, $C_{1-4}$ alkoxy, trifluoromethoxy and trifluoromethyl; and R⁴ and R⁵ taken together are —X(CH₂)ₘY— in which X is CH₂, Y is O, and m is 1.

7. The compound of claim 2 or 3 wherein R¹ is thienyl, phenyl or substituted phenyl in which said substituted phenyl is substituted with one or two substituents each independently selected from the group consisting of halogen, $C_{1-4}$ alkyl, $C_{1-4}$ alkoxy, trifluoromethoxy, trifluoromethyl and nitro; R⁴ is optionally substituted morpholin-4-yl with one or two substituents each independently selected from the group consisting of $C_{1-4}$ alkyl, aminomethyl, hydroxymethyl, chloro or fluoro; and R⁵ is hydrogen or fluoro.

8. The compound of claim 7 wherein R¹ is phenyl, fluorophenyl or difluorophenyl.

9. The compound of claim 2 wherein R¹ is substituted phenyl or 1,3-benzodioxol-5-yl in which said substituted phenyl is substituted with one or two substituents each independently selected from halogen or $C_{1-4}$ alkyl; and R⁴ and R⁵ taken together are —X(CH₂)ₘY— in which X and Y are O, and m is 2.

10. The compound of claim 2 wherein R¹ is phenyl or substituted phenyl in which said substituted phenyl is substituted with one or two substituents each independently selected from halogen or $C_{1-4}$ alkyl; R⁴ and R⁵ taken together are —X(CH₂)ₘY— in which X is (CH₂)ₙN(R⁹)—; Y is CH₂, and m and n are 1; and R⁹ is CO₂($C_{1-4}$alkyl).

11. The compound of claim 2 wherein R¹ is substituted phenyl in which said substituted phenyl is substituted with one or two substituents each independently selected from halogen; R⁴ and R⁵ taken together are —X(CH₂)ₘY— in which X is (CH₂)ₙN(R⁹)— and Y is O wherein m is 2 and n is 0; and R⁹ is hydrogen, cyclopropylmethyl or $C_{1-4}$alkyl.

12. The compound of claim 2 wherein R¹ is 3-quinolinyl or pyridinyl; R⁴ is trifluoromethoxy; and R⁵ is hydrogen.

13. The compound of claim 2 wherein R¹ is substituted phenyl in which said substituted phenyl is substituted with one or two substituents selected from halogen or $C_{1-4}$alkyl; R⁴ and R⁵ taken together are —X(CH₂)ₘY—, in which X is CH₂ and Y is (CH₂)ₙN(R⁹)— wherein m is 1 and n is 0; and R⁹ is CO₂($C_{1-4}$alkyl).

14. The compound of claim 2 wherein R¹ is phenyl or substituted phenyl in which said substituted phenyl is substituted with one or two substituents selected from halogen; R⁴ and R⁵ taken together are —X(CH₂)ₘY—, in which X is (CH₂)ₙN(R⁹)— and Y is CH₂ wherein m is 2 and n is 0; and R⁹ is hydrogen, $C_{1-4}$alkyl, acetyl, hydroxyethyl or methoxyethyl.

15. The compound of claim 2 wherein R¹ is phenyl or substituted phenyl in which said substituted phenyl is substituted with one or two substituents selected from halogen; R⁴ and R⁵ taken together are —X(CH₂)ₙY—, in which X is CH₂ and Y is (CH₂)ₙN(R⁹)— wherein m is 2 and n is 0; and R⁹ is hydrogen, $C_{1-4}$alkyl, acetyl, hydroxyethyl or methoxyethyl.

16. The compound of claim 2 or 3 wherein $R^1$ is pyridinyl, phenyl or substituted phenyl in which said substituted phenyl is substituted with one or two substituents selected from halogen; $R^4$ is optionally substituted pyridinyl with one or two substituents each independently selected from $C_{1-4}$ alkyl and halogen; and $R^5$ is hydrogen or fluoro.

17. The compound of claim 2 wherein $R^1$ is 1,3-benzodioxol-5-yl; $R^4$ is di($C_{1-4}$alkyl)amino; and $R^5$ is hydrogen or fluoro.

18. The compound of claim 2 wherein $R^1$ is phenyl or substituted phenyl in which said substituted phenyl is substituted with one or two substituents selected from halogen; $R^4$ is pyrimidinyl; and $R^5$ is hydrogen or fluoro.

19. The compound of claim 2 wherein $R^1$ is phenyl or substituted phenyl in which said substituted phenyl is substituted with one or two substituents selected from halogen; $R^4$ is pyrazinyl; and $R^5$ is hydrogen or fluoro.

20. The compound of claim 2 or 3 wherein $R^1$ is thienyl, phenyl or substituted phenyl in which said substituted phenyl is substituted with one or two substituents selected from $C_{1-4}$alkyl and halogen; $R^4$ is piperazinyl or 4-methylpiperazinyl; and $R^5$ is hydrogen or fluoro.

21. The compound of claim 2 selected from the group consisting of:

2-Methyl-3-phenyl-but-2-enoic acid (1-naphthalen-2-ylethyl)-amide;

N-(1-Benzo[1,3]dioxol-5-yl-ethyl)-3-(3-methoxy-phenyl)-acrylamide;

N-[1-(2,3-Dihydrobenzofuran-5-yl)ethyl]-3-(3-methoxyphenyl)-acrylamide;

(S)-3-Phenyl-N-[1-(3-morpholin-4-yl-phenyl)ethyl] acrylamide;

3-(3-Fluorophenyl)-N-[1-(2,3-dihydrobenzo[1,4]dioxin-6-yl)-ethyl]acrylamide;

(±)-7-{1-[3-(4-Fluorophenyl)acryloylamino]ethyl}-3,4-dihydro-1H-isoquinoline-2-carboxylic acid methyl ester;

3-(2-Fluorophenyl)-N-[1-(4-methyl-3,4-dihydro-2H-benzo[1,4]oxazin-6-yl)ethyl]-acrylamide;

(S)-N-(1-Naphthalen-2-yl-ethyl)-3-phenyl-acrylamide;

(S)-3-(4-Fluoro-phenyl)-N-(1-naphthalen-2-yl-ethyl)-acrylamide;

(±)-N-(1-Benzo[1,3]dioxol-5-yl-ethyl)-3-(2,4-difluoro-phenyl)-acrylamide;

(±)-N-[1-(2,3-Dihydro-benzofuran-5-yl)-ethyl]-3-(2-fluoro-phenyl)-acrylamide;

(±)-3-(2,4-Difluoro-phenyl)-N-[1-(2,3-dihydro-benzofuran-5-yl)-ethyl]-acrylamide;

(S)-3-(2,4-Difluoro-phenyl)-N-[1-(3-morpholin-4-yl-phenyl)-ethyl]-acrylamide;

(S)-N-[1-(3-(2,6-Dimethyl-morpholin)-4-yl-phenyl)-ethyl]-3-phenyl-acrylamide;

(S)-3-(2-Fluoro-phenyl)-N-[1-(3-morpholin-4-yl-phenyl)-ethyl]-acrylamide;

(S)-N-[1-(3-Morpholin-4-yl-phenyl)-ethyl]-3-thiophen-3-yl-acrylamide;

(S)-3-(4-Fluoro-phenyl)-N-[1-(3-morpholin-4-yl-phenyl)-ethyl]-acrylamide;

(S)-N-{1-[3-(cis-2,6-Dimethyl-morpholin-4-yl)-phenyl]-ethyl}-3-(4-fluoro-phenyl)-acrylamide;

(S)-3-(2,4-Difluoro-phenyl)-N-{1-[3-(cis-2,6-dimethyl-morpholin-4-yl)-phenyl]-ethyl}-acrylamide;

(S)-3-(3,4-Difluoro-phenyl)-N-{1-[3-(cis-2,6-dimethyl-morpholin-4-yl)-phenyl]-ethyl}-acrylamide;

(S)-3-(2,5-Difluoro-phenyl)-N-{1-[3-(cis-2,6-dimethyl-morpholin-4-yl)-phenyl]-ethyl}-acrylamide;

(S)-3-(2-Fluoro-phenyl)-N-{1-[3-(2-methyl-morpholin-4-yl)-phenyl]-ethyl}-acrylamide;

(S)-3-(3-Fluoro-phenyl)-N-{1-[3-(2-methyl-morpholin-4-yl)-phenyl]-ethyl}-acrylamide;

(S)-3-(4-Fluoro-phenyl)-N-{1-[3-(2-methyl-morpholin-4-yl)-phenyl]-ethyl}-acrylamide;

(S)-3-(2,4-Difluoro-phenyl)-N-{1-[3-(2-methyl-morpholin-4-yl)-phenyl]-ethyl}-acrylamide;

(S)-N-{1-[3-(2-Oxa-5-aza-bicyclo[2.2.1]hept-5-yl) phenyl]ethyl}-3-phenyl-acrylamide;

(S)-N-{1-[3-(2-Hydroxymethyl-morpholin-4-yl)-phenyl]-ethyl}-3-phenyl-acrylamide;

(±)-N-[1-(3-Morpholin-4-yl-phenyl)-propyl]-3-phenyl-acrylamide;

(±)-3-(2,4-Difluoro-phenyl)-N-[1-(3-morpholin-4-yl-phenyl)-propyl]-acrylamide;

(±)-3-(2-Fluoro-phenyl)-N-[1-(3-morpholin-4-yl-phenyl)-propyl]-acrylamide;

(±)-3-(3-Fluoro-phenyl)-N-[1-(3-morpholin-4-yl-phenyl)-propyl]-acrylamide;

(±)-N-[1-(4-Fluoro-3-morpholin-4-yl-phenyl)-ethyl]-3-(2-fluoro-phenyl)-acrylamide;

(±)-N-[1-(4-Fluoro-3-morpholin-4-yl-phenyl)-ethyl]-3-(4-fluoro-phenyl)-acrylamide;

(±)-3-(2,4-Difluoro-phenyl)-N-[1-(4-fluoro-3-morpholin-4-yl-phenyl)-ethyl]-acrylamide;

(±)-N-[1-(4-Fluoro-3-morpholin-4-yl-phenyl)-ethyl]-3-(4-fluoro-phenyl)-acrylamide;

(±)-3-(3,4-Difluoro-phenyl)-N-[1-(4-fluoro-3-morpholin-4-yl-phenyl)-ethyl]-acrylamide;

(±)-3-(2,5-Difluoro-phenyl)-N-[1-(4-fluoro-3-morpholin-4-yl-phenyl)-ethyl]-acrylamide;

(±)-N-[1-(4-Fluoro-3-morpholin-4-yl-phenyl)-ethyl]-3-(3-fluoro-phenyl)-acrylamide;

(±)-N-[1-(4-Fluoro-3-morpholin-4-yl-phenyl)-ethyl]-3-(2-fluoro-phenyl)-acrylamide;

(±)-3-(3-Fluoro-phenyl)-N-[1-(1,2,3,4-tetrahydro-quinolin-7-yl)-ethyl]-acrylamide;

(±)-3-(4-Fluoro-phenyl)-N-[1-(1,2,3,4-tetrahydro-quinolin-7-yl)ethyl]-acrylamide;

(±)-3-(2-Fluoro-phenyl)-N-[1-(1-methyl-1,2,3,4-tetrahydro-quinolin-7-yl)ethyl]acrylamide;

(±)-N-{1-[1-(2-Hydroxy-ethyl)-1,2,3,4-tetrahydro-quinolin-7-yl]-ethyl}-3-phenyl-acrylamide;

(±)-3-(2,5-Difluoro-phenyl)-N-{1-[1-(2-hydroxy-ethyl)-1,2,3,4-tetrahydro-quinolin-7-yl]-ethyl}-acrylamide;

(±)-3-(3,5-Difluoro-phenyl)-N-{1-[1-(2-hydroxy-ethyl)-1,2,3,4-tetrahydro-quinolin-6-yl]-ethyl}-acrylamide;

(S)-3-Phenyl-N-[1-(3-pyridyl-phenyl)-ethyl]acrylamide;

(S)-(2,4-Difluoro-phenyl)-N-[1-(3-pyridin-3-yl-phenyl)-ethyl]-acrylamide;

(S)-3-Phenyl-N-[1-(3-pyridin-4-yl-phenyl)-ethyl]-acrylamide;

(S)-N-{1-[3-(6-Chloro-pyridin-3-yl)-phenyl]-ethyl}-3-(2-fluoro-phenyl)-acrylamide;

(S)-3-Phenyl-N-[1-(3-pyrimidin-5-yl-phenyl)-ethyl]-acrylamide;

(S)-3-Phenyl-N-[1-(3-pyridin-2-yl-phenyl)-ethyl]-acrylamide;

(S)-3-(2-Fluoro-phenyl)-N-[1-(3-pyridin-2-yl-phenyl)-ethyl]-acrylamide;
(S)-3-(2-Fluoro-phenyl)-N-{1-[3-(6-fluoro-pyridin-3-yl)-phenyl]ethyl}-acrylamide;
(S)-3-(4-Fluoro-phenyl)-N-{1-[3-(6-fluoro-pyridin-3-yl)-phenyl]-ethyl}-acrylamide;
(S)-N-{1-[3-(6-Fluoro-pyridin-3-yl)-phenyl]-ethyl}-3-pyridin-3-yl-acrylamide;
(S)-N-{1-[3-(6-Fluoro-pyridin-3-yl)-phenyl]-ethyl}-3-pyridin-4-yl-acrylamide;
(S)-N-{1-[3-(6-Chloro-pyridin-3-yl)-phenyl]-ethyl}-3-(3-fluoro-phenyl)-acrylamide;
(S)-N-{1-[3-(6-Chloro-pyridin-3-yl)-phenyl]-ethyl}-3-pyridin-3-yl-acrylamide;
(S)-N-{1-[3-(6-Chloro-pyridin-3-yl)-phenyl]-ethyl}-3-pyridin-2-yl-acrylamide;
(S)-N-{1-[3-(6-Chloro-pyridin-3-yl)-phenyl]-ethyl}-3-pyridin-4-yl-acrylamide;
(S)-N-{1-[3-(6-Chloro-pyridin-3-yl)-phenyl]-ethyl}-3-(2-fluoro-phenyl)-acrylamide;
(S)-N-{1-[3-(6-Chloro-pyridin-3-yl)-phenyl]-ethyl}-3-(2,4-difluoro-phenyl)-acrylamide;
(S)-N-{1-[3-(6-Chloro-pyridin-3-yl)-phenyl]-ethyl}-3-(4-fluoro-phenyl)-acrylamide;
(S)-3-(2-Fluoro-phenyl)-N-[1-(3-pyridin-3-yl-phenyl)ethyl]acrylamide;
(S)-N-{1-[3-(6-Fluoro-pyridin-3-yl)-phenyl]-ethyl}-3-phenyl-acrylamide;
(S)-N-{1-[3-(6-Chloro-pyridin-3-yl)-phenyl]-ethyl}-3-phenyl-acrylamide;
(S)-3-(2-Fluoro-phenyl)-N-[1-(3-pyridin-4-yl-phenyl)ethyl]acrylamide;
(S)-3-(2-Fluoro-phenyl)-N-[1-(3-pyrazin-2-yl-phenyl)ethyl]acrylamide;
(S)-3-(2-Fluoro-phenyl)-N-[1-(3-pyrimidin-5-yl-phenyl)ethyl]acrylamide;
(S)-3-(2-Fluoro-phenyl)-N-{1-[3-(4-methyl-pyridin-3-yl)phenyl]ethyl}acrylamide;
(S)-3-(4-Fluorophenyl)-N-{1-[3-(4-methylpiperazin-1-yl)phenyl]ethyl}acrylamide; and
(S)-3-(2,3-Difluoro-phenyl)-N-{1-[3-(4-methyl-piperazin-1-yl)-phenyl]-ethyl}-acrylamide;
or a pharmaceutically acceptable salt thereof.

22. A pharmaceutical composition for the treatment of disorders responsive to opening of KCNQ potassium channels comprising a therapeutically effective amount of the compound of claim 1 in association with a pharmaceutically acceptable carrier, adjuvant or diluent.

23. A method of the treatment of disorders responsive to the opening of the KCNQ potassium channels in a mammal in need thereof, which comprises administering to said mammal a therapeutically effective amount of the compounds of claim 1, wherein said disorders are acute and chronic pain, migraine, neuropathic pain, bipolar disorders, convulsions, mania, epilepsy, anxiety, depression and neurodegenerative disorders.

24. The method of claim 23 wherein said disorder is migraine.

25. The method of claim 23 wherein said disorder is bipolar disorders.

26. The method of claim 23 wherein said disorder is neuropathic pain.

27. The method of claim 23 wherein said disorder is anxiety.

* * * * *